US012673925B2

(12) United States Patent
Hill et al.

(10) Patent No.: US 12,673,925 B2
(45) Date of Patent: Jul. 7, 2026

(54) COMPOUNDS AND COMPOSITIONS FOR EYE TREATMENTS

(71) Applicant: Avedro, Inc., Waltham, MA (US)

(72) Inventors: Jason Hill, Auburndale, MA (US); Desmond Adler, Bedford, MA (US); Marc D. Friedman, Needham, MA (US); Pavel Kamaev, Lexington, MA (US); Evan Sherr, Ashland, MA (US)

(73) Assignee: Avedro, Inc., Waltham, MA (US)

( * ) Notice: Subject to any disclaimer, the term of this patent is extended or adjusted under 35 U.S.C. 154(b) by 1016 days.

(21) Appl. No.: 17/311,150

(22) PCT Filed: Dec. 4, 2019

(86) PCT No.: PCT/US2019/064534
§ 371 (c)(1),
(2) Date: Jun. 4, 2021

(87) PCT Pub. No.: WO2020/117974
PCT Pub. Date: Jun. 11, 2020

(65) Prior Publication Data
US 2022/0041563 A1 Feb. 10, 2022

Related U.S. Application Data

(60) Provisional application No. 62/775,305, filed on Dec. 4, 2018.

(51) Int. Cl.

| | |
|---|---|
| ***C07D 241/44*** | (2006.01) |
| ***A61F 9/007*** | (2006.01) |
| ***A61F 9/008*** | (2006.01) |
| ***A61K 31/498*** | (2006.01) |
| ***A61K 31/506*** | (2006.01) |

(Continued)

(52) U.S. Cl.
CPC .......... *C07D 241/44* (2013.01); *A61F 9/0079* (2013.01); *A61F 9/008* (2013.01); *A61K 31/498* (2013.01); *A61K 31/506* (2013.01); *A61K 31/525* (2013.01); *A61K 31/5377* (2013.01); *A61K 31/675* (2013.01); *A61K 33/00* (2013.01); *A61K 41/00* (2013.01); *A61K 45/06* (2013.01); *A61P 27/02* (2018.01); *C07D 401/14* (2013.01); *C07D 403/04* (2013.01); *C07D 403/14* (2013.01); *C07D 413/04* (2013.01); *C07D 417/04* (2013.01); *C07F 9/6524* (2013.01)

(58) Field of Classification Search
CPC ..... A61F 9/0079; A61F 9/008; A61K 31/498; A61K 31/506; A61K 31/525; A61K 31/5377; A61K 31/675; A61K 33/00; A61K 41/00; A61K 45/06; A61K 31/519; A61K 9/0048; A61P 27/02; A61P 27/10; C07D 241/44; C07D 401/12; C07D 401/14; C07D 403/04; C07D 403/14; C07D 413/04; C07D 417/04; C07F 9/6524; A61N 2005/0661; A61N 5/0613
See application file for complete search history.

(56) References Cited

U.S. PATENT DOCUMENTS

| | | | |
|---|---|---|---|
| 8,574,277 | B2 | 11/2013 | Muller et al. |
| 2011/0237999 | A1 | 9/2011 | Muller et al. |

(Continued)

FOREIGN PATENT DOCUMENTS

| | | | |
|---|---|---|---|
| JP | 2014-519914 | A | 8/2014 |
| JP | 2018-501216 | A | 1/2018 |

(Continued)

OTHER PUBLICATIONS

Choi et al., "The interaction of flavins with egg white riboflavin-binding protein", Archives of Biochemistry and Biophysics (1980) 204(1):41-51.

(Continued)

*Primary Examiner* — Ellen M McAvoy
*Assistant Examiner* — Chantel Graham
(74) *Attorney, Agent, or Firm* — Knobbe Martens Olson & Bear LLP

(57) ABSTRACT

This disclosure features chemical entities (e.g., a compound or a pharmaceutically acceptable salt and/or hydrate and/or prodrug of the compound) that that generates cross-linking in the cornea in response to exposure to an electromagnetic irradiation. This disclosure also features compositions containing the same as well as other methods of using and making the same. The chemical entities are useful, e.g., for treating a subject (e.g., a human) having a disease, disorder, or condition in which in which abnormal shaping of the cornea (e.g., thinning of the cornea, e.g., bilateral thinning of the cornea, e.g., bilateral thinning of the central, paracentral, or peripheral cornea; or steepening (e.g., bulging) of the cornea) contributes to the pathology and/or symptoms and/or progression of the disease, disorder, or condition. Non-limiting examples of such diseases, disorders, or conditions include: (i) corneal ectatic disorders; (ii) vision conditions; and (iii) diseases, disorders, or conditions that are sequela or comorbid with any of the foregoing or any disclosed herein. More particular non-limiting examples of such diseases, disorders, or conditions include keratoconus, keratoglobus, pellucid marginal degeneration, corneal ectasia (e.g., post-operative ectasia, e.g., post-LASIK ectasia), Terrien's marginal degeneration, myopia, hyperopia, astigmatism, irregular astigmatism, and presbyopia.

20 Claims, No Drawings

(51) Int. Cl.

| | |
|---|---|
| ***A61K 31/525*** | (2006.01) |
| ***A61K 31/5377*** | (2006.01) |
| ***A61K 31/675*** | (2006.01) |
| ***A61K 33/00*** | (2006.01) |
| ***A61K 41/00*** | (2020.01) |
| ***A61K 45/06*** | (2006.01) |
| ***A61P 27/02*** | (2006.01) |
| ***C07D 401/14*** | (2006.01) |
| ***C07D 403/04*** | (2006.01) |
| ***C07D 403/14*** | (2006.01) |
| ***C07D 413/04*** | (2006.01) |
| ***C07D 417/04*** | (2006.01) |
| ***C07F 9/6524*** | (2006.01) |

(56) References Cited

U.S. PATENT DOCUMENTS

| | | | | |
|---|---|---|---|---|
| 2012/0215155 A1 | 8/2012 | Muller et al. | | |
| 2013/0060187 A1 | 3/2013 | Friedman et al. | | |
| 2013/0245536 A1 | 9/2013 | Friedman et al. | | |
| 2014/0343480 A1* | 11/2014 | Kamaev | A61K 31/519 | 514/249 |

FOREIGN PATENT DOCUMENTS

| | | | | |
|---|---|---|---|---|
| WO | WO 2011/130356 | 10/2011 | | |
| WO | WO 2012/167260 | 12/2012 | | |
| WO | WO 2015/130944 | 9/2015 | | |
| WO | WO 2016/090016 | 6/2016 | | |
| WO | WO-2016090016 A1 * | 6/2016 | A61F 9/0079 | |

OTHER PUBLICATIONS

Cresswell et al., "140. Pteridine Derivatives. Part VII. The synthesis of riboflavin 2-Imine and Related isoalloxaxine 2-Imines" J. Chem. Soc. (1959):698-704.

Matsui et al., "Formation Of Roseoflavin From Guanine Through Riboflavin", J. Biochem. (1979) 86(1): 167-175.

International Search Report and Written Opinion mailed Apr. 2, 2020 for PCT Application No. PCT/US2019/064534, filed Dec. 4, 2019.

International Preliminary Report on Patentability issued Jun. 8, 2021 for PCT Application No. PCT/US2019/064534, filed Dec. 4, 2019.

Office Action dated Aug. 31, 2023 for CN Application No. 201980091188.6, filed Dec. 4, 2019.

Office Action dated Sep. 12, 2023 for MX Application No. MX/a/2021/006642, filed Dec. 4, 2019.

Office Action dispatched Dec. 14, 2023 for JP 2021-554558, filed Dec. 4, 2019.

Examination Report dated Jul. 31, 2024 for Australian Patent Application, filed Dec. 4, 2019.

Office Action dated Nov. 7, 2024 for Korean Patent Application No. 10-2021-7021001, filed Dec. 4, 2019.

Office Action dated Feb. 15, 2024 for MX Application No. MX/a/2021/006642, filed Dec. 4, 2019.

Office Action dated Aug. 6, 2024 for MX Application No. MX/a/2021/006642, filed Dec. 4, 2019.

Office Action dated Jan. 6, 2025 for MX Application No. MX/a/2021/006642, filed Dec. 4, 2019.

* cited by examiner

COMPOUNDS AND COMPOSITIONS FOR EYE TREATMENTS

CROSS-REFERENCE TO RELATED APPLICATIONS

This application is a national phase filing under 35 U.S.C. § 371 of International Application No. PCT/US2019/064534, filed Dec. 4, 2019, which claims priority from U.S. Provisional Application Ser. No. 62/775,305, filed on Dec. 4, 2018. The entire contents of the prior applications are incorporated herein by reference in their entirety.

TECHNICAL FIELD

This disclosure features chemical entities (e.g., a compound or a pharmaceutically acceptable salt and/or hydrate and/or prodrug of the compound) that that generates cross-linking in the cornea in response to exposure to an electromagnetic irradiation. This disclosure also features compositions containing the same as well as other methods of using and making the same. The chemical entities are useful, e.g., for treating a subject (e.g., a human) having a disease, disorder, or condition in which in which abnormal shaping of the cornea (e.g., thinning of the cornea, e.g., bilateral thinning of the cornea, e.g., bilateral thinning of the central, paracentral, or peripheral cornea; or steepening (e.g., bulging) of the cornea) contributes to the pathology and/or symptoms and/or progression of the disease, disorder, or condition. Non-limiting examples of such diseases, disorders, or conditions include: (i) corneal ectatic disorders; (ii) vision conditions; and (iii) diseases, disorders, or conditions that are sequela or comorbid with any of the foregoing or any disclosed herein. More particular non-limiting examples of such diseases, disorders, or conditions include keratoconus, keratoglobus, pellucid marginal degeneration, corneal ectasia (e.g., post-operative ectasia, e.g., post-LASIK ectasia), Terrien's marginal degeneration, myopia, hyperopia, astigmatism, irregular astigmatism, and presbyopia.

BACKGROUND

A variety of eye disorders, such as myopia, keratoconus, and hyperopia, involve abnormal shaping of the cornea. Laser-assisted in-situ keratomileusis (LASIK), for example, is one of a number of corrective treatments that reshape the cornea so that light traveling through the cornea is properly focused onto the retina located in the back of the eye. The success of a particular treatment in addressing abnormal shaping of the cornea depends on the stability of the changes in the corneal structure after the treatment has been applied.

Although treatments may initially achieve desired reshaping of the cornea, the desired effects of reshaping the cornea may be mitigated or reversed at least partially if the collagen fibrils within the cornea continue to change after the desired reshaping has been achieved. For instance, a complication known as post-LASIK ectasia may occur due to the thinning and weakening of the cornea caused by LASIK surgery. In post-LASIK ectasia, the cornea experiences progressive steepening (bulging). To strengthen and stabilize the structure of the cornea after reshaping, some treatments may also initiate cross-linking in the corneal tissue. For example, a photosensitizing agent (e.g., riboflavin) is applied to the cornea as a cross-linking agent. Once the cross-linking agent has been applied to the cornea, the cross-linking agent is activated by a light source (e.g., ultraviolet (UV) light) to cause the cross-linking agent to absorb enough energy to cause the release of free oxygen radicals (e.g., singlet oxygen) and/or other radicals within the cornea. Once released, the radicals form covalent bonds between corneal collagen fibrils and thereby cause the corneal collagen fibrils to cross-link and strengthen and stabilize the structure of the cornea.

Due to the advantageous structural changes caused by the cross-linking agent, the cross-linking agent may be applied as the primary aspect of some treatments. For example, a cross-linking agent may be applied to treat keratoconus. Cross-linking treatments may also be employed to induce refractive changes in the cornea to correct disorders such as myopia, hyperopia, astigmatism, irregular astigmatism, presbyopia, etc.

U.S. Patent Application Publication No. 2011/0237999, filed Mar. 18, 2011; U.S. Patent Application Publication No. 2012/0215155, filed Apr. 3, 2012; U.S. Patent Application No. 2014/0343480, filed May 19, 2014; U.S. Patent Application No. 2013/0060187, filed Oct. 31, 2012; International Patent Application Publication No. 2011/130356, filed Apr. 13, 2011; International Patent Application Publication No. 2015/130944, filed Feb. 26, 2015; and International Patent Application No. 2016/090016, filed Dec. 2, 2015 described systems and compositions (e.g., ophthalmic solutions of riboflavin or riboflavin phosphate phosphate) for generating cross-linking activity in the cornea of an eye in treatment of eye disorders e.g., keratoconus (e.g., progressive keratoconus) or corneal ectasia following refractive surgery with or without the removal of corneal epithelium cells. PHOTREXA® VISCOUS (riboflavin 5'-phosphate in 20% dextran ophthalmic solution) 0.146% and PHOTREXA® (riboflavin 5'-phosphate ophthalmic solution) 0.146% are photo enhancers indicated for use with the KXL™ System in corneal collagen cross-linking for the treatment of progressive keratoconus.

SUMMARY

This disclosure features chemical entities (e.g., a compound or a pharmaceutically acceptable salt and/or hydrate and/or prodrug of the compound) that that generates cross-linking in the cornea in response to exposure to an electromagnetic irradiation. This disclosure also features compositions containing the same as well as other methods of using and making the same. The chemical entities are useful, e.g., for treating a subject (e.g., a human) having a disease, disorder, or condition in which abnormal shaping of the cornea (e.g., thinning of the cornea, e.g., bilateral thinning of the cornea, e.g., bilateral thinning of the central, paracentral, or peripheral cornea; or steepening (e.g., bulging) of the cornea) contributes to the pathology and/or symptoms and/or progression of the disease, disorder, or condition. Non-limiting examples of such diseases, disorders, or conditions include: (i) corneal ectatic disorders; (ii) vision conditions; and (iii) diseases, disorders, or conditions that are sequela or comorbid with any of the foregoing or any disclosed herein. More particular non-limiting examples of such diseases, disorders, or conditions include keratoconus, keratoglobus, pellucid marginal degeneration, corneal ectasia (e.g., post-operative ectasia, e.g., post-LASIK ectasia), Terrien's marginal degeneration, myopia, hyperopia, astigmatism, irregular astigmatism, and presbyopia.

In one aspect, the featured chemical entities include compounds of Formula I, or a pharmaceutically acceptable salt thereof:

(I)

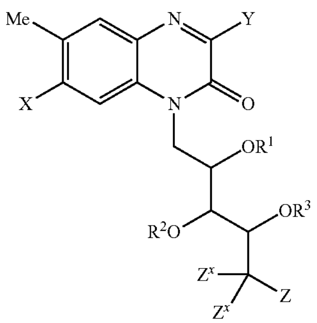

in which $R^1$, $R^2$, $R^3$, X, Y, Z, and $Z^X$ can be as defined anywhere herein.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for generating cross-linking in a cornea are featured that include contacting the cornea with a chemical entity described herein (e.g., a compound described generically or specifically herein or a pharmaceutically acceptable salt thereof or compositions containing the same); and applying an electromagnetic radiation to the cornea. Such methods can include, e.g., administering the chemical entity to a cornea of an eye in a subject (e.g., a human) having a disease, disorder, or condition in which abnormal shaping of the cornea (e.g., thinning of the cornea, e.g., bilateral thinning of the cornea, e.g., bilateral thinning of the central, paracentral, or peripheral cornea; or steepening (e.g., bulging) of the cornea) contributes to the pathology and/or symptoms and/or progression of the disease, disorder, or condition (e.g., keratoconus, keratoglobus, pellucid marginal degeneration, corneal ectasia (e.g., post-operative ectasia, e.g., post-LASIK ectasia), Terrien's marginal degeneration, myopia, hyperopia, astigmatism, irregular astigmatism, and presbyopia); and apply an electromagnetic radiation to the cornea. Methods can include, but are not limited to, providing refractive correction to a cornea (e.g., by imparting mechanical stiffness) and strengthen and stabilize the structure of a cornea.

In another aspect, methods of treatment of a disease, disorder, or condition are featured in which abnormal shaping of the cornea (e.g., thinning of the cornea, e.g., bilateral thinning of the cornea, e.g., bilateral thinning of the central, paracentral, or peripheral cornea; or steepening (e.g., bulging) of the cornea) contributes to the pathology and/or symptoms and/or progression of the disease, disorder, or condition. The methods include administering a chemical entity described herein (e.g., a compound described generically or specifically herein, a pharmaceutically acceptable salt thereof or compositions containing the same) in an amount effective to treat the disease, disorder, or condition.

In a further aspect, methods of treatment of a disease, disorder, or condition are featured in which abnormal shaping of the cornea (e.g., thinning of the cornea, e.g., bilateral thinning of the cornea, e.g., bilateral thinning of the central, paracentral, or peripheral cornea; or steepening (e.g., bulging) of the cornea) contributes to the pathology and/or symptoms and/or progression of the disease, disorder, or condition. The methods include administering to a cornea of an eye in a subject in need of such treatment an effective amount of a chemical entity described herein (e.g., a compound described generically or specifically herein, a pharmaceutically acceptable salt thereof, or compositions containing the same); and applying an electromagnetic radiation to the cornea.

A non-limiting example of such diseases, disorders, and conditions is a corneal ectatic disorder. In certain embodiments, the corneal ectatic disorder is keratoconus. In certain embodiments, the corneal ectatic disorder is keratoglobus. In certain embodiments, the corneal ectatic disorder is pellucid marginal degeneration. In certain embodiments, the corneal ectatic disorder is corneal ectasia (e.g., post-operative ectasia, e.g., post-LASIK ectasia). In certain embodiments, the corneal ectatic disorder is Terrien's marginal degeneration.

Another non-limiting example of such diseases, disorders, and conditions is a vision condition. In certain embodiments, the vision condition is myopia. In certain embodiments, the vision condition is hyperopia. In certain embodiments, the vision condition is myopia. In certain embodiments, the vision condition is hyperopia. In certain embodiments, the vision condition is astigmatism. In certain embodiments, the vision condition is irregular astigmatism. In certain embodiments, the vision condition is presbyopia.

Embodiments can include one of more of the following advantageous properties.

In some embodiments, chemical entities and compositions described herein can be applied to a cornea without prior removal of the corneal epithelial cells, thereby resulting in improved patient comfort.

In some embodiments, the chemical entities and compositions described herein can undergo cross-linking in the cornea using relatively short durations of electromagnetic radiation.

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

The term "acceptable" with respect to a formulation, composition or ingredient, as used herein, means having no persistent detrimental effect on the general health of the subject being treated.

The terms "effective amount" or "therapeutically effective amount," as used herein, refer to a sufficient amount of a chemical entity (e.g., a compound described generically or specifically herein, a pharmaceutically acceptable salt thereof, or compositions containing the same) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy, 21st ed.*; Lippincott Williams & Wilkins: Philadelphia, PA, 2005*; Handbook of Pharmaceutical Excipients, 6th ed.*; Rowe et al., Eds.; The Pharmaceutical Press and the American Pharmaceutical Association: 2009*; Handbook of Pharmaceutical Additives, 3rd ed.*; Ash and Ash Eds.; Gower Publishing Company: 2007*; Pharmaceutical Preformulation and Formulation, 2nd ed.*; Gibson Ed.; CRC Press LLC: Boca Raton, FL, 2009.

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt is not specifically limited as far as it can be used in medicaments. Examples of a salt that the compounds described herein form with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid: organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease, disorder, or condition, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., $—OCH_3$).

The term "haloalkoxy" refers to an —O-haloalkyl radical (e.g., $—OCF_3$).

The term "alkylene" refers to a branched or unbranched divalent alkyl (e.g., $—CH_2—$).

The term "arylene" and the like refer to divalent forms of the ring system, here divalent aryl.

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic e.g. tetrahydronaphthyl. Examples of aryl groups also include phenyl, naphthyl and the like.

The term "cycloalkyl" as used herein includes saturated cyclic hydrocarbon groups having 3 to 10 carbons, preferably 3 to 8 carbons, and more preferably 3 to 6 carbons, wherein the cycloalkyl group may be optionally substituted. Preferred cycloalkyl groups include, without limitation, cyclopropyl, cyclobutyl, cyclopentyl, cyclohexyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic (but does not have to be a ring which contains a heteroatom, e.g. tetrahydroisoquinolinyl. Exemplary heteroaryl systems are derived from, but not limited to, the following ring systems: pyrrole, furan, thiophene, imidazole, pyrazole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4]thiadiazole, [1,3,4]thiadiazole, tetrazole, pyridine, pyridazine, pyrimidine, pyrazine, [1,2,3]triazine, [1,2,4]triazine, [1,3,5]triazine, indole, isoindole, benzofuran, benzothiophene [1,3]benzoxazole, [1,3]benzothiazole, benzoimidazole, indazole, quinoline, isoquinoline, cinnoline, quinazoline, quinoxaline, phthalazine, different naphthyridines, e.g. [1,8]naphthyridine, different thienopyridines, e.g. thieno[2,3-b]pyridine and purine.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

The term "heterocycloalkenyl" as used herein means partially unsaturated cyclic ring system with 3-16 ring atoms (e.g., 5-8 membered monocyclic, 8-12 membered bicyclic, or 11-14 membered tricyclic ring system) having 1-3 heteroatoms if monocyclic, 1-6 heteroatoms if bicyclic, or 1-9 heteroatoms if tricyclic or polycyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocycloalkenyl groups include, without limitation, imidazolinyl, tetrahydropyridyl, dihydropyrazinyl, dihydropyridyl, dihydropyrrolyl, As used herein, when a ring is described as being "partially unsaturated", it means said ring has one or more additional degrees of unsaturation (in addition to the degree of unsaturation attributed to the ring itself; e.g., one or more double or triple bonds between constituent ring atoms), provided that the ring is not aromatic. Examples of such rings include: cyclopentene, cyclohexene, cycloheptene, dihydropyridine, tetrahydropyridine, dihydropyrrole, dihydrofuran, dihydrothiophene, and the like.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The details of one or more embodiments of the invention are set forth in the description below and in the accompanying Appendix, which is expressly considered part of this disclosure. Other features and advantages will also be apparent from the claims.

DETAILED DESCRIPTION

Formula (I) Compounds

In one aspect, the disclosure features compounds of formula (I):

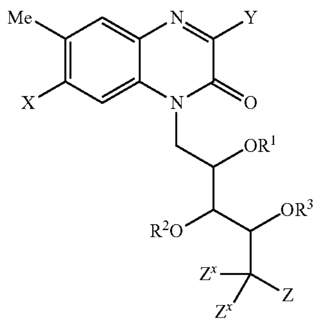

(I)

or a pharmaceutically acceptable salt thereof;

wherein:

X is selected from the group consisting of H, $NR^{4X}R^{5X}$, and $C_1$-$C_6$ alkyl which is optionally substituted with 1-3 $R^a$;

Y is selected from the group consisting of:

(i) $CO_2R^{6Y}$;

(ii) $C(O)NR^{4Y}R^{5Y}$;

(iii) heteroaryl including from 5-6 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-2 independently selected $R^c$; and (iv) heterocycloalkenyl including from 5-6 ring atoms, wherein from 1-4 ring atoms are heteroatoms, each independently selected from the group consisting of N, N(H), N($R^d$), O, and S, and wherein one or more of the heterocycloalkenyl ring carbon atoms are optionally substituted with from 1-2 independently selected $R^b$;

Z is selected from the group consisting of:

(i) H, (ii) $C_{1-6}$ alkyl, (iii) $NR^{4Z}R^{5Z}$, (iv) $OR^{6Z}$, (v) $OC(O)R^{7Z}$, (vi) $OP(O)OR^{8Z}OR^{9Z}$, and (vii); heterocyclyl including from 4-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^h$;

each $Z^x$ is H; or each $Z^x$ together with the carbon to which each is attached forms C═O;

each of $R^1$, $R^2$, and $R^3$ is independently selected from $R^{6A}$, $C(O)R^{7A}$, and $P(O)OR^{8A}OR^{9A}$;

each of $R^{4X}$ and $R^{5X}$ is independently selected from the group consisting of: H, $C_{1-6}$ alkyl; $C_{3-6}$ cycloalkyl;

—C(O)($C_{1-4}$ alkyl); —C(O)O($C_{1-4}$ alkyl); —CON(R')(R"); —$S(O)_{1-2}$(NR'R"); —$S(O)_{1-2}$($C_{1-4}$ alkyl); —OH; and $C_{1-4}$ alkoxy;

each of $R^{4Y}$ and $R^{5Y}$ is independently selected from the group consisting of:

(i) H;

(ii) $C_{1-12}$ alkyl, which is optionally substituted with 1-6 $R^a$;

(iii) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^h$;

(iv) —$(W^1—W^2)_n$—$W^3$, wherein:

$W^1$ is in each occurrence is independently $C_{1-3}$ alkylene, which is optionally substituted with from 1-4 $R^a$;

$W^2$ is in each occurrence independently —N(H)—, —N($R^d$)—, —O—, or —S—;

$W^3$ is H or $C_{1-7}$ alkyl, which is optionally substituted with from 1-4 $R^a$; and n is 2-4;

or (v) $R^{4Y}$ and $R^{5Y}$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to $R^{4Y}$ and $R^{5Y}$), which are each independently selected from the group consisting of N(H), N($R^d$), O, and S;

each of $R^{4Z}$ and $R^{5Z}$ is independently selected from the group consisting of:

(i) H;

(ii) $C_{1-10}$ alkyl which is optionally substituted with 1-6 independently selected $R^a$;

(iii) $C_{3-6}$ cycloalkyl;

(iv) —C(O)($C_{1-4}$ alkyl);

(v) —C(O)O($C_{1-4}$ alkyl);

(vi) —CON(R')(R");

(vii) —$S(O)_{1-2}$(NR'R");

(viii) —$S(O)_{1-2}$($C_{1-4}$ alkyl);

(ix) —OH;

(x) $C_{1-4}$ alkoxy; and (xi) —$(Q^1—Q^2)_q$—$Q^3$, wherein:

$Q^1$ in each occurrence is independently $C_{1-3}$ alkylene, which is optionally substituted with from 1-4 $R^a$;

$Q^2$ in each occurrence is independently —N(H)—, —N($R^d$)—, —O—, or —S—;

$Q^3$ is H or $C_{1-7}$ alkyl, which is optionally substituted with from 1-4 $R^a$; and q is 2-4;

$R^{6A}$ in each occurrence is independently selected from the group consisting of:

(i) H; and (ii) $C_{1-10}$ alkyl, optionally substituted with from 1-6 independently selected $R^a$;

$R^{6Z}$ is independently selected from the group consisting of:

(i) H;

(ii) $C_{1-10}$ alkyl, optionally substituted with from 1-6 independently selected $R^a$;

(iii) —($C_{0-2}$ alkylene)-($C_{6-10}$ aryl), wherein the $C_{6-10}$ aryl is optionally substituted with from 1-2 independently selected $R^h$;

(iv) —($C_{0-2}$ alkylene)-(heteroaryl), wherein the heteroaryl includes from 5-10 ring atoms, wherein from 1-4 ring atoms are heteroatoms, each independently selected from the group consisting of N, N(H), N($C_{1-3}$ alkyl), O, and S, and wherein one or more of the heteroaryl ring carbon atoms are optionally substituted with from 1-4 independently selected $R^h$;

(v) —($C_{1-2}$ alkylene)-C(═O)NH—($C_{1-3}$ alkylene)-$R^{6Z'}$ and (vi) -$(T^1\text{-}T^2)_t$-$T^3$, wherein:

$T^1$ in each occurrence is independently $C_{1-3}$ alkylene, which is optionally substituted with from 1-4 $R^a$;

$T^2$ in each occurrence is independently —N(H)—, —N($R^d$)—, —O—, or —S—;

$T^3$ is H or $C_{1-7}$ alkyl, which is optionally substituted with from 1-4 $R^a$; and t is 2-4;

$R^{6Z'}$ is selected from the group consisting of:

C(═O)OH, N($C_{1-4}$ alkyl)$_2$, $NH_2$, NH($C_{1-4}$ alkyl), and heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $C_{1-3}$ alkyl;

$R^{6Y}$ at each occurrence is independently selected from the group consisting of:

(i) H;

(ii) —$(Y^1)_m$—$Y^2$, wherein:

m is 0 or 1;

$Y^1$ is $C_{1-6}$ alkylene, which is optionally substituted with from 1-6 $R^a$; and $Y^2$ is:

(a) $C_{3-10}$ cycloalkyl, which is optionally substituted with from 1-4 $R^b$, (b) $C_{6-10}$ aryl, which is optionally substituted with from 1-4 $R^c$;

(c) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$, or (d) heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$;

(iii) $C_{1-12}$ alkyl, optionally substituted with from 1-6 independently selected $R^a$; and (iv) —$(Z^1—Z^2)_p$—$Z^3$, wherein:

$Z^1$ in each occurrence is independently $C_{1-3}$ alkylene, which is optionally substituted with from 1-4 $R^a$;

$Z^2$ in each occurrence is independently —N(H)—, —N($R^d$)—, —O—, or —S—;

$Z^3$ is H or $C_{1-7}$ alkyl, which is optionally substituted with from 1-4 $R^a$; and p is 2-4;

each of $R^{7Z}$ and $R^{7A}$, at each occurrence, is independently selected from the group consisting of:

(i) H;

(ii) $C_{1-10}$ alkyl, optionally substituted with from 1-6 independently selected $R^a$;

(iii) $C_{6-10}$ aryl, which is optionally substituted with from 1-4 $R^c$; and (iv) $C_{3-6}$ cycloalkyl, which is optionally substituted with from 1-4 $R^b$;

each of $R^{8A}$, $R^{8Z}$, $R^{9A}$, and $R^{9Z}$ in each occurrence is independently (i) H; or (ii) $C_{1-10}$ alkyl, optionally substituted with from 1-6 independently selected $R^a$;

each occurrence of $R^a$ is independently selected from the group consisting of: —OH; —F; —Cl; —Br; —$NR^eR^f$; $C_{1-4}$ alkoxy; $C_{1-4}$ haloalkoxy; —C(═O)O($C_{1-4}$ alkyl); —C(═O)($C_{1-4}$ alkyl); —C(═O)OH; —CON(R')(R"); —$S(O)_{1-2}$(NR'R"); —$S(O)_{0-2}$($C_{1-4}$ alkyl); C(═NH)N(R')(R"); cyano, and $C_{3-6}$ cycloalkyl optionally substituted with from 1-4 independently selected $C_{1-4}$ alkyl;

each occurrence of $R^b$ is independently selected from the group consisting of: $C_{1-6}$ alkyl; $C_{1-4}$ haloalkyl; —OH; oxo; —F; —Cl; —Br; —$NR^eR^f$; $C_{1-4}$ alkoxy; $C_{1-4}$ haloalkoxy; —C(═O)($C_{1-4}$ alkyl); —C(═O)O($C_{1-4}$ alkyl); —C(═O)OH; —C(═O)N(R')(R"); —$S(O)_{1-2}$(NR'R"); —$S(O)_{1-2}$($C_{1-4}$ alkyl); cyano; and $C_{3-6}$ cycloalkyl optionally substituted with from 1-4 independently selected $C_{1-4}$ alkyl;

each occurrence of $R^c$ is independently selected from the group consisting of:

(i) halo;

(ii) cyano;

(iii) $C_{1-10}$ alkyl;

(iv) $C_{1-10}$ alkyl which is substituted with from 1-6 independently selected $R^a$;

(v) $C_{3-6}$ cycloalkyl optionally substituted with from 1-3 independently selected $R^b$;

(vi) $C_{2-6}$ alkenyl;

(vii) $C_{2-6}$ alkynyl;

(viii) $C_{1-4}$ alkoxy;

(ix) $C_{1-4}$ haloalkoxy;

(x) —($C_{0-3}$ alkylene)-$C_{3-6}$ cycloalkyl optionally substituted with from 1-4 independently selected $C_{1-4}$ alkyl;

(xi) —$S(O)_{1-2}$($C_{1-4}$ alkyl);

(xii) —$NR^eR^f$;

(xiii) —OH;

(xiv) —$S(O)_{1-2}$(NR'R");

(xv) —$C_{1-4}$ thioalkoxy;

(xvi) —$NO_2$;

(xvii) —C(═O)($C_{1-4}$ alkyl);

(xviii) —C(═O)O($C_{1-4}$ alkyl);

(xix) —C(═O)OH; and (xx) —C(═O)N(R')(R");

$R^d$ is selected from the group consisting of: $C_{1-6}$ alkyl which is optionally substituted with from 1-3 independently selected $R^g$; $C_{3-6}$ cycloalkyl; —C(O)($C_{1-4}$ alkyl); —C(O)O($C_{1-4}$ alkyl); —CON(R')(R"); —$S(O)_{1-2}$(NR'R"); —$S(O)_{1-2}$($C_{1-4}$ alkyl); —OH; and $C_{1-4}$ alkoxy;

P each occurrence of $R^e$ and $R^f$ is independently selected from the group consisting of: H; $C_{1-6}$ alkyl; $C_{3-6}$ cycloalkyl; —C(O)($C_{1-4}$ alkyl); —C(O)O($C_{1-4}$ alkyl); —CON(R')(R"); —$S(O)_{1-2}$(NR'R"); —$S(O)_{1-2}$($C_{1-4}$ alkyl); —OH; and $C_{1-4}$ alkoxy;

or $R^e$ and $R^f$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to $R^e$ and $R^f$), which are each independently selected from the group consisting of N(H), N($R^d$), O, and S;

each occurrence of $R^g$ is independently selected from the group consisting of: —OH, —F, NR'R", $C_{1-3}$ alkoxy, —CON(R')(R"), —CONHS$(O)_2$($C_{1-4}$ alkyl), and —C(O)OH;

each occurrence of $R^h$ is independently selected from the group consisting of: $C_{1-3}$ alkyl, $C_{1-3}$ haloalkyl, $C_{1-3}$ alkoxy, $C_{1-3}$ haloalkoxy, and halo;

and each occurrence of R' and R" is independently selected from the group consisting of: H and $C_{1-4}$ alkyl; or R' and R" together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R"), which are each independently selected from the group consisting of N(H), N($R^d$), O, and S.

In some embodiments, the compound is other than one or more of the following:

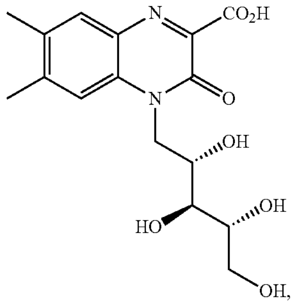

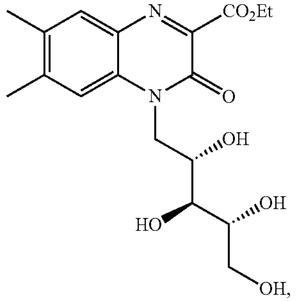

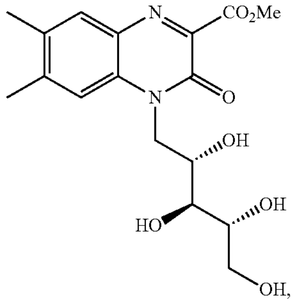

-continued
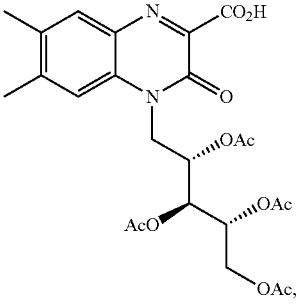
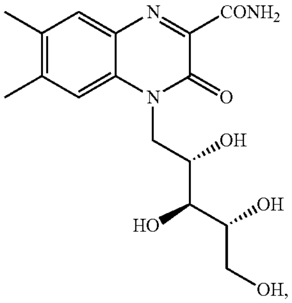
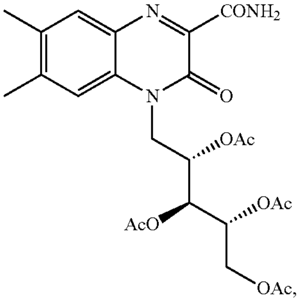
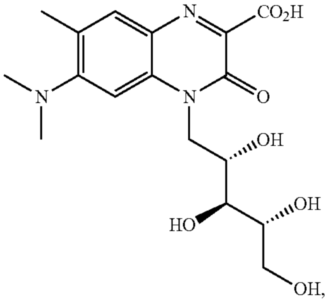
or
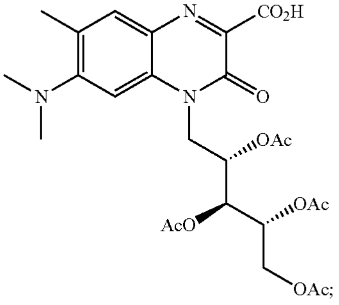
a pharmaceutically acceptable salt thereof.
In some embodiments, the compound is other than one or more of the following:
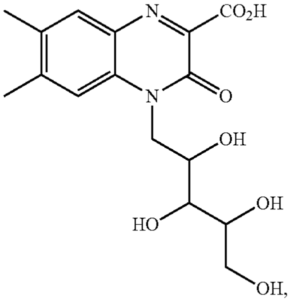
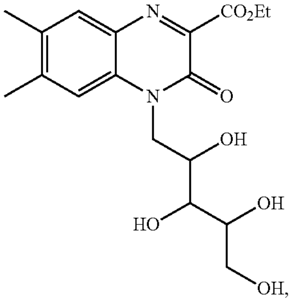
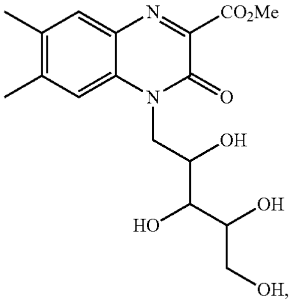
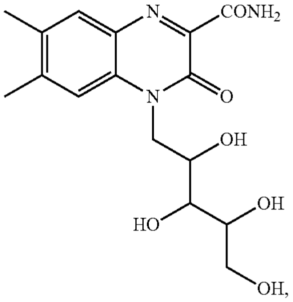
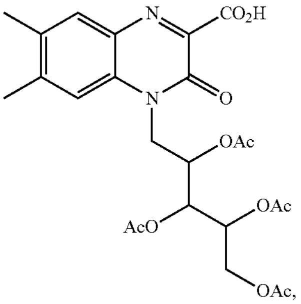

-continued

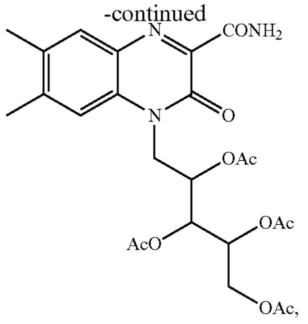

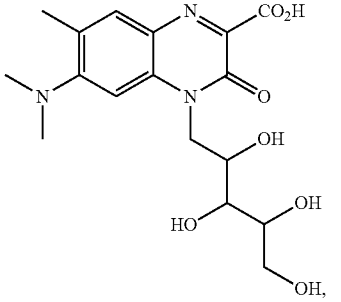

or

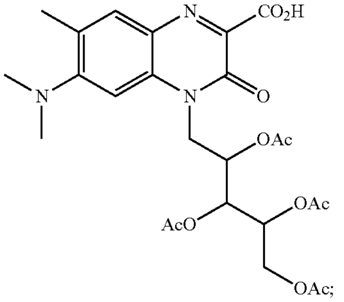

pharmaceutically acceptable salt thereof.

In another aspect, provided herein are compounds of formula (I):

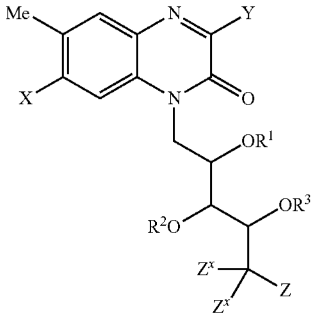

(I)

or a pharmaceutically acceptable salt thereof;

wherein:

X is selected from the group consisting of H, $NR^{4X}R^{5X}$, and $C_1$-$C_6$ alkyl which is optionally substituted with 1-3 $R^a$;

Y is selected from the group consisting of:

(i) $CO_2R^{6Y}$;

(ii) $C(O)NR^{4Y}R^{5Y}$; and (iii) heteroaryl including 5 ring atoms, wherein from 1-4 ring atoms are heteroatoms, each independently selected from the group consisting of N, N(H), $N(R^d)$, O, and S, and wherein one or more of the heteroaryl ring carbon atoms are optionally substituted with from 1-2 independently selected $R^c$;

Z is selected from H, $C_{1-6}$ alkyl, $NR^{4Z}R^{5Z}$, $OR^{6Z}$, $OC(O)R^{7Z}$, and $OP(O)OR^{8Z}OR^{9Z}$;

each Z is H; or each $Z^x$ together with the carbon to which each is attached forms C═O;

each of $R^1$, $R^2$, and $R^3$ is independently selected from $R^{6A}$, $C(O)R^{7A}$, and $P(O)OR^{8A}OR^{9A}$;

each of $R^{4X}$ and $R^{5X}$ is independently selected from the group consisting of: H, $C_{1-6}$ alkyl; $C_{3-6}$ cycloalkyl; —C(O)($C_{1-4}$ alkyl); —C(O)O($C_{1-4}$ alkyl); —CON(R')(R"); —$S(O)_{1-2}$(NR'R"); —$S(O)_{1-2}$($C_{1-4}$ alkyl); —OH; and $C_{1-4}$ alkoxy;

each of $R^{4Y}$ and $R^{5Y}$ is independently selected from the group consisting of:

(i) H;

(ii) $C_{1-12}$ alkyl, which is optionally substituted with 1-6 $R^a$;

(iii) —$(W^1—W^2)_n$—$W^3$, wherein:

$W^1$ is in each occurrence is independently $C_{1-3}$ alkylene, which is optionally substituted with from 1-4 $R^a$;

$W^2$ is in each occurrence independently —N(H)—, —N($R^d$)—, —O—, or —S—;

$W^3$ is H or $C_{1-7}$ alkyl, which is optionally substituted with from 1-4 $R^a$; and n is 2-4;

or (iv) $R^{4Y}$ and $R^{5Y}$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to $R^{4Y}$ and $R^{5Y}$), which are each independently selected from the group consisting of N(H), N($R^d$), O, and S;

each of $R^{4Z}$ and $R^{5Z}$ is independently selected from the group consisting of:

(i) H;

(ii) $C_{1-10}$ alkyl which is optionally substituted with 1-6 independently selected $R^a$;

(iii) $C_{3-6}$ cycloalkyl;

(iv) —C(O)($C_{1-4}$ alkyl);

(v) —C(O)O($C_{1-4}$ alkyl);

(vi) —CON(R')(R");

(vii) —$S(O)_{1-2}$(NR'R");

(viii) —$S(O)_{1-2}$($C_{1-4}$ alkyl);

(ix) —OH;

(x) $C_{1-4}$ alkoxy; and (xi) —$(Q^1—Q^2)_q$—$Q^3$, wherein:

$Q^1$ in each occurrence is independently $C_{1-3}$ alkylene, which is optionally substituted with from 1-4 $R^a$;

$Q^2$ in each occurrence is independently —N(H)—, —N($R^d$)—, —O—, or —S—;

$Q^3$ is H or $C_{1-7}$ alkyl, which is optionally substituted with from 1-4 $R^a$; and q is 2-4;

$R^{6A}$ in each occurrence is independently selected from the group consisting of:

(i) H; and (ii) $C_{1-10}$ alkyl, optionally substituted with from 1-6 independently selected $R^a$;

$R^{6Z}$ is independently selected from the group consisting of:
(i) H;
(ii) $C_{1-10}$ alkyl, optionally substituted with from 1-6 independently selected $R^a$; and
(iii) $-(T^1-T^2)_t-T^3$, wherein:
$T^1$ in each occurrence is independently $C_{1-3}$ alkylene, which is optionally substituted with from 1-4 $R^a$;
$T^2$ in each occurrence is independently —N(H)—, —N($R^d$)—, —O—, or —S—;
$T^3$ is H or $C_{1-7}$ alkyl, which is optionally substituted with from 1-4 $R^a$; and
t is 2-4;

$R^{6Y}$ at each occurrence is independently selected from the group consisting of:
(i) H;
(ii) —$(Y^1)_m$—$Y^2$, wherein:
m is 0 or 1;
$Y^1$ is $C_{1-6}$ alkylene, which is optionally substituted with from 1-6 $R^a$; and
$Y^2$ is:
(a) $C_{3-10}$ cycloalkyl, which is optionally substituted with from 1-4 $R^b$,
(b) $C_{6-10}$ aryl, which is optionally substituted with from 1-4 $R^c$;
(c) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$, or
(d) heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$;
(iii) $C_{1-12}$ alkyl, optionally substituted with from 1-6 independently selected $R^a$; and
(iv) —$(Z^1$—$Z^2)_p$—$Z^3$, wherein:
$Z^1$ in each occurrence is independently $C_{1-3}$ alkylene, which is optionally substituted with from 1-4 $R^a$;
$Z^2$ in each occurrence is independently —N(H)—, —N($R^d$)—, —O—, or —S—;
$Z^3$ is H or $C_{1-7}$ alkyl, which is optionally substituted with from 1-4 $R^a$; and
p is 2-4;

each of $R^{7Z}$ and $R^{7A}$, at each occurrence, is independently selected from the group consisting of:
(i) H;
(ii) $C_{1-10}$ alkyl, optionally substituted with from 1-6 independently selected $R^a$;
(iii) $C_{6-10}$ aryl, which is optionally substituted with from 1-4 $R^c$; and
(iv) $C_{3-6}$ cycloalkyl, which is optionally substituted with from 1-4 $R^b$;

each of $R^{8A}$, $R^{8Z}$, $R^{9A}$, and $R^{9Z}$ in each occurrence is independently
(i) H; or
(ii) $C_{1-10}$ alkyl, optionally substituted with from 1-6 independently selected $R^a$;

each occurrence of $R^a$ is independently selected from the group consisting of: —OH; —F; —Cl; —Br; —$NR^eR^f$; $C_{1-4}$ alkoxy; $C_{1-4}$ haloalkoxy; —C(═O)O($C_{1-4}$ alkyl); —C(═O)($C_{1-4}$ alkyl); —C(═O)OH; —CON(R')(R"); —$S(O)_{1-2}$(NR'R"); —$S(O)_{0-2}$($C_{1-4}$ alkyl); cyano, and $C_{3-6}$ cycloalkyl optionally substituted with from 1-4 independently selected $C_{1-4}$ alkyl;

each occurrence of $R^b$ is independently selected from the group consisting of: $C_{1-6}$ alkyl; $C_{1-4}$ haloalkyl; —OH; oxo; —F; —Cl; —Br; —$NR^eR^f$; $C_{1-4}$ alkoxy; $C_{1-4}$ haloalkoxy; —C(═O)($C_{1-4}$ alkyl); —C(═O)O($C_{1-4}$ alkyl); —C(═O)OH; —C(═O)N(R')(R"); —$S(O)_{1-2}$(NR'R"); —$S(O)_{1-2}$($C_{1-4}$ alkyl); cyano; and $C_{3-6}$ cycloalkyl optionally substituted with from 1-4 independently selected $C_{1-4}$ alkyl;

each occurrence of $R^c$ is independently selected from the group consisting of:
(i) halo;
(ii) cyano;
(iii) $C_{1-10}$ alkyl;
(iv) $C_{1-10}$ alkyl which is substituted with from 1-6 independently selected $R^a$;
(v) $C_{3-6}$ cycloalkyl optionally substituted with from 1-3 independently selected $R^b$;
(vi) $C_{2-6}$ alkenyl;
(vii) $C_{2-6}$ alkynyl;
(viii) $C_{1-4}$ alkoxy;
(ix) $C_{1-4}$ haloalkoxy;
(x) —($C_{0-3}$ alkylene)-$C_{3-6}$ cycloalkyl optionally substituted with from 1-4 independently selected $C_{1-4}$ alkyl;
(xi) —$S(O)_{1-2}$($C_{1-4}$ alkyl);
(xii) —$NR^eR^f$;
(xiii) —OH;
(xiv) —$S(O)_{1-2}$(NR'R");
(xv) —$C_{1-4}$ thioalkoxy;
(xvi) —$NO_2$;
(xvii) —C(═O)($C_{1-4}$ alkyl);
(xviii) —C(═O)O($C_{1-4}$ alkyl);
(xix) —C(═O)OH; and
(xx) —C(═O) N(R')(R");

$R^d$ is selected from the group consisting of: $C_{1-6}$ alkyl; $C_{3-6}$ cycloalkyl; —C(O)($C_{1-4}$ alkyl); —C(O)O($C_{1-4}$ alkyl); —CON(R')(R"); —$S(O)_{1-2}$(NR'R"); —$S(O)_{1-2}$($C_{1-4}$ alkyl); —OH; and $C_{1-4}$ alkoxy;

each occurrence of $R^e$ and $R^f$ is independently selected from the group consisting of: H; $C_{1-6}$ alkyl; $C_{3-6}$ cycloalkyl; —C(O)($C_{1-4}$ alkyl); —C(O)O($C_{1-4}$ alkyl); —CON(R')(R"); —$S(O)_{1-2}$(NR'R"); —$S(O)_{1-2}$($C_{1-4}$ alkyl); —OH; and $C_{1-4}$ alkoxy; and each occurrence of R' and R" is independently selected from the group consisting of: H and $C_{1-4}$ alkyl; or R' and R" together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to R' and R"), which are each independently selected from the group consisting of N(H), N($R^d$), O, and S.

In some embodiments, the compound is other than one or more of the following:
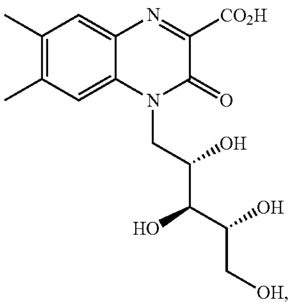
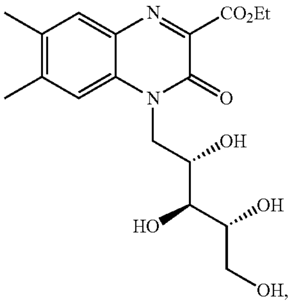
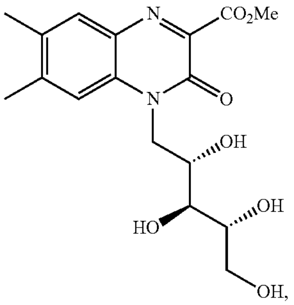
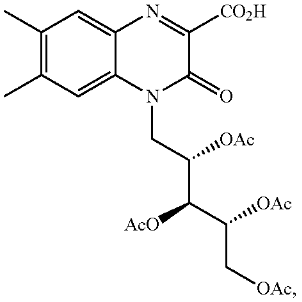
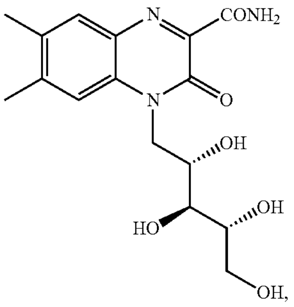
-continued
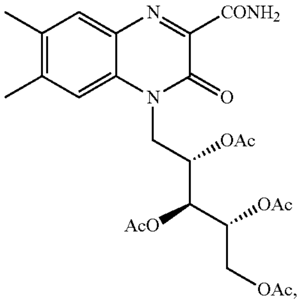
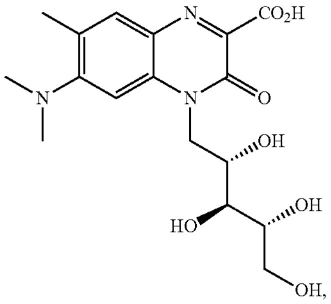
or
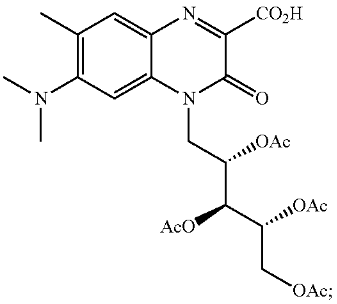
a pharmaceutically acceptable salt thereof.
In some embodiments, the compound is other than one or more of the following:
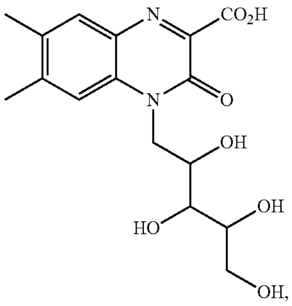
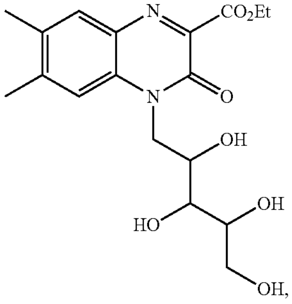

-continued

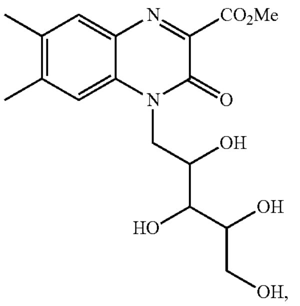

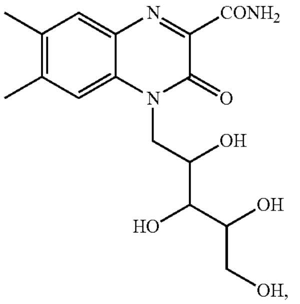

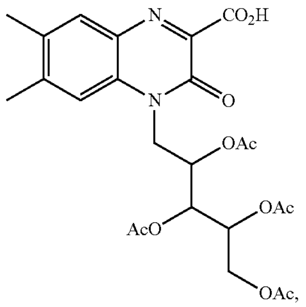

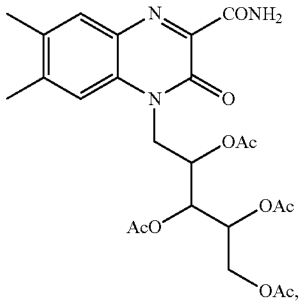

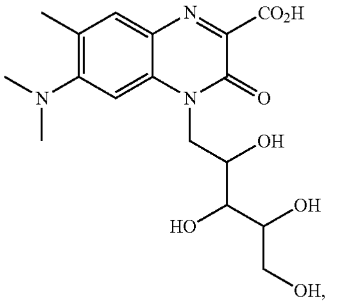

or

-continued

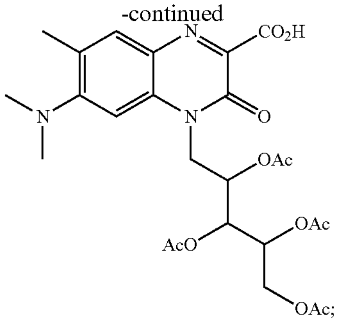

pharmaceutically acceptable salt thereof.

In some embodiments, when X is $C_1$-$C_6$ alkyl, which is optionally substituted with 1-3 $R^a$ (e.g., X is unsubstituted $C_1$-$C_6$ (e.g., $C_1$-$C_3$)alkyl, e.g., X is $CH_3$), then Y is other than $CO_2H$, $CO_2Me$, $CO_2Et$, or $CO_2NH_2$; or Y is other than $CO_2H$ or $CO_2NH_2$.

In some embodiments, when X is $C_1$-$C_6$ alkyl, which is optionally substituted with 1-3 $R^a$ (e.g., X is unsubstituted $C_1$-$C_6$ (e.g., $C_1$-$C_3$)alkyl, e.g., X is $CH_3$) and Z is OH, then Y is other than $CO_2H$, $CO_2Me$, $CO_2Et$, or $CO_2NH_2$.

In some embodiments, when X is $C_1$-$C_6$ alkyl, which is optionally substituted with 1-3 $R^a$ (e.g., X is unsubstituted $C_1$-$C_6$ (e.g., $C_1$-$C_3$)alkyl, e.g., X is $CH_3$), each of $R^1$, $R^2$, and $R^3$ is H, and Z is OH, then Y is other than $CO_2H$, $CO_2Me$, $CO_2Et$, or $CO_2NH_2$.

In some embodiments, when X is $C_1$-$C_6$ alkyl, which is optionally substituted with 1-3 $R^a$ (e.g., X is unsubstituted $C_1$-$C_6$ (e.g., $C_1$-$C_3$)alkyl, e.g., X is $CH_3$) and Z is OAc, then Y is other than $CO_2H$ or $CO_2NH_2$.

In some embodiments, when X is $C_1$-$C_6$ alkyl, which is optionally substituted with 1-3 $R^a$ (e.g., X is unsubstituted $C_1$-$C_6$ (e.g., $C_1$-$C_3$)alkyl, e.g., X is $CH_3$), each of $R^1$, $R^2$, and $R^3$ is C(O)Me, and Z is OAc, then Y is other than $CO_2H$ or $CO_2NH_2$.

In some embodiments, when X is $NR^{4X}R^{5X}$ (e.g., each of $R^{4X}$ and $R^{5X}$ is independently $C_{1-6}$ alkyl; e.g., each of $R^{4X}$ and $R^{5X}$ is $CH_3$), and Z is OH, then Y is other than $CO_2H$.

In some embodiments, when X is $NR^{4X}R^{5X}$ (e.g., each of $R^{4X}$ and $R^{5X}$ is independently $C_{1-6}$ alkyl; e.g., each of $R^{4X}$ and $R^{5X}$ is $CH_3$), each of $R^1$, $R^2$, and $R^3$ is H, and Z is OH, then Y is other than $CO_2H$.

In some embodiments, when X is $NR^{4X}R^{5X}$ (e.g., each of $R^{4X}$ and $R^{5X}$ is independently $C_{1-6}$ alkyl; e.g., each of $R^{4X}$ and $R^{5X}$ is $CH_3$), and Z is OAc, then Y is other than $CO_2H$.

In some embodiments, when X is $NR^{4X}R^{5X}$ (e.g., each of $R^{4X}$ and $R^{5X}$ is independently $C_{1-6}$ alkyl; e.g., each of $R^{4X}$ and $R^{5X}$ is $CH_3$), each of $R^1$, $R^2$, and $R^3$ is C(O)Me, and Z is OAc, then Y is other than $CO_2H$.

In some embodiments, it is provided when each of $R^1$, $R^2$, and $R^3$ is H; and when Z is OH, Y is other than $CO_2H$, $CO_2Me$, $CO_2Et$, or $CO_2NH_2$.

In some embodiments, it is provided when each of $R^1$, $R^2$, and $R^3$ is C(O)Me; and when Z is OAc (i.e., OC(O)Me), Y is other than $CO_2H$ or $CONH_2$.

Variable X

In some embodiments, X is H.

In some embodiments, X is $C_1$-$C_6$ alkyl, which is optionally substituted with 1-3 $R^a$.

In some embodiments, X is unsubstituted $C_1$-$C_6$ alkyl (e.g., unsubstituted $C_1$-$C_3$ alkyl). In certain embodiments, X is $CH_3$.

In some embodiments, X is $C_1$-$C_6$ alkyl which is substituted with 1-3 $R^a$. In some embodiments, X is methyl which is substituted with 1-3 $R^a$ (e.g., X is trifluoromethyl or difluoromethyl).

In some embodiments, X is $C_2$-$C_6$ alkyl, which is optionally substituted with 1-3 $R^a$.

In some embodiments, X is $C_2$-$C_6$ alkyl which is substituted with 1-3 $R^a$.

In some of the foregoing embodiments, wherein X is $C_1$-$C_6$ alkyl, which is optionally substituted with 1-3 $R^a$, each occurrence of $R^a$ is independently selected from the group consisting of: —OH; —F; —Cl; —Br; —$NR^eR^f$; $C_{1-4}$ alkoxy; $C_{1-4}$ haloalkoxy; —C(═O)O($C_{1-4}$ alkyl); —C(═O)($C_{1-4}$ alkyl); —C(═O)OH; —CON(R')(R"); —$S(O)_{1-2}$(NR'R"); —$S(O)_{1-2}$($C_{1-4}$ alkyl); cyano, and $C_{3-6}$ cycloalkyl optionally substituted with from 1-4 independently selected $C_{1-4}$ alkyl.

In certain of the foregoing embodiments, each occurrence of $R^a$ is independently selected from the group consisting of: —OH; —F; —Cl; —Br; —$NR^eR^f$; $C_{1-4}$ alkoxy; $C_{1-4}$ haloalkoxy; cyano, and $C_{3-6}$ cycloalkyl optionally substituted with from 1-4 independently selected $C_{1-4}$ alkyl.

In some embodiments, X is $NR^{4X}R^{5X}$.

In certain embodiments, both $R^{4X}$ and $R^{5X}$ are other than H (e.g., each of $R^{4X}$ and $R^{5X}$ is an independently selected $C_1$-$C_6$ alkyl).

In certain embodiments, one of $R^{4X}$ and $R^{5X}$ is H; and the other of $R^{4X}$ and $R^{5X}$ is other than H (e.g., one of $R^{4X}$ and $R^{5X}$ is H; and the other of $R^{4X}$ and $R^{5X}$ is an independently selected $C_1$-$C_6$ alkyl).

In certain embodiments, both $R^{4X}$ and $R^{5X}$ are H.

In certain embodiments, each of $R^{4X}$ and $R^{5X}$ is independently selected from the group consisting of: H; $C_{1-6}$ alkyl; $C_{3-6}$ cycloalkyl; and $C_{1-4}$ alkoxy.

In certain embodiments, one of $R^{4X}$ and $R^{5X}$ is independently selected from the group consisting of: H, $C_{1-6}$ alkyl; $C_{3-6}$ cycloalkyl; and $C_{1-4}$ alkoxy; and the other of $R^{4X}$ and $R^{5X}$ is independently selected from the group consisting of: —C(O)($C_{1-4}$ alkyl); —C(O)O($C_{1-4}$ alkyl); —CON(R')(R"); —$S(O)_{1-2}$(NR'R"); —S(O) 1-2 ($C_{1-4}$ alkyl); —OH.

In certain embodiments when X is $NR^{4X}R^{5X}$, each of $R^{4X}$ and $R^{5X}$ is independently H or $C_{1-6}$ alkyl.

In certain embodiments, each of $R^{4X}$ and $R^{5X}$ is an independently $C_{1-6}$ alkyl (e.g., an independently $C_{1-3}$ alkyl). In certain of these embodiments, each of $R^{4X}$ and $R^{5X}$ is the same $C_{1-6}$ alkyl. For example, each of $R^{4X}$ and $R^{5X}$ is $CH_3$. In other embodiments, each of $R^{4X}$ and $R^{5X}$ is a different $C_{1-6}$ alkyl.

Variable Y

In some embodiments, Y is $CO_2R^{6Y}$.

Variable $R^{6Y}$

In some embodiments, $R^{6Y}$ is H.

In some embodiments, $R^{6Y}$ is —$(Y^1)_m$—$Y^2$.

In some embodiments, m is 0.

In other embodiments, m is 1. In certain of the foregoing embodiments, $Y^1$ is $C_{1-6}$ alkylene, which is optionally substituted with from 1-6 $R^a$. As a non-limiting example, $Y^1$ can be ethylene or methylene (e.g., unsubstituted ethylene or methylene).

In some embodiments, $Y^2$ is $C_{3-10}$ cycloalkyl, which is optionally substituted with from 1-4 $R^b$.

In certain embodiments, $Y^2$ is $C_{3-8}$ cycloalkyl, which is optionally substituted with from 1-4 $R^b$.

In certain embodiments, $Y^2$ is $C_3$ cycloalkyl, which is optionally substituted with from 1-2 $R^b$.

In certain embodiments, $Y^2$ is $C_{5-6}$ cycloalkyl, which is optionally substituted with from 1-4 $R^b$.

In certain embodiments, $Y^2$ is $C_5$ cycloalkyl, which is optionally substituted with from 1-4 $R^b$.

In certain embodiments, $Y^2$ is $C_6$ cycloalkyl, which is optionally substituted with from 1-4 $R^b$.

In some embodiments, $Y^2$ is $C_{6-10}$ aryl, which is optionally substituted with from 1-4 $R^c$.

In certain embodiments, $Y^2$ is $C_6$ aryl, which is optionally substituted with from 1-4 $R^c$.

In certain embodiments, $Y^2$ is $C_{10}$ aryl, which is optionally substituted with from 1-4 $R^c$.

In some embodiments, $Y^2$ is heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$.

In certain embodiments, $Y^2$ is heteroaryl including from 5-6 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^c$.

In some embodiments, $Y^2$ is heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^b$.

In certain embodiments, $Y^2$ is heterocyclyl including from 4-6 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-2 independently selected $R^b$.

In some embodiments, $R^{6Y}$ is $C_{1-12}$ (e.g., $C_{1-6}$, $C_{2-6}$, $C_{2-3}$)alkyl, which is optionally substituted with from 1-6 (e.g., unsubstituted; or substituted with from 1-2, e.g., 1) independently selected $R^a$.

In some embodiments, $R^{6Y}$ is $C_{1-12}$ alkyl, optionally substituted with from 1-6 (e.g., from 1-2) independently selected $R^a$.

In some embodiments, $R^{6Y}$ is $C_{1-6}$ alkyl, optionally substituted with from 1-6 (e.g., from 1-2) independently selected $R^a$.

In some embodiments, $R^{6Y}$ is $C_{2-6}$ alkyl, optionally substituted with from 1-6 (e.g., from 1-2) independently selected $R^a$.

In some embodiments, $R^{6Y}$ is $C_{1-3}$ alkyl, optionally substituted with from 1-6 (e.g., from 1-2) independently selected $R^a$.

In certain embodiments, $R^{6Y}$ is $C_{2-3}$ alkyl, optionally substituted with from 1-6 (e.g., from 1-2) independently selected $R^a$ (e.g., $C_2$ alkyl optionally substituted with one $R^a$).

In certain embodiments, $R^{6Y}$ is $C_{1-3}$ alkyl, optionally substituted with from 1-2 independently selected $R^a$ (e.g., $C_2$ alkyl optionally substituted with one $R^a$).

In certain embodiments, $R^{6Y}$ is

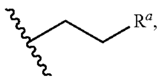

wherein $R^a$ is as defined elsewhere herein (in certain embodiments, $R^a$ is selected from the group consisting of: —OH; —F; —$NR^eR^f$ (e.g., $NMe_2$); $C_{1-4}$ alkoxy; and $C_{1-4}$ haloalkoxy).

In certain embodiments, $R^{6Y}$ is

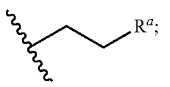

and $R^a$ is $NR^eR^f$. In certain of these embodiments, each of $R^e$ and $R^f$ is H or $C_{1-6}$ alkyl. For example, each of $R^e$ and $R^f$ can be $C_{1-3}$ alkyl.

In certain other embodiments, $R^e$ and $R^f$ together with the nitrogen atom to which each is attached forms a ring including from 3-8 (e.g., 5-6) ring atoms, wherein the ring includes: (a) from 1-7 (e.g., 1-5) ring carbon atoms, each of which is substituted with from 1-2 substituents independently selected from H and $C_{1-3}$ alkyl; and (b) from 0-3 ring heteroatoms (in addition to the nitrogen atom attached to $R^e$ and $R^f$), which are each independently selected from the group consisting of N(H), $N(R^d)$,O, and S;

As a non-limiting example, $R^{6Y}$ can be

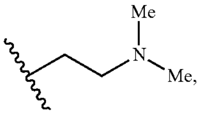

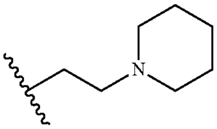

,

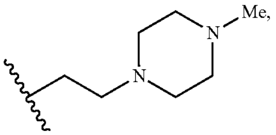

or

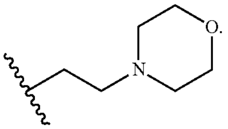

In certain of the foregoing embodiments when $R^{6Y}$ is $C_{1-12}$ alkyl, each occurrence of $R^a$ is independently selected from the group consisting of: —OH; —F; —Cl; —Br; —$NR^eR^f$; $C_{1-4}$ alkoxy; $C_{1-4}$ haloalkoxy; —C(═O)O($C_{1-4}$ alkyl); —C(═O)($C_{1-4}$ alkyl); —C(═O)OH; —CON(R')(R''); —$S(O)_{1-2}$(NR'R''); —$S(O)_{0-2}$($C_{1-4}$ alkyl); cyano, and $C_{3-6}$ cycloalkyl optionally substituted with from 1-4 independently selected $C_{1-4}$ alkyl.

In certain embodiments when $R^{6Y}$ is $C_{1-12}$ alkyl, each occurrence of $R^a$ is independently selected from the group consisting of: —OH; —F; —$NR^eR^f$ (e.g., $NMe_2$); $C_{1-4}$ alkoxy; and $C_{1-4}$ haloalkoxy.

In some embodiments, $R^{6Y}$ is unsubstituted $C_{1-12}$ alkyl.

In some embodiments, $R^{6Y}$ is unsubstituted $C_{1-6}$ alkyl.

In some embodiments, $R^{6Y}$ is unsubstituted $C_{1-4}$ alkyl (e.g., methyl or ethyl).

In some embodiments, $R^{6Y}$ is unsubstituted $C_{2-12}$ alkyl.

In some embodiments, $R^{6Y}$ is unsubstituted $C_{2-6}$ alkyl.

In some embodiments, $R^{6Y}$ is unsubstituted $C_{2-4}$ alkyl.

In some embodiments, $R^{6Y}$ is unsubstituted $C_{2-3}$ alkyl.

In some embodiments, $R^{6Y}$ is unsubstituted $C_{2-12}$ alkyl.

In some embodiments, $R^{6Y}$ is unsubstituted $C_{3-6}$ alkyl.

In some embodiments, $R^{6Y}$ is unsubstituted $C_{3-4}$ alkyl.

In some embodiments, $R^{6Y}$ is —$(Z^1$-$Z^2)_p$—$Z^3$.

In certain embodiments, p is 2-4 (e.g., 2-3). In certain of the foregoing embodiments, each occurrence of $Z^1$ is independently selected from $C_{1-3}$ alkylene (e.g., $C_2$ alkylene), which is optionally substituted with from 1-4 (e.g., from 1-2) $R^a$. As a non-limiting example, each $Z^1$ can be unsubstituted $C_2$ alkylene.

In some embodiments, each occurrence of $Z^2$ is independently selected from —N(H)—, —$N(R^d)$—, —O—, and —S—.

In certain embodiments, each occurrence of $Z^2$ is independently selected from —N(H)—, —N(Me)-, and —O—.

In some embodiments, $Z^3$ is H or $C_{1-3}$ alkyl, which is optionally substituted with from 1-4 $R^a$.

In certain embodiments, $Z^3$ is H or unsubstituted $C_{1-3}$ alkyl.

In certain embodiments, when $R^{6Y}$ is —$(Z^1$—$Z^2)_p$—$Z^3$, p is from 2-3; each occurrence of $Z^1$ is unsubstituted $C_2$ alkylene; each occurrence of $Z^2$ is independently selected from —N(H)—, —N(Me)-, and —O—; and $Z^3$ is H or unsubstituted $C_{1-3}$ alkyl.

In some embodiments when Y is $CO_2R^{6Y}$, Y is selected from $CO_2H$ and $CO_2Me$.

In some embodiments when Y is $CO_2R^{6Y}$, Y is

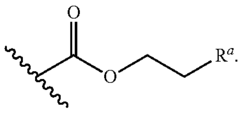

In certain embodiments of the foregoing, $R^a$ on Y is selected from —OH; —F; —$NR^eR^f$ (e.g., $NMe_2$); $C_{1-4}$ alkoxy; and $C_{1-4}$ haloalkoxy (e.g., Y can be

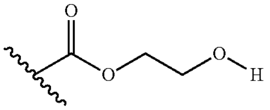

or

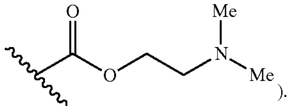

).

In some embodiments when Y is $CO_2R^{6Y}$, Y is other than $CO_2H$, $CO_2Me$, or $CO_2Et$.

In some embodiments, Y is C(O) $NR^4YR^{5Y}$.

Variable $R^{4Y}/R^{5Y}$.

In certain of the foregoing embodiments when Y is C(O) $NR^{4Y}R^{5Y}$, each of $R^{4Y}$ and $R^{5Y}$ is independently selected from the group consisting of:

(i) H;

(ii) $C_{1-12}$ alkyl, which is optionally substituted with 1-4 $R^a$;

(iii) —$(W^1$—$W^2)_n$—$W^3$, wherein:

$W^1$ is $C_{1-3}$ alkylene, which is optionally substituted with from 1-4 $R^a$;

$W^2$ is a —N(H)—, —$N(R^d)$—, —O—, or —S—;

$W^3$ is H or $C_2$-7 alkyl, which is optionally substituted with from 1-4 $R^a$; and n is 2-4;

or (iv) $R^{4Y}$ and $R^{5Y}$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to $R^{4Y}$ and $R^{5Y}$), which are each independently selected from the group consisting of N(H), N($R^d$), O, and S;

In some embodiments, $R^{4Y}$ is H.

In some embodiments, $R^{4Y}$ is $C_{1-12}$ alkyl, optionally substituted with from 1-6 independently selected $R^a$.

In certain embodiments, $R^{4Y}$ is $C_{1-6}$ alkyl, optionally substituted with from 1-3 independently selected $R^a$ (e.g., $C_2$ alkyl optionally substituted with one $R^a$).

In certain embodiments, $R^{4Y}$ is $C_{1-4}$ alkyl, optionally substituted with from 1-2 independently selected $R^a$ (e.g., $C_2$ alkyl optionally substituted with one $R^a$).

In certain embodiments, $R^{4Y}$ is

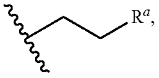

wherein $R^a$ is as defined elsewhere herein. In certain of the foregoing embodiments, $R^a$ is —OH, —$NR^eR^f$, $C_{1-4}$ alkoxy, or $C_{1-4}$ haloalkoxy. As non-limiting examples, $R^{4Y}$ can be

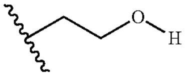 or 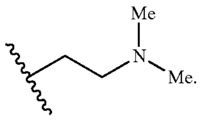

In certain of the foregoing embodiments when $R^{4Y}$ is $C_{1-12}$ alkyl, each occurrence of $R^a$ is independently selected from the group consisting of: —OH; —F; —Cl; —Br; —$NR^eR^f$; $C_{1-4}$ alkoxy; $C_{1-4}$ haloalkoxy; —C(═O)O($C_{1-4}$ alkyl); —C(═O)($C_{1-4}$ alkyl); —C(═O)OH; —CON(R')(R"); —$S(O)_{1-2}$(NR'R"); —$S(O)_{1-2}$($C_{1-4}$ alkyl); cyano, and $C_{3-6}$ cycloalkyl optionally substituted with from 1-4 independently selected $C_{1-4}$ alkyl.

In certain embodiments when $R^{4Y}$ is $C_{1-12}$ alkyl, each occurrence of $R^a$ is independently selected from the group consisting of: —OH; —F; —$NR^eR^f$ (e.g., $NMe_2$); $C_{1-4}$ alkoxy; and $C_{1-4}$ haloalkoxy.

In some embodiments, $R^{4Y}$ is unsubstituted $C_{1-12}$ alkyl.

In certain embodiments, $R^{4Y}$ is unsubstituted $C_{1-6}$ alkyl.

In certain embodiments, $R^{4Y}$ is unsubstituted $C_{1-4}$ alkyl (e.g., methyl, ethyl, n-propyl, or isopropyl).

In certain embodiments, $R^{4Y}$ is heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^h$. In certain of these embodiments, $R^{4Y}$ is heteroaryl including from 5-6 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^h$. For example, $R^{4Y}$ can be tetrazolyl wherein the ring nitrogen atom is optionally substituted with $R^d$. For example, $R^{4Y}$ can be

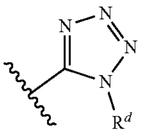 or 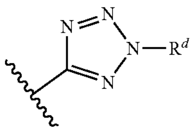

(e.g., 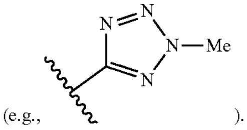).

In certain of the foregoing embodiments, $R^{5Y}$ is H.

In some embodiments, $R^{5Y}$ is H.

In some embodiments, RSY is $C_{1-12}$ alkyl, optionally substituted with from 1-6 independently selected $R^a$.

In certain embodiments, $R^{5Y}$ is $C_{1-6}$ alkyl, optionally substituted with from 1-3 independently selected $R^a$ (e.g., $C_2$ alkyl optionally substituted with one $R^a$).

In certain embodiments, $R^{5Y}$ is $C_{1-4}$ alkyl, optionally substituted with from 1-2 independently selected $R^a$ (e.g., $C_2$ alkyl optionally substituted with one $R^a$). wherein $R^a$ is as defined elsewhere In certain embodiments, $R^{5Y}$ is

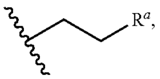

wherein $R^a$ is as defined elsewhere herein. In certain of the foregoing embodiments, $R^a$ is —OH, —$NR^eR^f$, $C_{1-4}$ alkoxy, or $C_{1-4}$ haloalkoxy. As non-limiting examples, $R^{5Y}$ can be

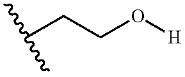 or 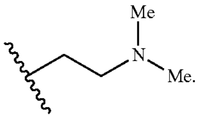

In certain of the foregoing embodiments when $R^{5Y}$ is $C_{1-12}$ alkyl, each occurrence of $R^a$ is independently selected from the group consisting of: —OH; —F; —Cl; —Br; —$NR^eR^f$; $C_{1-4}$ alkoxy; $C_{1-4}$ haloalkoxy; —C(═O)O($C_{1-4}$ alkyl); —C(═O)($C_{1-4}$ alkyl); —C(═O)OH; —CON(R')(R"); —$S(O)_{1-2}$(NR'R"); —$S(O)_{1-2}$($C_{1-4}$ alkyl); cyano, and $C_{3-6}$ cycloalkyl optionally substituted with from 1-4 independently selected $C_{1-4}$ alkyl.

In certain embodiments when $R^{5Y}$ is $C_{1-12}$ alkyl, each occurrence of $R^a$ is independently selected from the group consisting of: —OH; —F; —$NR^eR^f$ (e.g., $NMe_2$); $C_{1-4}$ alkoxy; and $C_{1-4}$ haloalkoxy.

In some embodiments, $R^{5Y}$ is unsubstituted $C_{1-12}$ alkyl.

In certain embodiments, $R^{5Y}$ is unsubstituted $C_{1-6}$ alkyl.

In certain embodiments, $R^{5Y}$ is unsubstituted $C_{1-4}$ alkyl (e.g., methyl, ethyl, n-propyl, or isopropyl).

In certain embodiments, $R^{5Y}$ is heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^h$. In certain of these embodiments, $R^{5Y}$ is heteroaryl including from 5-6 ring atoms, wherein from 1-4 ring atoms are heteroatoms, each independently selected from the group consisting of N, N(H), $N(R^d)$, O, and S, and wherein one or more of the heteroaryl ring carbon atoms are optionally substituted with from 1-4 independently selected $R^h$. For example, $R^{5Y}$ can be tetrazolyl wherein the ring nitrogen atom is optionally substituted with $R^d$. For example, $R^{5Y}$ can be

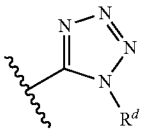 or 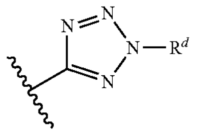

(e.g., 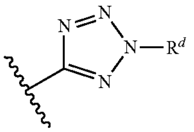 ).

In certain of the foregoing embodiments, $R^{4Y}$ is H.

In some embodiments, $R^{4Y}$ is $—(W^1—W^2)_n—W^3$.

In other embodiments, n is 2-4 (e.g., 2-3). In certain of the foregoing embodiments, each occurrence of $W^1$ is independently selected from $C_{1-3}$ alkylene (e.g., $C_2$ alkylene), which is optionally substituted with from 1-4 $R^a$.

In certain embodiments, $W^1$ is in each occurrence independently $C_{2-3}$ alkylene (e.g., $C_2$ alkylene).

In certain embodiments, $W^2$ is in each occurrence independently —N(H)—, —N(Me)-, or —O— (e.g., one $W^2$ is —O—; and another $W^2$ when present is —N(Me)-).

In certain embodiments, $W^3$ is selected from H and $C_{1-3}$ alkyl.

As a non-limiting example, $R^{4Y}$ can be selected from:

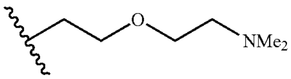 and

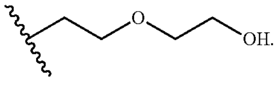

In some embodiments, $R^{5Y}$ is $—(W^1—W^2)_n—W^3$.

In other embodiments, n is 2-4 (e.g., 2-3). In certain of the foregoing embodiments, each occurrence of $W^1$ is independently selected from $C_{1-3}$ alkylene (e.g., $C_2$ alkylene), which is optionally substituted with from 1-4 $R^a$.

In certain embodiments, $W^1$ is in each occurrence independently $C_{2-3}$ alkylene (e.g., $C_2$ alkylene).

In certain embodiments, $W^2$ is in each occurrence independently —N(H)—, —N(Me)-, or —O— (e.g., one $W^2$ is —O—; and another $W^2$ when present is —N(Me)-).

In certain embodiments, $W^3$ is selected from H and $C_{1-3}$ alkyl.

As a non-limiting example, $R^{5Y}$ can be selected from:

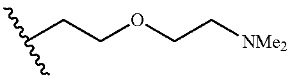 and

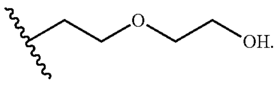

In some embodiments, one of $R^{4Y}$ and $R^{5Y}$ is $—(W^1—W^2)_n—W^3$. In certain embodiments of the foregoing, the other one of $R^{4Y}$ and $R^{5Y}$ is selected from H and $C_{1-3}$ alkyl.

In certain embodiments, n is 2-4 (e.g., n is 2; or n is 3).

In certain embodiments, n is 2 or 3.

In certain embodiments, $W^1$ is in each occurrence independently $C_{2-3}$ alkylene (e.g., $C_2$ alkylene).

In certain embodiments, $W^2$ is in each occurrence independently —N(H)—, —N(Me)-, or —O— (e.g., one $W^2$ is —O—; and another $W^2$ when present is —N(Me)-).

In certain embodiments, $W^3$ is selected from H and $C_{1-3}$ alkyl.

As non-limiting examples of the foregoing embodiments, one of $R^{4Y}$ and $R^{5Y}$ can be selected from:

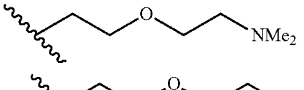 and

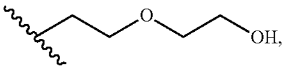

and the other one of $R^{4Y}$ and $R^{5Y}$ can be selected from H and $C_{1-3}$ alkyl.

In certain embodiments, both $R^{4Y}$ and $R^{5Y}$ are other than H (e.g., each of $R^{4Y}$ and $R^{5Y}$ is an independently selected $C_1$-$C_6$ alkyl which is optionally substituted with from 1-3 $R^a$).

In certain embodiments, one of $R^{4Y}$ and $R^{5Y}$ is H; and the other of $R^{4Y}$ and $R^{5Y}$ is other than H (e.g., one of $R^{4Y}$ and $R^{5Y}$ is H; and the other of $R^{4Y}$ and $R^{5Y}$ is an independently selected $C_1$-$C_6$ alkyl which is optionally substituted with from 1-3 $R^a$). As a non-limiting example, one of $R^{4Y}$ and $R^{5Y}$ can be H; and the other of $R^{4Y}$ and $R^{5Y}$ can be an independently selected $C_2$-$C_4$ alkyl (e.g., $C_2$ alkyl) which is optionally substituted with from 1-3 $R^a$.

In certain embodiments, both $R^{4Y}$ and $R^{5Y}$ are H.

In some embodiments, $R^{4Y}$ and $R^{5Y}$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to $R^{4Y}$ and $R^{5Y}$), which are each independently selected from the group consisting of N(H), $N(R^d)$, O, and S.

In certain embodiments, $R^{4Y}$ and $R^{5Y}$ together with the nitrogen atom to which each is attached forms a ring including 5 ring atoms, wherein the ring includes: (a) from 1-4 ring carbon atoms, each of which is substituted with from 1-2 substituents independently selected from H and $C_{1-3}$ alkyl; and (b) from 0-3 ring heteroatoms (in addition to the nitrogen atom attached to $R^{4Y}$ and $R^{5Y}$), which are each independently selected from the group consisting of N(H), $N(R^d)$, O, and S.

In certain embodiments, $R^{4Y}$ and $R^{5Y}$ together with the nitrogen atom to which each is attached forms a ring including 6 ring atoms, wherein the ring includes: (a) from 1-5 ring carbon atoms, each of which is substituted with from 1-2 substituents independently selected from H and $C_{1-3}$ alkyl; and (b) from 0-3 ring heteroatoms (in addition to the nitrogen atom attached to $R^{4Y}$ and $R^{5Y}$), which are each independently selected from the group consisting of N(H), $N(R^d)$, O, and S.

As non-limiting examples of the foregoing, Y can be:

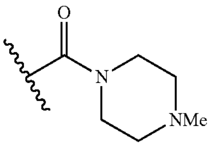 or 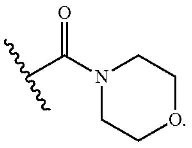

In some embodiments when Y is C(O) $NR^{4Y}R^{5Y}$, Y is $CONH_2$.

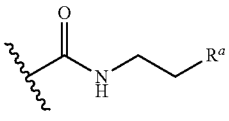

In some embodiments when Y is C(O) $NR^{4Y}R^{5Y}$, Y is selected from

In certain embodiments of the foregoing, $R^a$ is selected from —OH; —F; —$NR^eR^f$ (e.g., $NMe_2$); $C_{1-4}$ alkoxy; and $C_{1-4}$ haloalkoxy (e.g., Y can be

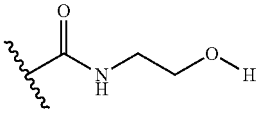 or

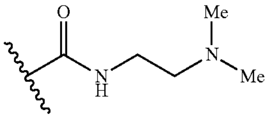).

In some embodiments when Y is C(O) $NR^{4Y}R^{5Y}$, Y is selected from:

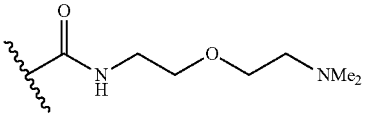 and

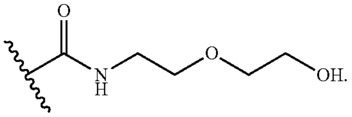

In some embodiments when Y is $CONR^{4Y}R^{5Y}$, Y is selected from:

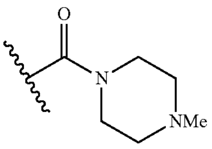 or 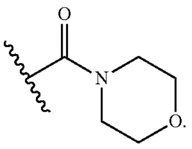

In some embodiments, Y is C(O)$NHR^{5Y}$. In certain of these embodiments, $R^{5Y}$ is $C_{1-6}$ alkyl, optionally substituted with from 1-3 independently selected $R^a$. In certain embodiments, $R^{5Y}$ is

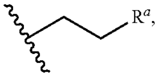

In certain of these embodiments, $R^a$ is $NR^eR^f$. In certain of these embodiments, each of $R^e$ and $R^f$ is H or $C_{1-6}$ alkyl. For example, each of $R^e$ and $R^f$ can be $C_{1-3}$ alkyl.

In certain other embodiments, $R^e$ and $R^f$ together with the nitrogen atom to which each is attached forms a ring including from 3-8 (e.g., 5-6) ring atoms, wherein the ring includes: (a) from 1-7 (e.g., 1-5) ring carbon atoms, each of which is substituted with from 1-2 substituents independently selected from H and $C_{1-3}$ alkyl; and (b) from 0-3 ring heteroatoms (in addition to the nitrogen atom attached to $R^e$ and $R^f$), which are each independently selected from the group consisting of N(H), N($R^d$), O, and S;

As a non-limiting example, $R^{5Y}$ can be

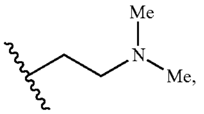 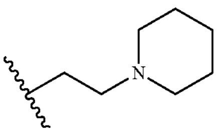,

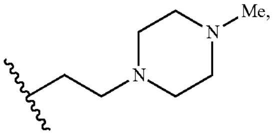 or 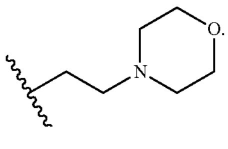

In certain embodiments, Y is C(O)$NHR^{5Y}$; and $R^{5Y}$ is heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^h$. In certain of these embodiments, $R^{5Y}$ is heteroaryl including from 5-6 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^h$. For example, $R^{5Y}$ can be tetrazolyl wherein the ring nitrogen atom is optionally substituted with $R^d$. For example, $R^{5Y}$ can be

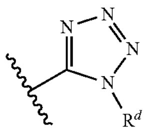 or 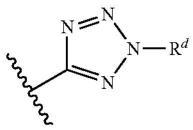

(e.g., 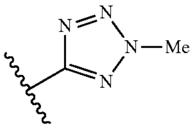).

In some embodiments, Y is heteroaryl including 5 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-2 independently selected $R^c$.

In some embodiments, Y is heteroaryl including 5 ring atoms, wherein from 2 ring atoms are heteroatom, each independently selected from the group consisting of N, N(H), N($R^d$), O, and S, and wherein one or more of the heteroaryl ring carbon atoms are optionally substituted with from 1-2 independently selected $R^c$.

In some embodiments, Y is heteroaryl including 5 ring atoms, wherein from 3-4 ring atoms are heteroatoms, each independently selected from the group consisting of N, N(H), N($R^d$), O, and S, and wherein one or more of the heteroaryl ring carbon atoms are optionally substituted with from 1-2 independently selected $R^c$.

In certain of the foregoing embodiments when Y is heteroaryl including 5 ring atoms, each occurrence of $R^e$ is independently selected from the group consisting of:

(i) halo;

(ii) cyano;

(iii) $C_{1-10}$ alkyl;

(iv) $C_{1-10}$ alkyl which is substituted with from 1-6 independently selected $R^a$;

(v) $C_{3-6}$ cycloalkyl optionally substituted with from 1-3 independently selected $R^b$ (vi) $C_{2-6}$ alkenyl;

(vii) $C_{2-6}$ alkynyl;

(viii) $C_{1-4}$ alkoxy;

(ix) $C_{1-4}$ haloalkoxy;

(x) —(Co-3 alkylene)-$C_{3-6}$ cycloalkyl optionally substituted with from 1-4 independently selected $C_{1-4}$ alkyl;

(xi) —$S(O)_{1-2}$($C_{1-4}$ alkyl);

(xii) —$NR^eR^f$;

(xiii) —OH;

In certain of the foregoing embodiments when Y is heteroaryl including 5 ring atoms, each occurrence of $R^d$ is selected from the group consisting of: $C_{1-6}$ alkyl; $C_{1-10}$ alkyl which is substituted with from 1-6 independently selected $R^a$; $C_{3-6}$ cycloalkyl optionally substituted with from 1-3 independently selected $R^b$; —C(O)($C_{1-4}$ alkyl); —C(O)O($C_{1-4}$ alkyl); —CON(R')(R"); —$S(O)_{1-2}$(NR'R"); and —$S(O)_{1-2}$($C_{1-4}$ alkyl).

In certain embodiments when Y is heteroaryl including 5 ring atoms, Y is selected from tetrazolyl, triazolyl, oxadiazolyl, imidazolyl, and oxazolyl, wherein one or more of the heteroaryl ring carbon atoms are optionally substituted with from 1-2 independently selected $R^c$; and one of the heteroaryl ring nitrogen atoms are optionally substituted with $R^d$ In certain embodiments when Y is heteroaryl including 5 ring atoms, Y is selected from tetrazolyl, triazolyl, oxadiazolyl, and oxazolyl, wherein one or more of the heteroaryl ring carbon atoms are optionally substituted with from 1-2 independently selected $R^c$; and one of the heteroaryl ring nitrogen atoms are optionally substituted with $R^d$.

In certain embodiments of the foregoing, each $R^c$ when present is independently selected from:

(i) halo;

(iii) $C_{1-10}$ alkyl;

(iv) $C_{1-10}$ alkyl which is substituted with from 1-6 (e.g., 1) independently selected $R^a$; and (v) $C_{3-6}$ cycloalkyl optionally substituted with from 1-3 independently selected $R^b$ (e.g., each $R^c$ can be independently (iii) $C_{1-10}$ alkyl or (iv) $C_{1-10}$ alkyl which is substituted with from 1-6 independently selected $R^a$).

In certain of the foregoing embodiments, $R^d$ is $C_{1-6}$ alkyl which is optionally substituted from 1-3 independently selected $R^g$. In certain of these embodiments, $R^d$ is unsubstituted $C_{1-3}$ alkyl.

In certain other embodiments, $R^d$ is $C_{1-3}$ alkyl which is optionally substituted with from 1-3 independently selected $R^g$. In certain of these embodiments, $R^g$ is selected from the group consisting of: —OH, —F, N($C_{1-3}$ alkyl)$_2$, $C_{1-3}$ alkoxy, —$CONH_2$, —CONHS(O)$_2$($C_{1-4}$ alkyl), and —C(O)OH.

Non-limiting examples of $R^d$ can include the following:

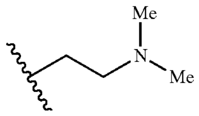
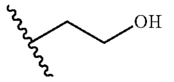
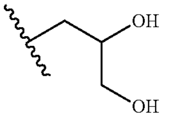
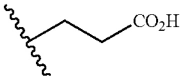
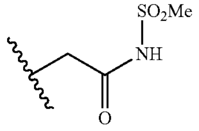
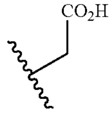

In certain embodiments of the foregoing, Y is selected from the group consisting

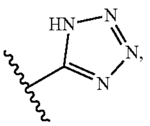
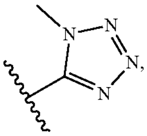
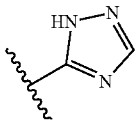
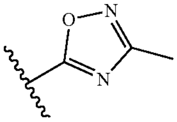
, and
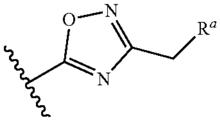

(e.g., $R^a$ can be selected from —OH, —OMe, and —$NMe_2$). For example, Y can be

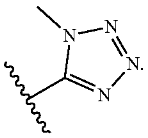 [SMILES: *c1nnnn1C]

In certain embodiments, Y is selected from the group consisting of:

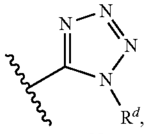
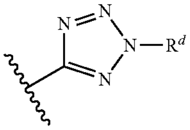
,
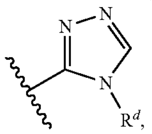
and
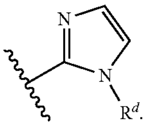

For example, Y can be

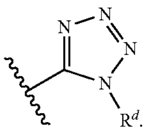

In certain embodiments, $R^d$ is unsubstituted $C_{1-3}$ alkyl, such as methyl.

In certain other of the foregoing embodiments, $R^d$ is $C_{1-3}$ alkyl which is optionally substituted with from 1-3 independently selected $R^g$. In certain of these embodiments, $R^g$ is selected from the group consisting of: —OH, —F, $N(C_{1-3}$ $alkyl)_2$, $C_{1-3}$ alkoxy, —$CONH_2$, —$CONHS(O)_2(C_{1-4}$ alkyl), and —C(O)OH. Non-limiting examples of $R^d$ can include the following:

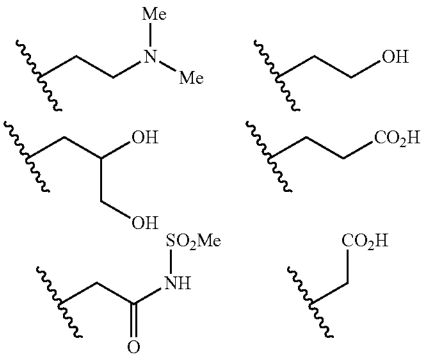

In certain embodiments, Y is

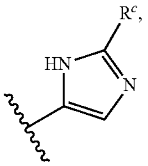

or

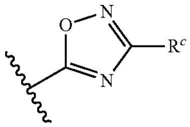

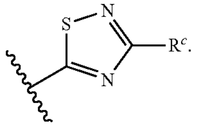

In certain of these embodiments, $R^c$ is $NH_2$, C(=O)N(R')(R"), C(=O)OH, or $C_{1-3}$ alkyl optionally substituted with $R^a$ (e.g., $R^c$ can be

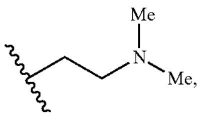

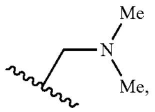

or

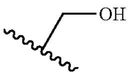

).

In some embodiments, Y is heteroaryl including 6 ring atoms, wherein from 1-3 ring atoms are ring nitrogen atoms, and wherein one or more of the heteroaryl ring carbon atoms are optionally substituted with from 1-2 independently selected $R^c$. For example, Y can be pyridyl or pyrimidyl, each of which is optionally substituted with from 1-2 independently selected $R^c$. As a non-limiting example, Y can be

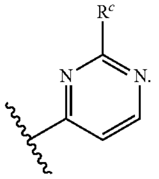

In some embodiments, Y is heterocycloalkenyl including from 5-6 ring atoms, wherein from 1-4 ring atoms are heteroatoms, each independently selected from the group consisting of N, N(H), $N(R^d)$, O, and S, and wherein one or more of the heterocycloalkenyl ring carbon atoms are optionally substituted with from 1-2 independently selected $R^b$. In certain of these embodiments, Y is imidazolinyl, wherein a ring nitrogen is optionally substituted with $R^d$ (e.g.,

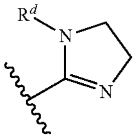

).

Variable Z

In some embodiments, Z is selected from H, $NR^{4Z}R^{5Z}$, $OR^{6Z}$ and $OC(O)R^{7Z}$.

In some embodiments Z is $NR^{4Z}R^{5Z}$.

Variable $R^{4Z}/R^{5Z}$

In some embodiments, $R^{4Z}$ is H.

In some embodiments, $R^{4Z}$ is $C_{1-10}$ alkyl which is optionally substituted with 1-6 independently selected $R^a$. In certain of the foregoing embodiments, $R^{4Z}$ is $C_{1-6}$ alkyl which is optionally substituted with 1-2 independently selected $R^a$.

In certain embodiments, $R^{4Z}$ is $C_{1-3}$ alkyl, optionally substituted with one $R^a$. As a non-limiting example, $R^{4Z}$ can be

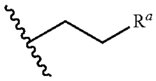

in certain embodiments, $R^a$ is selected from —OH, —$NR^eR^f$, $C_{1-4}$ alkoxy, and $C_{1-4}$ haloalkoxy, e.g., $R^{4Z}$ can be

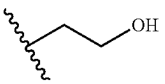

).

In some embodiments, $R^{4Z}$ is unsubstituted $C_{1-10}$ alkyl. In certain of the foregoing embodiments, $R^{4Z}$ is unsubstituted $C_{1-10}$ alkyl (e.g., unsubstituted $C_{1-6}$ alkyl, e.g., unsubstituted $C_{1-3}$ alkyl, e.g., methyl).

In some embodiments, $R^{4Z}$ is selected from the group consisting of: —C(O)($C_{1-4}$ alkyl); —C(O)O($C_{1-4}$ alkyl); —CON(R')(R"); —$S(O)_{1-2}$(NR'R"); —$S(O)_{1-2}$($C_{1-4}$ alkyl).

In some embodiments, $R^{5Z}$ is H.

In some embodiments, $R^{5Z}$ is $C_{1-10}$ alkyl which is optionally substituted with 1-6 independently selected $R^a$. In certain of the foregoing embodiments, $R^{5Z}$ is $C_{1-6}$ alkyl which is optionally substituted with 1-2 independently selected $R^a$.

In certain embodiments, $R^{5Z}$ is $C_{1-3}$ alkyl, optionally substituted with one $R^a$. As a non-limiting example, $R^{5Z}$ can be

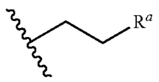

(in certain embodiments, $R^a$ is selected from —OH, —$NR^eR^f$, $C_{1-4}$ alkoxy, and $C_{1-4}$ haloalkoxy, e.g., $R^{5Z}$ can be

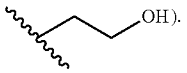 [SMILES: *CCO]

In some embodiments, $R^{5Z}$ is unsubstituted $C_{1-10}$ alkyl. In certain of the foregoing embodiments, $R^{5Z}$ is unsubstituted $C_{1-10}$ alkyl (e.g., unsubstituted $C_{1-6}$ alkyl, e.g., unsubstituted $C_{1-3}$ alkyl, e.g., methyl).

In some embodiments, $R^{5Z}$ is selected from the group consisting of: —C(O)($C_{1-4}$ alkyl); —C(O)O($C_{1-4}$ alkyl); —CON(R')(R"); —$S(O)_{1-2}$(NR'R"); —$S(O)_{1-2}$($C_{1-4}$ alkyl).

In certain embodiments, both $R^{4Z}$ and $R^{5Z}$ are other than H (e.g., each of $R^{4Z}$ and $R^{5Z}$ is an independently selected $C_1$-$C_6$ alkyl which is optionally substituted with from 1-3 $R^a$, e.g., each of $R^{4Z}$ and $R^{5Z}$ is an independently selected unsubstituted $C_1$-$C_6$ alkyl).

In certain embodiments, one of $R^{4Z}$ and $R^{5Z}$ is H; and the other of $R^{4Z}$ and $R^{5Z}$ is other than H (e.g., one of $R^{4Z}$ and $R^{5Z}$ is H; and the other of $R^{4Z}$ and $R^{5Z}$ is an independently selected $C_1$-$C_6$ alkyl which is optionally substituted with from 1-3 $R^a$, e.g., $R^{5Z}$ is an independently selected unsubstituted $C_1$-$C_6$ alkyl).

In certain embodiments, both $R^{4Z}$ and $R^{5Z}$ are H.

In certain embodiments when Z is $NR^{4Z}R^{5Z}$, each of $R^{4Z}$ and $R^{5Z}$ is independently selected from H and $C_{1-10}$ alkyl, optionally substituted with from 1-6 independently selected $R^a$.

In certain embodiments when Z is $NR^{4Z}R^{5Z}$, each of $R^{4Z}$ and $R^{5Z}$ is independently selected from H and $C_{1-6}$ alkyl, optionally substituted with from 1-2 independently selected $R^a$.

In certain embodiments when Z is $NR^{4Z}R^{5Z}$, each of $R^{4Z}$ and $R^{5Z}$ is independently selected from H and $C_{1-3}$ alkyl, optionally substituted with one $R^a$.

In certain embodiments when Z is $NR^{4Z}R^{5Z}$, each of $R^{4Z}$ and $R^{5Z}$ is independently selected from H and unsubstituted $C_{1-10}$ alkyl.

In certain of the foregoing embodiments, each of $R^{4Z}$ and $R^{5Z}$ is independently H or methyl.

In certain embodiments when Z is $NR^{4Z}R^{5Z}$, each of $R^{4Z}$ and $R^{5Z}$ is independently selected from H and

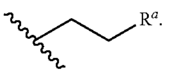

As a non-limiting example, the $R^a$ on $R^{4Z}$ and $R^{5Z}$ can be selected from —OH, —$NR^eR^f$, $C_{1-4}$ alkoxy, and $C_{1-4}$ haloalkoxy. For example, each of $R^{4Z}$ and $R^{5Z}$ can be independently selected from H and

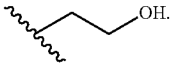 [SMILES: *CCO]

In certain embodiments, from 1-2 of $R^{4Z}$ and $R^{5Z}$ is H.

In certain embodiments, each of $R^{4Z}$ and $R^{5Z}$ is independently H or unsubstituted $C_{1-10}$ alkyl (e.g., unsubstituted $C_{1-6}$ alkyl, e.g., unsubstituted $C_{1-3}$ alkyl, e.g., methyl).

In some embodiments, Z is $OR^{6Z}$.

In certain embodiments, $R^{6Z}$ is selected from H and $C_{1-10}$ alkyl, optionally substituted with from 1-6 independently selected $R^a$.

In some embodiments, $R^{6Z}$ is H.

In some embodiments, $R^{6Z}$ is $C_{1-10}$ alkyl, optionally substituted with from 1-6 independently selected $R^a$.

In certain embodiments, $R^{6Z}$ is $C_{1-6}$ alkyl, optionally substituted with from 1-6 independently selected $R^a$.

In certain embodiments, $R^{6Z}$ is $C_{1-3}$ alkyl, optionally substituted with from 1-2 (e.g., 1) independently selected $R^a$ (in certain embodiments, $R^a$ on $R^{6Z}$ is selected from —OH, —$NR^eR^f$, $C_{1-4}$ alkoxy, and $C_{1-4}$ haloalkoxy).

As a non-limiting example of the foregoing, ROZ can be

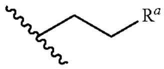

(e.g.,

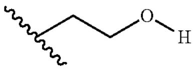

or

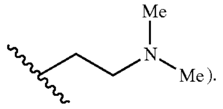

).

In certain embodiments when Z is $OR^{6Z}$, $R^{6Z}$ is selected from H and $C_{1-10}$ alkyl, optionally substituted with from 1-6 independently selected $R^a$.

In certain embodiments, Z is OH.

In certain embodiments, Z is —O($C_{1-3}$ alkyl), wherein the $C_{1-3}$ alkyl portion is optionally substituted with from 1-2 independently selected $R^a$.

As non-limiting examples of the foregoing embodiments, Z can be:

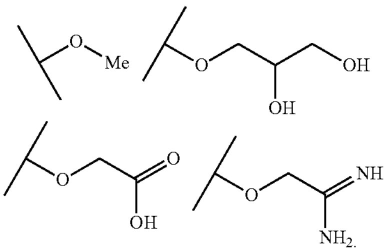

In some embodiments when Z is $OR^{6Z}$, $R^{6Z}$ is $-(T^1-T^2)_t-T^3$.

In certain embodiments of the foregoing, t is 2-3 (e.g., t is 2).

In certain embodiments, $T^1$ in each occurrence is independently $C_{2-3}$ alkylene (e.g., $C_2$ alkylene).

In certain embodiments, $T^2$ in each occurrence is independently —N(H)—, —N(Me)-, or —O—.

In certain embodiments, $T^3$ is H or $C_{1-3}$ alkyl (e.g., H or methyl).

As non-limiting examples of the foregoing embodiments, Z can be:

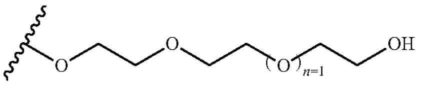

or

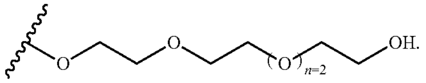

In some embodiments, Z is $OC(O)R^{7Z}$.

In some embodiments, $R^{7Z}$ is H.

In some embodiments, $R^{7Z}$ is $C_{1-10}$ alkyl (e.g., $C_{1-6}$ alkyl), optionally substituted with from 1-6 (e.g., from 1-4, e.g., from 1-3, e.g., 1) independently selected $R^a$. In certain of the foregoing embodiments, $R^{7Z}$ is $C_{1-6}$ alkyl, optionally substituted with from 1-3 (e.g., 1 or 2) independently selected $R^a$.

In certain of the foregoing embodiments when $R^{7Z}$ is $C_{1-10}$ alkyl optionally substituted with from 1-6 independently selected $R^a$, each occurrence of $R^a$ is independently selected from the group consisting of: —OH; —F; $—NR^eR^f$ (e.g., $NMe_2$); C(═O)OH; $C_{1-4}$ alkoxy; and $C_{1-4}$ haloalkoxy.

In certain of the foregoing embodiments when $R^{7Z}$ is $C_{1-10}$ alkyl optionally substituted with from 1-6 independently selected $R^a$, each occurrence of $R^a$ is independently selected from the group consisting of: —OH; —F; $—NR^eR^f$ (e.g., $NMe_2$); $C_{1-4}$ alkoxy; and $C_{1-4}$ haloalkoxy.

In some embodiments, $R^{7Z}$ is unsubstituted $C_{1-10}$ alkyl (e.g., unsubstituted $C_{1-6}$ alkyl, e.g., unsubstituted $C_{1-4}$ alkyl). As non-limiting examples, $R^{7Z}$ can be methyl, ethyl, or isopropyl.

In some embodiments, $R^{7Z}$ is $C_{6-10}$ aryl, which is optionally substituted with from 1-4 $R^c$.

In certain embodiments, $R^{7Z}$ is $C_6$ aryl, which is optionally substituted with from 1-4 $R^c$.

In certain of the foregoing embodiments when $R^{7Z}$ is $C_{6-10}$ aryl, which is optionally substituted with from 1-4 $R^c$, each occurrence of $R^c$ is independently selected from the group consisting of:

(i) halo;
(ii) cyano;
(iii) $C_{1-6}$ alkyl;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(xi) $—NR^eR^f$; and
(xii) —OH.

In some embodiments, $R^{7Z}$ is $C_{3-6}$ cycloalkyl, which is optionally substituted with from 1-4 $R^b$.

In certain of the foregoing embodiments when $R^{7Z}$ is $C_{3-6}$ cycloalkyl, which is optionally substituted with from 1-4 $R^b$, each occurrence of $R^b$ is independently selected from the group consisting of: $C_{1-6}$ alkyl; $C_{1-4}$ haloalkyl; —OH; oxo; —F; —Cl; —Br; $—NR^eR^f$; $C_{1-4}$ alkoxy; $C_{1-4}$ haloalkoxy; cyano; and $C_{3-6}$ cycloalkyl optionally substituted with from 1-4 independently selected $C_{1-4}$ alkyl.

In some embodiments, Z is $OP(O)OR^{8Z}OR^{9Z}$. For example, Z can be OP(O)OH(OH).

In some embodiments, $R^{8Z}$ is H.

In some embodiments, $R^{8Z}$ is $C_{1-10}$ alkyl, optionally substituted with from 1-6 independently selected $R^a$.

In some embodiments, $R^{9Z}$ is H.

In some embodiments, $R^{9Z}$ is $C_{1-10}$ alkyl, optionally substituted with from 1-6 independently selected $R^a$.

In some embodiments, Z is H.

In some embodiments, Z is heterocyclyl including from 4-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^h$.

In certain of these embodiments, Z is heterocyclyl including from 5-6 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^h$. For example, Z can be piperidinyl, pyrrolidinyl, piperazinyl, or morpholinyl, each of which is optionally substituted as defined supra. As a non-limiting example, Z can be morpholin-4-yl.

In some embodiments, Z is $OR^{6Z}$, wherein $R^{6Z}$ is:

(iii) —($C_{0-2}$ alkylene)-($C_{6-10}$ aryl), wherein the $C_{6-10}$ aryl is optionally substituted with from 1-2 independently selected $R^h$; or (iv) —($C_{0-2}$ alkylene)-(heteroaryl), wherein the heteroaryl includes from 5-10 ring atoms, wherein from 1-4 ring atoms are heteroatoms, each independently selected from the group consisting of N, N(H), N($C_{1-3}$ alkyl), O, and S, and wherein one or more of the heteroaryl ring carbon atoms are optionally substituted with from 1-4 independently selected $R^h$.

In certain of these embodiments, $R^{6Z}$ is (iv) —($C_{0-2}$ alkylene)-(heteroaryl), wherein the heteroaryl includes from 5-6 ring atoms, wherein from 1-4 ring atoms are heteroatoms, each independently selected from the group consisting of N, N(H), N($C_{1-3}$ alkyl), O, and S, and wherein one or more of the heteroaryl ring carbon atoms are optionally substituted with from 1-4 (e.g., 1, 2, 3, or 4) independently selected $R^h$. For example, Z can be

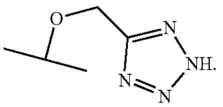

In some embodiments, Z is $R^{6Z}$, wherein $R^{6Z}$ is: —($C_{1-2}$ alkylene)-C(═O) NH—($C_{1-3}$ alkylene)-$R^{6Z'}$.

In certain of these embodiments, $R^{6Z'}$ is selected from the group consisting of: C(═O)OH, N($C_{1-4}$ alkyl)$_2$, $NH_2$, and NH($C_{1-4}$ alkyl).

As non-limiting examples, Z can be:

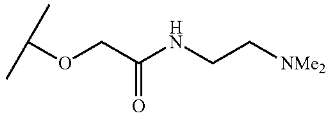

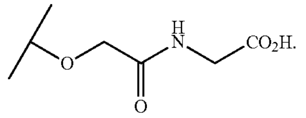

In certain embodiments, $R^{6Z'}$ is heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $C_{1-3}$ alkyl.

In certain of these embodiments, $R^{6Z'}$ is heterocyclyl including from 5-6 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $C_{1-3}$ alkyl.

As non-limiting examples, Z can be:

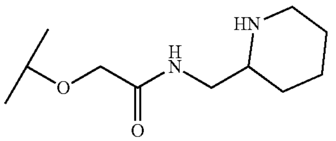

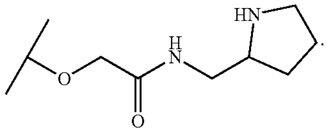

Variables $R^1$, $R^2$, and $R^3$

In some embodiments, $R^1$ is $R^{6A}$.

In certain embodiments, $R^1$ is $R^{6A}$; and each of $R^2$ and $R^3$ is other than $R^{6A}$.

In certain embodiments, $R^1$ is $R^{6A}$; $R^2$ is $R^{6A}$; and $R^3$ is other than $R^{6A}$.

In certain embodiments, $R^1$ is $R^{6A}$; $R^3$ is $R^{6A}$; and $R^2$ is other than $R^{6A}$.

In certain embodiments, $R^1$ is $R^{6A}$; and each of $R^2$ and $R^3$ is an independently selected $R^{6A}$.

In some embodiments, $R^2$ is $R^{6A}$.

In certain embodiments, $R^2$ is $R^{6A}$; and each of $R^1$ and $R^3$ is other than $R^{6A}$.

In certain embodiments, $R^2$ is $R^{6A}$; $R^3$ is $R^{6A}$; and $R^1$ is other than $R^{6A}$.

In some embodiments, $R^3$ is $R^{6A}$.

In certain embodiments, $R^3$ is $R^{6A}$; and each of $R^1$ and $R^3$ is other than $R^{6A}$.

In some embodiments, $R^{6A}$ is H.

In some embodiments, $R^{6A}$ is $C_{1-10}$ alkyl, optionally substituted with from 1-6 independently selected $R^a$.

In some embodiments, $R^1$ is $C(O)R^{7A}$.

In certain embodiments, $R^1$ is $C(O)R^{7A}$; and each of $R^2$ and $R^3$ is other than $C(O)R^{7A}$.

In certain embodiments, $R^1$ is $C(O)R^{7A}$; $R^2$ is $C(O)R^{7A}$; and $R^3$ is other than $C(O)R^{7A}$.

In certain embodiments, $R^1$ is $C(O)R^{7A}$; $R^3$ is $C(O)R^{7A}$; and $R^2$ is other than $C(O)R^{7A}$.

In certain embodiments, $R^1$ is $C(O)R^{7A}$; and each of $R^2$ and $R^3$ is $C(O)R^{7A}$.

In some embodiments, $R^2$ is $C(O)R^{7A}$.

In certain embodiments, $R^2$ is $C(O)R^{7A}$; and each of $R^1$ and $R^3$ is other than $C(O)R^{7A}$.

In certain embodiments, $R^2$ is $C(O)R^{7A}$; $R^3$ is $C(O)R^{7A}$; and $R^1$ is other than $C(O)R^{7A}$.

In some embodiments, $R^3$ is $C(O)R^{7A}$.

In certain embodiments, $R^3$ is $C(O)R^{7A}$; and each of $R^1$ and $R^3$ is other than $C(O)R^{7A}$.

In some embodiments, $R^{7A}$ is H.

In some embodiments, $R^{7A}$ is $C_{1-10}$ alkyl, optionally substituted with from 1-6 independently selected $R^a$ (e.g., $C_{1-6}$ or $C_{1-3}$ alkyl, optionally substituted with from 1-6 independently selected $R^a$; e.g., $C_{1-10}$ or $C_{1-6}$ or $C_{1-3}$ unsubstituted alkyl (e.g., $CH_3$)). In certain of the foregoing embodiments, $R^{7A}$ is $C_{1-6}$ alkyl, optionally substituted with from 1-6 (e.g., 1-3) independently selected $R^a$.

In certain of the foregoing embodiments when $R^{7A}$ is $C_{1-10}$ alkyl optionally substituted with from 1-6 independently selected $R^a$, each occurrence of $R^a$ is independently selected from the group consisting of: —OH; —F; —$NR^eR^f$ (e.g., $NMe_2$); $C_{1-4}$ alkoxy; and $C_{1-4}$ haloalkoxy.

In some embodiments, $R^{7A}$ is $C_{6-10}$ aryl, which is optionally substituted with from 1-4 $R^c$.

In certain embodiments, $R^{7A}$ is $C_6$ aryl, which is optionally substituted with from 1-4 $R^c$.

In certain of the foregoing embodiments when $R^{7A}$ is $C_{6-10}$ aryl, which is optionally substituted with from 1-4 $R^c$, each occurrence of $R^e$ is independently selected from the group consisting of:

(i) halo;

(ii) cyano;

(iii) $C_{1-6}$ alkyl;

(iv) $C_{2-6}$ alkenyl;

(v) $C_{2-6}$ alkynyl;

(vi) $C_{1-4}$ haloalkyl;

(vii) $C_{1-4}$ alkoxy;

(viii) $C_{1-4}$ haloalkoxy;

(ix) —($C_{0-3}$ alkylene)-$C_{3-6}$ cycloalkyl optionally substituted with from 1-4 independently selected $C_{1-4}$ alkyl;

(xi) —$NR^eR^f$; and (xii) —OH.

In some embodiments, $R^{7A}$ is $C_{3-6}$ cycloalkyl, which is optionally substituted with from 1-4 $R^b$.

In certain of the foregoing embodiments when $R^{7A}$ is $C_{3-6}$ cycloalkyl, which is optionally substituted with from 1-4 $R^b$, each occurrence of $R^b$ is independently selected from the group consisting of: $C_{1-6}$ alkyl; $C_{1-4}$ haloalkyl; —OH; oxo; —F; —Cl; —Br; —$NR^eR^f$; $C_{1-4}$ alkoxy; $C_{1-4}$ haloalkoxy; cyano; and $C_{3-6}$ cycloalkyl optionally substituted with from 1-4 independently selected $C_{1-4}$ alkyl.

In some embodiments, $R^1$ is $OP(O)OR^{8A}OR^{9A}$.

In certain embodiments, $R^1$ is $OP(O)OR^{8A}OR^{9A}$; and each of $R^2$ and $R^3$ is other than $OP(O)OR^{8A}OR^{9A}$.

In certain embodiments, $R^1$ is $OP(O)OR^{8A}OR^{9A}$; $R^2$ is $OP(O)OR^{8A}OR^{9A}$; and $R^3$ is other than $OP(O)OR^{8A}OR^{9A}$.

In certain embodiments, $R^1$ is $OP(O)OR^{8A}OR^{9A}$; $R^3$ is $OP(O)OR^{8A}OR^{9A}$; and $R^2$ is other than $OP(O)OR^{8A}OR^{9A}$.

In certain embodiments, $R^1$ is $OP(O)OR^{8A}OR^{9A}$; and each of $R^2$ and $R^3$ is $OP(O)OR^{8A}OR^{9A}$.

In some embodiments, $R^2$ is $OP(O)OR^{8A}OR^{9A}$.

In certain embodiments, $R^2$ is $OP(O)OR^{8A}OR^{9A}$; and each of $R^1$ and $R^3$ is other than $OP(O)OR^{8A}OR^{9A}$.

In certain embodiments, $R^2$ is $OP(O)OR^{8A}OR^{9A}$; $R^3$ is $OP(O)OR^{8A}OR^{9A}$; and $R^1$ is other than $OP(O)OR^{8A}OR^{9A}$.

In some embodiments, $R^3$ is $OP(O)OR^{8A}OR^{9A}$.

In certain embodiments, $R^3$ is $OP(O)OR^{8A}OR^{9A}$; and each of $R^1$ and $R^3$ is other than $OP(O)OR^{8A}OR^{9A}$.

In some embodiments, $R^{8A}$ is H.

In some embodiments, $R^{8A}$ is $C_{1-10}$ alkyl, optionally substituted with from 1-6 independently selected $R^a$.

In some embodiments, $R^{9A}$ is H.

In some embodiments, $R^{9A}$ is $C_{1-10}$ alkyl, optionally substituted with from 1-6 independently selected $R^a$.

In some embodiments, each of $R^1$, $R^2$, and $R^3$ is independently selected from H and $C(O)R^{7A}$.

In certain embodiments of the foregoing, each occurrence of $R^{7A}$ is independently $C_{1-10}$ alkyl, optionally substituted with from 1-6 independently selected $R^a$ (e.g., $C_{1-6}$ or $C_{1-3}$ alkyl, optionally substituted with from 1-6 independently selected $R^a$; e.g., $C_{1-10}$ or $C_{1-6}$ or $C_{1-3}$ unsubstituted alkyl (e.g., $CH_3$)).

In some embodiments, each of $R^1$, $R^2$, and $R^3$ is independently selected from H and C(O)Me (e.g., $R^1$, $R^2$, and $R^3$ are each H; or $R^1$, $R^2$, and $R^3$ are each C(O)Me).

In certain embodiments, one or more of $R^1$, $R^2$, and $R^3$ is H. In certain of these embodiments, each one of $R^1$, $R^2$, and $R^3$ is H.

In certain other embodiments, each one of $R^1$, $R^2$, and $R^3$ is C(O)Me.

Variable $Z^x$

In some embodiments, each $Z^x$ is H.

In some embodiments, each $Z^x$ together with the carbon to which each is attached forms C═O.

Non-Limiting Combinations

Non-Limiting Combination [1]

In some embodiments, a compound of formula (I) is a compound having formula (I-a):

(I-a)

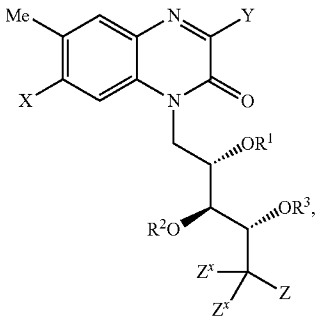

wherein X, Y, Z, $Z^x$, $R^1$, $R^2$, and $R^3$ are as defined elsewhere herein.

Non-Limiting Combination [2]

In some embodiments:

X is $C_1$-$C_6$ alkyl which is optionally substituted with from 1-3 $R^a$; and

Y is $CO_2R^{6Y}$.

In certain embodiments of [2], $R^{6Y}$ is $C_{1-12}$ alkyl, optionally substituted with from 1-6 independently selected $R^a$. In certain embodiments, $R^{6Y}$ is $C_{1-6}$ alkyl, optionally substituted with from 1-3 independently selected $R^a$ (e.g., $C_2$ alkyl optionally substituted with one $R^a$). In certain embodiments, $R^{6Y}$ is $C_{1-4}$ alkyl, optionally substituted with from 1-2 independently selected $R^a$ (e.g., $C_2$ alkyl optionally substituted with one $R^a$). In certain embodiments, $R^{6Y}$ is

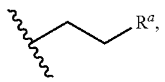

wherein $R^a$ is as defined elsewhere herein (in certain embodiments, $R^a$ is selected from —OH; —F; —$NR^eR^f$ (e.g., $NMe_2$); $C_{1-4}$ alkoxy; and $C_{1-4}$ haloalkoxy). For example, $R^{6Y}$ is methyl, 2-(dimethylamino)-eth-1-yl, or 2-(hydroxyl)-eth-1-yl. In certain embodiments of [2], $R^{6Y}$ is unsubstituted $C_{1-12}$ alkyl.

In certain other embodiments of [2], $R^{6Y}$ is H.

In certain embodiments of [2], $R^{6Y}$ is H.

In certain embodiments of [2], $R^{6Y}$ is $C_{1-12}$ (e.g., $C_{1-6}$, $C_{2-6}$, $C_{2-3}$)alkyl, which is optionally substituted with from 1-6 (e.g., unsubstituted; or substituted with from 1-2, e.g., 1) independently selected $R^a$.

In certain embodiments of [2], Y is $CO_2R^{6Y}$, wherein Y is selected from $CO_2H$ and $CO_2Me$.

In certain embodiments of [2], Y is $CO_2R^{6Y}$, wherein Y is

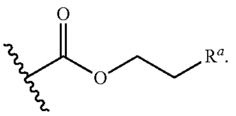

For example, Y can be

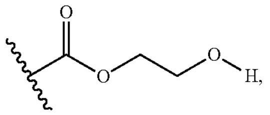 or 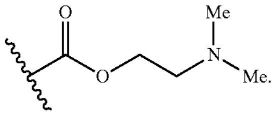

In certain embodiments of [2], Y is

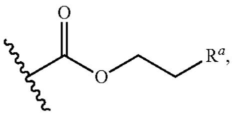

wherein the $R^a$ on Y is selected from —OH; —F; —$NR^eR^f$ (e.g., $NMe_2$); $C_{1-4}$ alkoxy; and $C_{1-4}$ haloalkoxy (e.g., Y can be

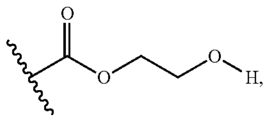 or

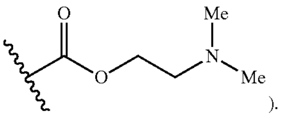

).

As a non-limiting example, Y can be

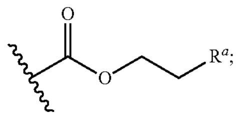

and $R^a$ can be —OH or —$NR^eR^f$ (e.g., $NMe_2$).

In certain embodiments of [2], X is $C_{1-3}$ alkyl; and Y is

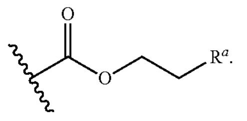

In certain of these embodiments, X is methyl. In certain embodiments, $R^a$ is —OH or —$NR^eR^f$ (e.g., $NMe_2$).

In certain embodiments of [2], Z is $OR^{6Z}$. For example, Z can be OH.

In certain embodiments of [2], each $Z^x$ is H.

In certain embodiments of [2], each $Z^x$ together with the carbon to which each is attached forms C═O.

In certain embodiments of [2], each of $R^1$, $R^2$, and $R^3$ is independently selected from H and $C(O)R^{7A}$. For example, each of $R^1$, $R^2$, and $R^3$ can be H. In another non-limiting example, each of $R^1$, $R^2$, and $R^3$ can be independently selected $C(O)R^{7A}$ (e.g., C(O)Me).

Non-Limiting Combination [3]

In some embodiments:

X is $C_1$-$C_6$ alkyl which is optionally substituted with from 1-3 $R^a$; and

Y is $C(O)NR^{4Y}R^{5Y}$.

In certain embodiments of [3], $R^{4Y}$ is H. In certain other embodiments of [3], $R^{4Y}$ is $C_{1-12}$ (e.g., $C_{1-6}$, $C_{1-4}$)alkyl, optionally substituted with from 1-6 independently selected $R^a$. In certain of the foregoing embodiments, $R^{4Y}$ is $C_{1-6}$ alkyl, optionally substituted with from 1-3 independently selected $R^a$ (e.g., $C_2$ alkyl optionally substituted with one $R^a$). In certain of the foregoing embodiments, embodiments, $R^{4Y}$ is $C_{1-4}$ alkyl, optionally substituted with from 1-2 independently selected $R^a$ (e.g., $C_2$ alkyl optionally substituted with one $R^a$). In certain embodiments, $R^{4Y}$ is

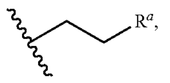

wherein $R^a$ is as defined elsewhere herein (in certain embodiments, $R^a$ is selected from —OH; —F; —$NR^eR^f$ (e.g., $NMe_2$); $C_{1-4}$ alkoxy; and $C_{1-4}$ haloalkoxy). For example, $R^{4Y}$ is methyl, 2-(dimethylamino)-eth-1-yl, or 2-(hydroxyl)-eth-1-yl. In certain embodiments of [3], $R^{4Y}$ is unsubstituted $C_{1-12}$ alkyl (e.g., $C_{1-6}$, $C_{2-6}$, $C_{2-3}$).

In certain embodiments of [3], $R^{5Y}$ is H. In certain other embodiments of [3], $R^{5Y}$ is $C_{1-12}$ (e.g., $C_{1-6}$, $C_{1-4}$)alkyl, optionally substituted with from 1-6 independently selected $R^a$. In certain of the foregoing embodiments, $R^{5Y}$ is $C_{1-6}$ alkyl, optionally substituted with from 1-3 independently selected $R^a$ (e.g., $C_2$ alkyl optionally substituted with one $R^a$). In certain of the foregoing embodiments, embodiments, $R^{5Y}$ is $C_{1-4}$ alkyl, optionally substituted with from 1-2 independently selected $R^a$ (e.g., $C_2$ alkyl optionally substituted with one $R^a$). In certain embodiments, $R^{5Y}$ is

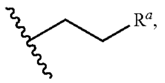

wherein $R^a$ is as defined elsewhere herein (in certain embodiments, $R^a$ is selected from —OH; —F; —$NR^eR^f$ (e.g., $NMe_2$); $C_{1-4}$ alkoxy; and $C_{1-4}$ haloalkoxy). For example, $R^{5Y}$ is methyl, 2-(dimethylamino)-eth-1-yl, or 2-(hydroxyl)-eth-1-yl. In certain embodiments of [3], $R^{5Y}$ is unsubstituted $C_{1-12}$ alkyl (e.g., $C_{1-6}$, $C_{2-6}$, $C_{2-3}$).

In certain embodiments of [3], both $R^{4Y}$ and $R^{5Y}$ are other than H (e.g., each of $R^{4Y}$ and $R^{5Y}$ is an independently selected $C_1$-$C_6$ alkyl).

In certain embodiments of [3], one of $R^{4Y}$ and $R^{5Y}$ is H; and the other of $R^{4Y}$ and $R^{5Y}$ is other than H (e.g., one of $R^{4Y}$ and $R^{5Y}$ is H; and the other of $R^{4Y}$ and $R^{5Y}$ is an independently selected $C_1$-$C_6$ alkyl).

In certain embodiments of [3], both $R^{4Y}$ and $R^{5Y}$ are H.

In certain embodiments of [3], one of $R^{4Y}$ and $R^{5Y}$ is $—(W^1—W^2)_n—W^3$.

In certain embodiments of the foregoing of [3], n is 2-3 (e.g., n is 2; or n is 3).

In certain embodiments of [3], $W^1$ is in each occurrence independently $C_{2-3}$ alkylene (e.g., $C_2$ alkylene).

In certain embodiments of [3], $W^2$ is in each occurrence independently —N(H)—,—N(Me)-, or —O— (e.g., one $W^2$ is —O—; and another $W^2$ when present is —N(Me)-).

In certain embodiments of [3], $W^3$ is selected from H and $C_{1-3}$ alkyl.

As non-limiting examples of the foregoing embodiments, one of $R^{4Y}$ and $R^{5Y}$ can be selected from:

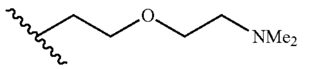

and

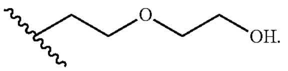

In certain embodiments of [3] when one of $R^{4Y}$ and $R^{5Y}$ is $—(W^1—W^2)_n—W^3$, the other one of $R^{4Y}$ and $R^{5Y}$ is selected from H and $C_{1-3}$ alkyl.

In certain embodiments, one of $R^{4Y}$ and $R^{5Y}$ is other than H.

In certain embodiments of [3], wherein each of $R^{4Y}$ and $R^{5Y}$ is independently H or $C_{1-12}$ alkyl (e.g., $C_{1-6}$, $C_{1-4}$), optionally substituted with from 1-6 (e.g., from 1-3 or from 1-2) independently selected $R^a$.

In certain embodiments of [3], wherein each of $R^{4Y}$ and $R^{5Y}$ is independently H or

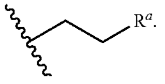

In certain of these embodiments, one of $R^{4Y}$ and $R^{5Y}$ is H; and the other one of $R^{4Y}$ and $R^{5Y}$ is

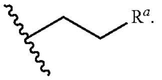

In certain of the foregoing embodiments of [3] (wherein when each of $R^{4Y}$ and $R^{5Y}$ is independently H or

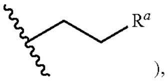

), wherein the $R^a$ on $R^{4Y}$ or $R^{5Y}$ is selected from —OH; —F; —$NR^eR^f$ (e.g., $NMe_2$); $C_{1-4}$ alkoxy; and $C_{1-4}$ haloalkoxy.

In certain of these embodiments ((e.g., when one of $R^{4Y}$ and $R^{5Y}$ is H; and the other one of $R^{4Y}$ and $R^{5Y}$ is

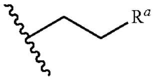

), $R^a$ is selected from —OH; —F; —$NR^eR^f$ (e.g., $NMe_2$); $C_{1-4}$ alkoxy; and $C_{1-4}$ haloalkoxy.

In certain embodiments of [3], wherein each of $R^{4Y}$ and $R^{5Y}$ is independently H,

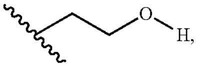

or

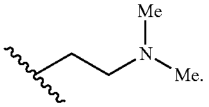

In certain embodiments of [3], Y is $CONH_2$.

In certain other embodiments of [3], Y is

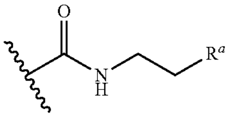

(e.g., $R^a$ is selected from —OH; —F; —$NR^eR^f$ (e.g., $NMe_2$); $C_{1-4}$ alkoxy; and $C_{1-4}$ haloalkoxy). As a non-limiting example, Y can be

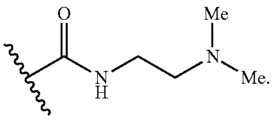 [SMILES: *C(=O)NCCN(C)C]

In certain embodiments of [3], wherein one of $R^{4Y}$ and $R^{5Y}$ is —$(W^1—W^2)_n$—$W^3$; and the other one of $R^{4Y}$ and $R^{5Y}$ is selected from H and $C_{1-3}$ alkyl.

In certain embodiments of [3], wherein one of $R^{4Y}$ and $R^{5Y}$ is —$(W^1—W^2)_n$—$W^3$; and the other one of $R^{4Y}$ and $R^{5Y}$ is selected from H and $C_{1-3}$ alkyl; and n is 2 or 3.

In certain embodiments of [3] (when one of $R^{4Y}$ and $R^{5Y}$ is —$(W^1—W^2)_n$—$W^3$; and the other one of $R^{4Y}$ and $R^{5Y}$ is selected from H and $C_{1-3}$ alkyl), $W^1$ is in each occurrence independently $C_{2-3}$ alkylene (e.g., $C_2$ alkylene).

In certain embodiments of [3] (when one of $R^{4Y}$ and $R^{5Y}$ is —$(W^1—W^2)_n$—$W^3$; and the other one of $R^{4Y}$ and $R^{5Y}$ is selected from H and $C_{1-3}$ alkyl), $W^2$ is in each occurrence independently —N(H)—, —N(Me)-, or —O—.

In certain embodiments of [3] (when one of $R^{4Y}$ and $R^{5Y}$ is —$(W^1—W^2)_n$—$W^3$; and the other one of $R^{4Y}$ and $R^{5Y}$ is selected from H and $C_{1-3}$ alkyl), $W^3$ is selected from H and $C_{1-3}$ alkyl.

In certain embodiments of [3], one of $R^{4Y}$ and $R^{5Y}$ is —$(W^1—W^2)_n$—$W^3$; and the other one of $R^{4Y}$ and $R^{5Y}$ is selected from H and $C_{1-3}$ alkyl, wherein one of $R^{4Y}$ and $R^{5Y}$ is selected from:

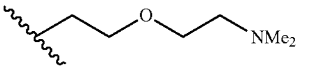

and

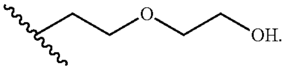

In certain embodiments of [3], one of $R^{4Y}$ and $R^{5Y}$ is —$(W^1—W^2)_n$—$W^3$; and the other one of $R^{4Y}$ and $R^{5Y}$ is H, wherein n is 2 or 3; $W^1$ is in each occurrence independently $C_{2-3}$ alkylene (e.g., $C_2$ alkylene); $W^2$ is in each occurrence independently —N(H)—, —N(Me)-, or —O—; and $W^3$ is selected from H and $C_{1-3}$ alkyl.

As a non-limiting example of the foregoing embodiments, when Y is C(O) $NR^{4Y}R^{5Y}$; Y can be

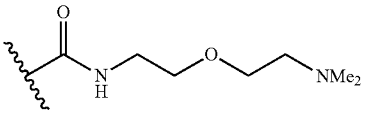

or

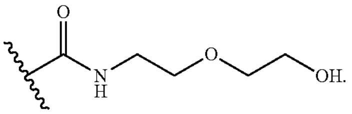

In certain embodiments of [3], In some embodiments, $R^{4Y}$ and $R^{5Y}$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to $R^{4Y}$ and $R^{5Y}$), which are each independently selected from the group consisting of N(H), $N(R^d)$, O, and S.

In certain embodiments of the foregoing, $R^{4Y}$ and $R^{5Y}$ together with the nitrogen atom to which each is attached forms a ring including 6 ring atoms, wherein the ring includes: (a) from 1-5 ring carbon atoms, each of which is substituted with from 1-2 substituents independently selected from H and $C_{1-3}$ alkyl; and (b) from 0-3 ring heteroatoms (in addition to the nitrogen atom attached to $R^{4Y}$ and $R^{5Y}$), which are each independently selected from the group consisting of N(H), $N(R^d)$, O, and S.

As non-limiting examples of the foregoing, Y can be:

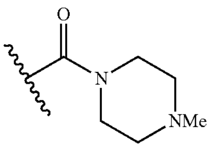 or 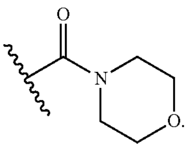

In certain embodiments of [3], X is $C_1$-$C_3$ alkyl; and Y is C(O)NHR$^{5Y}$. In certain of these embodiments, X is methyl. In certain of the foregoing embodiments, R$^{5Y}$ is $C_{1-12}$ alkyl (e.g., $C_{1-6}$, $C_{1-4}$), optionally substituted with from 1-6 (e.g., from 1-3 or from 1-2) independently selected R$^a$. As a non-limiting example, R$^{5Y}$ can be

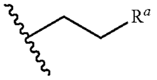

(e.g., R$^a$ can be —OH; —F; —NR$^e$R$^f$ (e.g., NMe$_2$); $C_{1-4}$ alkoxy; or $C_{1-4}$ haloalkoxy). For example, R$^{5Y}$ can be

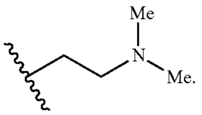 [SMILES: *CCN(C)C]

In certain embodiments of [3], X is $C_1$-$C_3$ alkyl; Y is C(O)NHR$^{5Y}$; and R$^{5Y}$ is —(W$^1$—W$^2$)$_n$—W$^3$; wherein n is 2 or 3; W$^1$ is in each occurrence independently $C_{2-3}$ alkylene (e.g., $C_2$ alkylene); W$^2$ is in each occurrence independently —N(H)—, —N(Me)-, or —O—; and W$^3$ is selected from H and $C_{1-3}$ alkyl.

In certain embodiments of [3], Z is OR$^{6Z}$. For example, Z can be OH.

In certain embodiments of [3], each Z$^x$ is H.

In certain embodiments of [3], each Z$^x$ together with the carbon to which each is attached forms C═O.

In certain embodiments of [3], each of R$^1$, R$^2$, and R$^3$ is independently selected from H and C(O)R$^{7A}$. For example, each of R$^1$, R$^2$, and R$^3$ can be H. In another non-limiting example, each of R$^1$, R$^2$, and R$^3$ can be independently selected C(O)R$^{7A}$ (e.g., C(O)Me).

Non-Limiting Combination [4]

In some embodiments:

X is $C_1$-$C_6$ alkyl which is optionally substituted with 1-3 R$^a$; and

Y is heteroaryl including 5 ring atoms, wherein from 1-4 ring atoms are heteroatoms, each independently selected from the group consisting of N, N(H), N(R$^d$), O, and S, and wherein one or more of the heteroaryl ring carbon atoms are optionally substituted with from 1-2 independently selected R$^c$.

In certain embodiments of [4], Y is heteroaryl including 5 ring atoms, wherein from 1-4 ring atoms are heteroatoms, each independently selected from the group consisting of N, N(H), N(R$^d$), O, and S, and wherein one or more of the heteroaryl ring carbon atoms are optionally substituted with from 1-2 independently selected R$^c$.

In certain embodiments of [4], Y is heteroaryl including 5 ring atoms, wherein from 1 ring atom is a heteroatom, selected from the group consisting of N, N(H), N(R$^d$), O, and S, and wherein one or more of the heteroaryl ring carbon atoms are optionally substituted with from 1-2 independently selected R$^c$.

In certain embodiments of [4], Y is heteroaryl including 5 ring atoms, wherein from 3-4 ring atoms are heteroatoms, each independently selected from the group consisting of N, N(H), N(R$^d$), O, and S, and wherein one or more of the heteroaryl ring carbon atoms are optionally substituted with from 1-2 independently selected R$^c$.

In certain embodiments of [4], Y is selected from tetrazolyl, triazolyl, oxadiazolyl, and oxazolyl, wherein one or more of the heteroaryl ring carbon atoms are optionally substituted with from 1-2 independently selected R$^c$; and one of the heteroaryl ring nitrogen atoms are optionally substituted with R$^d$.

In certain embodiments of the foregoing, each R$^c$ when present is independently selected from:

(i) halo;

(iii) $C_{1-10}$ alkyl;

(iv) $C_{1-10}$ alkyl which is substituted with from 1-6 (e.g., 1) independently selected R$^a$; and (v) $C_{3-6}$ cycloalkyl optionally substituted with from 1-3 independently selected R$^b$ (e.g., each R$^c$ can be independently (iii) $C_{1-10}$ alkyl or (iv) $C_{1-10}$ alkyl which is substituted with from 1-6 independently selected R$^a$).

In certain embodiments of the foregoing, Y is selected from the group consisting of

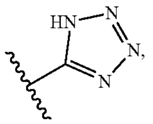 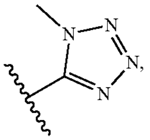 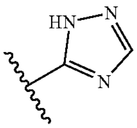,

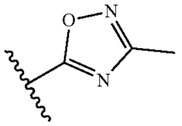, and 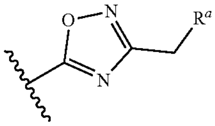

(e.g., R$^a$ can be selected from —OH, —OMe, and —NMe$_2$).

In certain embodiments of [4], Y is selected from tetrazolyl, triazolyl, oxadiazolyl, and oxazolyl, wherein one or more of the heteroaryl ring carbon atoms are optionally substituted with from 1-2 independently selected R$^c$; and one of the heteroaryl ring nitrogen atoms is optionally substituted with R$^d$.

In certain embodiments of [4], Y is selected from the group consisting of:

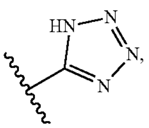 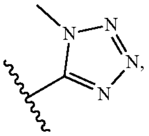 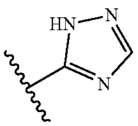

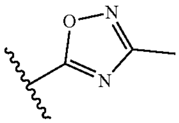, and 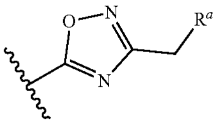

(e.g., R$^a$ can be selected from —OH, —OMe, and —NMe$_2$).

In certain embodiments of [4], X is $C_{1-3}$ alkyl; and Y is selected from the group consisting of tetrazolyl and triazolyl, wherein one or more of the heteroaryl ring carbon atoms are optionally substituted with from 1-2 independently selected $R^c$; and one of the heteroaryl ring nitrogen atoms are optionally substituted with $R^d$.

In certain of these embodiments, X is methyl.

In certain of the foregoing embodiments, Y is

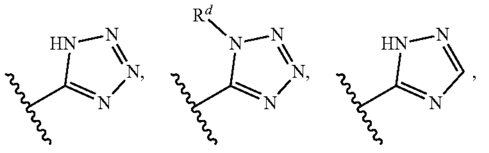

or

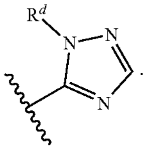

As a non-limiting example, Y is

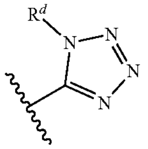

(e.g.,

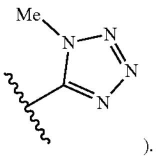

).

In certain embodiments of [4], Z is $OR^{6Z}$. For example, Z can be OH.

In certain embodiments of [4], each $Z^x$ is H.

In certain embodiments of [4], each $Z^x$ together with the carbon to which each is attached forms C═O.

In certain embodiments of [4], each of $R^1$, $R^2$, and $R^3$ is independently selected from H and $C(O)R^{7A}$. For example, each of $R^1$, $R^2$, and $R^3$ can be H. In another non-limiting example, each of $R^1$, $R^2$, and $R^3$ can be independently selected $C(O)R^{7A}$ (e.g., C(O)Me).

Non-Limiting Combination [5]

In some embodiments:

X is $NR^{4X}R^{5X}$; and

Y is $CO_2R^{6Y}$.

In certain embodiments of [5], both $R^{4X}$ and $R^{5X}$ are other than H (e.g., each of $R^{4X}$ and $R^{5X}$ is an independently selected $C_1$-$C_6$ alkyl, e.g., each of $R^{4X}$ and $R^{5X}$ is methyl).

In certain embodiments of [5], one of $R^{4X}$ and $R^{5X}$ is H; and the other of $R^{4X}$ and $R^{5X}$ is other than H (e.g., one of $R^{4X}$ and $R^{5X}$ is H; and the other of $R^{4X}$ and $R^{5X}$ is an independently selected $C_1$-$C_6$ alkyl).

In certain embodiments of [5], both $R^{4X}$ and $R^{5X}$ are H.

In certain embodiments of [5], $R^{6Y}$ is $C_{1-12}$ alkyl, optionally substituted with from 1-6 independently selected $R^a$. In certain embodiments, $R^{6Y}$ is $C_{1-6}$ alkyl, optionally substituted with from 1-3 independently selected $R^a$ (e.g., $C_2$ alkyl optionally substituted with one $R^a$). In certain embodiments, $R^{6Y}$ is $C_{1-4}$ alkyl, optionally substituted with from 1-2 independently selected $R^a$ (e.g., $C_2$ alkyl optionally substituted with one $R^a$). In certain embodiments, $R^{6Y}$ is

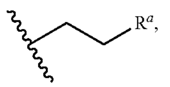

wherein $R^a$ is as defined elsewhere herein (in certain embodiments, $R^a$ is selected from —OH; —F; —$NR^eR^f$ (e.g., $NMe_2$); $C_{1-4}$ alkoxy; and $C_{1-4}$ haloalkoxy). For example, $R^{6Y}$ is methyl, 2-(dimethylamino)-eth-1-yl, or 2-(hydroxyl)-eth-1-yl. In certain embodiments of [5], $R^{6Y}$ is unsubstituted $C_{1-12}$ alkyl.

In certain other embodiments of [5], $R^{6Y}$ is H.

In certain embodiments of [5], $R^{6Y}$ is H.

In certain embodiments of [5], $R^{6Y}$ is $C_{1-12}$ (e.g., $C_{1-6}$, $C_{2-6}$, $C_{2-3}$)alkyl, which is optionally substituted with from 1-6 (e.g., unsubstituted; or substituted with from 1-2, e.g., 1) independently selected $R^a$.

In certain embodiments of [5], Y is selected from $CO_2H$ and $CO_2Me$.

In certain embodiments of [5], Y is

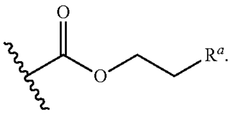

For example, Y can be

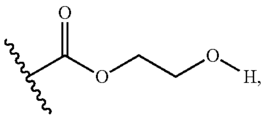

or

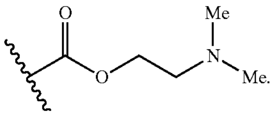

In certain embodiments of [5], Y is

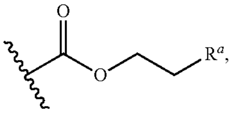

wherein the $R^a$ on Y is selected from —OH; —F; —$NR^eR^f$ (e.g., $NMe_2$); $C_{1-4}$ alkoxy; and $C_{1-4}$ haloalkoxy (e.g., Y can be

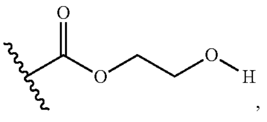

, or

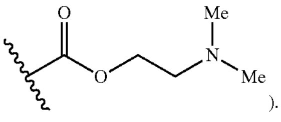

).

As a non-limiting example, Y can be

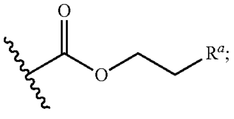

and $R^a$ can be —OH or —$NR^eR^f$ (e.g., $NMe_2$).

In certain embodiments of [5], X is $N(C_{1-3}$ alkyl) 2; and Y is

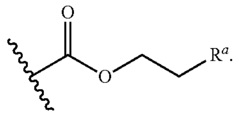

In certain of these embodiments, X is $NMe_2$. In certain embodiments, Y is

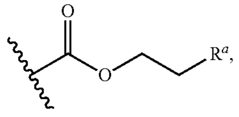

wherein $R^a$ can be —OH or —$NR^eR^f$ (e.g., $NMe_2$).

In certain embodiments of [5], Z is $OR^{6Z}$. For example, Z can be OH.

In certain embodiments of [5], each $Z^x$ is H.

In certain embodiments of [5], each $Z^x$ together with the carbon to which each is attached forms C═O.

In certain embodiments of [5], each of $R^1$, $R^2$, and $R^3$ is independently selected from H and $C(O)R^{7A}$. For example, each of $R^1$, $R^2$, and $R^3$ can be H. In another non-limiting example, each of $R^1$, $R^2$, and $R^3$ can be independently selected $C(O)R^{7A}$ (e.g., C(O)Me).

Non-Limiting Combination [6]

In some embodiments:

X is $NR^{4X}R^{5X}$; and

Y is $C(O)NR^{4Y}R^{5Y}$.

In certain embodiments of [6], both $R^{4X}$ and $R^{5X}$ are other than H (e.g., each of $R^{4X}$ and $R^{5X}$ is an independently selected $C_1$-$C_6$ alkyl).

In certain embodiments of [6], one of $R^{4X}$ and $R^{5X}$ is H; and the other of $R^{4X}$ and $R^{5X}$ is other than H (e.g., one of $R^{4X}$ and $R^{5X}$ is H; and the other of $R^{4X}$ and $R^{5X}$ is an independently selected $C_1$-$C_6$ alkyl).

In certain embodiments of [6], both $R^{4X}$ and $R^{5X}$ are H.

In certain embodiments of [6], $R^{4Y}$ is H. In certain other embodiments of [6], $R^{4Y}$ is $C_{1-12}$ (e.g., $C_{1-6}$, $C_{1-4}$)alkyl, optionally substituted with from 1-6 independently selected $R^a$. In certain of the foregoing embodiments, $R^{4Y}$ is $C_{1-6}$ alkyl, optionally substituted with from 1-3 independently selected $R^a$ (e.g., $C_2$ alkyl optionally substituted with one $R^a$). In certain of the foregoing embodiments, embodiments, $R^{4Y}$ is $C_{1-4}$ alkyl, optionally substituted with from 1-2 independently selected $R^a$ (e.g., $C_2$ alkyl optionally substituted with one $R^a$). In certain embodiments, $R^{4Y}$ is

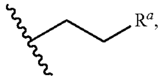

wherein $R^a$ is as defined elsewhere herein (in certain embodiments, $R^a$ is selected from —OH; —F; —$NR^eR^f$ (e.g., $NMe_2$); $C_{1-4}$ alkoxy; and $C_{1-4}$ haloalkoxy). For example, $R^{4Y}$ is methyl, 2-(dimethylamino)-eth-1-yl, or 2-(hydroxyl)-eth-1-yl. In certain embodiments of [6], $R^{4Y}$ is unsubstituted $C_{1-12}$ alkyl (e.g., $C_{1-6}$, $C_{2-6}$, $C_{2-3}$).

In certain embodiments of [6], $R^{5Y}$ is H. In certain other embodiments of [6], $R^{5Y}$ is $C_{1-12}$ (e.g., $C_{1-6}$, $C_{1-4}$)alkyl, optionally substituted with from 1-6 independently selected $R^a$. In certain of the foregoing embodiments, $R^{5Y}$ is $C_{1-6}$ alkyl, optionally substituted with from 1-3 independently selected $R^a$ (e.g., $C_2$ alkyl optionally substituted with one $R^a$). In certain of the foregoing embodiments, embodiments, $R^{5Y}$ is $C_{1-4}$ alkyl, optionally substituted with from 1-2 independently selected $R^a$ (e.g., $C_2$ alkyl optionally substituted with one $R^a$). In certain embodiments, $R^{5Y}$ is

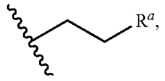

wherein $R^a$ is as defined elsewhere herein (in certain embodiments, $R^a$ is selected from —OH; —F; —$NR^eR^f$ (e.g., $NMe_2$); $C_{1-4}$ alkoxy; and $C_{1-4}$ haloalkoxy). For example, $R^{5Y}$ is methyl, 2-(dimethylamino)-eth-1-yl, or 2-(hydroxyl)-eth-1-yl. In certain embodiments of [6], $R^{5Y}$ is unsubstituted $C_{1-12}$ alkyl (e.g., $C_{1-6}$, $C_{2-6}$, $C_{2-3}$).

In certain embodiments of [6], both $R^{4Y}$ and $R^{5Y}$ are other than H (e.g., each of $R^{4Y}$ and $R^{5Y}$ is an independently selected $C_1$-$C_6$ alkyl).

In certain embodiments of [6], one of $R^{4Y}$ and $R^{5Y}$ is H; and the other of $R^{4Y}$ and $R^{5Y}$ is other than H (e.g., one of $R^{4Y}$ and $R^{5Y}$ is H; and the other of $R^{4Y}$ and $R^{5Y}$ is an independently selected $C_1$-$C_6$ alkyl).

In certain embodiments of [6], both $R^{4Y}$ and $R^{5Y}$ are H.

In certain embodiments of [6], one of $R^{4Y}$ and $R^{5Y}$ is —$(W^1—W^2)_n$—$W^3$.

In certain embodiments of the foregoing of [6], n is 2-3 (e.g., n is 2; or n is 3).

In certain embodiments of [6], $W^1$ is in each occurrence independently $C_{2-3}$ alkylene (e.g., $C_2$ alkylene).

In certain embodiments of [6], $W^2$ is in each occurrence independently —N(H)—,—N(Me)-, or —O— (e.g., one $W^2$ is —O—; and another $W^2$ when present is-N(Me)-).

In certain embodiments of [6], $W^3$ is selected from H and $C_{1-3}$ alkyl.

As non-limiting examples of the foregoing embodiments, one of $R^{4Y}$ and $R^{5Y}$ can be selected from:

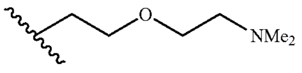

and

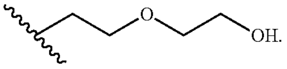

In certain embodiments of [6] when one of $R^{4Y}$ and $R^{5Y}$ is —$(W^1—W^2)_n$—$W^3$, the other one of $R^{4Y}$ and $R^{5Y}$ is selected from H and $C_{1-3}$ alkyl.

In certain embodiments, one of $R^{4Y}$ and $R^{5Y}$ is other than H.

In certain embodiments of [6], wherein each of $R^{4Y}$ and $R^{5Y}$ is independently H or $C_{1-12}$ alkyl (e.g., $C_{1-6}$, $C_{1-4}$), optionally substituted with from 1-6 (e.g., from 1-3 or from 1-2) independently selected $R^a$.

In certain embodiments of [6], wherein each of $R^{4Y}$ and $R^{5Y}$ is independently H or

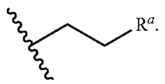

In certain of these embodiments, one of $R^{4Y}$ and $R^{5Y}$ is H; and the other one of $R^{4Y}$ and $R^{5Y}$ is

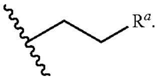

In certain of the foregoing embodiments of [6] (when each of $R^{4Y}$ and $R^{5Y}$ is independently H or

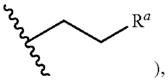

), wherein the $R^a$ on $R^{4Y}$ or $R^{5Y}$ is selected from —OH; —F; —$NR^eR^f$ (e.g., $NMe_2$); $C_{1-4}$ alkoxy; and $C_{1-4}$ haloalkoxy.

In certain of these embodiments ((e.g., when one of $R^{4Y}$ and $R^{5Y}$ is H; and the other one of $R^{4Y}$ and $R^{5Y}$ is

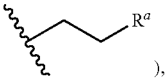

), $R^a$ is selected from —OH; —F; —$NR^eR^f$ (e.g., $NMe_2$); $C_{1-4}$ alkoxy; and $C_{1-4}$ haloalkoxy.

In certain embodiments of [6], each of $R^{4Y}$ and $R^{5Y}$ is independently H,

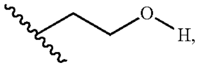

or

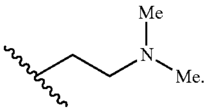

In certain embodiments of [6], Y is $CONH_2$.

In certain other embodiments of [6], Y is

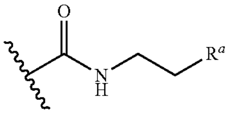

(e.g., $R^a$ is selected from —OH; —F; —$NR^eR^f$ (e.g., $NMe_2$); $C_{1-4}$ alkoxy; and $C_{1-4}$ haloalkoxy). As a non-limiting example, Y can be

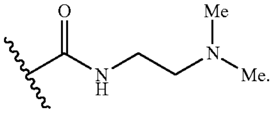

In certain embodiments of [6], wherein one of $R^{4Y}$ and $R^{5Y}$ is —$(W^1—W^2)_n$—$W^3$; and the other one of $R^{4Y}$ and $R^{5Y}$ is selected from H and $C_{1-3}$ alkyl.

In certain embodiments of [6], wherein one of $R^{4Y}$ and $R^{5Y}$ is —$(W^1—W^2)_n$—$W^3$; and the other one of $R^{4Y}$ and $R^{5Y}$ is selected from H and $C_{1-3}$ alkyl; and n is 2 or 3.

In certain embodiments of [6] (wherein one of $R^{4Y}$ and $R^{5Y}$ is —$(W^1—W^2)_n$—$W^3$; and the other one of $R^{4Y}$ and $R^{5Y}$ is selected from H and $C_{1-3}$ alkyl), $W^1$ is in each occurrence independently $C_{2-3}$ alkylene (e.g., $C_2$ alkylene).

In certain embodiments of [6] (wherein one of $R^{4Y}$ and $R^{5Y}$ is —$(W^1—W^2)_n$—$W^3$; and the other one of $R^{4Y}$ and $R^{5Y}$ is selected from H and $C_{1-3}$ alkyl), $W^2$ is in each occurrence independently —N(H)—, —N(Me)-, or —O—.

In certain embodiments of [6] (wherein one of $R^{4Y}$ and $R^{5Y}$ is —$(W^1—W^2)_n$—$W^3$; and the other one of $R^{4Y}$ and $R^{5Y}$ is selected from H and $C_{1-3}$ alkyl), $W^3$ is is selected from H and $C_{1-3}$ alkyl.

In certain embodiments of [6], one of $R^{4Y}$ and $R^{5Y}$ can be selected from:

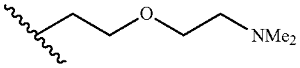

and

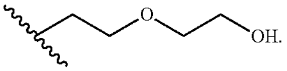

In certain embodiments of [6], one of $R^{4Y}$ and $R^{5Y}$ is —$(W^1—W^2)_n$—$W^3$; and the other one of $R^{4Y}$ and $R^{5Y}$ is H, wherein n is 2 or 3; $W^1$ is in each occurrence independently $C_{2-3}$ alkylene (e.g., $C_2$ alkylene); $W^2$ is in each occurrence independently —N(H)—, —N(Me)-, or —O—; and $W^3$ is selected from H and $C_{1-3}$ alkyl.

As a non-limiting example of the foregoing embodiments, when Y is $C(O)NR^{4Y}R^{5Y}$; Y can be

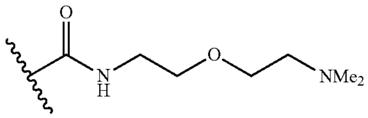

or

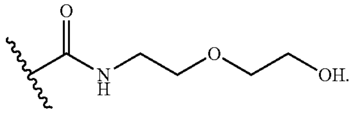

In certain embodiments of [6], In some embodiments, $R^{4Y}$ and $R^{5Y}$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms (in addition to the nitrogen atom attached to $R^{4Y}$ and $R^{5Y}$), which are each independently selected from the group consisting of N(H), $N(R^d)$, O, and S.

In certain embodiments of the foregoing, $R^{4Y}$ and $R^{5Y}$ together with the nitrogen atom to which each is attached forms a ring including 6 ring atoms, wherein the ring includes: (a) from 1-5 ring carbon atoms, each of which is substituted with from 1-2 substituents independently selected from H and $C_{1-3}$ alkyl; and (b) from 0-3 ring heteroatoms (in addition to the nitrogen atom attached to $R^{4Y}$ and $R^{5Y}$), which are each independently selected from the group consisting of N(H), $N(R^d)$, O, and S.

As non-limiting examples of the foregoing, Y can be: NMe or

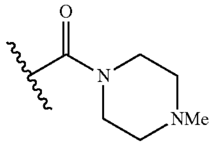 or 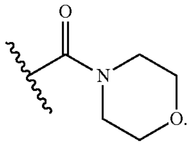

In certain embodiments of [5], X is $N(C_{1-3}\ alkyl)_2$; and Y is $C(O)NHR^{5Y}$. In certain of these embodiments, X is $NMe_2$.

In certain of the foregoing embodiments, Y is

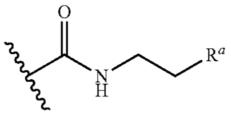

(e.g., $R^a$ is selected from —OH; —F; —$NR^eR^f$ (e.g., $NMe_2$); $C_{1-4}$ alkoxy; and $C_{1-4}$ haloalkoxy). As a non-limiting example, Y can be

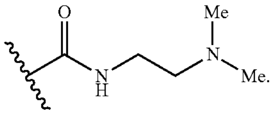 [SMILES: *C(=O)NCCN(C)C]

In certain embodiments of [6], $R^{5Y}$ is —$(W^1—W^2)_n$—$W^3$; wherein n is 2 or 3; $W^1$ is in each occurrence independently $C_{2-3}$ alkylene (e.g., $C_2$ alkylene); $W^2$ is in each occurrence independently —N(H)—, —N(Me)-, or —O—; and $W^3$ is selected from H and $C_{1-3}$ alkyl.

In certain embodiments of [6], Z is $OR^{6Z}$. For example, Z can be OH.

In certain embodiments of [6], each $Z^x$ is H.

In certain embodiments of [6], each $Z^x$ together with the carbon to which each is attached forms C═O.

In certain embodiments of [6], each of $R^1$, $R^2$, and $R^3$ is independently selected from H and $C(O)R^{7A}$. For example, each of $R^1$, $R^2$, and $R^3$ can be H. In another non-limiting example, each of $R^1$, $R^2$, and $R^3$ can be independently selected $C(O)R^{7A}$ (e.g., C(O)Me).

Non-Limiting Combination [7]

In some embodiments:

X is $NR^{4X}R^{5X}$; and

Y is heteroaryl including 5 ring atoms, wherein from 1-4 ring atoms are heteroatoms, each independently selected from the group consisting of N, N(H), $N(R^d)$, O, and S, and wherein one or more of the heteroaryl ring carbon atoms are optionally substituted with from 1-2 independently selected $R^c$.

In certain embodiments of [7], both $R^{4X}$ and $R^{5X}$ are other than H (e.g., each of $R^{4X}$ and $R^{5X}$ is an independently selected $C_1$-$C_6$ alkyl). As a non-limiting example, each of $R^{4X}$ and $R^{5X}$ can be methyl.

In certain embodiments of [7], one of $R^{4X}$ and $R^{5X}$ is H; and the other of $R^{4X}$ and $R^{5X}$ is other than H (e.g., one of $R^{4X}$ and $R^{5X}$ is H; and the other of $R^{4X}$ and $R^{5X}$ is an independently selected $C_1$-$C_6$ alkyl).

In certain embodiments of [7], both $R^{4X}$ and $R^{5X}$ are H.

In certain embodiments of [7], Y is heteroaryl including 5 ring atoms, wherein from 1-4 ring atoms are heteroatoms, each independently selected from the group consisting of N, N(H), $N(R^a)$, O, and S, and wherein one or more of the heteroaryl ring carbon atoms are optionally substituted with from 1-2 independently selected $R^c$.

In certain embodiments of [7], Y is heteroaryl including 5 ring atoms, wherein from 1 ring atom is a heteroatom, selected from the group consisting of N, N(H), $N(R^d)$, O, and S, and wherein one or more of the heteroaryl ring carbon atoms are optionally substituted with from 1-2 independently selected $R^c$.

In certain embodiments of [7], Y is heteroaryl including 5 ring atoms, wherein from 3-4 ring atoms are heteroatoms, each independently selected from the group consisting of N, N(H), $N(R^d)$, O, and S, and wherein one or more of the heteroaryl ring carbon atoms are optionally substituted with from 1-2 independently selected $R^c$.

In certain embodiments of [7], Y is selected from tetrazolyl, triazolyl, oxadiazolyl, and oxazolyl, wherein one or more of the heteroaryl ring carbon atoms are optionally substituted with from 1-2 independently selected $R^c$; and one of the heteroaryl ring nitrogen atoms are optionally substituted with $R^d$.

In certain embodiments of the foregoing, each $R^c$ when present is independently selected from:

(i) halo;

(iii) $C_{1-10}$ alkyl;

(iv) $C_{1-10}$ alkyl which is substituted with from 1-6 (e.g., 1) independently selected $R^a$; and (v) $C_{3-6}$ cycloalkyl optionally substituted with from 1-3 independently selected $R^b$ (e.g., each $R^a$ can be independently (iii) $C_{1-10}$ alkyl or (iv) $C_{1-10}$ alkyl which is substituted with from 1-6 independently selected $R^a$.

In certain embodiments of the foregoing, Y is selected from the group consisting of:

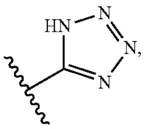, 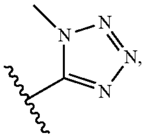, 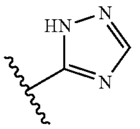

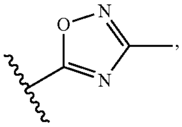, and 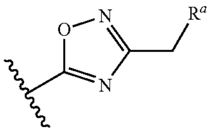

(e.g., $R^a$ can be selected from —OH, —OMe, and —$NMe_2$).

In certain embodiments of [7], Y is selected from tetrazolyl, triazolyl, oxadiazolyl, and oxazolyl, wherein one or more of the heteroaryl ring carbon atoms are optionally substituted with from 1-2 independently selected $R^c$; and one of the heteroaryl ring nitrogen atoms is optionally substituted with $R^d$.

In certain embodiments of [4], Y is selected from the group consisting of:

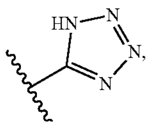, 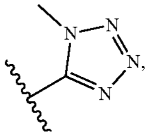, 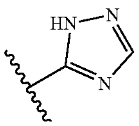

-continued

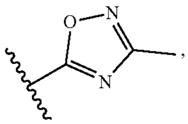, and 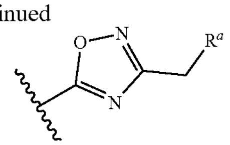

(e.g., $R^a$ can be selected from —OH, —OMe, and —$NMe_2$).

In certain embodiments of [7], X is N($C_{1-3}$ alkyl) 2; and Y is selected from the group consisting of tetrazolyl and triazolyl, wherein one or more of the heteroaryl ring carbon atoms are optionally substituted with from 1-2 independently selected $R^c$; and one of the heteroaryl ring nitrogen atoms are optionally substituted with $R^d$.

In certain of these embodiments, X is $NMe_2$.

In certain of the foregoing embodiments, Y is

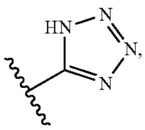, 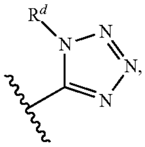, 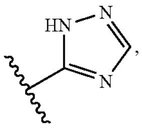, or

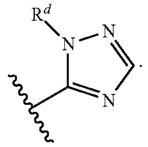.

As a non-limiting example, Y is

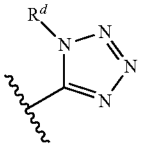 (e.g., 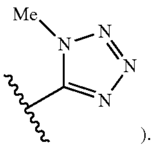).

In certain embodiments of [7], Z is $OR^{6Z}$. For example, Z can be OH.

In certain embodiments of [7], each $Z^x$ is H.

In certain embodiments of [7], each $Z^x$ together with the carbon to which each is attached forms C═O.

In certain embodiments of [7], each of $R^1$, $R^2$, and $R^3$ is independently selected from H and C(O)$R^{7A}$. For example, each of $R^1$, $R^2$, and $R^3$ can be H. In another non-limiting example, each of $R^1$, $R^2$, and $R^3$ can be independently selected C(O)$R^{7A}$ (e.g., C(O)Me).

Further Exemplary Embodiments of Z, $R^1$, $R^2$, and $R^3$ in Non-Limiting Combinations [1]-[7]

In certain embodiments of [1]-[7], Z is selected from H, $NR^{4Z}R^{5Z}$, $OR^{6Z}$ and OC(O)$R^{7Z}$.

In certain embodiments of [1]-[7], Z is $NR^{4Z}R^{5Z}$.

In certain of these embodiments, wherein each of $R^{4Z}$ and $R^{5Z}$ is independently selected from H and $C_{1-10}$ alkyl, optionally substituted with from 1-6 independently selected $R^a$. In certain of these embodiments, each of $R^{4Z}$ and $R^{5Z}$ is independently selected from H and $C_{1-6}$ alkyl, optionally substituted with from 1-2 independently selected $R^a$. In certain of these embodiments, each of $R^{4Z}$ and $R^{5Z}$ is independently selected from H and $C_{1-3}$ alkyl, optionally substituted with one $R^a$. In certain of these embodiments, each of $R^{4Z}$ and $R^{5Z}$ is independently selected from H and

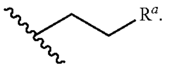

In certain of the foregoing embodiments when each of $R^{4Z}$ and $R^{5Z}$ is independently selected from H and

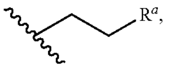

wherein the $R^a$ on $R^{4Z}$ and $R^{5Z}$ is selected from —OH, —$NR^eR^f$, $C_{1-4}$ alkoxy, and $C_{1-4}$ haloalkoxy. In certain embodiments of [1]-[7], each of $R^{4Z}$ and $R^{5Z}$ is independently selected from H and

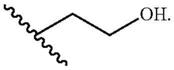 [SMILES: *CCO]

In certain embodiments of [1]-[7], Z is $NR^{4Z}R^{5Z}$; and wherein from 1-2 of $R^{4Z}$ and $R^{5Z}$ is H.

In certain embodiments of [1]-[7], Z is $NR^{4Z}R^{5Z}$; and wherein each of $R^{4Z}$ and $R^{5Z}$ is independently H or unsubstituted $C_{1-10}$ alkyl (e.g., unsubstituted $C_{1-6}$ alkyl, e.g., unsubstituted $C_{1-3}$ alkyl, e.g., methyl).

In certain embodiments of [1]-[7], Z is $OR^{6Z}$. In certain of these embodiments, ROZ is selected from H and $C_{1-10}$ alkyl, optionally substituted with from 1-6 independently selected $R^a$. In certain of these embodiments, $R^{6Z}$ is H. In certain other embodiments, $R^{6Z}$ is $C_{1-6}$ alkyl, optionally substituted with from 1-6 independently selected $R^a$. For example, $R^{6Z}$ can be $C_{1-6}$ alkyl, optionally substituted with from 1-6 independently selected $R^a$ or $C_{1-3}$ alkyl, optionally substituted with from 1-2 (e.g., 1) independently selected $R^a$. As a non-limiting example, $R^{6Z}$ can be

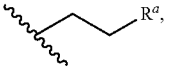

In certain embodiments of [1]-[7], Z is $OR^{6Z}$; $R^{6Z}$ is

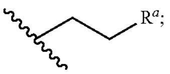

and $R^a$ on $R^{6Z}$ is selected from —OH, —$NR^eR^f$, $C_{1-4}$ alkoxy, and $C_{1-4}$ haloalkoxy. For example, $R^{6Z}$ can be selected from

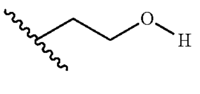 and 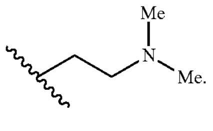

In certain embodiments of [1]-[7], Z is OC(O)$R^{7Z}$. In certain of these embodiments, $R^{7Z}$ is $C_{1-10}$ alkyl, optionally substituted with from 1-6 independently selected $R^a$. For example, $R^{7Z}$ can be an unsubstituted $C_{1-10}$ alkyl (e.g., methyl, ethyl, and isopropyl).

In certain of these embodiments, each of $R^1$, $R^2$, and $R^3$ is independently selected from H and $C(O)R^{7A}$.

In certain of these embodiments, each occurrence of $R^{7A}$ is independently $C_1$-10 alkyl, optionally substituted with from 1-6 independently selected $R^a$ (e.g., $C_{1-6}$ or $C_{1-3}$ alkyl, optionally substituted with from 1-6 independently selected $R^a$; e.g., $C_{1-10}$ or $C_{1-6}$ or $C_{1-3}$ unsubstituted alkyl (e.g., $CH_3$)).

In certain of the foregoing embodiments, $R^1$, $R^2$, and $R^3$ is independently selected from H and C(O)Me (e.g., $R^1$, $R^2$, and $R^3$ are each H; or $R^1$, $R^2$, and $R^3$ are each C(O)Me).

In certain embodiments of [1]-[7], each of $R^1$, $R^2$, and $R^3$ is independently selected from H and C(O)Me. For example, $R^1$, $R^2$, and $R^3$ can each be H. As another example, $R^1$, $R^2$, and $R^3$ can each be C(O)Me).

Non-Limiting Combination [8]

In some embodiments:

X is $C_1$-$C_6$ alkyl which is optionally substituted with 1-3 $R^a$; and

Z is $OR^{6Z}$.

In certain embodiments, $R^{6Z}$ is H.

In certain embodiments of [8], X is $C_{1-3}$ alkyl which is optionally substituted with 1-3 $R^a$. For example, X is methyl or trifluoromethyl. In certain of these embodiments, Z is OH.

Non-Limiting Combination [9]

In some embodiments:

X is $C_1$-$C_6$ alkyl which is optionally substituted with 1-3 $R^a$; and

Z is $OC(O)R^{7Z}$.

In certain embodiments of [9], $R^{7Z}$ is H.

In certain embodiments of [9], $R^{7Z}$ is $C_{1-10}$ alkyl, optionally substituted with from 1-6 independently selected $R^a$. In certain of the foregoing embodiments, $R^{7Z}$ is $C_{1-6}$ alkyl, optionally substituted with from 1-6 (e.g., 1-3) independently selected $R^a$.

In certain of the foregoing embodiments of [9] when $R^{7Z}$ is $C_{1-10}$ alkyl optionally substituted with from 1-6 independently selected $R^a$, each occurrence of $R^a$ is independently selected from the group consisting of: —OH; —F; —$NR^eR^f$ (e.g., $NMe_2$); $C_{1-4}$ alkoxy; and $C_{1-4}$ haloalkoxy.

In certain embodiments of [9] when $R^{7Z}$ is unsubstituted $C_{1-10}$ alkyl (e.g., unsubstituted $C_{1-6}$ alkyl).

Non-Limiting Combination [10]

In some embodiments:

X is $NR^{4X}R^{5X}$; and

Z is $OR^{6Z}$.

In certain embodiments, $R^{6Z}$ is H.

In certain embodiments of [10], both $R^{4X}$ and $R^{5X}$ are other than H (e.g., each of $R^{4X}$ and $R^{5X}$ is an independently selected $C_1$-$C_6$ alkyl). As a non-limiting example, each of $R^{4X}$ and $R^{5X}$ can be methyl.

In certain embodiments of [10], one of $R^{4X}$ and $R^{5X}$ is H; and the other of $R^{4X}$ and $R^{5X}$ is other than H (e.g., one of $R^{4X}$ and $R^{5X}$ is H; and the other of $R^{4X}$ and $R^{5X}$ is an independently selected $C_1$-$C_6$ alkyl).

In certain embodiments of [10], both $R^{4X}$ and $R^{5X}$ are H.

Non-Limiting Combination [11]

In some embodiments:

X is $NR^{4X}R^{5X}$; and

Z is $OC(O)R^{7Z}$.

In certain embodiments of [11], both $R^{4X}$ and $R^{5X}$ are other than H (e.g., each of $R^{4X}$ and $R^{5X}$ is an independently selected $C_1$-$C_6$ alkyl). As a non-limiting example, each of $R^{4X}$ and $R^{5X}$ can be methyl.

In certain embodiments of [11], one of $R^{4X}$ and $R^{5X}$ is H; and the other of $R^{4X}$ and $R^{5X}$ is other than H (e.g., one of $R^{4X}$ and $R^{5X}$ is H; and the other of $R^{4X}$ and $R^{5X}$ is an independently selected $C_1$-$C_6$ alkyl). As a non-limiting example, each of $R^{4X}$ and $R^{5X}$ can be methyl.

In certain embodiments of [11], both $R^{4X}$ and $R^{5X}$ are H.

In certain embodiments of [11], $R^{7Z}$ is H.

In certain embodiments of [11], $R^{7Z}$ is $C_{1-10}$ alkyl, optionally substituted with from 1-6 independently selected $R^a$. In certain of the foregoing embodiments, $R^{7Z}$ is $C_{1-6}$ alkyl, optionally substituted with from 1-6 (e.g., 1-3) independently selected $R^a$.

In certain of the foregoing embodiments of [11] when $R^{7Z}$ is $C_{1-10}$ alkyl optionally substituted with from 1-6 independently selected $R^a$, each occurrence of $R^a$ is independently selected from the group consisting of: —OH; —F; —$NR^eR^f$ (e.g., $NMe_2$); $C_{1-4}$ alkoxy; and $C_{1-4}$ haloalkoxy.

In certain embodiments of [8]-[11], Y is $CO_2R^{6Y}$.

In certain embodiments of [8]-[11], $R^{6Y}$ is H. In certain other embodiments, $R^{6Y}$ is $C_{1-12}$ (e.g., $C_{1-6}$, $C_{2-6}$, $C_{2-3}$)alkyl, which is optionally substituted with from 1-6 (e.g., unsubstituted; or substituted with from 1-2, e.g., 1) independently selected $R^a$.

In certain embodiments of [8]-[11], Y is selected from $CO_2H$ and $CO_2Me$.

In certain embodiments of [8]-[11], Y is

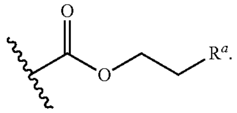

In certain embodiments of [8]-[11], Y is

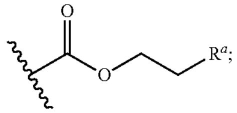

and wherein the $R^a$ on Y is selected from —OH; —F; —$NR^eR^f$ (e.g., $NMe_2$); $C_{1-4}$ alkoxy; and $C_{1-4}$ haloalkoxy (e.g., Y can be

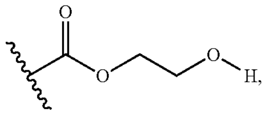
, or

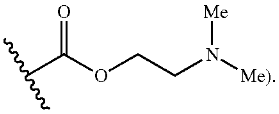
).

For example, Y can be

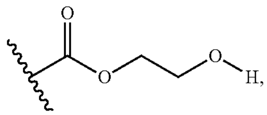
, or

-continued

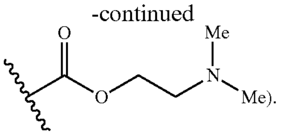

In certain embodiments of [8]-[11], Y is $CONR^{4Y}R^{5Y}$. In certain of these embodiments, each of $R^{4Y}$ and $R^{5Y}$ is independently H or $C_1$-12 alkyl (e.g., $C_{1-6}$, $C_{1-4}$), optionally substituted with from 1-6 (e.g., from 1-3 or from 1-2) independently selected $R^a$. In certain of the foregoing embodiments, each of $R^{4Y}$ and $R^{5Y}$ is independently H or

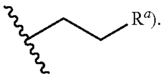

In certain of these embodiments, wherein the $R^a$ on $R^{4Y}$ or $R^{5Y}$ is selected from —OH; —F; —$NR^eR^f$ (e.g., $NMe_2$); $C_{1-4}$ alkoxy; and $C_{1-4}$ haloalkoxy.

In certain embodiments of [8]-[11], Y is $CONR^{4Y}R^{5Y}$; and each of $R^{4Y}$ and $R^{5Y}$ is independently H,

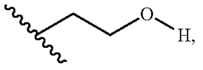
or
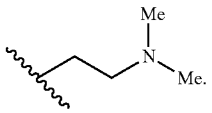

For example, Y can be $CONH_2$.

As another non-limiting example, Y can be

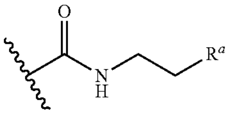

(e.g., $R^a$ is selected from —OH; —F; —$NR^eR^f$ (e.g., $NMe_2$); $C_{1-4}$ alkoxy; and $C_{1-4}$ haloalkoxy).

In certain embodiments of [8]-[11], Y is $CONR^{4Y}R^{5Y}$.

In certain embodiments of [8]-[11], Y is $CONR^{4Y}R^{5Y}$, wherein one of $R^{4Y}$ and $R^{5Y}$ is —$(W^1—W^2)_n$—$W^3$; and the other one of $R^{4Y}$ and $R^{5Y}$ is selected from H and $C_{1-3}$ alkyl.

In certain of these embodiments, n is 2 or 3.

In certain embodiments when one of $R^{4Y}$ and $R^{5Y}$ is —$(W^1—W^2)_n$—$W^3$, $W^1$ is in each occurrence independently $C_{2-3}$ alkylene (e.g., $C_2$ alkylene).

In certain embodiments when one of $R^{4Y}$ and $R^{5Y}$ is —$(W^1—W^2)_n$—$W^3$, $W^2$ is in each occurrence independently —N(H)—, —N(Me)-, or —O—.

In certain embodiments when one of $R^{4Y}$ and $R^{5Y}$ is —$(W^1—W^2)_n$—$W^3$ w3 is selected from H and $C_{1-3}$ alkyl.

In certain embodiments, wherein one of $R^{4Y}$ and $R^{5Y}$ is selected from:

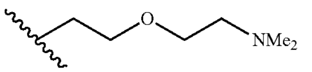
and
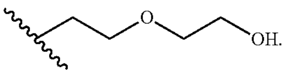

In certain embodiments of [8]-[11], Y is $CONR^{4Y}R^{5Y}$; one of $R^{4Y}$ and $R^{5Y}$ is —$(W^1—W^2)_n$—$W^3$; and the other one of $R^{4Y}$ and $R^{5Y}$ is selected from H and $C_{1-3}$ alkyl, wherein:

n is 2 or 3; $W^1$ is in each occurrence independently $C_{2-3}$ alkylene (e.g., $C_2$ alkylene); $W^2$ is in each occurrence independently —N(H)—, —N(Me)-, or —O—; and $W^3$ is selected from H and $C_{1-3}$ alkyl.

As a non-limiting example, one of $R^{4Y}$ and $R^{5Y}$ can be selected from:

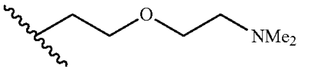
and
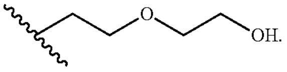

In certain embodiments, Y is heteroaryl including from 5 ring atoms, wherein from 1-4 ring atoms are heteroatoms, each independently selected from the group consisting of N, N(H), $N(R^d)$, O, and S, and wherein one or more of the heteroaryl ring carbon atoms are optionally substituted with from 1-2 independently selected $R^c$.

In certain of these embodiments, Y is selected from tetrazolyl, triazolyl, oxadiazolyl, and oxazolyl, wherein one or more of the heteroaryl ring carbon atoms are optionally substituted with from 1-2 independently selected $R^c$; and one of the heteroaryl ring nitrogen atoms is optionally substituted with $R^d$.

In certain of the foregoing embodiments, Y is selected from the group consisting of

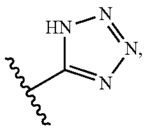
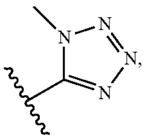
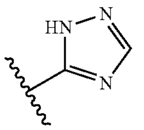

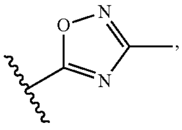
, and
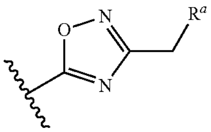

(e.g., $R^a$ can be selected from —OH, —OMe, and —$NMe_2$).

As a non-limiting example, Y can be

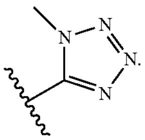 [SMILES: *c1nnnn1C]

In certain of these embodiments, each of $R^1$, $R^2$, and $R^3$ is independently selected from H and $C(O)R^{7A}$.

In certain of these embodiments, each occurrence of $R^{7A}$ is independently $C_1$-10 alkyl, optionally substituted with from 1-6 independently selected $R^a$ (e.g., $C_{1-6}$ or $C_{1-3}$ alkyl, optionally substituted with from 1-6 independently selected $R^a$; e.g., $C_{1-10}$ or $C_{1-6}$ or $C_{1-3}$ unsubstituted alkyl (e.g., $CH_3$)).

In certain of the foregoing embodiments, each of $R^1$, $R^2$, and $R^3$ is independently selected from H and C(O)Me (e.g., $R^1$, $R^2$, and $R^3$ are each H; or $R^1$, $R^2$, and $R^3$ are each C(O)Me).

In certain embodiments of [8]-[11], each of $R^1$, $R^2$, and $R^3$ is independently selected from H and C(O)Me. For example, $R^1$, $R^2$, and $R^3$ can each be H. As another example, $R^1$, $R^2$, and $R^3$ can each be C(O)Me).

In certain embodiments of [1]-[11], each $Z^x$ is H.

In certain other embodiments of [1]-[11], each $Z^x$ together with the carbon to which each is attached forms C=O.

In some embodiments, the compound is selected from Table A-1, below:

TABLE A-1

| Example # | Compound | Name/ID # |
|---|---|---|
| 1 | 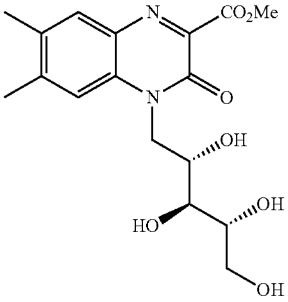 [SMILES: COC(=O)c1nc2cc(C)c(C)cc2n(C[C@H](O)[C@H](O)[C@H](O)CO)c1=O] | Compound 3 |
| 2 | 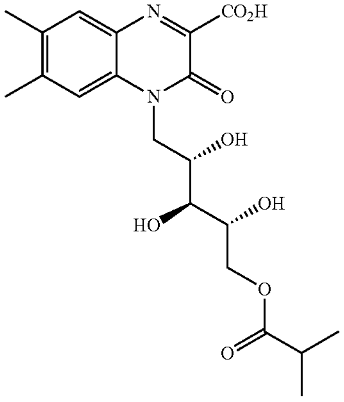 [SMILES: Cc1cc2nc(C(=O)O)c(=O)n(C[C@H](O)[C@H](O)[C@H](O)COC(=O)C(C)C)c2cc1C] | Compound 10 |
| 3 | 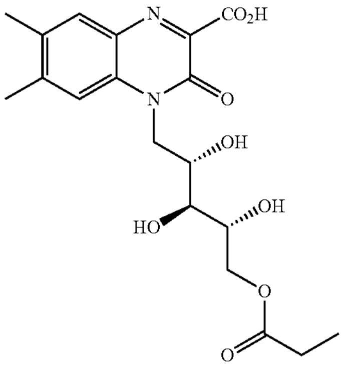 [SMILES: CCC(=O)OC[C@@H](O)[C@@H](O)[C@@H](O)Cn1c(=O)c(C(=O)O)nc2cc(C)c(C)cc21] | Compound 12 |

TABLE A-1-continued
| Example # | Compound | Name/ID # |
| --- | --- | --- |
| 4 | 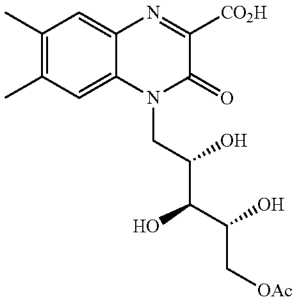 [SMILES: CC(=O)OC[C@@H](O)[C@@H](O)[C@@H](O)Cn1c(=O)c(C(=O)O)nc2cc(C)c(C)cc21] | Compound 14 |
| 5 | 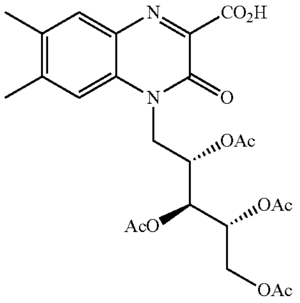 [SMILES: CC(=O)OC[C@@H](OC(C)=O)[C@@H](OC(C)=O)[C@H](Cn1c(=O)c(C(=O)O)nc2cc(C)c(C)cc21)OC(C)=O] | Compound 4 |
| 6 | 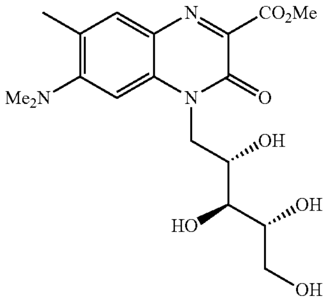 [SMILES: COC(=O)c1nc2cc(C)c(N(C)C)cc2n(C[C@H](O)[C@H](O)[C@H](O)CO)c1=O] | Compound 7 |
| 7 | 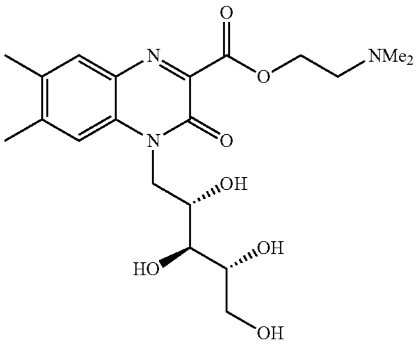 [SMILES: Cc1cc2nc(C(=O)OCCN(C)C)c(=O)n(C[C@H](O)[C@H](O)[C@H](O)CO)c2cc1C] | Compound 44 |
| 8 | 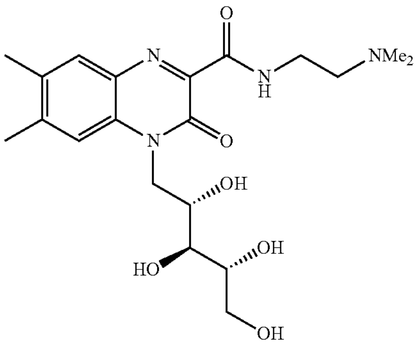 [SMILES: Cc1cc2nc(C(=O)NCCN(C)C)c(=O)n(C[C@H](O)[C@H](O)[C@H](O)CO)c2cc1C] | Compound 15 |

TABLE A-1-continued
| Example # | Compound | Name/ID # |
|---|---|---|
| 9 | 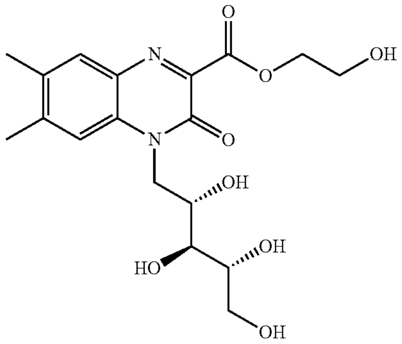 [SMILES: Cc1cc2nc(C(=O)OCCO)c(=O)n(C[C@H](O)[C@H](O)[C@H](O)CO)c2cc1C] | Compound 16 |
| 10 | 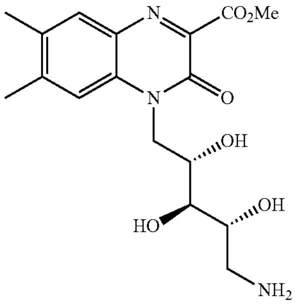 [SMILES: COC(=O)c1nc2cc(C)c(C)cc2n(C[C@H](O)[C@H](O)[C@H](O)CN)c1=O] | Compound 24 |
| 11 | 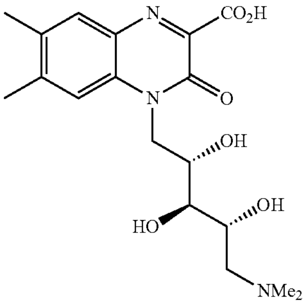 [SMILES: Cc1cc2nc(C(=O)O)c(=O)n(C[C@H](O)[C@H](O)[C@H](O)CN(C)C)c2cc1C] | Compound 27 |
| 12 | 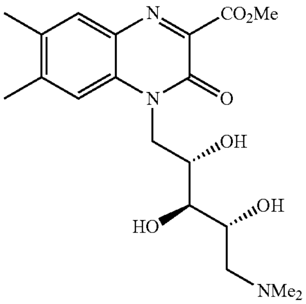 | Compound 26 |
| 13 | 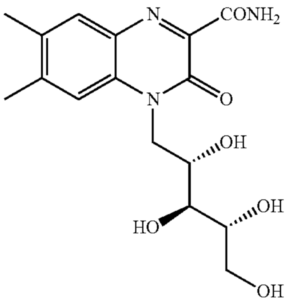 [SMILES: Cc1cc2nc(C(N)=O)c(=O)n(C[C@H](O)[C@H](O)[C@H](O)CO)c2cc1C] | Compound 17 |

TABLE A-1-continued
| Example # | Compound | Name/ID # |
|---|---|---|
| 14 | 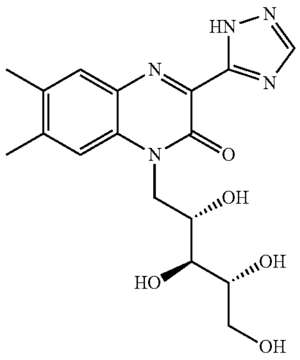 [SMILES: Cc1cc2nc(-c3ncn[nH]3)c(=O)n(C[C@H](O)[C@H](O)[C@H](O)CO)c2cc1C] | Compound 31 |
| 15 | 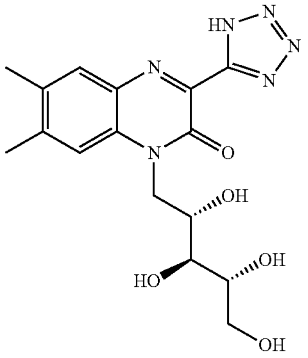 [SMILES: Cc1cc2nc(-c3nnn[nH]3)c(=O)n(C[C@H](O)[C@H](O)[C@H](O)CO)c2cc1C] | Compound 37 |
| 16 | 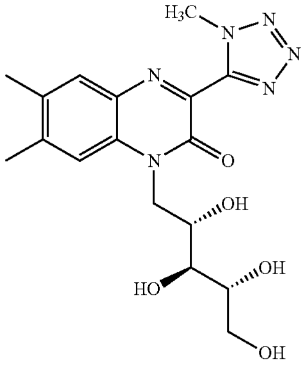 [SMILES: Cc1cc2nc(-c3nnnn3C)c(=O)n(C[C@H](O)[C@H](O)[C@H](O)CO)c2cc1C] | Compound 40 |
| 17 | 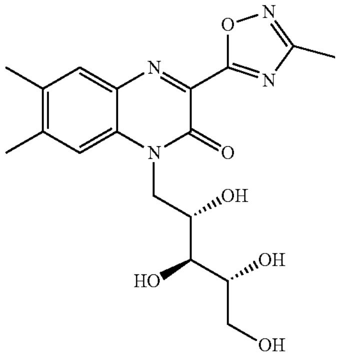 | Compound 43 |

TABLE A-1-continued
| Example # | Compound | Name/ID # |
|---|---|---|
| 18 | 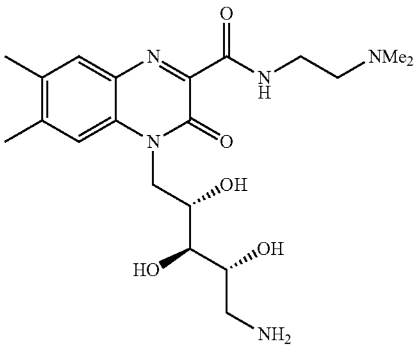 [SMILES: Cc1cc2nc(C(=O)NCCN(C)C)c(=O)n(C[C@H](O)[C@H](O)[C@H](O)CN)c2cc1C] | Compound 50 |
| 19 | 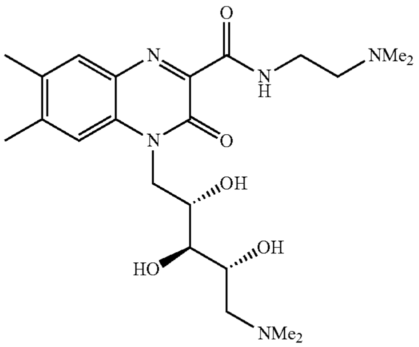 [SMILES: Cc1cc2nc(C(=O)NCCN(C)C)c(=O)n(C[C@H](O)[C@H](O)[C@H](O)CN(C)C)c2cc1C] | Compound 52 |
| 20 | 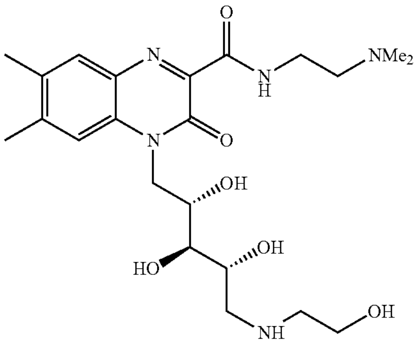 [SMILES: Cc1cc2nc(C(=O)NCCN(C)C)c(=O)n(C[C@H](O)[C@H](O)[C@H](O)CNCCO)c2cc1C] | Compound 54 |
| 21 | 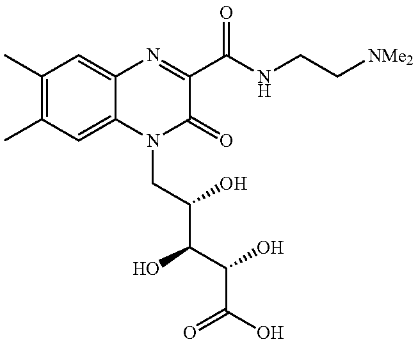 [SMILES: Cc1cc2nc(C(=O)NCCN(C)C)c(=O)n(C[C@H](O)[C@H](O)[C@H](O)C(=O)O)c2cc1C] | Compound 56 |

TABLE A-1-continued
| Example # | Compound | Name/ID # |
|---|---|---|
| 22 | 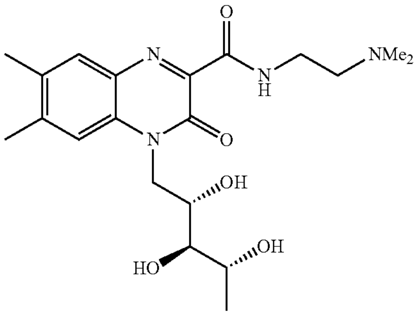 [SMILES: Cc1cc2nc(C(=O)NCCN(C)C)c(=O)n(C[C@H](O)[C@H](O)[C@@H](C)O)c2cc1C] | Compound 59 |
| 23 | 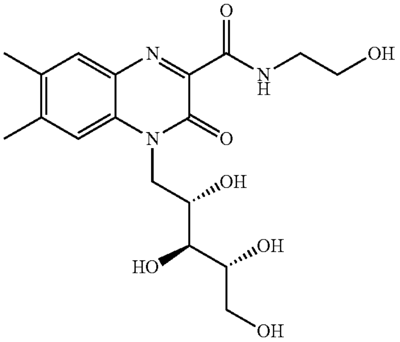 [SMILES: Cc1cc2nc(C(=O)NCCO)c(=O)n(C[C@H](O)[C@H](O)[C@H](O)CO)c2cc1C] | Compound 61 |
| 24 | 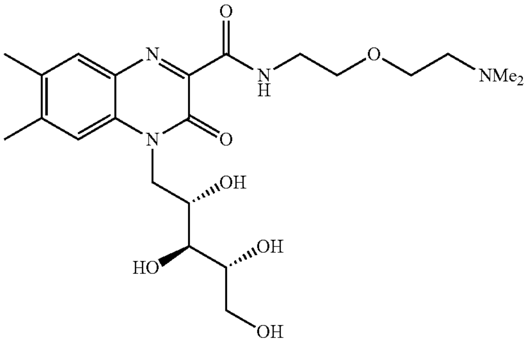 [SMILES: Cc1cc2nc(C(=O)NCCOCCN(C)C)c(=O)n(C[C@H](O)[C@H](O)[C@H](O)CO)c2cc1C] | Compound 63 |
| 25 | 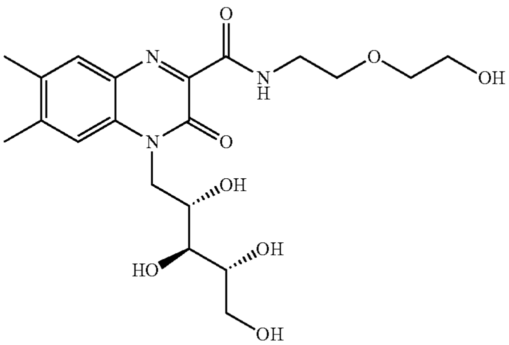 [SMILES: Cc1cc2nc(C(=O)NCCOCCO)c(=O)n(C[C@H](O)[C@H](O)[C@H](O)CO)c2cc1C] | Compound 65 |

TABLE A-1-continued
| Example # | Compound | Name/ID # |
|---|---|---|
| 26 | 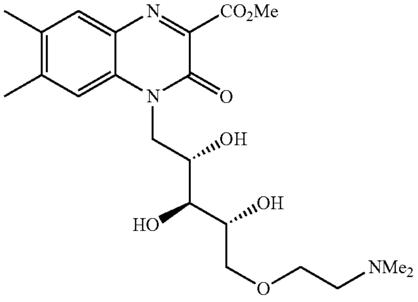 [SMILES: COC(=O)c1nc2cc(C)c(C)cc2n(C[C@H](O)[C@H](O)[C@H](O)COCCN(C)C)c1=O] | Compound 69 |
| 27 | 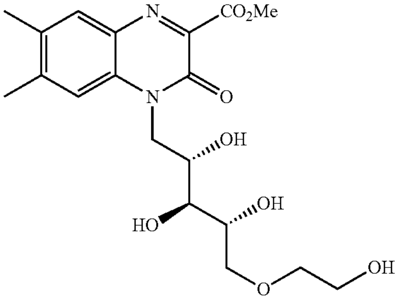 [SMILES: COC(=O)c1nc2cc(C)c(C)cc2n(C[C@H](O)[C@H](O)[C@H](O)COCCO)c1=O] | Compound 67 |
| 28 | 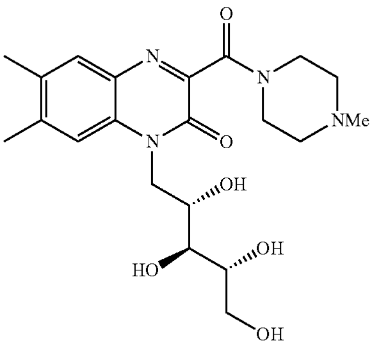 [SMILES: Cc1cc2nc(C(=O)N3CCN(C)CC3)c(=O)n(C[C@H](O)[C@H](O)[C@H](O)CO)c2cc1C] | Compound 71 |
| 29 | 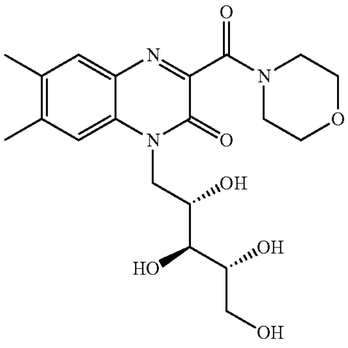 [SMILES: Cc1cc2nc(C(=O)N3CCOCC3)c(=O)n(C[C@H](O)[C@H](O)[C@H](O)CO)c2cc1C] | Compound 73 |

TABLE A-1-continued
| Example # | Compound | Name/ID # |
|---|---|---|
| 30 | 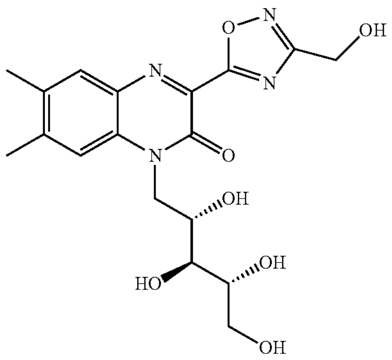 [SMILES: Cc1cc2nc(-c3nc(CO)no3)c(=O)n(C[C@H](O)[C@H](O)[C@H](O)CO)c2cc1C] | Compound 75 |
| 31 | 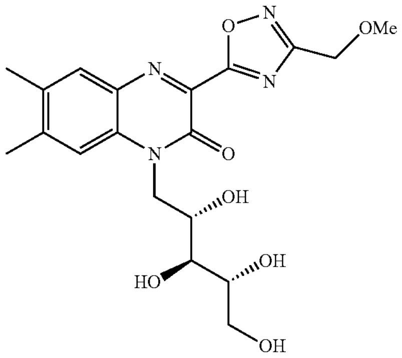 [SMILES: COCc1noc(-c2nc3cc(C)c(C)cc3n(C[C@H](O)[C@H](O)[C@H](O)CO)c2=O)n1] | Compound 79 |
| 32 | 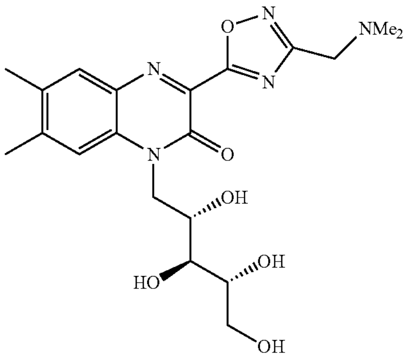 [SMILES: Cc1cc2nc(-c3nc(CN(C)C)no3)c(=O)n(C[C@H](O)[C@H](O)[C@H](O)CO)c2cc1C] | Compound 78 |
| 33 | 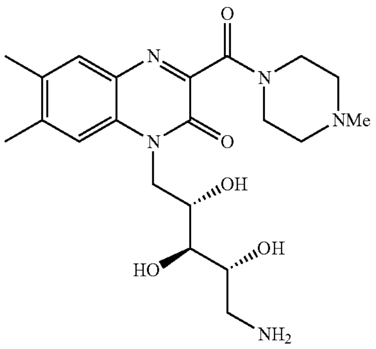 [SMILES: Cc1cc2nc(C(=O)N3CCN(C)CC3)c(=O)n(C[C@H](O)[C@H](O)[C@H](O)CN)c2cc1C] | Compound 83 |

TABLE A-1-continued
| Example # | Compound | Name/ID # |
| --- | --- | --- |
| 34 | 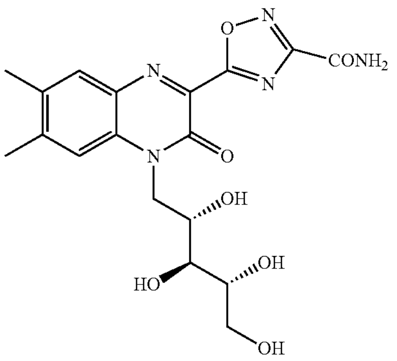 [SMILES: Cc1cc2nc(-c3nc(C(N)=O)no3)c(=O)n(C[C@H](O)[C@H](O)[C@H](O)CO)c2cc1C] | Compound 84 |
| 35 | 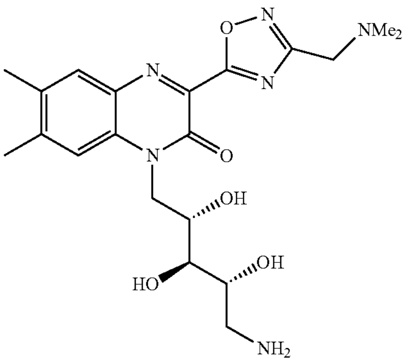 [SMILES: Cc1cc2nc(-c3nc(CN(C)C)no3)c(=O)n(C[C@H](O)[C@H](O)[C@H](O)CN)c2cc1C] | Compound 92 |
| 36 | 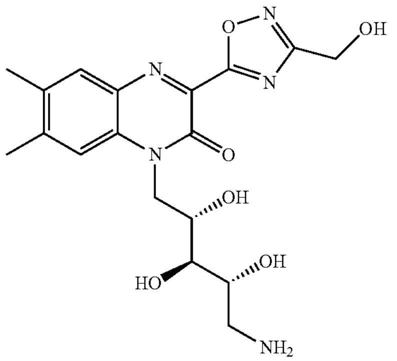 [SMILES: Cc1cc2nc(-c3nc(CO)no3)c(=O)n(C[C@H](O)[C@H](O)[C@H](O)CN)c2cc1C] | Compound 97 |
| 37 | 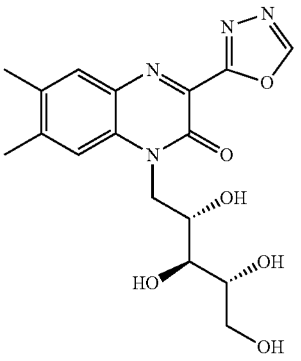 [SMILES: Cc1cc2nc(-c3nnco3)c(=O)n(C[C@H](O)[C@H](O)[C@H](O)CO)c2cc1C] | Compound 99 |

TABLE A-1-continued
| Example # | Compound | Name/ID # |
|---|---|---|
| 38 | 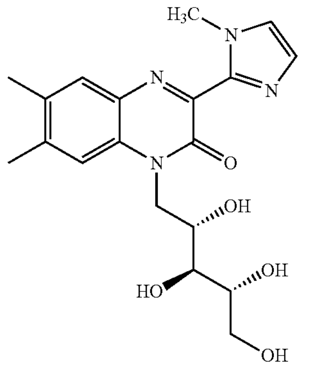 [SMILES: Cc1cc2nc(-c3nccn3C)c(=O)n(C[C@H](O)[C@H](O)[C@H](O)CO)c2cc1C] | Compound 104 |
| 39 | 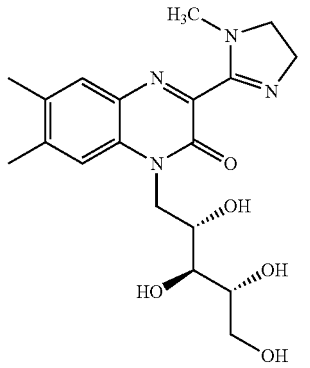 [SMILES: Cc1cc2nc(C3=NCCN3C)c(=O)n(C[C@H](O)[C@H](O)[C@H](O)CO)c2cc1C] | Compound 105 |
| 40 | 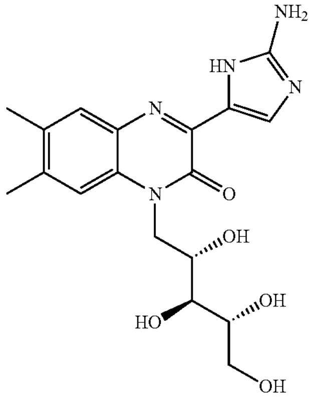 [SMILES: Cc1cc2nc(-c3cnc(N)[nH]3)c(=O)n(C[C@H](O)[C@H](O)[C@H](O)CO)c2cc1C] | Compound 110 |
| 41 | 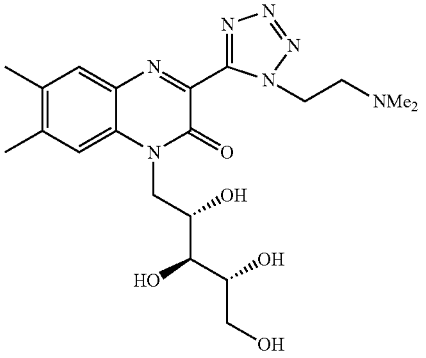 [SMILES: Cc1cc2nc(-c3nnnn3CCN(C)C)c(=O)n(C[C@H](O)[C@H](O)[C@H](O)CO)c2cc1C] | Compound 113 |

TABLE A-1-continued
| Example # | Compound | Name/ID # |
| --- | --- | --- |
| 42 | 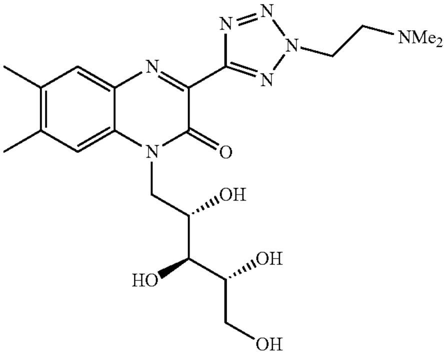 [SMILES: Cc1cc2nc(-c3nnn(CCN(C)C)n3)c(=O)n(C[C@H](O)[C@H](O)[C@H](O)CO)c2cc1C] | Compound 116 |
| 43 | 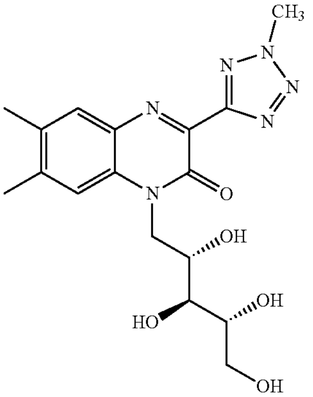 [SMILES: Cc1cc2nc(-c3nnn(C)n3)c(=O)n(C[C@H](O)[C@H](O)[C@H](O)CO)c2cc1C] | Compound 117 |
| 44 | 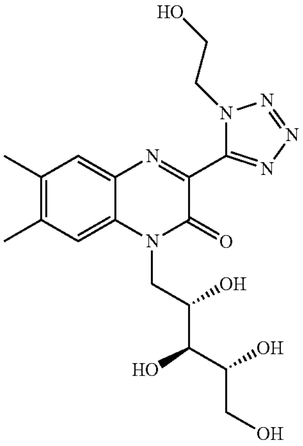 [SMILES: Cc1cc2nc(-c3nnnn3CCO)c(=O)n(C[C@H](O)[C@H](O)[C@H](O)CO)c2cc1C] | Compound 121 |
| 45 | 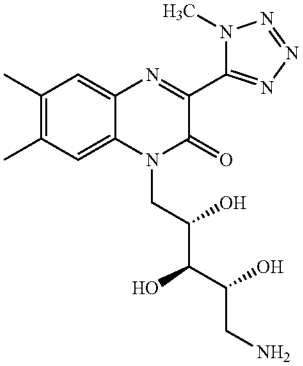 [SMILES: Cc1cc2nc(-c3nnnn3C)c(=O)n(C[C@H](O)[C@H](O)[C@H](O)CN)c2cc1C] | Compound 129 |

TABLE A-1-continued
| Example # | Compound | Name/ID # |
|---|---|---|
| 46 | 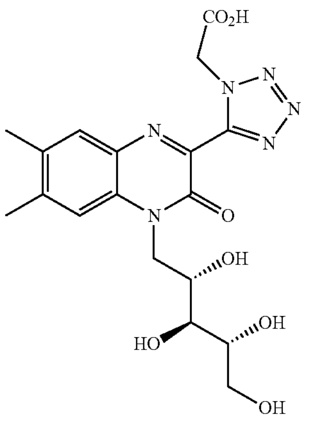 [SMILES: Cc1cc2nc(-c3nnnn3CC(=O)O)c(=O)n(C[C@H](O)[C@H](O)[C@H](O)CO)c2cc1C] | Compound 132 |
| 47 | 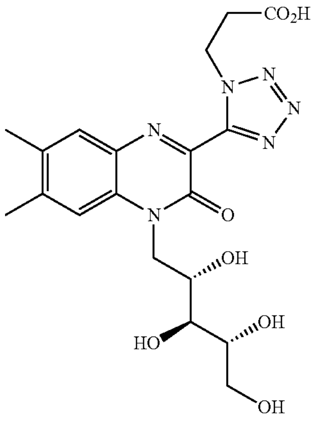 [SMILES: Cc1cc2nc(-c3nnnn3CCC(=O)O)c(=O)n(C[C@H](O)[C@H](O)[C@H](O)CO)c2cc1C] | Compound 135 |
| 48 | 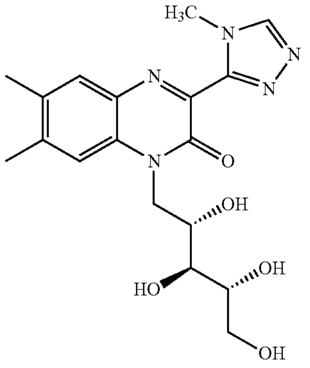 [SMILES: Cc1cc2nc(-c3nncn3C)c(=O)n(C[C@H](O)[C@H](O)[C@H](O)CO)c2cc1C] | Compound 137 |

TABLE A-1-continued
| Example # | Compound | Name/ID # |
|---|---|---|
| 49 | 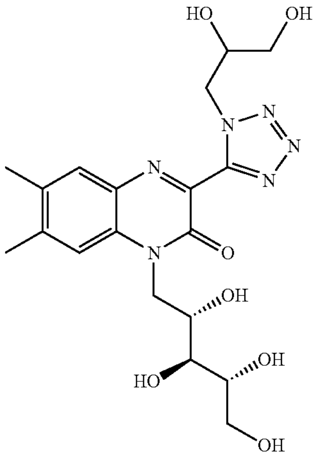 [SMILES: Cc1cc2nc(-c3nnnn3CC(O)CO)c(=O)n(C[C@H](O)[C@H](O)[C@H](O)CO)c2cc1C] | Compound 141 |
| 50 | 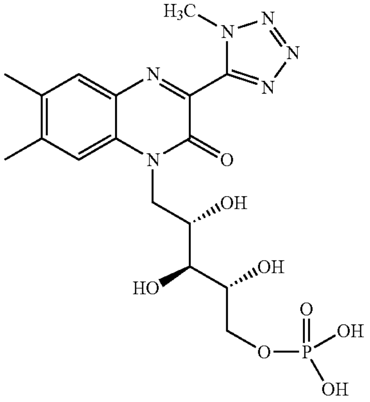 [SMILES: Cc1cc2nc(-c3nnnn3C)c(=O)n(C[C@H](O)[C@H](O)[C@H](O)COP(=O)(O)O)c2cc1C] | Compound 143 |
| 51 | 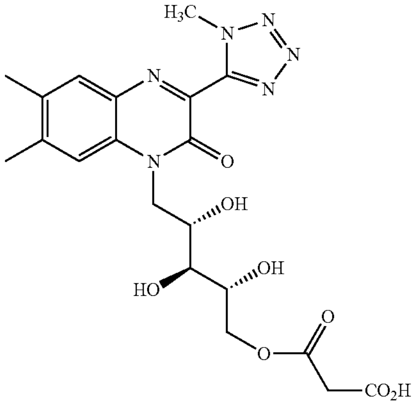 [SMILES: Cc1cc2nc(-c3nnnn3C)c(=O)n(C[C@H](O)[C@H](O)[C@H](O)COC(=O)CC(=O)O)c2cc1C] | Compound 145 |

TABLE A-1-continued
| Example # | Compound | Name/ID # |
|---|---|---|
| 52 | 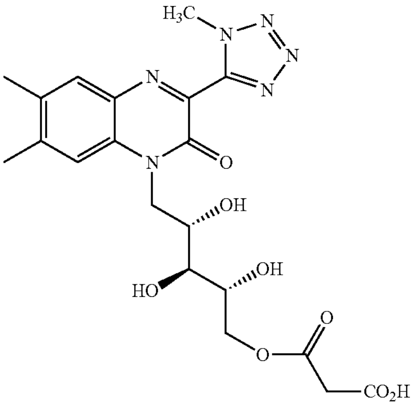 [SMILES: Cc1cc2nc(-c3nnnn3C)c(=O)n(C[C@H](O)[C@H](O)[C@H](O)COC(=O)CC(=O)O)c2cc1C] | Compound 147 |
| 53 | 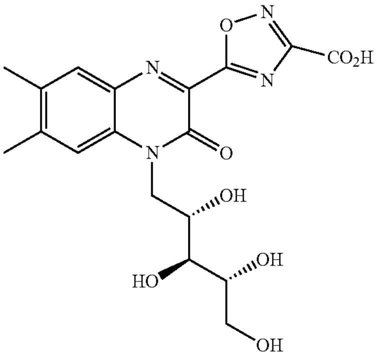 [SMILES: Cc1cc2nc(-c3nc(C(=O)O)no3)c(=O)n(C[C@H](O)[C@H](O)[C@H](O)CO)c2cc1C] | Compound 150 |
| 54 | 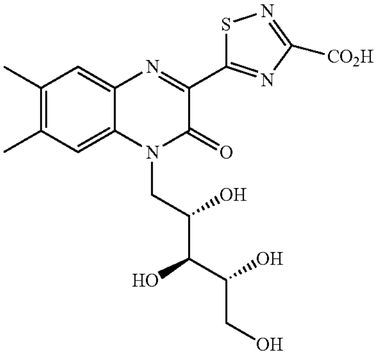 | Compound 153 |
| 55 | 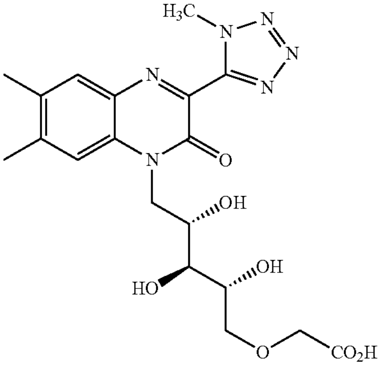 [SMILES: Cc1cc2nc(-c3nnnn3C)c(=O)n(C[C@H](O)[C@H](O)[C@H](O)COCC(=O)O)c2cc1C] | Compound 158 |

TABLE A-1-continued
| Example # | Compound | Name/ID # |
|---|---|---|
| 56 | 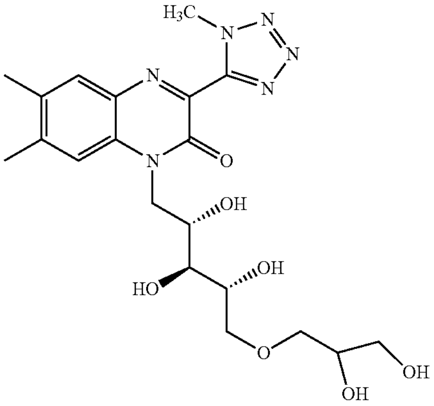 [SMILES: Cc1cc2nc(-c3nnnn3C)c(=O)n(C[C@H](O)[C@H](O)[C@H](O)COCC(O)CO)c2cc1C] | Compound 160 |
| 57 | 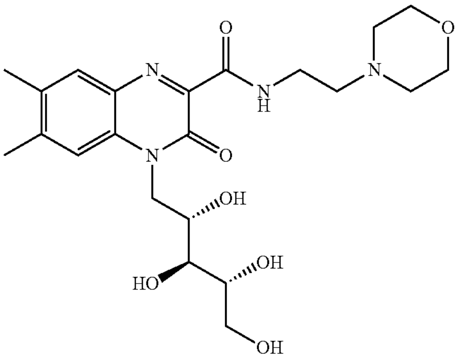 [SMILES: Cc1cc2nc(C(=O)NCCN3CCOCC3)c(=O)n(C[C@H](O)[C@H](O)[C@H](O)CO)c2cc1C] | Compound 161 |
| 58 | 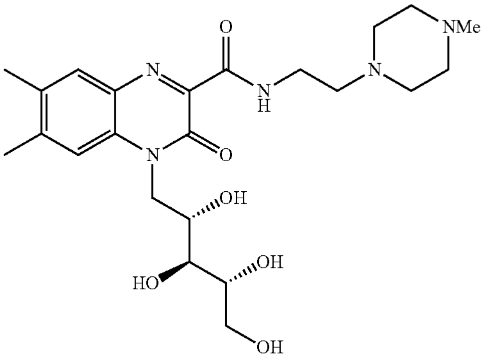 [SMILES: Cc1cc2nc(C(=O)NCCN3CCN(C)CC3)c(=O)n(C[C@H](O)[C@H](O)[C@H](O)CO)c2cc1C] | Compound 162 |
| 59 | 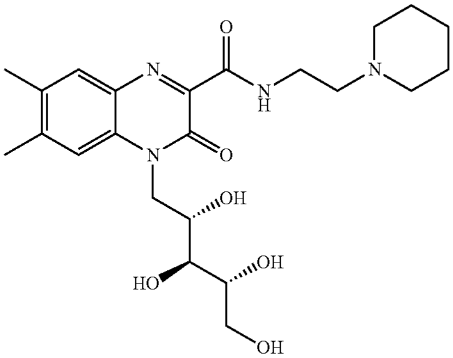 [SMILES: Cc1cc2nc(C(=O)NCCN3CCCCC3)c(=O)n(C[C@H](O)[C@H](O)[C@H](O)CO)c2cc1C] | Compound 163 |

TABLE A-1-continued
| Example # | Compound | Name/ID # |
|---|---|---|
| 60 | 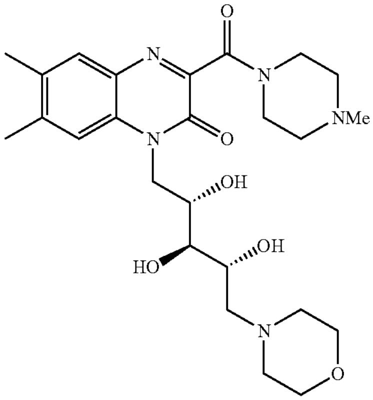 [SMILES: Cc1cc2nc(C(=O)N3CCN(C)CC3)c(=O)n(C[C@H](O)[C@H](O)[C@H](O)CN3CCOCC3)c2cc1C] | Compound 165 |
| 61 | 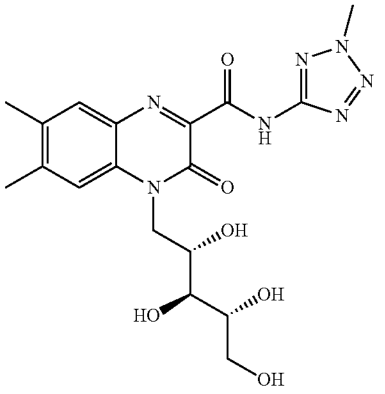 [SMILES: Cc1cc2nc(C(=O)Nc3nnn(C)n3)c(=O)n(C[C@H](O)[C@H](O)[C@H](O)CO)c2cc1C] | Compound 167 |
| 62 | 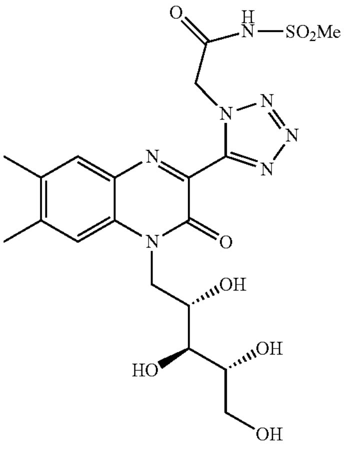 [SMILES: Cc1cc2nc(-c3nnnn3CC(=O)NS(C)(=O)=O)c(=O)n(C[C@H](O)[C@H](O)[C@H](O)CO)c2cc1C] | Compound 170 |

TABLE A-1-continued
| Example # | Compound | Name/ID # |
|---|---|---|
| 63 | 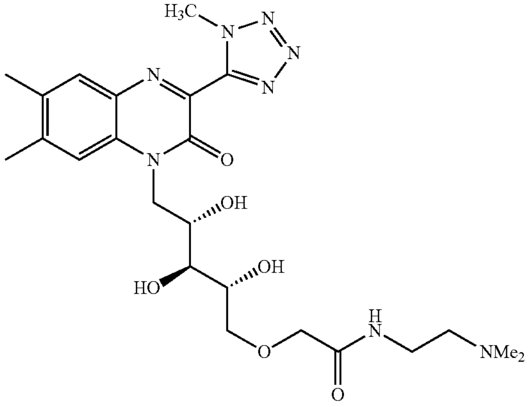 [SMILES: Cc1cc2nc(-c3nnnn3C)c(=O)n(C[C@H](O)[C@H](O)[C@H](O)COCC(=O)NCCN(C)C)c2cc1C] | Compound 171 |
| 64 | 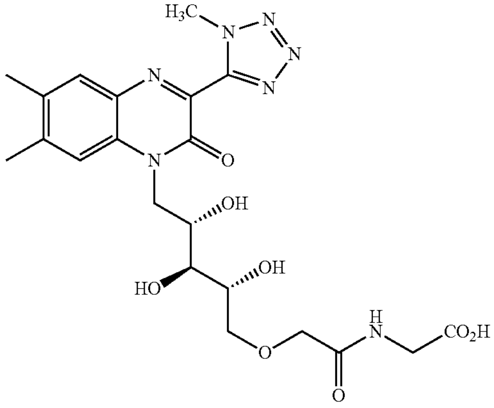 [SMILES: Cc1cc2nc(-c3nnnn3C)c(=O)n(C[C@H](O)[C@H](O)[C@H](O)COCC(=O)NCC(=O)O)c2cc1C] | Compound 173 |
| 65 | 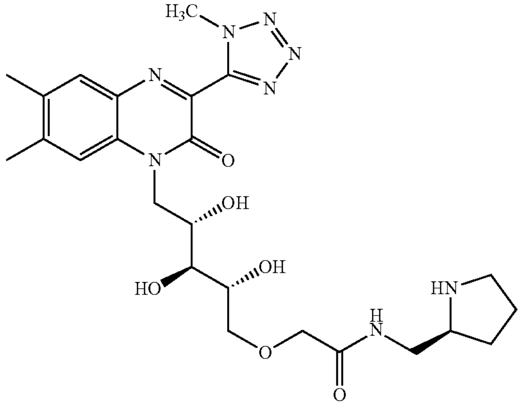 [SMILES: Cc1cc2nc(-c3nnnn3C)c(=O)n(C[C@H](O)[C@H](O)[C@H](O)COCC(=O)NC[C@@H]3CCCN3)c2cc1C] | Compound 175 |

TABLE A-1-continued
| Example # | Compound | Name/ID # |
|---|---|---|
| 66 | 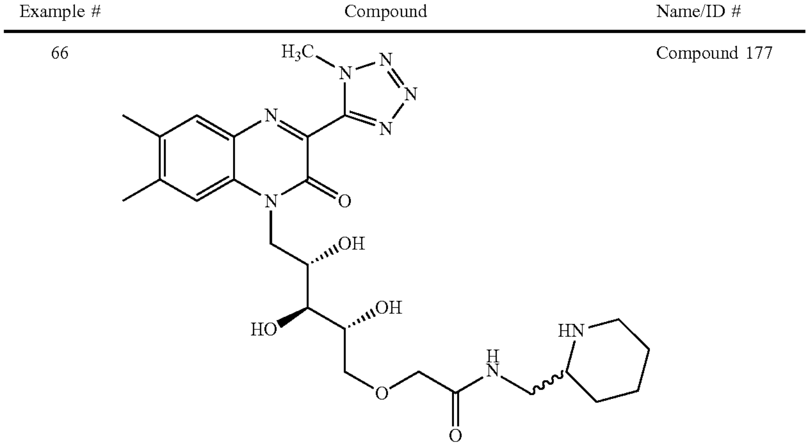 | Compound 177 |
| 67 | 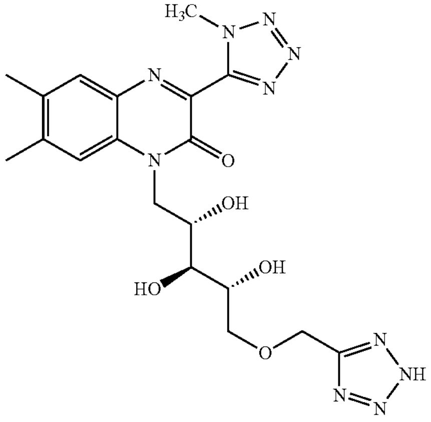 [SMILES: Cc1cc2nc(-c3nnnn3C)c(=O)n(C[C@H](O)[C@H](O)[C@H](O)COCc3nn[nH]n3)c2cc1C] | Compound 180 |
| 68 | 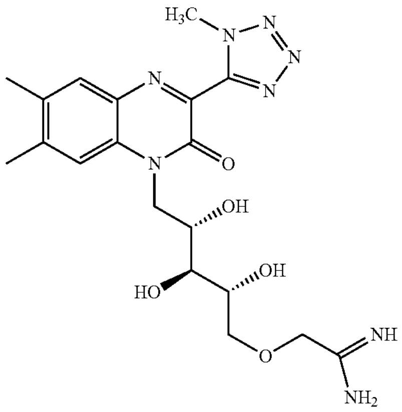 [SMILES: Cc1cc2nc(-c3nnnn3C)c(=O)n(C[C@H](O)[C@H](O)[C@H](O)COCC(=N)N)c2cc1C] | Compound 181 |

TABLE A-1-continued
| Example # | Compound | Name/ID # |
|---|---|---|
| 69 | 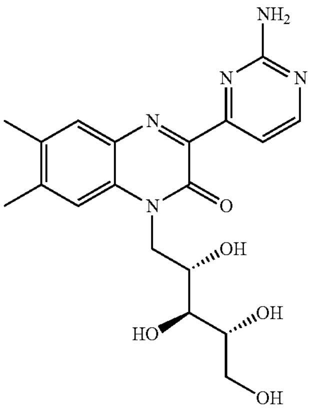 [SMILES: Cc1cc2nc(-c3ccnc(N)n3)c(=O)n(C[C@H](O)[C@H](O)[C@H](O)CO)c2cc1C] | Compound 183 |
or a pharmaceutically acceptable salt thereof.
In some embodiments, the compound is selected from Table A-2, below:
TABLE A-2
| Example # | Compound | Name/ID # |
|---|---|---|
| 2 | 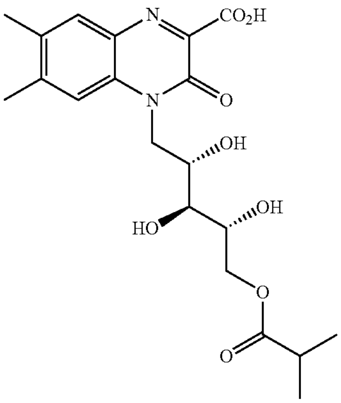 [SMILES: Cc1cc2nc(C(=O)O)c(=O)n(C[C@H](O)[C@H](O)[C@H](O)COC(=O)C(C)C)c2cc1C] | Compound 10 |
| 3 | 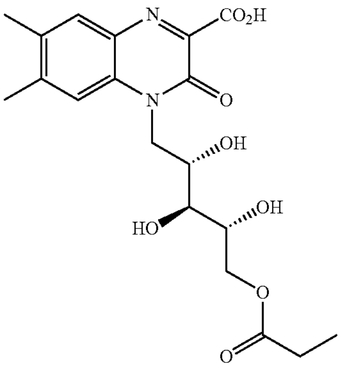 [SMILES: CCC(=O)OC[C@@H](O)[C@@H](O)[C@@H](O)Cn1c(=O)c(C(=O)O)nc2cc(C)c(C)cc21] | Compound 12 |

TABLE A-2-continued
| Example # | Compound | Name/ID # |
| --- | --- | --- |
| 4 | 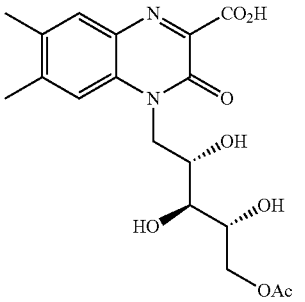 [SMILES: CC(=O)OC[C@@H](O)[C@@H](O)[C@@H](O)Cn1c(=O)c(C(=O)O)nc2cc(C)c(C)cc21] | Compound 14 |
| 6 | 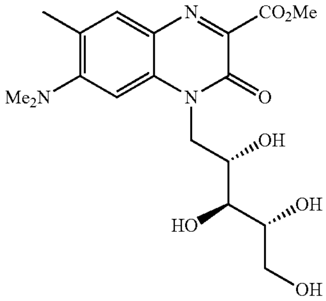 [SMILES: COC(=O)c1nc2cc(C)c(N(C)C)cc2n(C[C@H](O)[C@H](O)[C@H](O)CO)c1=O] | Compound 7 |
| 7 | 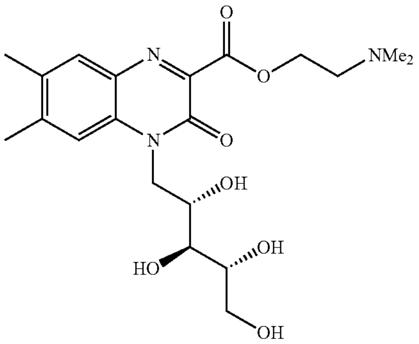 [SMILES: Cc1cc2nc(C(=O)OCCN(C)C)c(=O)n(C[C@H](O)[C@H](O)[C@H](O)CO)c2cc1C] | Compound 44 |
| 8 | 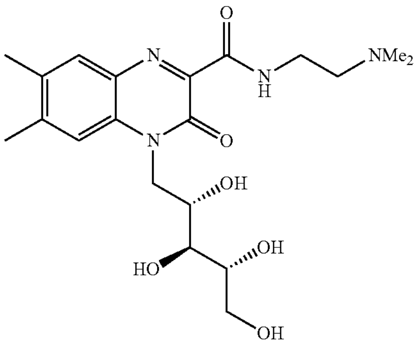 [SMILES: Cc1cc2nc(C(=O)NCCN(C)C)c(=O)n(C[C@H](O)[C@H](O)[C@H](O)CO)c2cc1C] | Compound 15 |

TABLE A-2-continued
| Example # | Compound | Name/ID # |
|---|---|---|
| 9 | 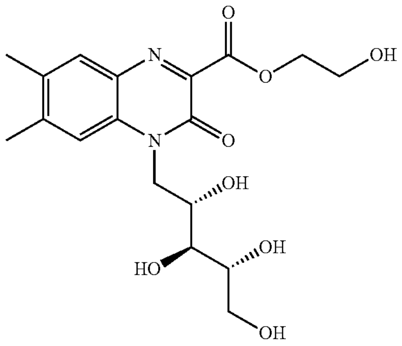 [SMILES: Cc1cc2nc(C(=O)OCCO)c(=O)n(C[C@H](O)[C@H](O)[C@H](O)CO)c2cc1C] | Compound 16 |
| 10 | 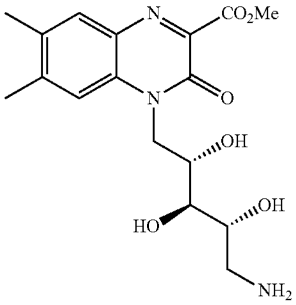 [SMILES: COC(=O)c1nc2cc(C)c(C)cc2n(C[C@H](O)[C@H](O)[C@H](O)CN)c1=O] | Compound 24 |
| 11 | 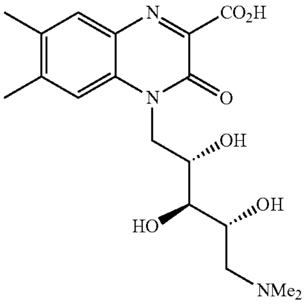 [SMILES: Cc1cc2nc(C(=O)O)c(=O)n(C[C@H](O)[C@H](O)[C@H](O)CN(C)C)c2cc1C] | Compound 27 |
| 12 | 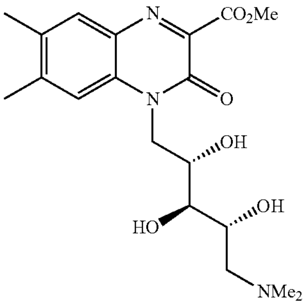 [SMILES: COC(=O)c1nc2cc(C)c(C)cc2n(C[C@H](O)[C@H](O)[C@H](O)CN(C)C)c1=O] | Compound 26 |

TABLE A-2-continued
| Example # | Compound | Name/ID # |
|---|---|---|
| 14 | 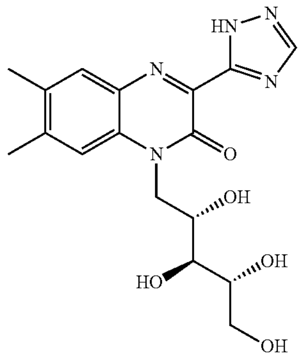 [SMILES: Cc1cc2nc(-c3ncn[nH]3)c(=O)n(C[C@H](O)[C@H](O)[C@H](O)CO)c2cc1C] | Compound 31 |
| 15 | 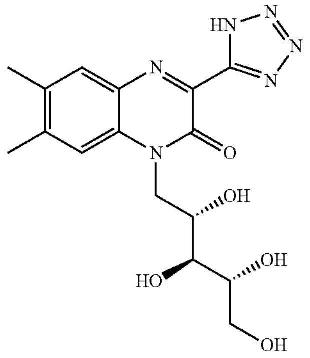 [SMILES: Cc1cc2nc(-c3nnn[nH]3)c(=O)n(C[C@H](O)[C@H](O)[C@H](O)CO)c2cc1C] | Compound 37 |
| 16 | 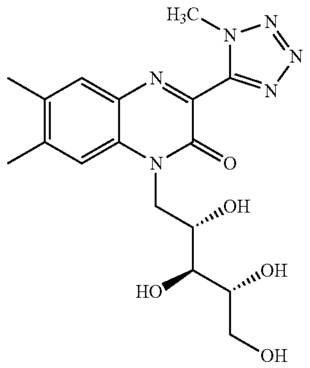 [SMILES: Cc1cc2nc(-c3nnnn3C)c(=O)n(C[C@H](O)[C@H](O)[C@H](O)CO)c2cc1C] | Compound 40 |
| 17 | 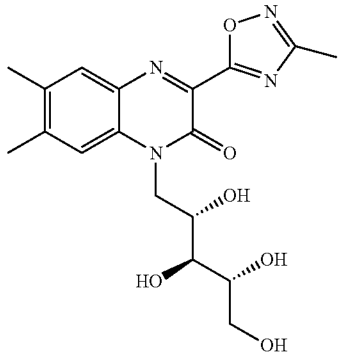 | Compound 43 |

TABLE A-2-continued
| Example # | Compound | Name/ID # |
| --- | --- | --- |
| 18 | 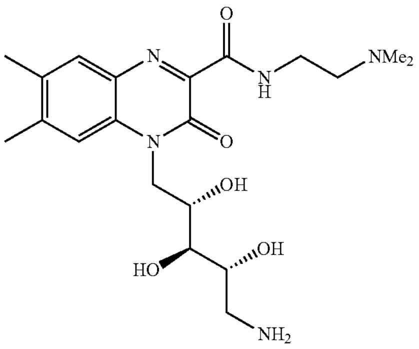 [SMILES: Cc1cc2nc(C(=O)NCCN(C)C)c(=O)n(C[C@H](O)[C@H](O)[C@H](O)CN)c2cc1C] | Compound 50 |
| 19 | 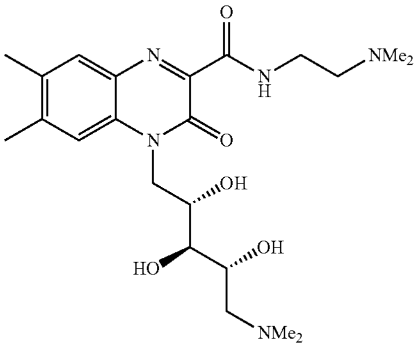 [SMILES: Cc1cc2nc(C(=O)NCCN(C)C)c(=O)n(C[C@H](O)[C@H](O)[C@H](O)CN(C)C)c2cc1C] | Compound 52 |
| 20 | 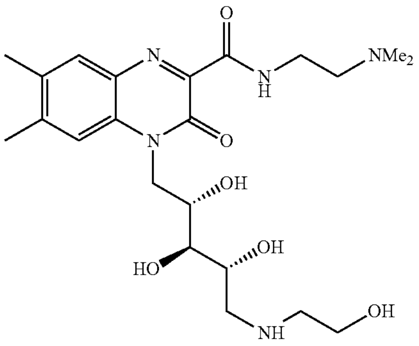 [SMILES: Cc1cc2nc(C(=O)NCCN(C)C)c(=O)n(C[C@H](O)[C@H](O)[C@H](O)CNCCO)c2cc1C] | Compound 54 |
| 21 | 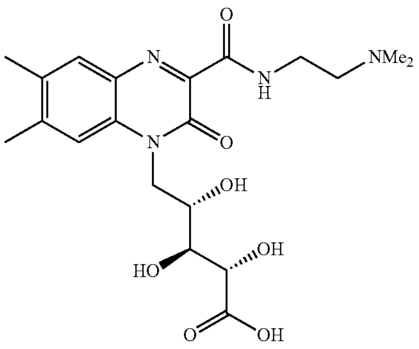 [SMILES: Cc1cc2nc(C(=O)NCCN(C)C)c(=O)n(C[C@H](O)[C@H](O)[C@H](O)C(=O)O)c2cc1C] | Compound 56 |

TABLE A-2-continued
| Example # | Compound | Name/ID # |
|---|---|---|
| 22 | 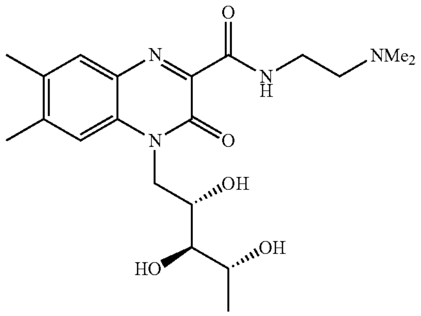 [SMILES: Cc1cc2nc(C(=O)NCCN(C)C)c(=O)n(C[C@H](O)[C@H](O)[C@@H](C)O)c2cc1C] | Compound 59 |
| 23 | 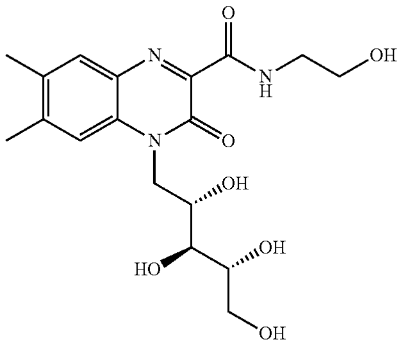 [SMILES: Cc1cc2nc(C(=O)NCCO)c(=O)n(C[C@H](O)[C@H](O)[C@H](O)CO)c2cc1C] | Compound 61 |
| 24 | 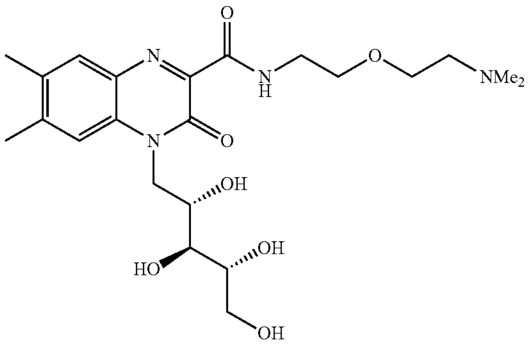 [SMILES: Cc1cc2nc(C(=O)NCCOCCN(C)C)c(=O)n(C[C@H](O)[C@H](O)[C@H](O)CO)c2cc1C] | Compound 63 |
| 25 | 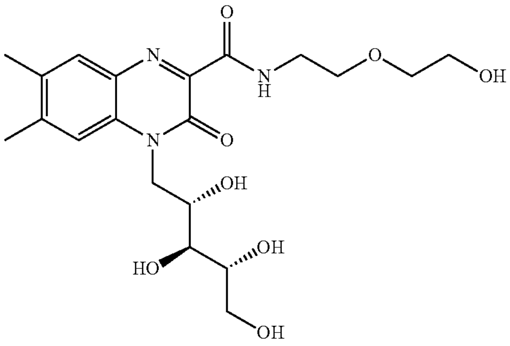 [SMILES: Cc1cc2nc(C(=O)NCCOCCO)c(=O)n(C[C@H](O)[C@H](O)[C@H](O)CO)c2cc1C] | Compound 65 |

TABLE A-2-continued
| Example # | Compound | Name/ID # |
|---|---|---|
| 26 | 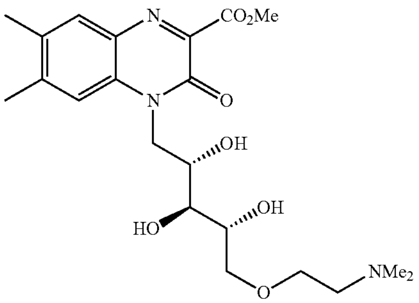 [SMILES: COC(=O)c1nc2cc(C)c(C)cc2n(C[C@H](O)[C@H](O)[C@H](O)COCCN(C)C)c1=O] | Compound 69 |
| 27 | 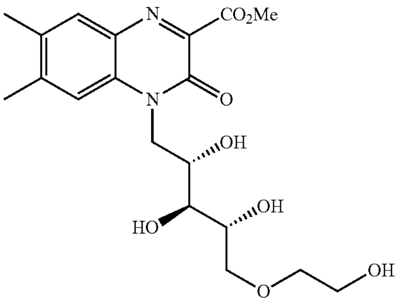 [SMILES: COC(=O)c1nc2cc(C)c(C)cc2n(C[C@H](O)[C@H](O)[C@H](O)COCCO)c1=O] | Compound 67 |
| 28 | 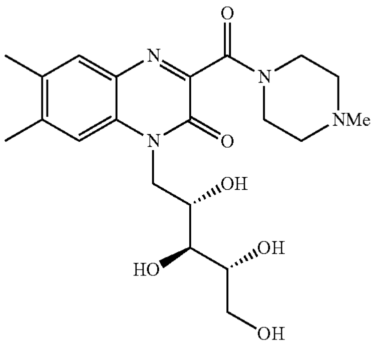 [SMILES: Cc1cc2nc(C(=O)N3CCN(C)CC3)c(=O)n(C[C@H](O)[C@H](O)[C@H](O)CO)c2cc1C] | Compound 71 |
| 29 | 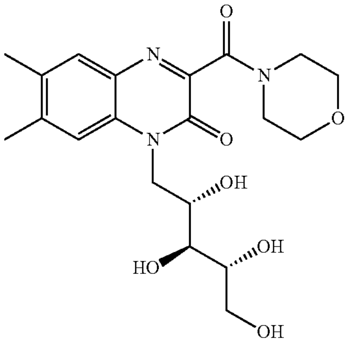 [SMILES: Cc1cc2nc(C(=O)N3CCOCC3)c(=O)n(C[C@H](O)[C@H](O)[C@H](O)CO)c2cc1C] | Compound 73 |

TABLE A-2-continued
| Example # | Compound | Name/ID # |
| --- | --- | --- |
| 30 | 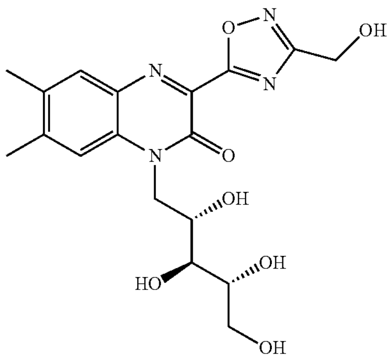 [SMILES: Cc1cc2nc(-c3nc(CO)no3)c(=O)n(C[C@H](O)[C@H](O)[C@H](O)CO)c2cc1C] | Compound 75 |
| 31 | 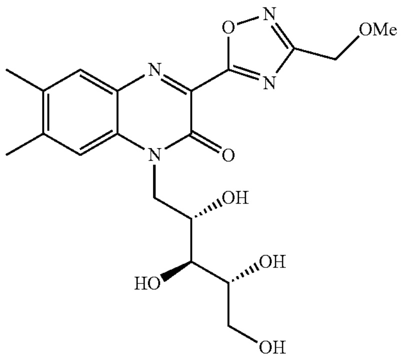 [SMILES: COCc1noc(-c2nc3cc(C)c(C)cc3n(C[C@H](O)[C@H](O)[C@H](O)CO)c2=O)n1] | Compound 79 |
| 32 | 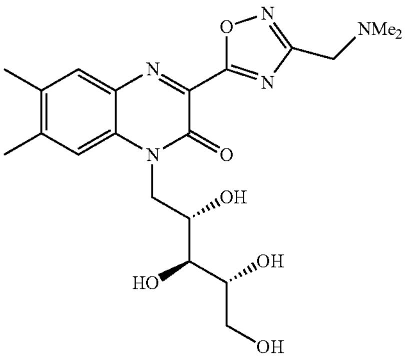 [SMILES: Cc1cc2nc(-c3nc(CN(C)C)no3)c(=O)n(C[C@H](O)[C@H](O)[C@H](O)CO)c2cc1C] | Compound 78 |
| 33 | 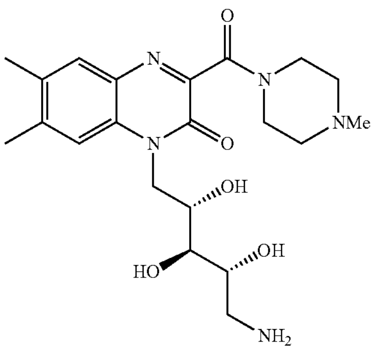 [SMILES: Cc1cc2nc(C(=O)N3CCN(C)CC3)c(=O)n(C[C@H](O)[C@H](O)[C@H](O)CN)c2cc1C] | Compound 83 |

TABLE A-2-continued
| Example # | Compound | Name/ID # |
|---|---|---|
| 34 | 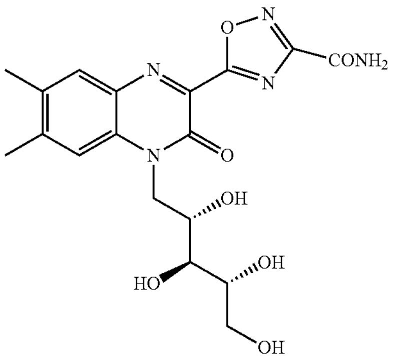 [SMILES: Cc1cc2nc(-c3nc(C(N)=O)no3)c(=O)n(C[C@H](O)[C@H](O)[C@H](O)CO)c2cc1C] | Compound 84 |
| 35 | 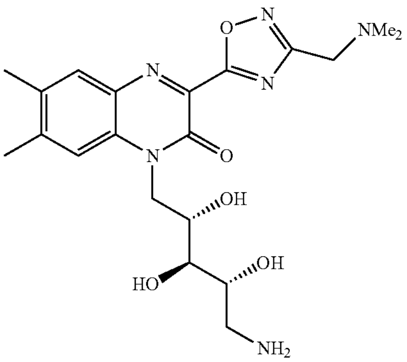 [SMILES: Cc1cc2nc(-c3nc(CN(C)C)no3)c(=O)n(C[C@H](O)[C@H](O)[C@H](O)CN)c2cc1C] | Compound 92 |
| 36 | 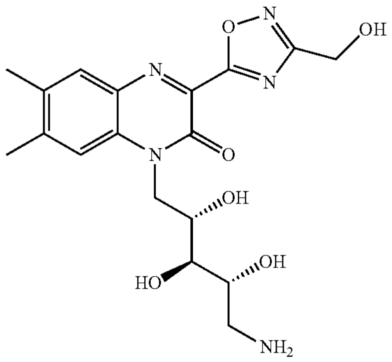 [SMILES: Cc1cc2nc(-c3nc(CO)no3)c(=O)n(C[C@H](O)[C@H](O)[C@H](O)CN)c2cc1C] | Compound 97 |
| 37 | 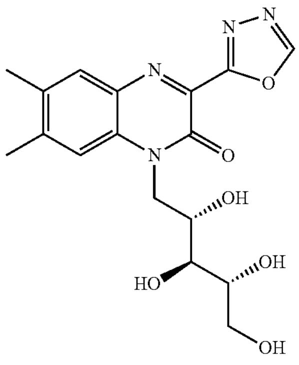 [SMILES: Cc1cc2nc(-c3nnco3)c(=O)n(C[C@H](O)[C@H](O)[C@H](O)CO)c2cc1C] | Compound 99 |

TABLE A-2-continued
| Example # | Compound | Name/ID # |
|---|---|---|
| 38 | 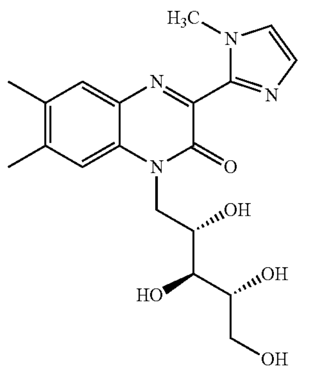 [SMILES: Cc1cc2nc(-c3nccn3C)c(=O)n(C[C@H](O)[C@H](O)[C@H](O)CO)c2cc1C] | Compound 104 |
| 39 | 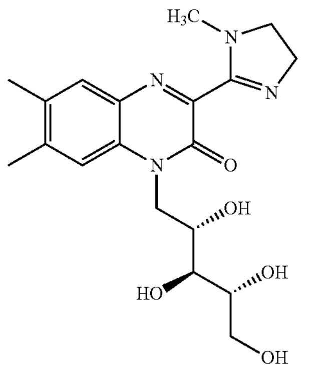 [SMILES: Cc1cc2nc(C3=NCCN3C)c(=O)n(C[C@H](O)[C@H](O)[C@H](O)CO)c2cc1C] | Compound 105 |
| 40 | 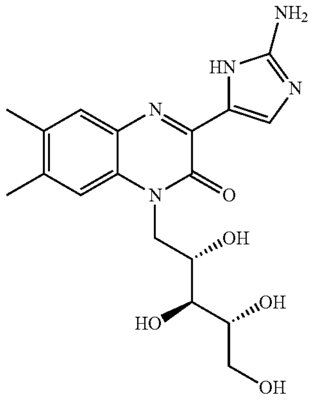 [SMILES: Cc1cc2nc(-c3cnc(N)[nH]3)c(=O)n(C[C@H](O)[C@H](O)[C@H](O)CO)c2cc1C] | Compound 110 |
| 41 | 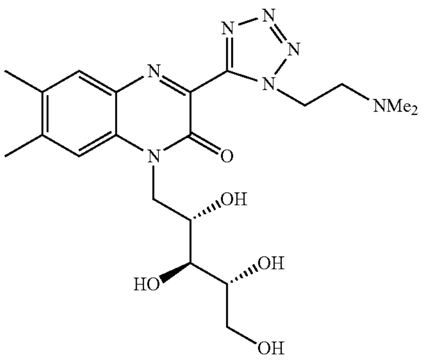 [SMILES: Cc1cc2nc(-c3nnnn3CCN(C)C)c(=O)n(C[C@H](O)[C@H](O)[C@H](O)CO)c2cc1C] | Compound 113 |

TABLE A-2-continued
| Example # | Compound | Name/ID # |
|---|---|---|
| 42 | 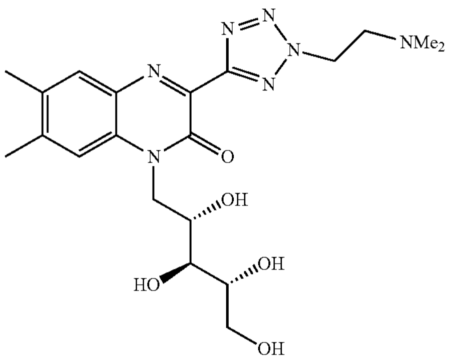 [SMILES: Cc1cc2nc(-c3nnn(CCN(C)C)n3)c(=O)n(C[C@H](O)[C@H](O)[C@H](O)CO)c2cc1C] | Compound 116 |
| 43 | 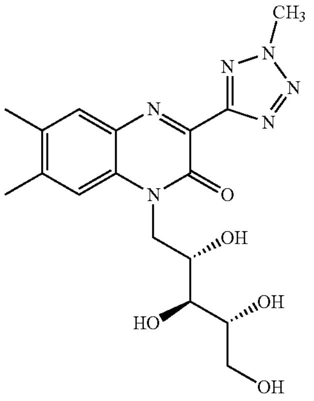 [SMILES: Cc1cc2nc(-c3nnn(C)n3)c(=O)n(C[C@H](O)[C@H](O)[C@H](O)CO)c2cc1C] | Compound 117 |
| 44 | 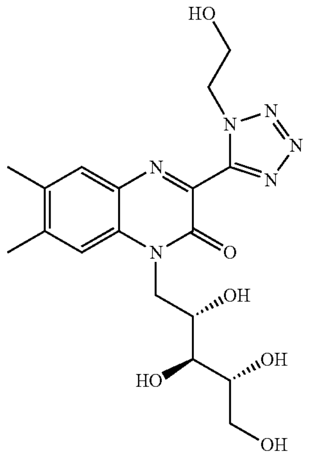 [SMILES: Cc1cc2nc(-c3nnnn3CCO)c(=O)n(C[C@H](O)[C@H](O)[C@H](O)CO)c2cc1C] | Compound 121 |
| 45 | 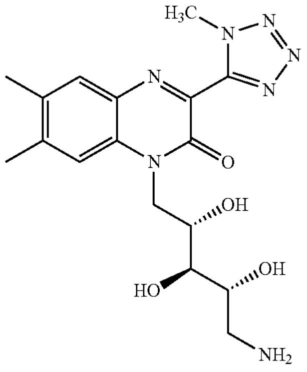 [SMILES: Cc1cc2nc(-c3nnnn3C)c(=O)n(C[C@H](O)[C@H](O)[C@H](O)CN)c2cc1C] | Compound 129 |

TABLE A-2-continued
| Example # | Compound | Name/ID # |
| --- | --- | --- |
| 46 | 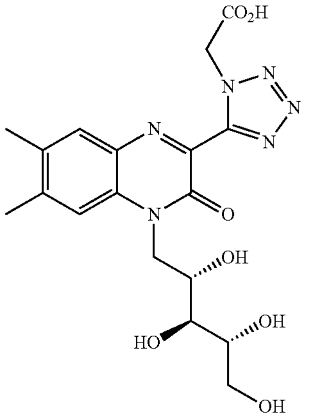 [SMILES: Cc1cc2nc(-c3nnnn3CC(=O)O)c(=O)n(C[C@H](O)[C@H](O)[C@H](O)CO)c2cc1C] | Compound 132 |
| 47 | 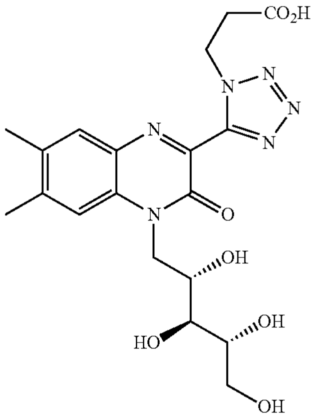 [SMILES: Cc1cc2nc(-c3nnnn3CCC(=O)O)c(=O)n(C[C@H](O)[C@H](O)[C@H](O)CO)c2cc1C] | Compound 135 |
| 48 | 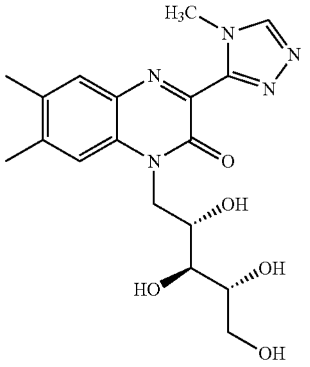 [SMILES: Cc1cc2nc(-c3nncn3C)c(=O)n(C[C@H](O)[C@H](O)[C@H](O)CO)c2cc1C] | Compound 137 |

TABLE A-2-continued
| Example # | Compound | Name/ID # |
| --- | --- | --- |
| 49 | 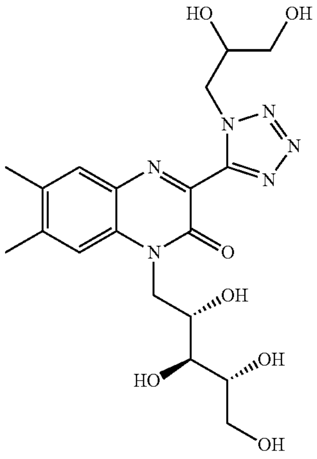 [SMILES: Cc1cc2nc(-c3nnnn3CC(O)CO)c(=O)n(C[C@H](O)[C@H](O)[C@H](O)CO)c2cc1C] | Compound 141 |
| 50 | 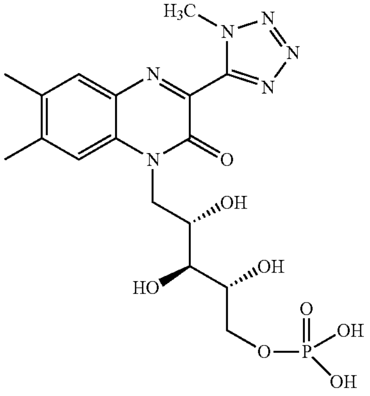 [SMILES: Cc1cc2nc(-c3nnnn3C)c(=O)n(C[C@H](O)[C@H](O)[C@H](O)COP(=O)(O)O)c2cc1C] | Compound 143 |
| 51 | 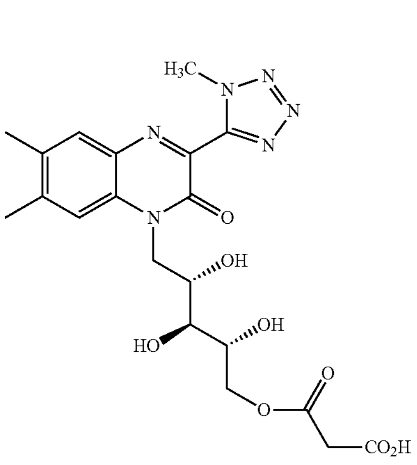 [SMILES: Cc1cc2nc(-c3nnnn3C)c(=O)n(C[C@H](O)[C@H](O)[C@H](O)COC(=O)CC(=O)O)c2cc1C] | Compound 145 |

TABLE A-2-continued
| Example # | Compound | Name/ID # |
| --- | --- | --- |
| 52 | 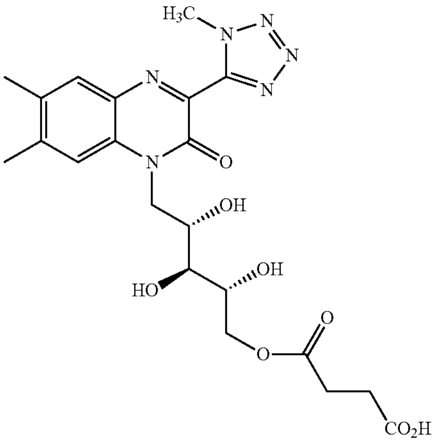 [SMILES: Cc1cc2nc(-c3nnnn3C)c(=O)n(C[C@H](O)[C@H](O)[C@H](O)COC(=O)CCC(=O)O)c2cc1C] | Compound 147 |
| 53 | 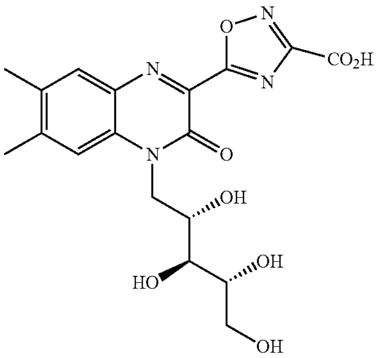 [SMILES: Cc1cc2nc(-c3nc(C(=O)O)no3)c(=O)n(C[C@H](O)[C@H](O)[C@H](O)CO)c2cc1C] | Compound 150 |
| 54 | 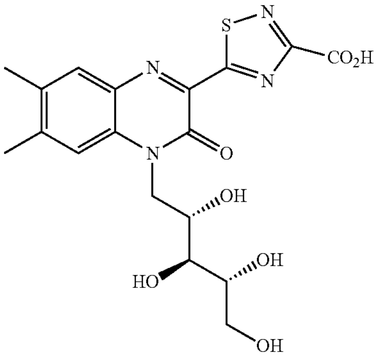 [SMILES: Cc1cc2nc(-c3nc(C(=O)O)ns3)c(=O)n(C[C@H](O)[C@H](O)[C@H](O)CO)c2cc1C] | Compound 153 |
| 55 | 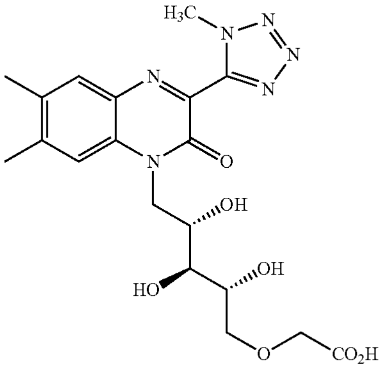 [SMILES: Cc1cc2nc(-c3nnnn3C)c(=O)n(C[C@H](O)[C@H](O)[C@H](O)COCC(=O)O)c2cc1C] | Compound 158 |

TABLE A-2-continued
| Example # | Compound | Name/ID # |
|---|---|---|
| 56 | 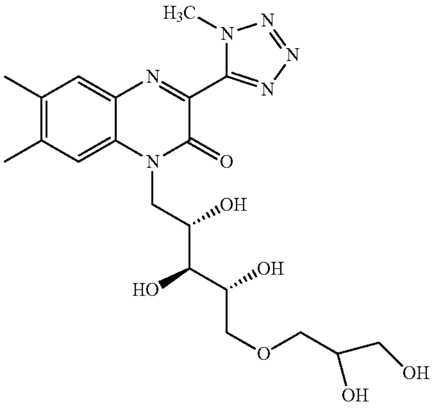 [SMILES: Cc1cc2nc(-c3nnnn3C)c(=O)n(C[C@H](O)[C@H](O)[C@H](O)COCC(O)CO)c2cc1C] | Compound 160 |
| 57 | 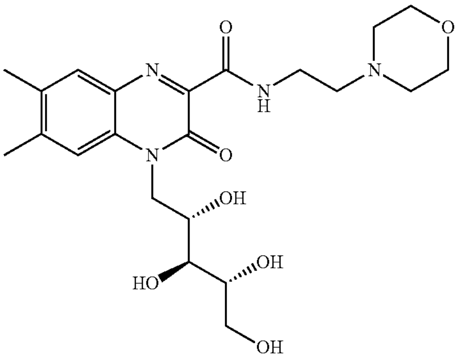 [SMILES: Cc1cc2nc(C(=O)NCCN3CCOCC3)c(=O)n(C[C@H](O)[C@H](O)[C@H](O)CO)c2cc1C] | Compound 161 |
| 58 | 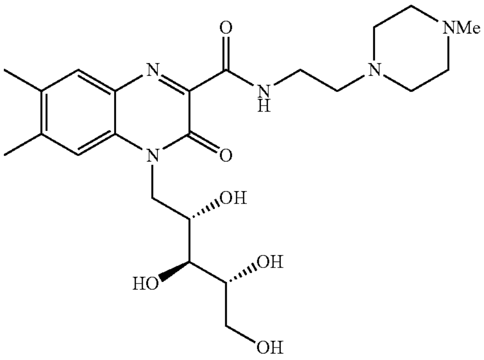 [SMILES: Cc1cc2nc(C(=O)NCCN3CCN(C)CC3)c(=O)n(C[C@H](O)[C@H](O)[C@H](O)CO)c2cc1C] | Compound 162 |
| 59 | 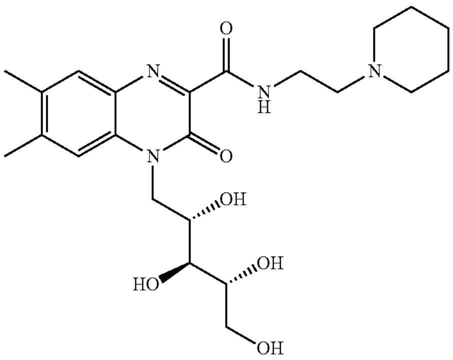 [SMILES: Cc1cc2nc(C(=O)NCCN3CCCCC3)c(=O)n(C[C@H](O)[C@H](O)[C@H](O)CO)c2cc1C] | Compound 163 |

TABLE A-2-continued
| Example # | Compound | Name/ID # |
|---|---|---|
| 60 | 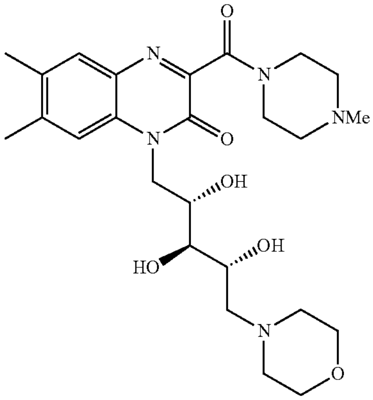 [SMILES: Cc1cc2nc(C(=O)N3CCN(C)CC3)c(=O)n(C[C@H](O)[C@H](O)[C@H](O)CN3CCOCC3)c2cc1C] | Compound 165 |
| 61 | 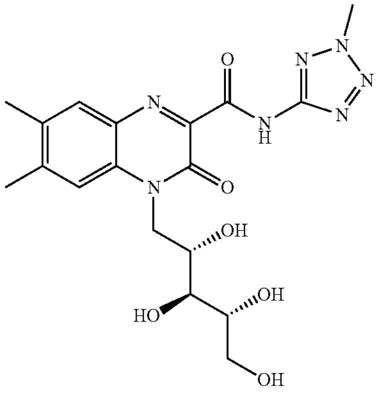 [SMILES: Cc1cc2nc(C(=O)Nc3nnn(C)n3)c(=O)n(C[C@H](O)[C@H](O)[C@H](O)CO)c2cc1C] | Compound 167 |
| 62 | 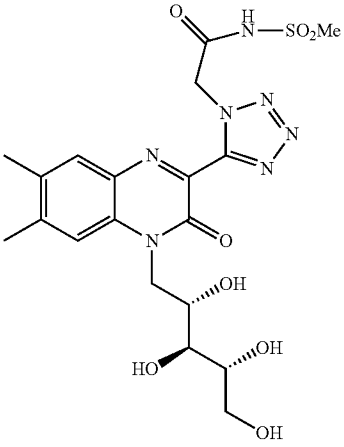 [SMILES: Cc1cc2nc(-c3nnnn3CC(=O)NS(C)(=O)=O)c(=O)n(C[C@H](O)[C@H](O)[C@H](O)CO)c2cc1C] | Compound 170 |

TABLE A-2-continued
| Example # | Compound | Name/ID # |
| --- | --- | --- |
| 63 | 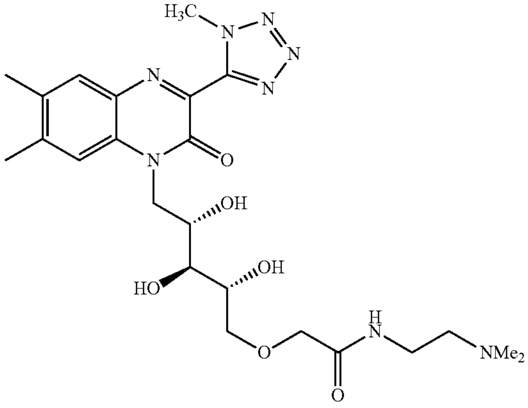 [SMILES: Cc1cc2nc(-c3nnnn3C)c(=O)n(C[C@H](O)[C@H](O)[C@H](O)COCC(=O)NCCN(C)C)c2cc1C] | Compound 171 |
| 64 | 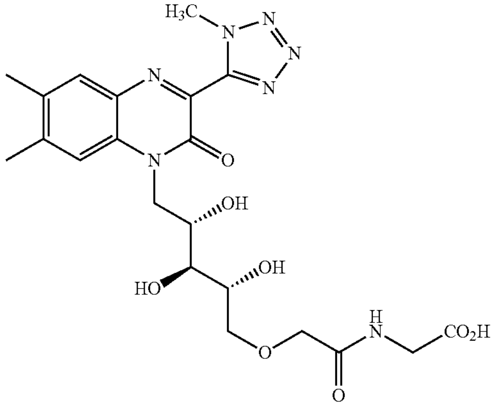 [SMILES: Cc1cc2nc(-c3nnnn3C)c(=O)n(C[C@H](O)[C@H](O)[C@H](O)COCC(=O)NCC(=O)O)c2cc1C] | Compound 173 |
| 65 | 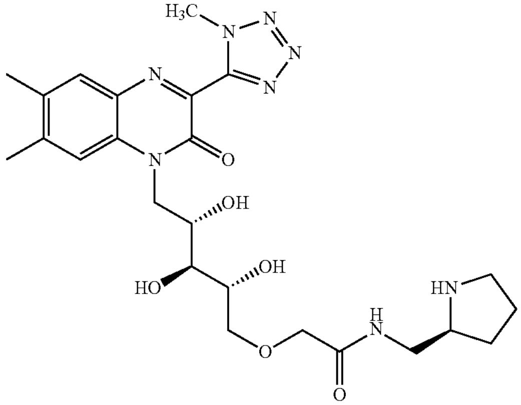 [SMILES: Cc1cc2nc(-c3nnnn3C)c(=O)n(C[C@H](O)[C@H](O)[C@H](O)COCC(=O)NC[C@@H]3CCCN3)c2cc1C] | Compound 175 |

TABLE A-2-continued
| Example # | Compound | Name/ID # |
| --- | --- | --- |
| 66 | 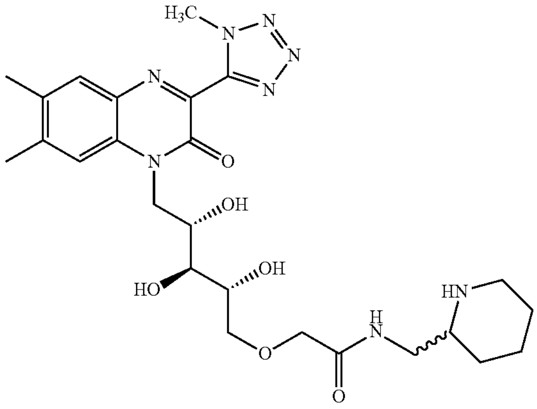 [SMILES: Cc1cc2nc(-c3nnnn3C)c(=O)n(C[C@H](O)[C@H](O)[C@H](O)COCC(=O)NCC3CCCCN3)c2cc1C] | Compound 177 |
| 67 | 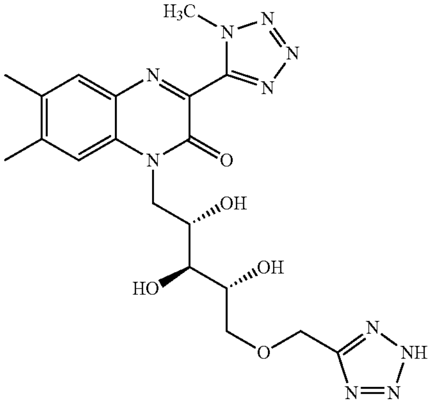 [SMILES: Cc1cc2nc(-c3nnnn3C)c(=O)n(C[C@H](O)[C@H](O)[C@H](O)COCc3nn[nH]n3)c2cc1C] | Compound 180 |
| 68 | 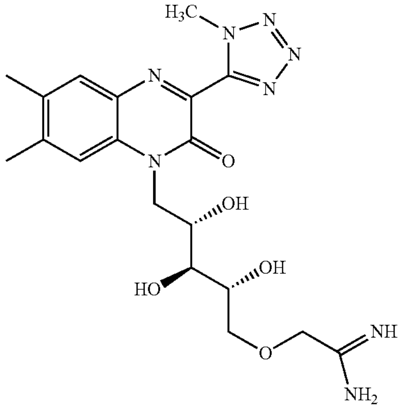 [SMILES: Cc1cc2nc(-c3nnnn3C)c(=O)n(C[C@H](O)[C@H](O)[C@H](O)COCC(=N)N)c2cc1C] | Compound 181 |

TABLE A-2-continued

| Example # | Compound | Name/ID # |
|---|---|---|
| 69 | 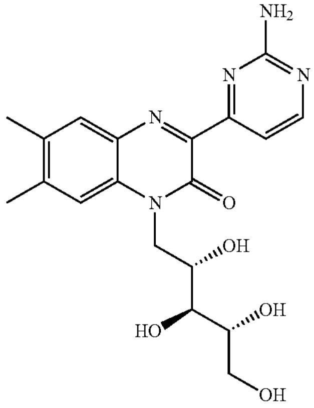 [SMILES: Cc1cc2nc(-c3ccnc(N)n3)c(=O)n(C[C@H](O)[C@H](O)[C@H](O)CO)c2cc1C] | Compound 183 |

or a pharmaceutically acceptable salt thereof.

The specification as-filed concludes with 95 claims. For ease of exposition, certain variable definitions refer to one or more specific claim numbers, and as such, it is understood that the entire subject matter of each claim referenced is incorporated by reference in its entirety into the portion of the disclosure, in which it is referenced. For the avoidance of doubt and as a non-limiting example, use of a phrase, such as "Y is as defined in claims 52-53" is intended to represent the short-hand recitation for the following set of definitions:

Y is selected from tetrazolyl, triazolyl, oxadiazolyl, and oxazolyl, wherein one or more of the heteroaryl ring carbon atoms are optionally substituted with from 1-2 independently selected $R^c$; and one of the heteroaryl ring nitrogen atoms is optionally substituted with $R^d$; and/or Y is selected from the group consisting of:

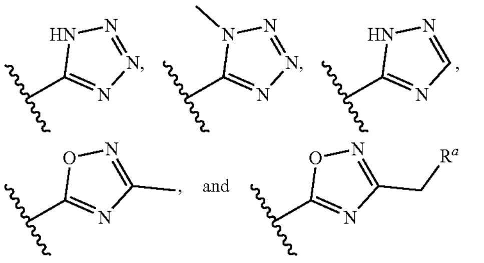

(e.g., $R^a$ can be selected from —OH, —OMe, and —$NMe_2$).

Pharmaceutical Compositions and Administration

General

In some embodiments, a chemical entity (e.g., a compound or a pharmaceutically acceptable salt and/or hydrate and/or prodrug of the compound) that generates cross-linking in the cornea in response to exposure to photoactivating light is administered as a pharmaceutical composition that includes the chemical entity and one or more pharmaceutically acceptable excipients, and optionally one or more additional therapeutic agents as described herein.

In some embodiments, the pharmaceutical composition is as described in U.S. 2018/0236077 which is incorporated herein by reference in its entirety.

In some embodiments, the chemical entities described herein can be administered in combination with one or more delivery agents. Delivery agents include, but are not limited to, anesthetic agents, analgesic agents, tonicity agents, shear-thinning, viscosity-increasing agents, surfactants (e.g., ionic surfactants or non-ionic surfactants), or chelating agents. Non-limiting examples of anesthetic agents may include pilocarpine, proparacaine, tetracaine, or oxybuprocaine. Non-limiting examples of analgesic agents include menthol, benzyl alcohol, or phenylethyl alcohol. Non-limiting examples of tonicity agents include glycerin, propylene glycol, polyethylene glycol (PEG)-8, ethanol, benzyl alcohol, phenylethyl alcohol, or triacetin. Non-limiting examples of shear-thinning, viscosity-increasing agents include carbomer, polycarbophil, gellan gum, xanthan gum, carboxymethyl cellulose sodium, or sodium hyaluronate. Non-limiting examples of ionic surfactants include benzalkonium chloride. Non-limiting examples of non-ionic surfactants include poloxamer 407, tetronic 1107, tetronic 1304, polysorbate 80, polyethylene glycol (PEG)-40 hydrogenated castor oil, lecithin, polysorbate 60, polyethylene glycol (PEG)-35 castor oil, tocophersolan (TPGS), nonoxynol-9, or tyloxapol. Non-limiting examples of chelating agents include ethylenediaminetetraacetic acid (EDTA) or citrate.

In some embodiments, the chemical entities described herein can be administered in combination with one or more preparatory formulations to an epithelium of a cornea. In certain embodiments, the preparatory formulations increase a permeability of the epithelium of the cornea. As non-limiting examples of the foregoing, preparatory formulations can include one or more of: zinc metalloproteinase, copper metalloproteinase, papain, bromelain, actinidin, ficain, N-acetylcysteine, ambroxol, carbocisteine, or erdosteine. In certain embodiments, the one or more preparatory formulations can further include one or more anesthetic agents (e.g., pilocarpine, proparacaine, tetracaine, or oxybuprocaine).

In some embodiments, the chemical entities described herein can be administered in combination with one or more enhancement formulations which are configured to one or more of: (i) remove the one or more therapeutic formulations from the epithelium of the cornea without diluting the one or more therapeutic agents delivered to the stroma; (ii) close tight junctions of the epithelium to control hydration of the cornea; (iii) promote oxidation for the one or more therapeutic agents delivered to the stroma; or (iv) further deliver the one or more therapeutic formulations from the epithelium to the stroma. As non-limiting examples of the foregoing, the enhancement formulations may include one or more of: divalent metal salts, one or more pro-oxidants, or one or more glycosaminoglycans.

In some embodiments, the chemical entities described herein can be administered in combination with one or more post-treatment formulations in response to applying the one or more enhancement formulations, and the one or more post-treatment formulations may include at least one of one or more divalent metal salts, one or more viscosity agents, one or more glycosaminoglycans, or one or more antibiotics.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy,* 22$^{nd}$ Edition (Pharmaceutical Press, London, U K. 2012).

Routes of Administration and Composition Components

Compositions can be prepared as liquid solutions or suspensions; solid forms suitable for use to prepare solutions or suspensions upon the addition of a liquid prior to administration can also be prepared; and the preparations can also be emulsified. The preparation of such formulations will be known to those of skill in the art in light of the present disclosure.

Compositions can be administered topically (e.g., intaocularly as a topical instillation).

The pharmaceutical forms suitable for intraocular use include sterile aqueous solutions (e.g., buffers, e.g., citrate buffers; e.g., ophthalmic solutions, e.g., 20% dextran ophthalmic solution) or dispersions; formulations including sesame oil, peanut oil, or aqueous propylene glycol; and sterile powders for the extemporaneous preparation of sterile solutions or dispersions. In general, the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the compositions can be brought about by the use in the compositions of agents delaying absorption, for example, aluminum monostearate and gelatin.

Sterile solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile solutions, the preferred methods of preparation are vacuum-drying and freeze-drying techniques, which yield a powder of the active ingredient, plus any additional desired ingredient from a previously sterile-filtered solution thereof.

In certain embodiments the excipients are sterile and generally free of undesirable matter. These compositions can be sterilized by conventional, well-known sterilization techniques. For various oral dosage form excipients such as tablets and capsules, sterility is not required. The USP/NF standard is usually sufficient.

Ocular compositions can include, without limitation, one or more of any of the following: dextran, viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In certain embodiments, the compounds and compositions disclosed herein can be applied to a cornea of an eye using an applicator. Non-limiting examples of applicators can include eyedropper or syringe.

In certain embodiments, the compounds and compositions described herein can be administered in a formulation that allows the compound of composition to pass through the corneal epithelium to underlying regions in the corneal stroma. In other embodiments, the corneal epithelium may be removed or otherwise incised to allow the compound or compositions provided herein to be applied more directly to the underlying tissue.

Accordingly, in some embodiments the compounds and compositions described herein are directly applied to the cornea (e.g., without removing or otherwise incising corneal epithelium). In other embodiments, the corneal epithelium is be removed or otherwise incised before the compounds and compositions described herein are applied.

Dosages

The dosages may be varied depending on the requirement of the patient, the severity of the condition being treated and the particular compound being employed. Proper dosage for a particular situation can be determined by one skilled in the medical arts. In some cases, the total dosage may be divided and administered in portions throughout the procedure or by means providing continuous delivery.

In some embodiments, the composition is a solution (e.g., buffers, e.g., citrate buffers; e.g., ophthalmic solutions, e.g., 20% dextran ophthalmic solution) that comprises from 0.01-100 mg/mL of a chemical entity described herein (e.g., from 0.02-50 mg/mL, from 0.04-25 mg/mL, from 0.08-12.5 mg/mL, from 0.16-6.25 mg/mL, from 0.2-5 mg/mL). In certain embodiments of the foregoing, a unit dosage is from 0.001-1 mL (e.g., from 0.002-0.5 mL, from 0.010-0.25 mL, e.g., from 0.020-0.1 mL).

In some embodiments, the composition is a solution (e.g., buffers, e.g., citrate buffers; e.g., ophthalmic solutions, e.g., 20% dextran ophthalmic solution) that comprises from 0.001%-20% of a chemical entity described herein (e.g., from 0.002%-10%, from 0.004%-5%, from 0.008%-2.5%). In certain embodiments of the foregoing, a unit dosage is from 0.001-1 mL (e.g., from 0.002-0.5 mL, from 0.010-0.25 mL, e.g., from 0.020-0.2 mL).

Regimens

The foregoing dosages can be administered periodically for a specific duration of time. In some embodiments, a unit dosage can be administered every 1-1200 seconds (e.g., every 2-300 seconds, every 2-150 seconds, every 5-150 seconds, every 5-100 seconds, every 5-10 seconds, every 10-150 seconds, every 50-150 seconds). In certain embodiments of the foregoing, the dosages are administered over a period of from 1-1200 minutes (e.g., from 1-600 minutes, from 5-120 minutes, from 10-120 minutes).

Methods of Treatment

General

This disclosure features methods for treating a subject (e.g., a human) having a disease, disorder, or condition in which abnormal shaping of the cornea (e.g., thinning of the cornea, e.g., bilateral thinning of the cornea, e.g., bilateral thinning of the central, paracentral, or peripheral cornea; or steepening (e.g., bulging) of the cornea) contributes to the pathology and/or symptoms and/or progression of the disease, disorder, or condition. In certain embodiments, the methods described herein can include or further include treating one or more conditions associated, co-morbid or sequela with any one or more of the conditions described herein.

In some embodiments, the method further comprises identifying the subject.

In certain embodiments, the chemical entities described herein provide refractive correction to the cornea (e.g., by imparting mechanical stiffness). In certain embodiments, the chemical entities described herein strengthen and stabilize the structure of the cornea. In certain embodiments, the chemical entities described herein can be used for vision correction.

Method

In some embodiments, the method comprises administering a compound disclosed herein or a pharmaceutical composition thereof to a cornea of an eye in a subject in need thereof; and applying an electromagnetic radiation (e.g., a light) to the cornea, thereby generating cross-linking in the cornea.

In certain embodiments of the foregoing, the method comprises administering a compound disclosed herein or a pharmaceutical composition thereof to the stroma of the cornea of a subject in need thereof.

In certain embodiments, the compound disclosed herein, or a pharmaceutical composition thereof is administered to the cornea without removing corneal epithelial cells.

In certain embodiments, the method further comprises increasing or decreasing the concentration of $O_2$ at the cornea during irradiation.

In certain embodiments, the method further comprises administering to the cornea one or more delivery agents, wherein the one or more delivery agents are as described elsewhere herein.

In certain embodiments, the method further comprises administering to a subject in need thereof (e.g., the cornea of a subject in need thereof) one or more preparatory formulations that increases a permeability of the epithelium of the cornea, wherein the one or more preparatory formulations are as described elsewhere herein.

In certain embodiments, the method further comprises administering to the epithelium of the cornea one or more enhancement formulations, wherein the one or more enhancement formulations configured to one or more of:

(i) remove the one or more therapeutic formulations from the epithelium of the cornea without diluting the one or more therapeutic agents delivered to the stroma;
(ii) close tight junctions of the epithelium to control hydration of the cornea;
(iii) promote oxidation for the one or more therapeutic agents delivered to the stroma; or
(iv) further deliver the one or more therapeutic formulations from the epithelium to the stroma, wherein the one or more enhancement formulations are as described elsewhere herein.

In certain embodiments, the method further comprises administering to the subject in need thereof one or more post-treatment formulations in response to applying one or more enhancement formulations, wherein the one or more enhancement formulations are as described elsewhere herein.

Electromagnetic Radiation

In some embodiments, the electromagnetic radiation applied to the cornea of an eye in a subject in need thereof is a light radiation. In certain embodiments, the light radiation has appropriate wavelength, energy, and duration, to cause a compound described herein to undergo a reaction (e.g., photoinduced electron transfer and/or fragmentation), thereby allowing cross-linking.

In some embodiments, wavelength of light can be chosen so that it corresponds to or encompasses the absorption of the compounds described herein, and reaches the area of the tissue that has been contacted with the compounds described herein, e.g., penetrates into the region where the compound described herein presents.

In some embodiments, the energy of the electromagnetic radiation applied is less than 2000 $J/cm^2$. In certain embodiments of the foregoing, the electromagnetic energy applied is between 1 and 500 $J/cm^2$. The total dose of energy absorbed in the cornea can be described as an effective dose, which is an amount of energy absorbed through an area of the corneal epithelium. For example, the effective dose for a region of the corneal surface can be, for example, between 5 $J/cm^2$ and 20 $J/cm^2$ or 30 $J/cm^2$ (e.g., 5.4 $J/cm^2$).

In some embodiments, the electromagnetic radiation is applied at an irradiance of about 1-100 $mW/cm^2$. In certain embodiments, the electromagnetic radiation is applied at an irradiance of about 1-5 $mW/cm^2$ (e.g., 3 $mW/cm^2$).

In some embodiments, the electromagnetic radiation has wavelengths within the visible, infrared, or ultraviolet spectra. In some embodiments, the electromagnetic radiation includes radiations of wavelengths from about 300 nm to about 800 nm (e.g., from 300 nm to 700 nm). In certain embodiments, the electromagnetic radiation includes ultraviolet A (UVA) light (e.g., of wavelength between 350 and 380 nm e.g., 360-370 nm, e.g., 365 nm). In certain embodiments, the electromagnetic radiation includes a visible wavelength (e.g., of wavelength between 400 nm and 550 nm, e.g., approximately 452 nm). In some embodiments, the electromagnetic radiation is laser radiation. In certain embodiments, the laser radiation is applied at an average power of 1-100 mW.

In some embodiments, the duration of radiation is between 30 seconds to 1 hour. In certain embodiments, the duration of irradiation is between 1 minute to 1 hour (e.g., 30 minutes).

In some embodiments, the cornea of an eye can be more broadly treated with a compound or composition described herein; and the radiation can be selectively directed to regions of the treated cornea according to a particular pattern.

In certain embodiments, the electromagnetic radiation may be directed and focused with one or more mirrors or lenses to a particular pattern on the cornea (e.g., at particular focal planes within the cornea, e.g., at particular depths in the underlying region wherein cross-linking activity is desired).

In some embodiments, specific regimes of electromagnetic radiation can be modulated to achieve a desired degree of cross-linking in the selected regions of the cornea. For example, electromagnetic radiation may be delivered according to any combination of: wavelength, bandwidth, intensity, power, location, depth of penetration, and/or duration of treatment (the duration of the exposure cycle, the dark cycle, and the ratio of the exposure cycle to the dark cycle duration).

In some embodiments, the electromagnetic irradiation is delivered using a system that comprises a digital micromirror device (DMD) to modulate the application of electromagnetic radiation spatially and temporally. In certain embodiments of the foregoing, light is projected in a precise spatial pattern that is created by microscopically small mirrors laid out in a matrix on a semiconductor chip. Each mirror represents one or more pixels in the pattern of projected light. With the DMD one can perform topography guided cross-linking. The control of the DMD according to topography may employ several different spatial and temporal irradiance and dose profiles. These spatial and temporal dose profiles may be created using continuous wave illumination but may also be modulated via pulsed illumination by pulsing the illumination source under varying frequency and duty cycle regimes as described above. Alternatively, the DMD can modulate different frequencies and duty cycles on a pixel by pixel basis to give ultimate flexibility using continuous wave illumination. Or alternatively, both pulsed illumination and modulated DMD frequency and duty cycle combinations may be combined. This allows for specific amounts of spatially determined corneal cross-linking. This spatially determined cross-linking may be combined with dosimetry, interferometry, optical coherence tomography (OCT), corneal topography, etc., for pre-treatment planning and/or real-time monitoring and modulation of corneal cross-linking during treatment. Additionally, pre-clinical patient information may be combined with finite element biomechanical computer modeling to create patient specific pre-treatment plans.

In some embodiments, the electromagnetic radiation is delivered using multiphoton excitation microscopy. In particular, rather than delivering a single photon of a particular wavelength to the cornea, multiple photons of longer wavelengths, i.e., lower energy, are delivered that combine to initiate the cross-linking. Advantageously, longer wavelengths are scattered within the cornea to a lesser degree than shorter wavelengths, which allows longer wavelengths of light to penetrate the cornea more efficiently than shorter wavelength light. Shielding effects of incident irradiation at deeper depths within the cornea are also reduced over conventional short wavelength illumination since the absorption of the light by the photosensitizer is much less at the longer wavelengths. This allows for enhanced control over depth specific cross-linking. For example, in some embodiments, two photons may be employed, where each photon carries approximately half the energy necessary to excite the molecules of the compounds or compositions disclosed herein to generate the photochemical kinetic reactions described further below. When a compound disclosed herein simultaneously absorbs both photons, it absorbs enough energy to release reactive radicals in the corneal tissue. Embodiments may also utilize lower energy photons such that a molecule of a compound disclosed herein must simultaneously absorb, for example, three, four, or five, photons to release a reactive radical. The probability of the near-simultaneous absorption of multiple photons is low, so a high flux of excitation photons may be required, and the high flux may be delivered through a femtosecond laser.

In some embodiments, the electromagnetic radiation is applied continuously (continuous wave (CW)) or as pulsed radiation. In certain embodiments, this selection has an effect on the amount, the rate, and the extent of cross-linking. In certain embodiments, when the electromagnetic radiation light is applied as pulsed radiation, the duration of the exposure cycle, the dark cycle, and the ratio of the exposure cycle to the dark cycle duration have an effect on the resulting corneal stiffening. Pulsed radiation can be used to create greater or lesser stiffening of corneal tissue than may be achieved with continuous wave illumination for the same amount or dose of energy delivered. Light pulses of suitable length and frequency may be used to achieve more optimal chemical amplification. For pulsed light treatment, the on/off duty cycle may be between approximately 1000/1 to approximately 1/1000; the irradiance may be between approximately 0.1 $mW/cm^2$ to approximately 1000 $mW/cm^2$ average irradiance, and the pulse rate may be between approximately 0.01 HZ to approximately 1000 Hz or between approximately 1000 Hz to approximately 100,000 Hz.

In some embodiments, pulsed radiation can be delivered by employing a DMD, electronically turning the light source 110 on and off, and/or using a mechanical or optoelectronic (e.g., Pockels cells) shutter or mechanical chopper or rotating aperture. Because of the pixel specific modulation capabilities of the DMD and the subsequent stiffness impartment based on the modulated frequency, duty cycle, irradiance and dose delivered to the cornea, complex biomechanical stiffness patterns may be imparted to the cornea to allow for various amounts of refractive correction. These refractive corrections, for example, may involve combinations of myopia, hyperopia, astigmatism, irregular astigmatism, presbyopia and complex corneal refractive surface corrections because of ophthalmic conditions such as keratoconus, pellucid marginal disease, post-lasik ectasia, and other conditions of corneal biomechanical alteration/degeneration, etc. A specific advantage of the DMD system and method is that it allows for randomized asynchronous pulsed topographic patterning, creating a non-periodic and uniformly appearing illumination which eliminates the possibility for triggering photosensitive epileptic seizures or flicker vertigo for pulsed frequencies between 2 Hz and 84 Hz.

Examples of systems and methods for delivering electromagnetic radiation are described, for example, in U.S. Patent Application Publication No. 2011/0237999, filed Mar. 18, 2011 and titled "Systems and Methods for Applying and Monitoring Eye Therapy," U.S. Patent Application Publication No. 2012/0215155, filed Apr. 3, 2012 and titled "Systems and Methods for Applying and Monitoring Eye Therapy," and U.S. Patent Application Publication No. 2013/0245536, filed Mar. 15, 2013 and titled "Systems and Methods for Corneal Cross-Linking with Pulsed Light," the contents of these applications being incorporated entirely herein by reference.

Oxygen

In some embodiments, the concentration of $O_2$ is increased or decreased (e.g., increased) actively during irradiation to control the rate of cross-linking. Oxygen may be applied during the cross-linking treatments in a number of different ways. In some embodiments, a pharmaceutical composition comprising compounds described herein can be supersaturated with $O_2$. Thus, when the compound described herein is applied to the eye, a higher concentration of $O_2$ is delivered directly into the cornea with the riboflavin and affects the reactions involving $O_2$ when the riboflavin is exposed to the electromagnetic radiation. According to another approach, a steady state of $O_2$ (at a selected concentration, e.g., >21%) may be maintained at the surface of the cornea to expose the cornea to a selected amount of $O_2$ and cause $O_2$ to enter the cornea. Example systems and methods for applying oxygen during cross-linking treatments are described, for example, in U.S. Pat. No. 8,574,277, filed Oct. 21, 2010 and titled "Eye Therapy," U.S. Patent Application Publication No. 2013/0060187, filed Oct. 31, 2012 and titled "Systems and Methods for Corneal Cross-Linking with Pulsed Light," the contents of these applications being incorporated entirely herein by reference.

Accordingly, in some embodiments, the method may further include applying a selected concentration of oxygen to the eye, where the selected concentration is greater than a concentration of oxygen in atmosphere.

Indications

In some embodiments, the condition, disease or disorder is an ophthalmic disorder.

In some embodiments, the ophthalmic disorder involves reduced corneal rigidity.

Ectatic Disorder

In certain embodiments, the condition, disease or disorder is a corneal ectatic disorder. Non-limiting examples of ectatic disorders include keratoconus (e.g., keratoconus with nipple cones, oval cones, or globus cones; e.g., progressive keratoconus), keratoglobus, pellucid marginal degeneration, corneal ectasia (e.g., post-operative ectasia, e.g., post-LASIK ectasia), and Terrien's marginal degeneration.

In certain embodiments, the condition, disease or disorder is a corneal ectatic disorder developed following a refractive surgical procedure (e.g., post-operative corneal ectasis). Non-limiting examples of refractive surgical procedures include radial keratotomy (RK), photorefractive keratectomy (PRK), or laser in-situ keratomileusis (LASIK).

In certain embodiments, the condition, disease or disorder is bacterial keratitis.

Vision Conditions

In some embodiments, the disease, condition or disorder is myopia, hyperopia, astigmatism, irregular astigmatism, presbyopia.

In some embodiments, the ophthalmic disorder is cataract (e.g., nuclear, cortical, posterior, secondary, traumatic, or radiation cataract) or a lens disorder.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In some embodiments, the compound described herein can be administered in combination with one or more of additional therapeutic agents. Representative additional therapeutic agents include, but are not limited to, therapeutic agents for inflammation, cataracts, lens disorder, or ectatic disorders, including but not limited to keratoconus (e.g., keratoconus with nipple cones, oval cones, or globus cones), keratoglobus, pellucid marginal degeneration, corneal ectasia (e.g., post-operative ectasia, e.g., post-LASIK ectasia), and Terrien's marginal degeneration.

In some embodiments, the one or more additional therapeutic agents include those useful, e.g., as cross-linking agents, including those described in U.S. Patent Application Publication No. 2014/0343480, filed on May 19, 2014, which is incorporated in its entirety by reference herein. Non-limiting examples include:

riboflavin (e.g., riboflavin or riboflavin phosphate);
2,3-butandione;
folic acid;
quinoxalines (e.g., Olaquidox);
quinolines (e.g., chloroquinine, hydroxychloroquinine, and quinine);
dibucaine;
methotrexate;
menadione; and
verteporfin
and derivatives thereof.

Additional non-limiting examples of cross-linking agents can include photosensitizers such as Rose Bengal, methylene blue, and N-hydroxypyridine-2-(1H)-thione. Further non-limiting examples of cross-linking agents can also include photosensitizers such as Photofrin™, synthetic diporphyrins and dichlorins, phthalocyanines with or without metal substituents, chloroaluminum phthalocyanine with or without varying substituents, O-substituted tetraphenyl porphyrins, 3,1-meso tetrakis (o-propionamido phenyl) porphyrin, verdins, purpurins, tin and zinc derivatives of octaethylpurpurin, etiopurpurin, hydroporphyrins, bacteriochlorins of the tetra (hydroxyphenyl) porphyrin series (e.g., protoporphyrin I through protoporphyrin IX, coproporphyrins, uroporphyrins, mesoporphyrins, hematoporphyrins and sapphyrins), chlorins, chlorine6, mono-1-aspartyl derivative of chlorine6, di-1-aspartyl derivative of chlorine6, tin (IV) chlorine6, meta-tetrahydroxphenylchlorin, benzoporphyrin derivatives, benzoporphyrin monoacid derivatives, tetracyanoethylene adducts of benzoporphyrin, dimethyl acetylenedicarboxylate adducts of benzoporphyrin, Diels-Adler adducts, monoacid ring "a" derivative of benzoporphyrin, sulfonated aluminum PC, sulfonated AlPc, disulfonated, tetrasulfonated derivative, sulfonated aluminum naphthalocyanines, naphthalocyanines with or without metal substituents and with or without varying substituents, chlorophylis, bacteriochlorophyll A, anthracenediones, anthrapyrazoles, aminoanthraquinone, phenoxazine dyes, thiazines, methylene blue, phenothiazine derivatives, chalcogenapyrylium dyes, cationic selena and tellurapyrylium derivatives, ring-substituted cationic PC, pheophorbide derivative, naturally occurring porphyrins, hematoporphyrin, ALA-induced protoporphyrin IX, endogenous metabolic precursors, 5-aminolevulinic acid, benzonaphthoporphyrazines, cationic imminium salts, tetracyclines, lutetium texaphyrin, texaphyrin, tin-etio-purpurin, porphycenes, benzophenothiazinium, xanthenes, rose bengal, eosin, erythrosin, cyanines, merocyanine 540, selenium substitued cyanines, flavins, riboflavin, proflavin, quinones, anthraquinones, benzoquinones, naphthaldiimides, naphthalimides, victoria blue, toluidine blue, dianthroquinones (e.g., hypericin), fullerenes, rhodamines and photosensitive derivatives thereof.

In some embodiments, the one or more additional agents include metals (including elemental and ionic forms) (e.g., metal salts, e.g., divalent metal salts). Non-limiting examples include:

iron (e.g., iron (II), e.g., $FeSO_4$) (in certain embodiments, the iron additive may be dissolved in the citrate buffer);
copper;
manganese;
chromium;
vanadium;
aluminum;
cobalt;
mercury;
cadmium;
nickel; and
arsenic;
optionally in combination with hydrogen peroxide.

In some embodiments, the one or more additional therapeutic agents include those useful, e.g., as anesthetic agents. Non-limiting examples include: pilocarpine, proparacaine, tetracaine, or oxybuprocaine.

In some embodiments, the one or more additional therapeutic agents include those useful, e.g., as analgesic agents. Non-limiting examples include: menthol, benzyl alcohol, or phenylethyl alcohol.

In some embodiments, the one or more additional therapeutic agents include those useful, e.g., for increasing a permeability of the epithelium of the cornea. Non-limiting examples include: zinc metalloproteinase, copper metalloproteinase, papain, bromelain, actinidin, ficain, N-acetylcysteine, ambroxol, carbocisteine, or erdosteine.

In some embodiments, the one or more additional therapeutic agents include those useful, e.g., as therapeutics for cataract and/or lens disorders.

In some embodiments, the one or more additional therapeutic agents include those useful, e.g., as antibiotics.

In some embodiments, the one or more additional therapeutic agents include those useful, e.g., in gene therapy.

In some embodiments, the one or more additional therapeutic regimens include therapeutic regimens for inflammation, cataracts, lens disorder, or ectatic disorders, including but not limited to keratoconus (e.g., keratoconus with nipple cones, oval cones, or globus cones), keratoglobus, pellucid marginal degeneration, corneal ectasia (e.g., post-operative ectasia, e.g., post-LASIK ectasia), and Terrien's marginal degeneration.

In some embodiments, the one or more additional therapeutic regimens include therapeutic regimens for myopia, hyperopia, astigmatism, irregular astigmatism, and presbyopia.

In some embodiments, the one or more additional therapeutic regimens include ophthalmic surgical procedures. Non-limiting examples include:

corneal transplant surgery;
cataract surgery;
laser surgery;
keratoplasty (e.g., penetrating keratoplasty or lamellar keratoplasty);
refractive surgery (e.g., keratotomy (RK), photorefractive keratectomy (PRK), or laser in-situ keratomileusis (LASIK));
cornea reshaping; and
treatment of corneal laceration.

Additional non-limiting examples of the one or more additional therapeutic regiments include contact lens therapy, amniotic membrane therapy, LASIK therapy, and administration of antibiotics.

Compound Preparation and Biological Assays

As can be appreciated by the skilled artisan, methods of synthesizing the compounds of the formulae herein will be evident to those of ordinary skill in the art. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and RGM. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

In some embodiments, intermediates useful for preparing the compounds described herein can be prepared using the chemistries delineated in any one or more of the following schemes and non-limiting examples.

Abbreviations

| | |
|---|---|
| $Ac_2O$ | acetic anhydride |
| AcOH | acetic acid |
| AllOH | allyl alcohol |
| Aq | aqueous |
| CDI | carbonyldiimidazole |
| DCM | dichloromethane |
| DIPEA | N,N-Diisopropylethylamine |
| DMAP | 4-dimethylaminopyridine |
| DMF | dimethyformamide |
| DMFDMA | dimethylformamide dimethylacetal |
| EDCI | N-(3-Dimethylaminopropyl)-N'-ethylcarbodiimide |
| Eq | equivalent |
| EtOAc | ethyl acetate |
| HOBt or HOBT | hydroxybenzotriazole |
| HPLC | high pressure liquid chromatography |
| LC/MS or LCMS | liquid chromatography/mass spectrometry |
| MeCN or ACN | acetonitrile |
| MOM | methoxymethyl |
| Ms (e.g., in MsCl) | methanesulfonate |

-continued

| | |
|---|---|
| NMR | nuclear magnetic resonance spectroscopy |
| Py | pyridine |
| STAB | sodium triacetoxyborohydride |
| TBAF | tetrabutyl ammonium fluoride |
| TBTU | O-(Benzotriazol-1-yl)-N,N,N',N'-tetramethyluronium tetrafluoroborate |
| TEA | triethylamine |
| Tf (e.g., in $Tf_2O$) | trifluoromethanesulfonate |
| TFA | trifluoroacetic acid |
| THF | tetrahydrofuran |
| TLC | thin layer chromatography |
| TMS | trimethylsilyl |
| Tr | trityl (triphenylmethyl) |
| Ts (e.g., in TsCl) | p-Toluenesulfonate |

Compound Preparation

Compounds of the invention can be obtained according to the following procedures General Procedures General procedure 1

Step1

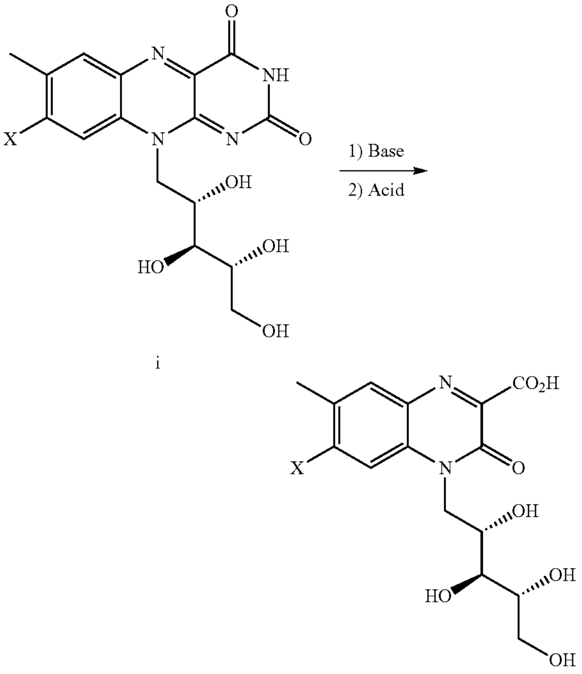

i ii

Commercially available compound (i) such as Riboflavin or Roseoflavin can be converted to compound (ii) by treatment with a base such as NaOH or KOH in an appropriate solvent such as water or ethanol, at temperatures ranging from room temperature to the boiling point of the solvent, followed by neutralization to pH6 with an acid such as acetic, citric or hydrochloric acid at temperatures ranging from 0° C. to room temperature.

Wherein X is as defined elsewhere herein.

Step2

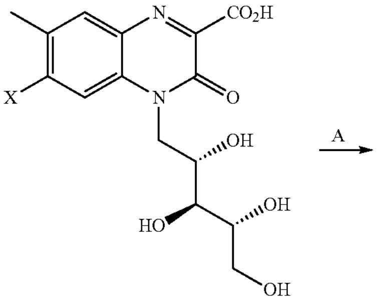

ii

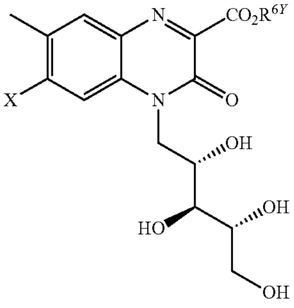

iii

Compound (ii) can be converted to compound (iii) by treatment with A and a coupling reagent such as thionyl chloride, CDI or EDCI in an appropriate solvent such as methanol, ethanol, THF or dioxane at temperatures ranging from room temperature to the boiling point of the solvent.

Wherein X and $R^{6Y}$ are as defined elsewhere herein, and A is an alcohol such as methanol, allyl alcohol or ethylene glycol.

General procedure 2

Step1

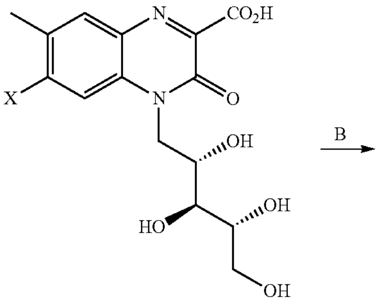

ii

-continued

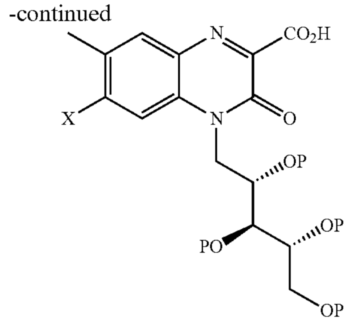

iv

Compound (ii) can be converted to compound (iv) by treatment with B and if necessary a base such as TEA or DIPEA in an appropriate solvent such as DCM, THF or dioxane at temperatures ranging from room temperature to the boiling point of the solvent.

Wherein X is as defined elsewhere herein, B is a hydroxyl protecting group reagent such as acetic anhydride, MOM-$C_1$ or MEM-$C_1$ and P is a hydroxy protecting group such as acetyl, MOM or MEM Step2

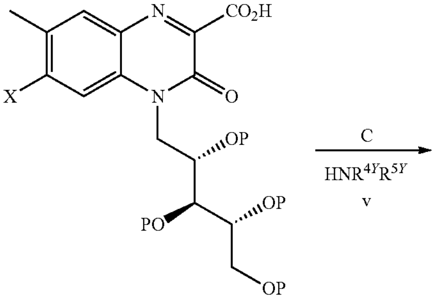

iv

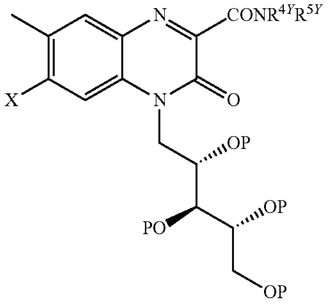

vi

Compound (iv) can be converted to compound (vi) by treatment with an amine (v) such as methylamine, dimethylamine or N,N-dimethylethane-1,2-diamine, C, and if necessary a base such as TEA or DIPEA in an appropriate solvent such as DMF, DCM, THF or dioxane at temperatures ranging from room temperature to the boiling point of the solvent.

Wherein X, $R^{4Y}$, $R^{5Y}$ and P as defined elsewhere herein and C is a coupling reagent such as EDCI, CDI or PyBOP.

Step3

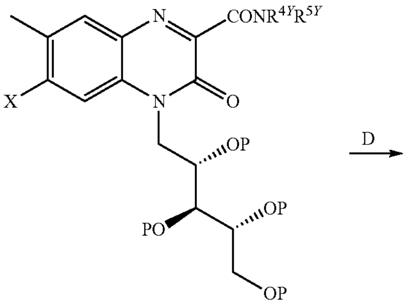

vi

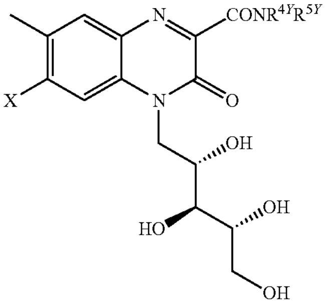

vii

Compound (vi) can be converted to compound (vii) by treatment with D in an appropriate solvent such as MeOH, DCM, THF or dioxane at temperatures ranging from 0° C. to the boiling point of the solvent.

Wherein X, $R^{4Y}$ and $R^{5Y}$ as defined elsewhere herein and D is a reagent capable of removing the protecting groups P such as sodium methoxide, HCl (gas) in dioxane, HBr or $NH_4OH$ General procedure 3

Step1

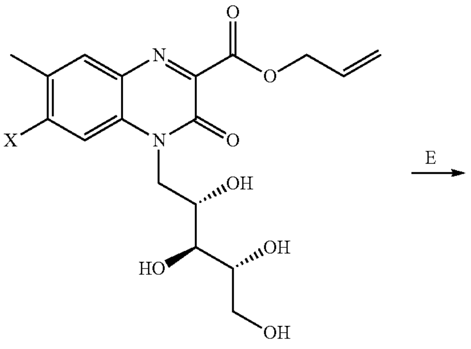

viii

-continued

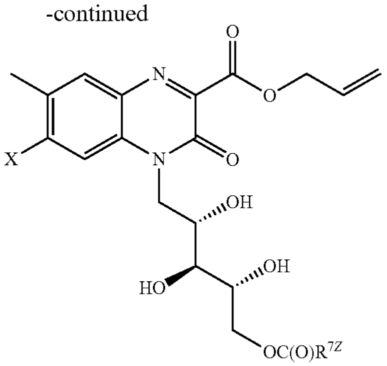

ix

Compound (viii) obtained using General procedure 1 can be converted to compound (ix) by treatment with E and if necessary a base such as TEA or DIPEA in an appropriate solvent such as MeOH, DCM, THF or dioxane at temperatures ranging from −70° C. to room temperature.

Wherein X and $R^{7Z}$ are as defined elsewhere herein and E is an anhydride such as acetic anhydride, propionic anhydride or isopropyl anhydride or an activated ester or acid such as acetic acid pentafluorophenol ester or acetic acid activated with CDI.

Step2

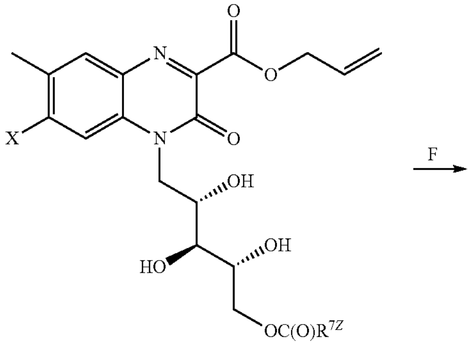

ix

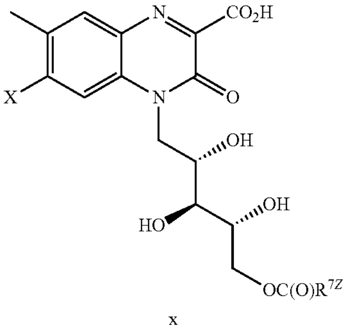

x

Compound (ix) can be converted to compound (x) by treatment with F and if necessary a base such as TEA, pyrrolidine or DIPEA in an appropriate solvent such as MeCN, DCM, THF or dioxane at temperatures ranging from 0° C. to room temperature.

Wherein X and $R^{7Z}$ are as defined elsewhere herein and F is a regent capable of selectively removing an allyl ester protecting group such as $Pd(PPh_3)_4$ or $Pd(OAc)_2$ General procedure 4

Step1

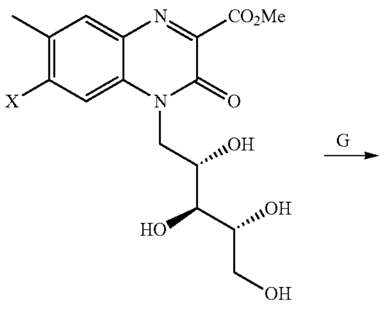

xi

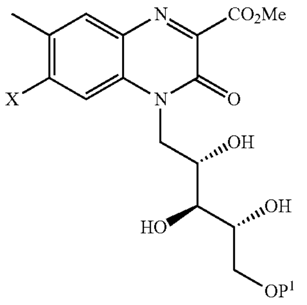

xii

Compound (xi) obtained using General procedure 1 can be converted to compound (xii) by treatment with G and if necessary a base such as TEA, N,N-dimethylaminopyridine or DIPEA in an appropriate solvent such as pyridine, DCM, THF or dioxane at temperatures ranging from 0° C. to the boiling point of the solvent.

Wherein X is as defined elsewhere herein, G is a protecting group reagent capable of selectively reacting at a primary hydroxy group such as trityl-chloride or 2-chlorotrityl chloride and $P^1$ is a primary hydroxy protecting group such as trityl or 2-chlorotrityl.

Step2

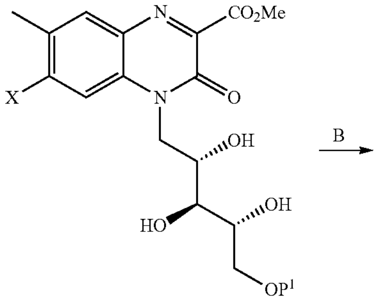

xii

-continued

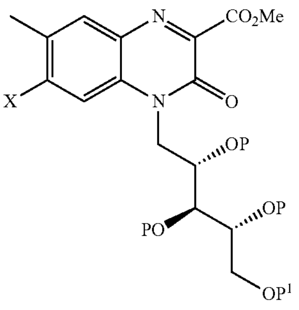

xiii

Compound (xii) can be converted to compound (xiii) by treatment with B according to general procedure 2 step 1.

Wherein X, P and $P^1$ are as defined elsewhere herein.

Step3

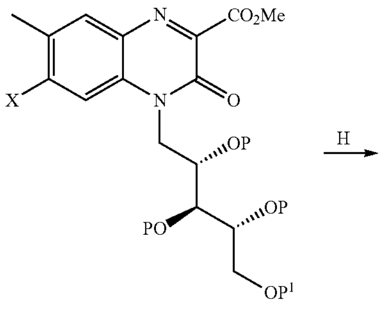

xiii

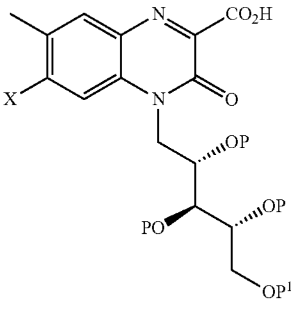

xix

Compound (xiii) can be converted to compound (xix) by treatment with H in an appropriate solvent such as Water, MeOH, THF or dioxane at temperatures ranging from 0° C. to the boiling point of the solvent.

Wherein X, P and $P^1$ are as defined elsewhere herein and H is a reagent capable of hydrolyzing a methyl ester such NaOH, LiOH or $NH_4OH$.

Step4

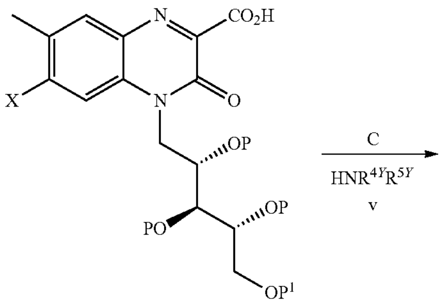

xix

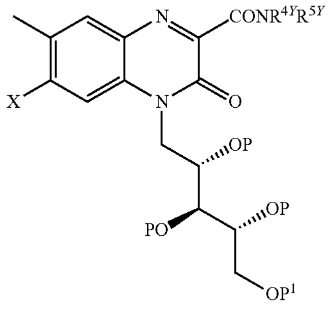

xx

Compound (xix) can be converted to compound (xx) by treatment with C according to general procedure 2 step 2

Wherein X, $R^{4Y}$, $R^{5Y}$, P, $P^1$ and C are as defined elsewhere herein.

Step5

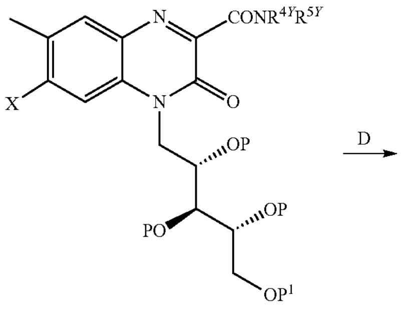

xx

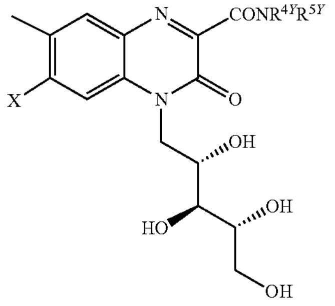

xxi

Compound (xx) can be converted to compound (xxi) by treatment with D according to general procedure 2 step 3.

Wherein X, $R^{4Y}$, $R^{5Y}$, P, $P^1$ and D are as defined elsewhere herein.

General procedure 5

Step1

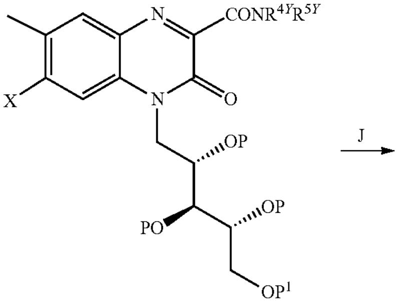

xx

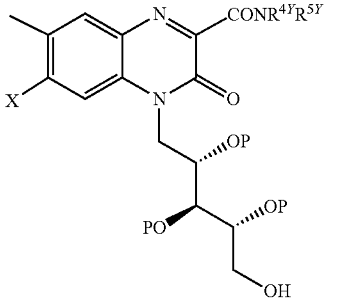

xxii

Compound (xx) can be converted to compound (xxii) by treatment with J in an appropriate solvent such as diethylether, MeOH, THF or dioxane at temperatures ranging from 0° C. to room temperature.

Wherein X, $R^{4Y}$, $R^{5Y}$, P and $P^1$ are as defined elsewhere herein and J is a reagent capable of removing a trityl or 2-chlorotrityl protecting group selectively such as pentafluoroethanol, silica gel-supported ceric ammonium nitrate formic or acetic acid.

Step2

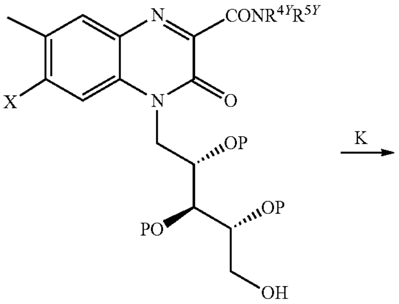

xxii

-continued

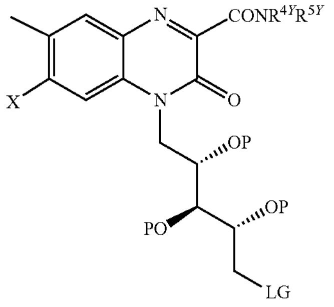

xxiii

Compound (xxii) can be converted to compound (xxiii) by treatment with K and if necessary a base such as TEA, N,N-dimethylaminopyridine or DIPEA in an appropriate solvent such as DMF, DCM, MeOH, THF or dioxane at temperatures ranging from 0° C. to room temperature.

Wherein X, $R^{4Y}$, $R^{5Y}$ and P are as defined elsewhere herein and K is a reagent capable of converting a hydroxy group to a leaving group such as Ms-$C_1$, TsCl or methyltriphenoxyphosphonium iodide. LG is a leaving group such as mesylate, tosylate or iodo.

Step3

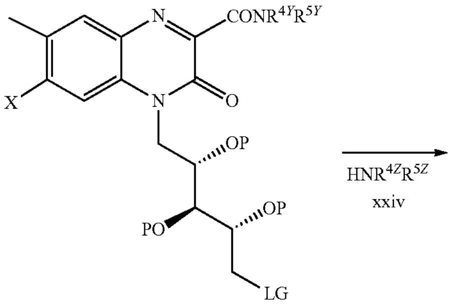

xxiii

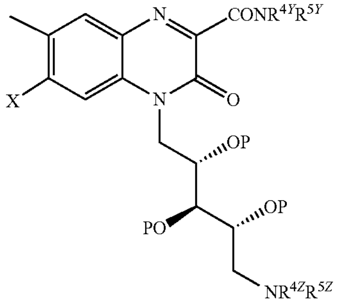

xxv

Compound (xxiii) can be converted to compound (xxv) by treatment with amine (xxiv) methylamine, dimethylamine, morpholine or N,N-dimethylethane-1,2-diamine, and if necessary a base such as TEA, N,N-dimethylaminopyridine or DIPEA in an appropriate solvent such as DMF, DCM, MeOH, THF or dioxane at temperatures ranging from 0° C. to the boiling point of the solvent.

Wherein X, $R^{4Y}$, $R^{5Y}$, $R^{4Z}$, $R^{5Z}$, LG and P are as defined elsewhere herein.

Step4

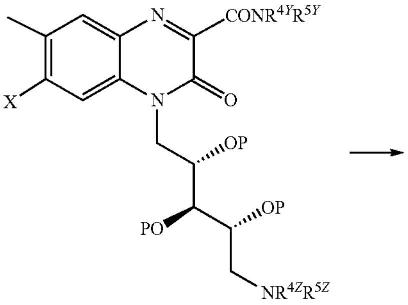

xxv

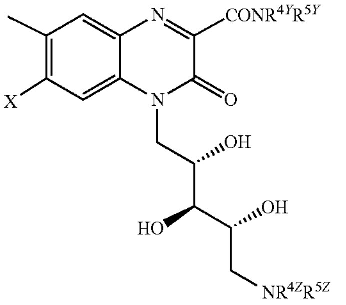

xxvi

Compound (xxv) can be converted to compound (xxvi) by treatment with D according to general procedure 2 step 3.

Wherein X, $R^{4Y}$, $R^{5Y}$, $R^{4Z}$, $R^{5Z}$, P and D are as defined elsewhere herein.

Reactions sensitive to moisture or air were performed under nitrogen or argon using anhydrous solvents and reagents. The progress of reactions was determined by either analytical thin layer chromatography (TLC) usually performed with Sanpont precoated TLC plates, silica gel GF-254, layer thickness 0.25 mm or liquid chromatography-mass spectrometry (LC-MS).

Typically, the analytical LC-MS system used consisted of an Agilent 6120 platform with electrospray ionization in positive ion detection mode with an Agilent 1260 series HPLC with autosampler. The column was usually an Agilent poroshell C18, 3.0×50 mm, 2.7 μm. The flow rate was 0.6 mL/min, and the injection volume was 5 μL. UV detection was in the range 190-400 nm. The mobile phase consisted of solvent A (water plus 0.1% TFA) and solvent B (acetonitrile plus 0.05% TFA) with a gradient of 90% solvent A changing to 95% solvent B over 1.7 min, maintained for 1.8 min, then reverting to 90% solvent A over 0.1 min and maintained for 1.4 mins.

Preparative HPLC purifications were usually performed Waters 2555-2767 system with a 2489 UV detector. The column was Welch C-18, 21.2×150 mm, 5 μm. The mobile phases consisted of mixtures of acetonitrile (5-95%) in water containing 0.05% TFA. Flow rates were maintained at 20 mL/min, the injection volume was 1800 μL, and the UV detector used two channels 254 nm and 280 nm. Mobile phase gradients were optimized for the individual compounds.

Reactions performed using microwave irradiation were normally carried out using an Initiator manufactured by Biotage. Concentration of solutions was carried out on a rotary evaporator under reduced pressure. Flash chromatography was usually performed using a Biotage Flash Chromatography apparatus (Dyax Corp.) on silica gel (40-63 mM, 60 Å pore size) in pre-packed cartridges of the size noted. $^{1}H$ NMR spectra were acquired at 400 MHz spectrometers in $CDCl_3$ solutions unless otherwise noted. Chemical shifts were reported in parts per million (ppm). Tetramethylsilane (TMS) was used as internal reference in $CD_3Cl$ solutions, and residual $CH_3OH$ peak or TMS was used as internal reference in $CD_3OD$ solutions. Coupling constants (J) were reported in hertz (Hz). Chiral analytical chromatography was performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of Chiralpak AS, Chiralpak AD, Chiralcel OD, Ciralcel IA, or Chiralcel OJ columns (20×250 mm) (Daicel Chemical Industries, Ltd.) with desired isocratic solvent systems identified on chiral analytical chromatography or by supercritical fluid (SFC) conditions.

SYNTHETIC EXAMPLES

Synthesis of Compound 3 (Example 1) and Compound 4 (Example 5)

Examples 1 and 5 were synthesized according to the scheme below:

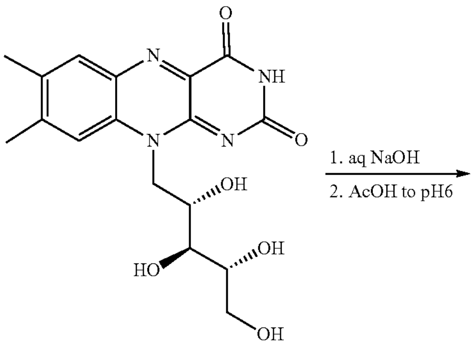

1

-continued

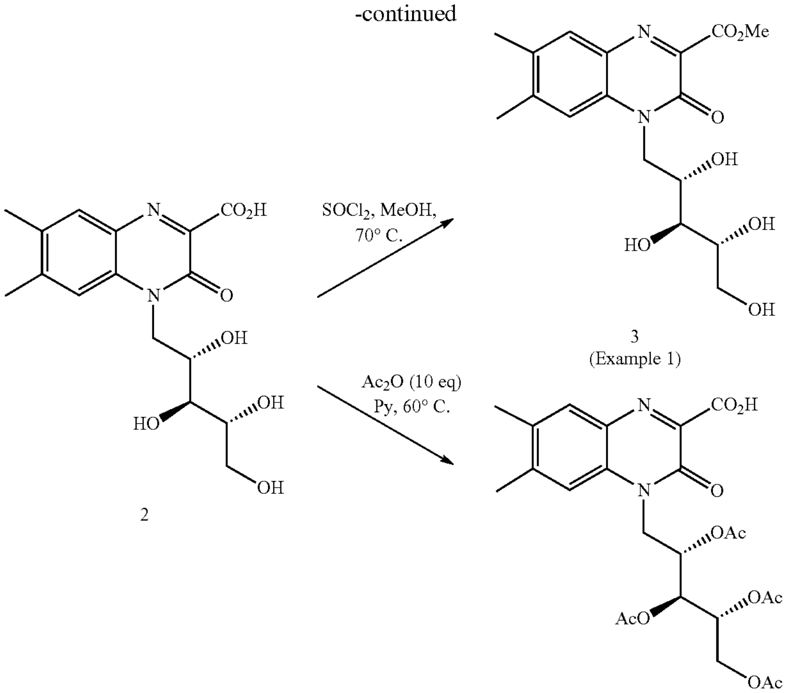

2

3
(Example 1)

4
(Example 5)

Compound 2

1200 mL of 1M aq NaOH was added to Riboflavin (1) (50 g, 133 mmol) and the mixture was stirred at 90° C. for 2 h. The mixture was cooled down to 20° C., and glacial acetic acid was added to adjust the pH to 6. The mixture was partially evaporated to 800 mL volume and left overnight in a fridge at 5° C. for crystallization. The pellet thus formed was filtered off, washed with water and dried to give compound (2) 41 g.

$^1$H-NMR (DMSO-$d_6$, δ, ppm): 2.25 (s, 3H), 2.31 (s, 3H), 3.42-3.48 (m, 1H), 3.55-3.66 (m, 2H), 4.53 (dd, 1H, $J_1$=3.9 Hz, $J_2$=9.8 Hz), 4.62 (br.s, 1H), 4.72 (br.d, 1H, J=6.0 Hz), 5.02 (br.s, 1H), 5.14 (br.s, 1H), 7.41 (s, 1H), 7.46 (s, 1H).

LCMS, m/z: 353.4 $(M+H)^+$.

Compound 3 (Example 1)

To a suspension of compound (2) (1.5 g, 4.3 mmol) in 100 mL MeOH, neat $SOCl_2$ (0.51 g, 4.3 mmol) was added dropwise at ambient temperature. The reaction mixture was stirred at reflux overnight and evaporated to dryness. The residue was passed through a silica gel pad eluting with 20% MeOH in chloroform giving compound (3) (Example 1) 1.0 g.

$^1$H-NMR (DMSO-$d_6$, δ, ppm): 2.30 (s, 3H), 2.38 (s, 3H), 3.41-3.49 (m, 1H), 3.55-3.65 (m, 3H), 4.07-4.14 (m, 1H), 4.18 (br.d, 1H, J=14.0 Hz), 4.47 (dd, 1H, $J_1$=$J_2$=5.8 Hz), 4.59 (dd, 1H, $J_1$=3.6 Hz, $J_2$=14.0 Hz), 4.72 (d, 1H, J=5.8 Hz), 4.82 (d, 1H, J=2.7 Hz), 4.97 (d, 1H, J=4.3 Hz), 7.61 (br.s, 2H).

$^{13}$C-NMR (DMSO-$d_6$, δ, ppm): 18.63, 20.33, 44.50, 52.61, 63.51, 68.60, 72.76, 73.83, 116.26, 129.66, 129.96, 132.34, 132.68, 142.20, 147.65, 152.41, 164.54.

LCMS, m/z: 367.0 $(M+H)^+$, 389.5 $(M+Na)^+$.

Compound 4 (Example 5)

Compound (2) (2.5 g, 7.1 mmol) was suspended in 20 mL pyridine, and acetic anhydride (7.2 g, 71 mmol) was added. The mixture was stirred at 70° C. overnight and evaporated to dryness. The residue was passed through a silica gel pad eluting with 25% MeOH in chloroform giving compound (4) (Example 5) 0.77 g.

$^1$H-NMR (DMSO-$d_6$, δ, ppm): 1.70 (3, 3H), 2.00 (s, 3H), 2.11 (s, 3H), 2.13 (s, 3H), 2.31 (s, 3H), 2.40 (s, 3H), 4.19 (dd, 1H, $J_1$=5.4 Hz, $J_2$=12.2 Hz), 4.32 (br.d, 1H, J=12.2 Hz), 4.42 (br.d, 1H, J=14.0 Hz), 4.60-4.68 (m, 1H), 5.30-5.42 (m, 3H), 7.40 (s, 1H), 7.52 (s, 1H).

$^{13}$C-NMR (DMSO-$d_6$, δ, ppm): 18.67, 20.10, 20.19, 20.51, 20.57, 20.73, 41.78, 61.56, 68.99, 69.15, 70.17, 115.00, 129.60, 130.30, 130.72, 132.48, 140.35, 152.58, 152.70, 166.26, 169.33, 169.56, 169.62, 170.16.

LCMS, m/z: 521.4 $(M+H)^+$, 543.5 $(M+Na)^+$.

Synthesis of Compound 7 (Example 6)

Example 6 can be synthesized according to the scheme below:

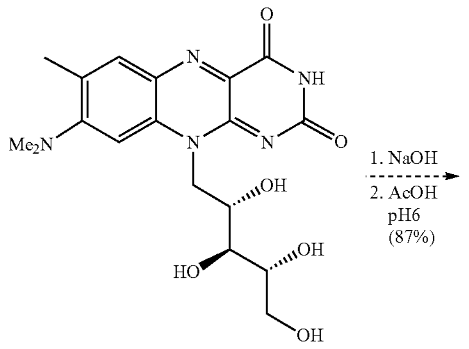

5

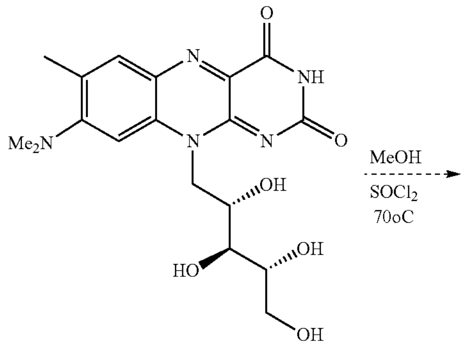

6

-continued

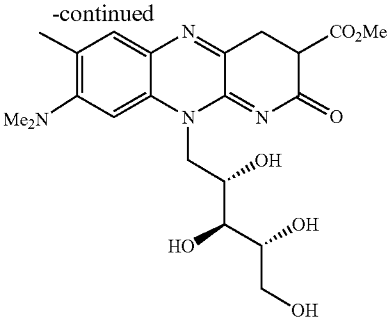

7
(Example 6)

Roseoflavin (5) (CAS #51093-55-1) is hydrolyzed with NaOH, whereupon the resulting carboxylate moiety is re-acidified with acetic acid to afford compound (6). Compound (6) is subjected to esterification conditions with methanol (e.g., with thionyl chloride) to afford compound (7) (Example 6).

Synthesis of Compound 10 (Example 2), Compound 12 (Example 3), and Compound 14 (Example 4)

Examples 2-4 were synthesized according to the scheme below:

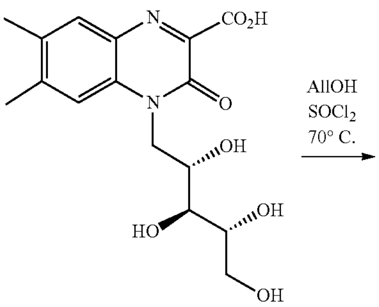

2

-continued

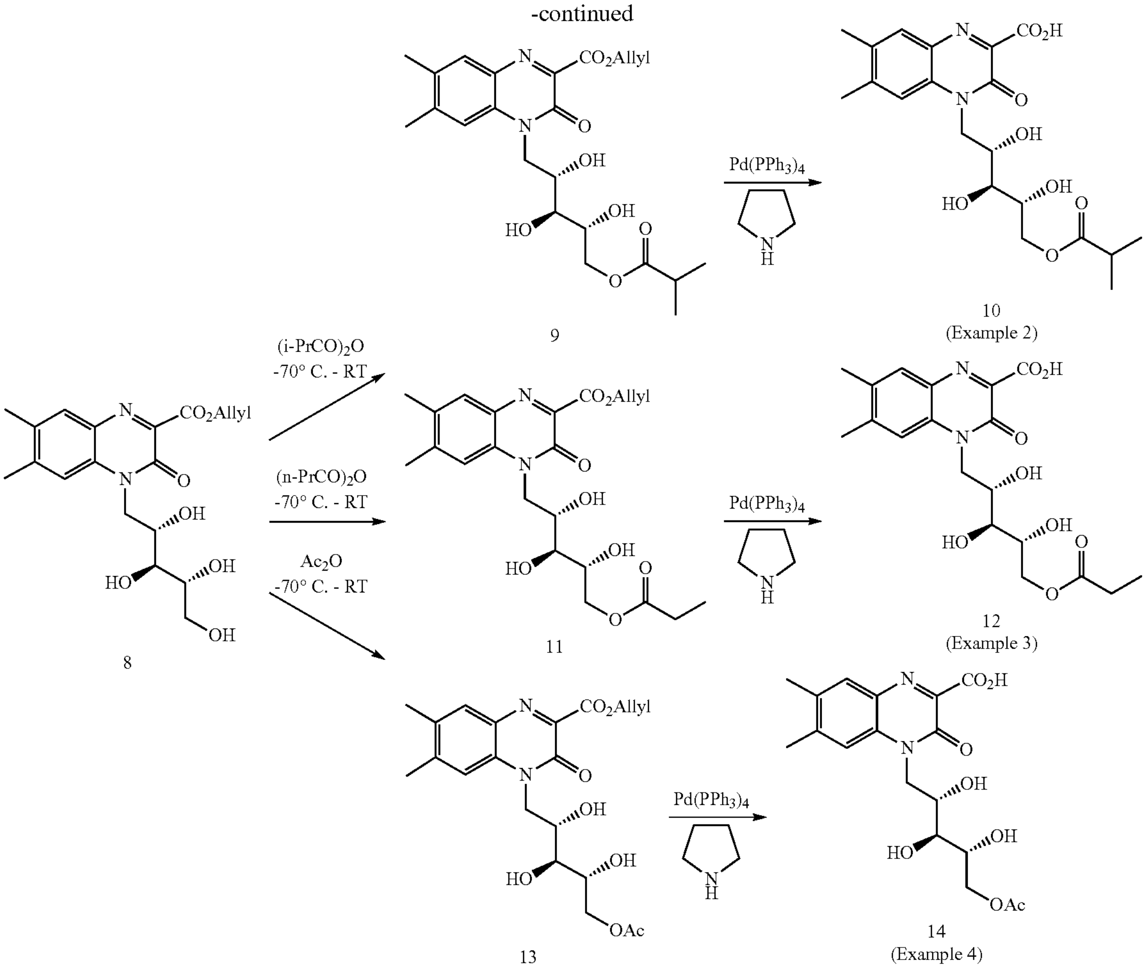

8

9

10 (Example 2)

11

12 (Example 3)

13

14 (Example 4)

Compound 8

To a suspension of compound (2) (31.5 g, 89.4 mmol) in allyl alcohol (200 mL), neat $SOCl_2$ (10.6 g, 89.4 mmol) was added dropwise at ambient temperature. The reaction mixture was stirred at 80-90° C. for 4 h and evaporated to dryness. The residue was purified by column chromatography on silica gel eluting with 20-100% EtOAc in hexane→10% i-PrOH in EtOAc giving compound (8) 16.0 g.

$^{1}$H-NMR (DMSO-$d_6$, δ, ppm): 2.30 (s, 3H), 2.39 (s, 3H), 3.42-3.49 (m, 1H), 3.58-3.66 (m, 3H), 4.10-4.14 (m, 1H), 4.20 (br.d, 1H, J=12.3 Hz), 4.60 (dd, 1H, $J_1$=3.5 Hz, $J_2$=13.6 Hz), 4.72 (br.s, 1H), 4.82 (br.s, 1H), 4.85 (d, 2H, J=5.3 Hz), 4.97 (br.s, 1H), 5.30 (d, 1H, J=10.7 Hz), 5.50 (d, 1H, J=17.2 Hz), 5.98-6.08 (m, 1H), 7.60 (s, 1H), 7.62 (s, 1H).

LCMS, m/z: 393.5 $(M+H)^+$.

Compound 9

To a suspension of compound (8) (14.1 g, 35.9 mmol) in DCM (500 mL), DIPEA (23.2 g, 179.5 mmol) was added. The mixture was cooled down to −70° C., and isobutyric anhydride (5.7 g, 35.9 mmol) was added in one portion. The mixture was stirred at −70° C. for 5 h and then for 48 h at ambient temperature. The reaction mixture was quenched with 5% aq citric acid, the organic layer separated, and the aqueous layer extracted with DCM. The combined organic extracts were dried over $Na_2SO_4$ and evaporated. The residue was purified by column chromatography on silica gel eluting with 30→70% EtOAc in hexane giving compound (9) 3.6 g.

$^{1}$H-NMR (DMSO-$d_6$, δ, ppm): 1.10 (dd, 6H, $J_1$=1.8 Hz, $J_2$=7.0 Hz), 2.31 (s, 3H), 2.39 (s, 3H), 2.52-2.59 (m, 1H), 3.59-3.64 (m, 1H), 3.80-3.87 (m, 1H), 4.02 (dd, 1H, $J_1$=7.1 Hz, $J_2$=11.3 Hz), 4.07-4.14 (m, 1H), 4.20-4.26 (m, 2H), 4.55 (dd, 1H, $J_1$=3.8 Hz, $J_2$=13.5 Hz), 4.83-4.88 (m, 3H), 5.16 (dd, 1H, $J_1$=5.4 Hz, $J_2$=16.4 Hz), 5.30 (dd, 1H, $J_1$=1.3 Hz, $J_2$=10.5 Hz), 5.49 (dd, 1H, $J_1$=1.3 Hz, $J_2$=17.2 Hz), 5.97-6.06 (m, 1H), 7.57 (s, 1H), 7.62 (s, 1H).

LCMS, m/z: 445.0 $(M-H_2O)$, 463.5 $(M+H)^+$, 485.3 $(M+Na)^+$.

Compound 10 (Example 2)

Compound (9) (3.6 g, 7.7 mmol) was dissolved in MeCN (50 mL). The solution was purged with nitrogen gas, and Pd $(PPh_3)_4$ was added (0.89 g, 0.77 mmol) followed by pyrrolidine (0.66 g, 9.2 mmol). After 16 h at room temperature the MeCN was evaporated, EtOAc was added and the formed pellet filtered off and washed with EtOAc. The pellet was dissolved in water, and the pH adjusted to 2 by the addition of 10% HCl. The formed pellet was filtered off, washed with water and dried giving compound (10) (Example 2) 1.56 g.

$^1$H-NMR (DMSO-$d_6$, δ, ppm): 1.10 (dd, 6H, $J_1$=1.7 Hz, $J_2$=7.1 Hz), 2.32 (s, 3H), 2.40 (s, 3H), 2.52-2.59 (m, 1H), 3.60-3.62 (m, 1H), 3.81-3.88 (m, 1H), 4.02 (dd, 6H, $J_1$=7.0 Hz, $J_2$=10.9 Hz), 4.10-4.12 (m, 1H), 4.20-4.30 (m, 2H), 4.58 (dd, 6H, $J_1$=10.2 Hz, $J_2$=13.7 Hz), 4.82-4.89 (m, 1H), 5.12-5.23 (m, 2H), 7.60 (s, 1H), 7.65 (s, 1H), 13.98 (br.s, 1H).

$^{13}$C-NMR (DMSO-$d_6$, δ, ppm): 18.67, 18.91 (2×), 20.38, 33.31, 44.84, 66.28, 68.44, 69.74, 73.78, 116.26, 129.79, 130.41, 132.07, 132.98, 142.11, 147.51, 153.54, 165.03, 176.39.

LCMS, m/z: 423.5 $(M+H)^+$, 445.3 $(M+Na)^+$.

Compound 11

To a suspension of compound (8) (8.9 g, 22.7 mmol) in DCM (400 mL), DIPEA (14.7 g, 113.5 mmol) was added. The mixture was cooled to −70° C., and propionic anhydride (3.0 g, 22.7 mmol) was added in one portion. The mixture was stirred at −70° C. for 5 h and then for 48 h at ambient temperature. The reaction mixture was quenched with 5% aq citric acid, the organic layer was separated, and the aqueous layer extracted with DCM. The combined organic extracts were dried over $Na_2SO_4$ and evaporated. The residue was purified by column chromatography on silica gel eluting with 30→70% EtOAc in hexane giving compound (11) 2.6 g.

$^1$H-NMR (DMSO-$d_6$, δ, ppm): 1.02 (t, 3H, J=7.4 Hz), 2.30-2.42 (m, 8H), 3.58-3.62 (m, 1H), 3.80-3.87 (m, 1H), 4.00-4.05 (m, 1H), 4.09-4.12 (m, 1H), 4.20-4.24 (m, 2H), 4.55 (dd, 1H, $J_1$=3.3 Hz, $J_2$=10.4 Hz), 4.85-4.90 (m, 3H), 5.18 (dd, 1H, $J_1$=5.9 Hz, $J_2$=16.3 Hz), 5.30 (dd, 1H, $J_1$=1.3 Hz, $J_2$=10.5 Hz), 5.49 (dd, 1H, $J_1$=1.3 Hz, $J_2$=17.2 Hz), 5.97-6.05 (m, 1H), 7.57 (s, 1H), 7.63 (s, 1H).

LCMS, m/z: 431.3 $(M-H_2O)$, 449.4 $(M+H)^+$, 471.0 $(M+Na)^+$.

Compound 12 (Example 3)

Compound (11) (2.6 g, 5.8 mmol) was dissolved in MeCN (50 mL). The solution was purged with nitrogen gas, and Pd $(PPh_3)_4$ was added (0.68 g, 0.58 mmol) followed by pyrrolidine (0.62 g, 8.7 mmol). After 16 h at room temperature the MeCN was evaporated, EtOAc was added and the formed pellet filtered off and washed with EtOAc. The pellet was dissolved in water, and the pH was adjusted to 2 by addition of 10% HCl, the formed pellet was filtered off, washed with water and dried giving compound (12) (Example 3) 0.84 g.

$^1$H-NMR (DMSO-$d_6$, δ, ppm): 1.03 (t, 3H, J=7.4 Hz), 2.30-2.43 (m, 8H), 3.60-3.63 (m, 1H), 3.82-3.89 (m, 1H), 4.03 (dd, 6H, $J_1$=7.0 Hz, $J_2$=10.9 Hz), 4.10-4.13 (m, 1H), 4.21-4.30 (m, 2H), 4.57 (dd, 6H, $J_1$=10.2 Hz, $J_2$=13.7 Hz), 4.82 (br.d, 1H, J=4.6 Hz), 5.12-5.21 (m, 2H), 7.60 (s, 1H), 7.65 (s, 1H), 13.95 (br.s, 1H).

$^{13}$C-NMR (DMSO-$d_6$, δ, ppm): 9.07, 18.67, 20.38, 26.91, 44.83, 66.25, 68.45, 69.70, 73.79, 116.25, 129.79, 130.41, 132.07, 132.99, 142.11, 147.53, 153.53, 165.04, 173.88.

LCMS, m/z: 409.5 $(M+H)^+$, 431.5 $(M+Na)^+$.

Compound 13

To a suspension of compound (8) (16.1 g, 41.0 mmol) in DCM (600 mL), DIPEA (26.5 g, 205.0 mmol) was added. The mixture was cooled down to −70° C., and acetic anhydride (4.2 g, 41.0 mmol) was added in one portion. The mixture was stirred at −70° C. for 5 h and then for 24 h at ambient temperature. The reaction mixture was quenched with 5% aq citric acid, the organic layer was separated, and the aqueous layer was extracted with DCM. The combined organic extracts were dried over $Na_2SO_4$ and evaporated. The residue was purified by column chromatography on silica gel eluting with 30→100% EtOAc in hexane giving compound (13) 2.5 g.

$^1$H-NMR (DMSO-$d_6$, δ, ppm): 2.01 (s, 3H), 2.31 (s, 3H), 2.40 (s, 3H), 3.58-3.62 (m, 1H), 3.81-3.88 (m, 1H), 4.00-4.05 (m, 1H), 4.09-4.12 (m, 1H), 4.20-4.24 (m, 2H), 4.55 (dd, 1H, $J_1$=3.3 Hz, $J_2$=10.4 Hz), 4.85-4.90 (m, 3H), 5.18 (dd, 1H, $J_1$=5.9 Hz, $J_2$=16.3 Hz), 5.30 (dd, 1H, $J_1$=1.3 Hz, $J_2$=10.5 Hz), 5.49 (dd, 1H, $J_1$=1.3 Hz, $J_2$=17.2 Hz), 5.97-6.05 (m, 1H), 7.57 (s, 1H), 7.62 (s, 1H).

LCMS, m/z: 417.5 $(M-H_2O)^+$, 435.0 $(M+H)^+$.

Compound 14 (Example 4)

Compound (13) (2.5 g, 5.8 mmol) was dissolved in MeCN (50 mL). The solution was purged with nitrogen gas, and Pd (PPh3) 4 was added (0.68 g, 0.58 mmol) followed by pyrrolidine (0.62 g, 8.7 mmol). After 16 h at room temperature the MeCN was evaporated, EtOAc was added and the formed pellet was filtered off and washed with EtOAc. The residue was dissolved in water, and the pH adjusted to 2 by addition of 10% HCl, the formed pellet was filtered off, washed with water and dried giving compound (14) (Example 4) 1.56 g.

$^1$H-NMR (DMSO-$d_6$, δ, ppm): 2.02 (s, 3H), 2.32 (s, 3H), 2.39 (s, 3H), 3.60-3.63 (m, 1H), 3.82-3.85 (m, 1H), 4.03 (dd, 6H, $J_1$=7.0 Hz, $J_2$=10.9 Hz), 4.08-4.12 (m, 1H), 4.20-4.28 (m, 2H), 4.57 (dd, 6H, $J_1$=10.2 Hz, $J_2$=13.7 Hz), 4.80-4.90 (m, 1H), 5.10-5.29 (m, 2H), 7.59 (s, 1H), 7.64 (s, 1H), 13.96 (br.s, 1H).

$^{13}$C-NMR (DMSO-$d_6$, δ, ppm): 18.67, 20.38, 20.91, 44.83, 66.35, 68.44, 69.65, 73.78, 116.24, 129.79, 130.40, 132.07, 132.99, 142.13, 147.50, 153.53, 165.03, 170.60. LCMS, m/z: 395.3 $(M+H)^+$, 417.5 $(M+Na)^+$.

Synthesis of Compound 15 (Example 8), Compound 16 (Example 9), and Compound 17 (Example 13)

Examples 8, 9, and 13 were synthesized according to the scheme below:

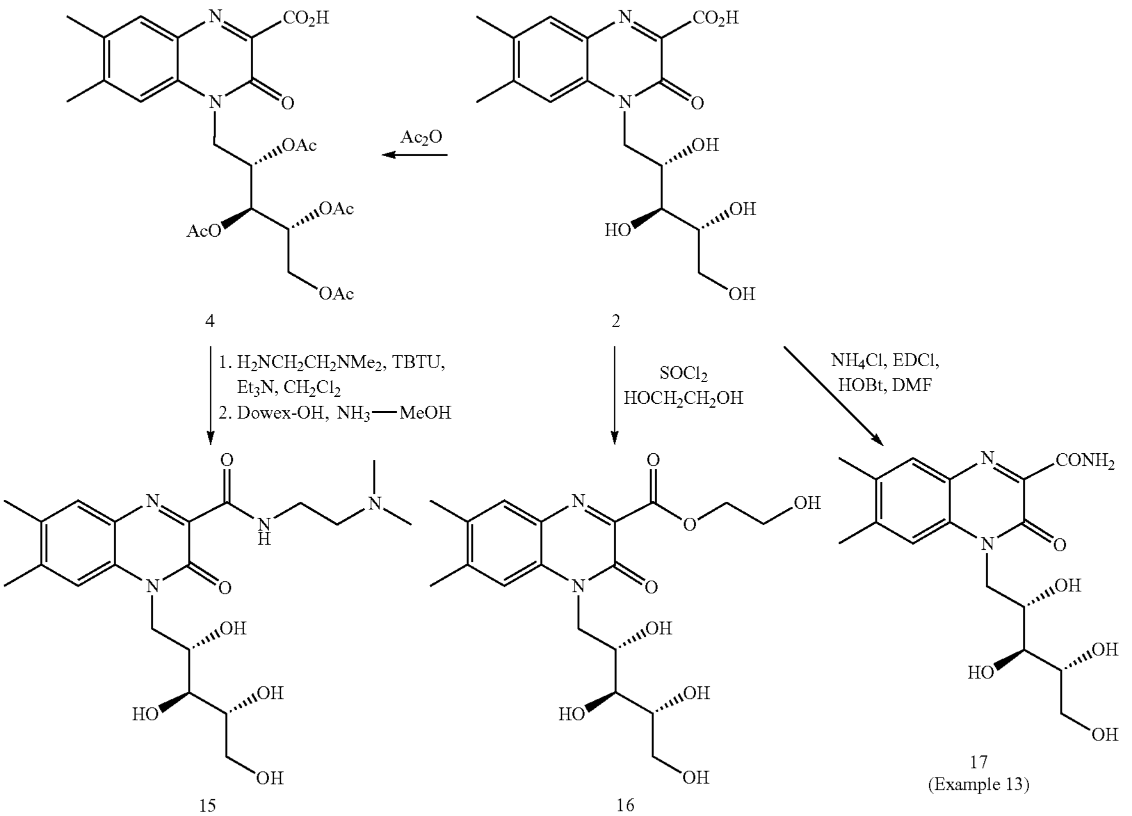

4

2

15
(Example 8)

16
(Example 9)

17
(Example 13)

Compound 15 (Example 8)

To a solution of compound (4) (1.7 g, 3.3 mmol) in DCM, $Et_3N$ (1 mL), N,N-dimethylethane-1,2-diamine (1.2 g, 4.3 mmol), and TBTU (1.68 g, 5.3 mmol) were added. The mixture was stirred at ambient temperature for 15 h and quenched with sat aq $NaHCO_3$. The organic layer was separated, and the aqueous layer was extracted with DCM. The combined organic layers were dried with $Na_2SO_4$ and evaporated. The residue was purified by column chromatography on silica gel eluting with 10-20% EtOAc in DCM giving a mixture of di-tri- and tetraacetates of compound (12). The mixture was dissolved in MeOH, Dowex-OH resin and aq $NH_3$ were added, and the mixture was stirred at ambient temperature for 15 h. The resin was filtered off, and the filtrate was evaporated giving compound (15) (Example 8) 0.12 g.

$^1$H-NMR (DMSO-$d_6$, δ, ppm): 2.30 (s, 6H), 2.32 (s, 3H), 2.40 (s, 3H), 2.56 (dd, 1H, $J_1$=$J_2$=5.8 Hz), 3.40-3.48 (m, 3H), 3.60-3.65 (m, 3H), 4.10-4.15 (m, 1H), 4.24 (br.d, 1H, J=13.5 Hz), 4.45-4.48 (m, 1H), 4.58-4.68 (m, 2H), 4.82 (br.s, 1H), 4.97 (br.s, 1H), 7.61 (s, 1H), 7.66 (s, 1H), 9.19 (t, 1H, J=4.7 Hz).

$^{13}$C-NMR (DMSO-$d_6$, δ, ppm): 18.69, 20.34, 37.06, 45.23, 57.92, 63.52, 68.73, 72.78, 73.81, 116.13, 129.95, 130.53, 132.10, 132.67, 141.90, 147.25, 154.20, 162.81.

LCMS, m/z: 378.2 ($M-NMe_2$), 423.5 $(M+H)^+$, 445.3 $(M+Na)^+$.

Compound 16 (Example 9)

To a solution of compound (2) (1.0 g, 2.8 mmol) in 1.76 g (28 mmol) of ethylene glycol, thionyl chloride (0.68 g, 5.6 mmol) was added dropwise. The mixture was stirred at reflux for 2 h and allowed to cool to room temperature. Excess of the solvent was evaporated in vacuo, and the oily residue was washed with $Et_2O$ and DCM. The residue was crystallized from THE-MeCN, the formed pellet was washed with MeCN and $Et_2O$ and dried giving compound (16) (Example 9) 0.70 g.

$^1$H-NMR (DMSO-$d_6$, δ, ppm): 2.31 (s, 3H), 2.39 (s, 3H), 3.40-3.48 (m, 1H), 3.58-3.65 (m, 3H), 3.66-3.71 (m, 2H), 4.10-4.15 (m, 1H), 4.20 (br.d, 1H, J=12.9 Hz), 4.30-4.34 (m, 2H), 4.45-4.50 (m, 1H), 4.60 (dd, 1H, $J_1$=2.8 Hz, $J_2$=10.4 Hz), 4.74 (d, 1H, J=6.4 Hz), 4.84 (br.s, 1H), 4.92 (dd, 1H, $J_1$=$J_2$=5.3 Hz), 4.98 (d, 1H, J=3.1 Hz), 7.61 (s, 1H), 7.62 (s, 1H).

$^{13}$C-NMR (DMSO-$d_6$, δ, ppm): 18.65, 20.34, 44.53, 58.81, 63.51, 67.30, 68.59, 72.75, 73.84, 116.31, 129.63, 129.96, 132.32, 132.70, 142.11, 147.91, 152.43, 164.24.

LCMS, m/z: 379.5 $(M-H_2O)^+$, 397.3 $(M+H)^+$, 419.5 $(M+Na)^+$.

Compound 17 (Example 13)

To a solution of compound (2) (1.0 g, 2.8 mmol) in 5 mL DMF, ammonium chloride (0.64 g, 11.8 mmol) was added followed by EDCI (0.65 g, 3.4 mmol) and HOBt (0.5 g, 3.6 mmol). The mixture was stirred at ambient temperature for 15 h, diluted with water and extracted with EtOAc. The combined organic extracts were dried with $Na_2SO_4$ and evaporated. The residue was purified by column chromatography on silica gel eluting with 10% EtOAc in DCM giving compound (17) (Example 13) 0.62 g.

$^1$H-NMR (DMSO-$d_6$, δ, ppm): 2.32 (s, 3H), 2.38 (s, 3H), 3.16 (br.s, 1H), 3.40-3.48 (m, 1H), 3.57-3.67 (m, 3H), 4.10-4.18 (m, 1H), 4.21 (br.d, 1H, J=13.4 Hz), 4.45-4.51 (m, 1H), 4.56-4.70 (m, 2H), 4.82 (br.s, 1H), 5.00 (br.s, 1H), 7.60 (s, 1H), 7.62 (s, 1H), 7.79 (br.s, 1H), 8.35 (br.s, 1H).
$^{13}$C-NMR (DMSO-$d_6$, δ, ppm): 18.69, 20.32, 44.52, 63.50, 68.85, 72.76, 73.83, 116.10, 129.79, 130.38, 132.10, 132.53, 141.60, 148.83, 153.81, 164.93.
LCMS, m/z: 352.6 $(M+H)^+$, 374.5 $(M+Na)^+$.
Synthesis of Compound 24 (Example 10)
Example 10 was synthesized according to the scheme below:
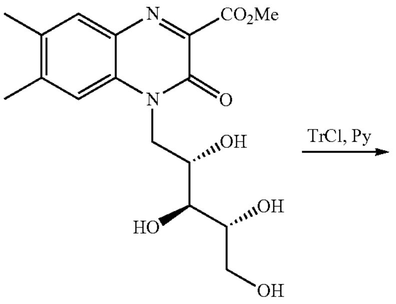
3
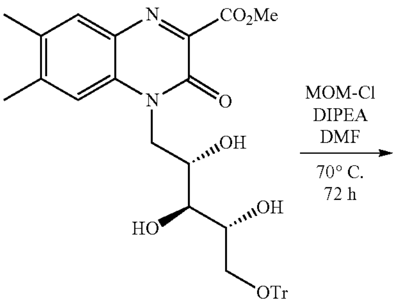
18
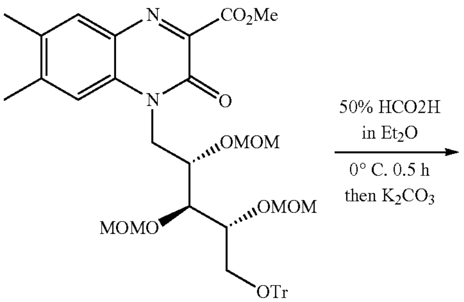
19
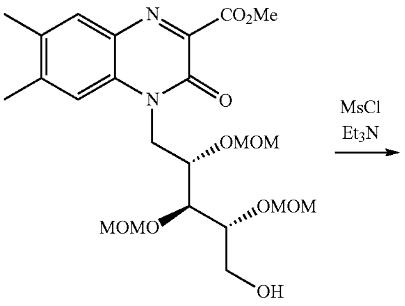
20
-continued
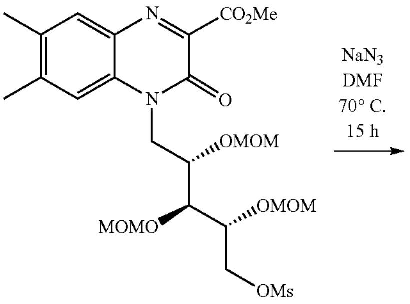
21
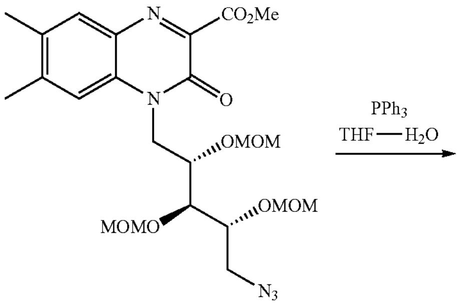
22
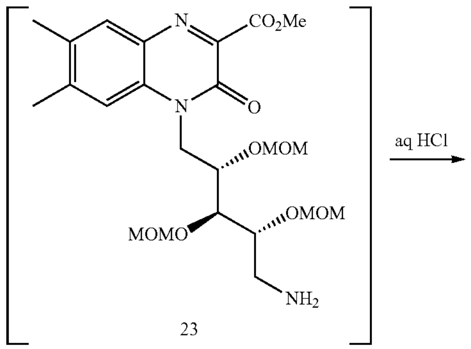
23
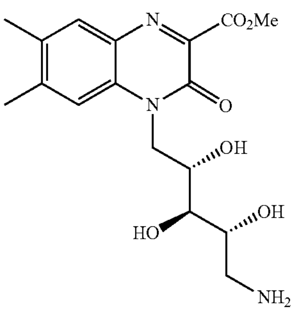
24
(Example 10)

Compound 18

Compound (3) (5.2 g, 14.2 mmol) was dissolved in pyridine (50 mL), and trityl chloride (6.3 g, 22.7 mmol) was added. The mixture was stirred at 50° C. for 15 h. Pyridine was evaporated, the residue diluted with 5% aq citric acid, and extracted with EtOAc. The combined organic extracts were dried with $Na_2SO_4$ and evaporated. The residue was purified by column chromatography on silica gel eluting with EtOAc-hexane, 1:2→2:1 giving compound (18) 4.1 g.

$^1$H-NMR (DMSO-$d_6$, δ, ppm): 2.30 (s, 6H), 2.32 (s, 3H), 3.06 (dd, 1H, $J_1$=2.4 Hz, $J_2$=6.8 Hz), 3.18 (dd, 1H, $J_1$=2.8 Hz, $J_2$=9.0 Hz), 3.56-3.62 (m, 1H), 4.07-4.13 (m, 1H), 4.20 (br.d, 1H, J=13.9 Hz), 4.58 (dd, 1H, $J_1$=3.9 Hz, $J_2$=9.9 Hz), 4.75 (d, 1H, J=6.1 Hz), 4.94 (d, 1H, J=5.3 Hz), 5.20 (d, 1H, J=5.8 Hz), 7.22-7.28 (m, 3H), 7.29-7.35 (m, 6H), 7.42-7.47 (m, 6H), 7.52 (s, 1H), 7.62 (s, 1H).

LCMS, m/z: 631.5 $(M+Na)^+$.

Compound 19

Compound (18) (6.6 g, 10.8 mmol) was dissolved in 100 mL DMF, and DIPEA (16.8 g, 129.6 mmol) was added followed by MOM-$C_1$ (5.2 g, 64.8 mmol). The mixture was stirred at 70° C. for 72 h. The mixture was cooled down to room temperature, diluted with 5% aq citric acid, and extracted with EtOAc. The combined organic extracts were dried with $Na_2SO_4$ and evaporated. The residue was purified by column chromatography on silica gel eluting with 5-30% EtOAc-hexane, giving compound (19) 5.2 g.

$^1$H-NMR (DMSO-$d_6$, δ, ppm): 2.28 (s, 6H), 2.30 (s, 3H), 2.70 (s, 3H), 3.24 (s, 3H), 3.11-3.17 (m, 1H), 3.23 (s, 3H), 3.29-3.31 (m, 1H), 3.33 (s, 3H), 3.89 (s, 3H), 3.95-4.04 (m, 2H), 4.15 (d, 1H, J=6.9 Hz), 4.21-4.35 (m, 3H), 4.56 (d, 1H, J=6.4 Hz), 4.66 (d, 1H, J=6.6 Hz), 4.72-4.83 (m, 3H), 7.22-7.28 (m, 3H), 7.29-7.34 (m, 6H), 7.37-7.42 (m, 6H), 7.47 (s, 1H), 7.66 (s, 1H).

LCMS, m/z: 741.8 $(M+H)^+$, 763.7 $(M+Na)^+$.

Compound 20

Compound (19) (4.8 g, 6.5 mmol) was dissolved in 50 mL $Et_2O$, and formic acid (50 mL) was added in 10 mL portions at 5° C. The mixture was stirred at 5° C. for 1 h and poured into saturated aq $Na_2CO_3$ at 5° C. portion wise. The mixture was extracted with EtOAc, the combined organic extracts dried with $Na_2SO_4$ and evaporated. The residue was purified by column chromatography on silica gel eluting with 5-30% EtOAc-hexane giving compound (20) 2.6 g.

$^1$H-NMR (DMSO-$d_6$, δ, ppm): 2.32 (s, 6H), 2.39 (s, 3H), 2.64 (s, 3H), 3.36 (s, 3H), 3.38 (s, 3H), 3.59-3.62 (m, 2H), 3.80-3.82 (m, 1H), 3.89 (s, 3H), 4.00-4.02 (m, 1H), 4.20 (d, 1H, J=6.9 Hz), 4.22-4.34 (m, 2H), 4.41 (d, 1H, J=6.4 Hz), 4.72-4.85 (m, 6H), 7.50 (s, 1H), 7.64 (s, 1H).

LCMS, m/z: 499.5 $(M+H)^+$, 521.3 $(M+Na)^+$.

Compound 21

To a solution of compound (20) (1.4 g, 2.8 mmol) in 50 mL DCM, $Et_3N$ (0.58 g, 5.6 mmol) was added followed by MsCl (0.39 g, 3.4 mmol) in 10 mL DCM dropwise at 5-10° C. The mixture was stirred at ambient temperature for 1 h and quenched with saturated aq $NaHCO_3$. The mixture was extracted with EtOAc, the combined organic extracts were dried with $Na_2SO_4$ and evaporated giving compound (21) that was used for the next step without further purification 1.6 g.

$^1$H-NMR (DMSO-$d_6$, δ, ppm): 2.33 (s, 6H), 2.41 (s, 3H), 2.71 (s, 3H), 3.06-3.12 (m, 1H), 3.23 (s, 3H), 3.37 (s, 3H), 3.38 (s, 3H), 3.89 (s, 3H), 3.98-4.00 (m, 1H), 4.08-4.12 (m, 1H), 4.20-4.35 (m, 4H), 4.41-4.52 (m, 2H), 4.70-4.82 (m, 4H), 4.85-4.89 (m, 1H), 7.50 (s, 1H), 7.65 (s, 1H).

LCMS, m/z: 577.3 $(M+H)^+$, 599.3 $(M+Na)^+$.

Compound 22

To a solution of compound (21) (2.4 g, 4.1 mmol) in 80 mL DMF, sodium azide (1.9 g, 28.7 mmol) was added and the mixture was stirred at 70° C. for 15 h. Water was added, and the mixture was extracted with EtOAc, the combined organic extracts were dried with $Na_2SO_4$ and evaporated giving compound (22) that was used for the next step without further purification 2.1 g.

$^1$H-NMR (DMSO-$d_6$, δ, ppm): 2.32 (s, 6H), 2.40 (s, 3H), 2.70 (s, 3H), 3.36 (s, 3H), 3.39 (s, 3H), 3.46-3.52 (m, 1H), 3.72-3.77 (m, 1H), 3.89 (s, 3H), 3.95-4.00 (m, 2H), 4.20-4.34 (m, 3H), 4.42 (d, 1H, J=7.2 Hz), 4.68-4.72 (m, 1H), 4.76 (s, 2H), 4.81 (d, 1H, J=6.2 Hz), 4.88 (d, 1H, J=6.1 Hz), 7.49 (s, 1H), 7.65 (s, 1H).

LCMS, m/z: 524.7 $(M+H)^+$, 546.2 $(M+Na)^+$.

Compound 24 (Example 10)

To a solution of compound (22) (0.31 g, 0.59 mmol) in 20 mL THF, triphenylphosphine (0.31 g, 1.18 mmol) was added and the mixture was stirred at 60° C. for 4 h. 10% HCl (5 mL) was added, and the mixture was stirred at 60° C. for 2 h. The mixture was diluted with water, extracted with chloroform, and the combined organic extracts were discarded. The aqueous layer was evaporated to dryness, and the solid residue was washed with chloroform and $Et_2O$ giving compound (24) (Example 10) 0.13 g.

$^1$H-NMR (DMSO-$d_6$, δ, ppm): 2.31 (s, 3H), 2.40 (s, 3H), 2.80-2.84 (m, 1H), 2.98-3.02 (m, 1H), 3.32-3.40 (m, 2H), 3.60-3.65 (m, 1H), 3.89 (s, 3H), 3.90-3.92 (m, 1H), 3.95-4.02 (m, 1H), 4.28 (br.d, 1H, J=13.4 Hz), 4.48 (dd, 1H, $J_1$=3.8 Hz, $J_2$=9.7 Hz), 5.10 (d, 1H, J=6.5 Hz), 5.48 (d, 1H, J=5.8 Hz), 7.61 (s, 1H), 7.62 (s, 1H), 7.88 (br.s, 3H, $NH_2 \cdot HCl$).

$^{13}$C-NMR (DMSO-$d_6$, δ, ppm): 18.63, 20.33, 41.74, 45.32, 52.64, 68.29, 68.71, 74.62, 116.30, 129.65, 129.96, 132.45, 132.77, 142.32, 146.51, 152.34, 164.49.

LCMS, m/z: 348.6 $(M-H_2O)^+$, 366.1 $(M+H)^+$, 388.3 $(M+Na)^+$.

Synthesis of Compound 27 (Example 11) and Compound 26 (Example 12)

Examples 11-12 can be synthesized according to the scheme below:

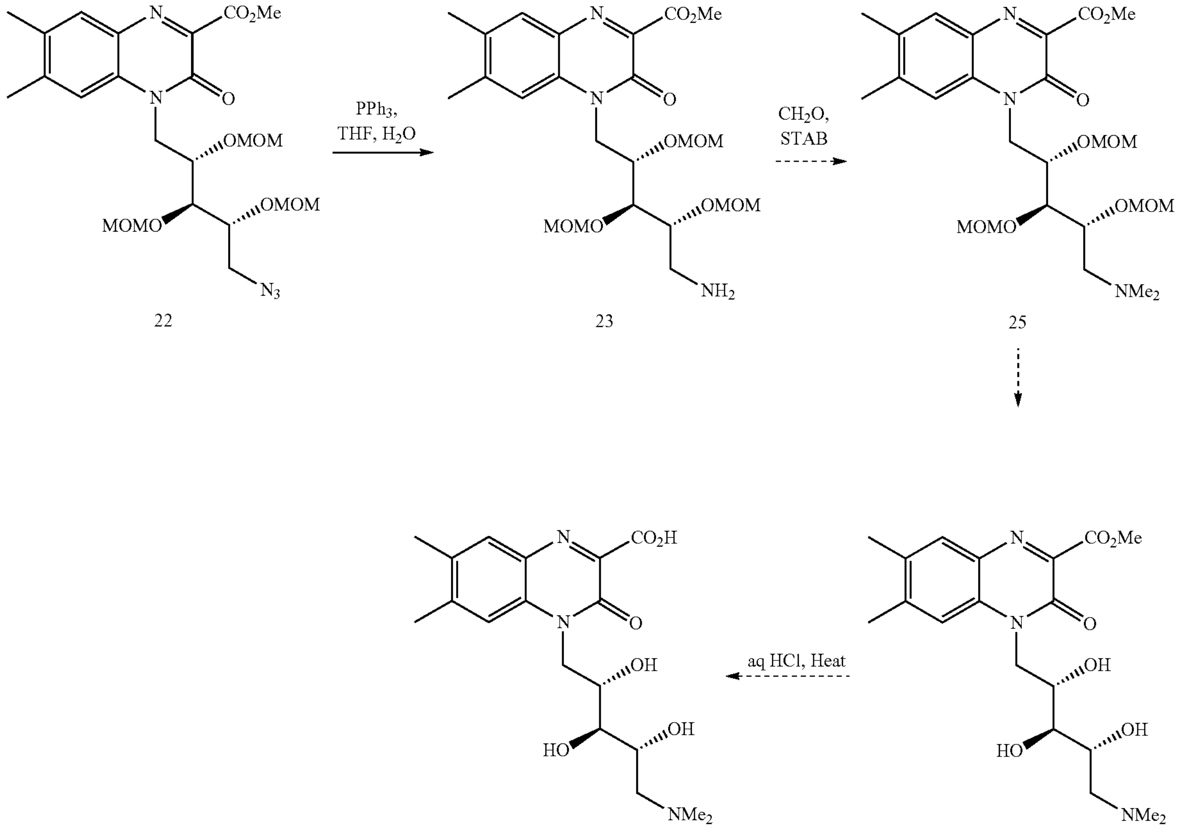

22

23

25

27
(Example 11)

26
(Example 12)

Staudinger reduction of the azide moiety on compound (22) with triphenylphosphine and water affords compound (23). Compound (23) undergoes reductive amination with formaldehyde and STAB to afford compound (25), whereupon removal of the MOM groups leads to compound (26) (Example 12). Hydrolysis of the ester group in compound (26) (Example 12) with aq. HCl and heat yields compound (27) (Example 11).

Synthesis of Compound 31 (Example 14)

Example 14 was synthesized according to the scheme below:

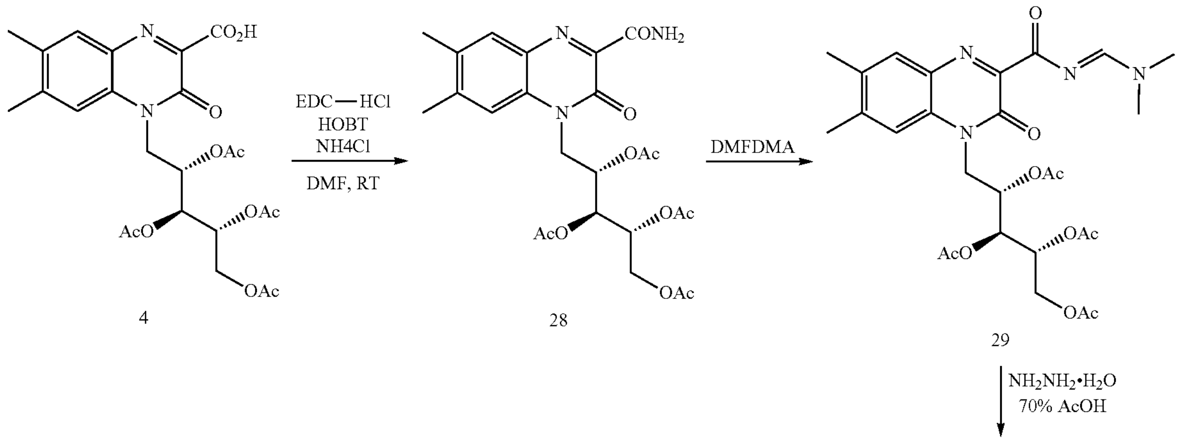

4

28

29

-continued

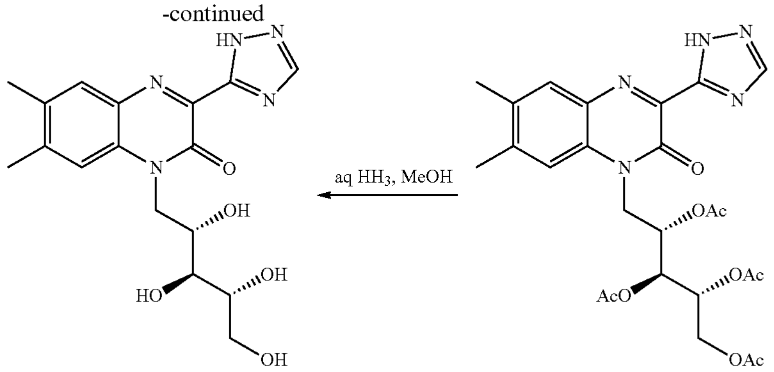

31
(Example 14)

30

Compound 28

To a solution of compound (4) (3.0 g, 5.7 mmol) in DMF (15 mL) at ambient temperature was added EDC-HCl (1.3 g, 6.8 mmol), and HOBt (1.5 g, 11.4 mmol), followed by $NH_4Cl$ (1.3 g, 24.0 mmol). The reaction mixture was stirred at ambient temperature for 12 h, ice-cold water was added and the mixture extracted with EtOAc. The combined organic layers were dried with $Na_2SO_4$ and evaporated to dryness. The residue was passed through a silica gel pad eluting with 4% MeOH in DCM giving compound (28) 0.95 g.

$^1$H-NMR (DMSO-$d_6$, δ, ppm): 1.70 (s, 3H), 2.00 (s, 3H), 2.11 (s, 3H), 2.13 (s, 3H), 2.33 (s, 3H), 2.42 (s, 3H), 4.18 (dd, 1H, $J_1$=5.4 Hz, $J_2$=12.0 Hz), 4.33-4.37 (m, 1H), 4.46-4.50 (m, 1H), 4.64-4.70 (m, 1H), 5.31-5.40 (m, 3H), 7.47 (s, 1H), 7.64 (s, 1H), 7.80 (s, 1H), 8.22 (s, 1H).

LCMS, m/z: 520 $(M+H)^+$, 542.5 $(M+Na)^+$.

Compound 29

To a solution of compound (28) (0.95 g, 1.9 mmol) in THF (25 mL) at ambient temperature, DMFDMA (0.24 g, 2.0 mmol) was added, and reaction mixture heated to reflux for 3 h. The reaction mixture was evaporated to dryness to afford the desired compound (29). The crude product was used in the next step without further purification 1.05 g.

LCMS, m/z: 575.3 $(M+H)^+$, 597.3 $(M+Na)^+$.

Compound 30

To a solution of compound (29) (1.05 g, 1.8 mmol) in 70% AcOH (10 mL) at ambient temperature, hydrazine hydrate (0.22 g, 4.3 mmol) was added, and the reaction mixture heated to reflux for 2 h. The reaction mixture was evaporated to dryness and co-evaporated with toluene. The residue was dissolved in EtOAc, washed with water, dried with $Na_2SO_4$ and evaporated to dryness. The residue was passed through a silica gel pad eluting with 5% MeOH in DCM giving compound (30) 0.18 g.

$^1$H-NMR (DMSO-$d_6$, δ, ppm): 1.67 (s, 3H), 1.99 (s, 3H), 2.11 (s, 3H), 2.13 (s, 3H), 2.35 (s, 3H), 2.44 (s, 3H), 4.15-4.19 (m, 1H), 4.34-4.37 (m, 1H), 4.56-4.61 (m, 1H), 4.72-4.78 (m, 1H), 5.32-5.35 (m, 1H), 5.40-5.48 (m, 2H), 7.46-7.54 (m, 1H), 7.62-7.72 (m, 1H), 8.15-8.59 (m, 1H), 14.32-14.47 (m, 1H).

LCMS, m/z: 544.5.0 $(M+H)^+$, 566.7 $(M+Na)^+$.

Compound 31 (Example 14)

To a solution of compound (30) (0.18 g, 0.33 mmol) in MeOH (3.5 mL) at ambient temperature, aqueous $NH_3$ (3.5 mL) was added. The reaction mixture was stirred at ambient temperature for 12 h. The reaction mixture was evaporated to ½ volume, and the pellet formed was filtered off and dried giving compound (31) (Example 14) 0.099 g.

$^1$H-NMR (DMSO-$d_6$, δ, ppm): 2.34 (s, 3H), 2.40 (s, 3H), 3.43-3.48 (m, 1H), 3.59-3.66 (m, 3H), 4.15-4.21 (m, 1H), 4.29-4.32 (m, 1H), 4.46-4.49 (m, 1H), 4.64-4.73 (m, 2H), 4.81-4.82 (m, 1H), 4.98-4.99 (m, 1H), 7.62 (s, 1H), 7.68 (s, 1H), 8.23 (br.s, 1H), 14.36 (br.s, 1H).

$^{13}$C-NMR (DMSO-$d_6$, δ, ppm): 18.70, 20.34, 44.68, 63.50, 68.65, 72.73, 73.83, 116.08, 129.82, 131.09, 131.71, 132.63, 141.53, 142.20 (br), 150.16 (br), 151.42 (br), 153.79.

LCMS, m/z: 376.5 $(M+H)^+$, 398.4 $(M+Na)^+$.

Synthesis of Compound 37 (Example 15)

Example 15 was synthesized according to the scheme below:

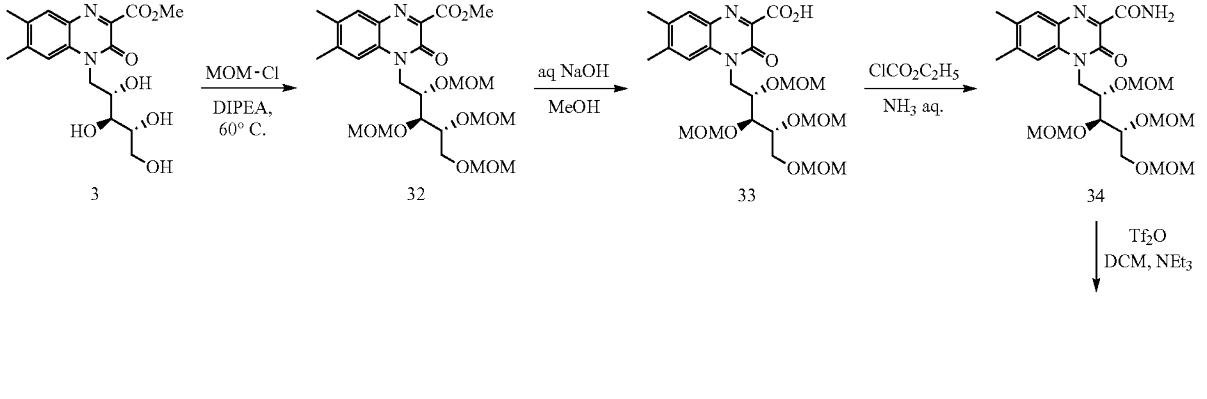

3 32 33 34

-continued

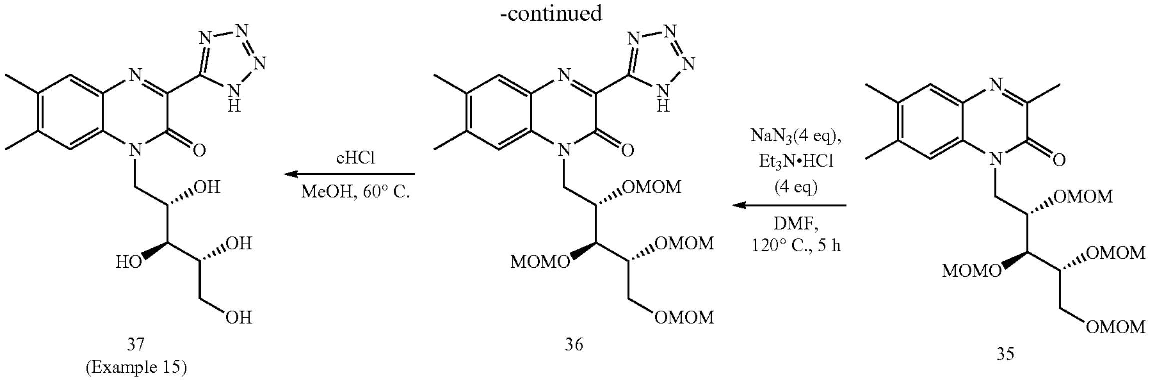

37
(Example 15)

36

35

Compound 32

Compound (3) (10.1 g, 27.5 mmol) was dissolved in DMF (100 ml), MOM chloride (16.75 ml, 220 mmol) and DIPEA (38 ml, 220 mmol) were added and the reaction mixture stirred overnight at 60° C. The reaction mixture was concentrated in vacuo, diluted with water and extracted with EtOAc. The combined organic extracts were dried with $Na_2SO_4$ and evaporated to give compound (32) 12.1 g. Compound (32) was used for the next step without further purification.

$^1$H-NMR (DMSO-$d_6$, δ, ppm): 2.39 (s, 3H), 2.67 (s, 3H), 3.27 (s, 3H), 3.31 (s, 3H), 3.37 (s, 3H), 3.38 (s, 2H), 3.62-3.73 (m, 2H), 3.89 (s, 3H), 3.96-4.06 (m, 2H), 4.21-4.25 (m, 2H), 4.3 (br.d, 1H, J=13.2 Hz), 4.41 (d, 1H, J=7.4 Hz), 4.6 (s, 2H), 4.74-4.80 (m, 6H), 7.49 (s, 1H), 7.64 (s, 1H).

LCMS, m/z: 543.5 $(M+H)^+$, 565.5 $(M+Na)^+$.

Compound 33

Compound (32) (12.1 g, 22.3 mmol) was dissolved in MeOH (150 ml), and a solution of NaOH (2.2 g, 55.75 mmol) in water (15 ml) added. The reaction mixture was stirred at room temperature overnight. MeOH was evaporated and the residue diluted with water, acidified with 10% $H_2SO_4$ to pH 2 and extracted with EtOAc. The combined organic extracts were dried with $Na_2SO_4$ and evaporated to dryness to give compound (33) 10.8 g.

$^1$H-NMR (DMSO-$d_6$, δ, ppm): 2.33 (s, 3H), 2.4 (s, 3H), 2.69 (s, 3H), 3.28 (s, 3H), 3.37 (s, 3H), 3.38 (s, 3H), 3.65 (dd, 1H, $J_1$=10.5 Hz, $J_2$=4.5 Hz), 3.72 (dd, 1H, $J_1$=11 Hz, $J_2$=4 Hz), 3.96-4.04 (m, 2H), 4.21-4.43 (m, 4H), 4.6 (s, 2H), 4.74-4.80 (m, 5H), 7.5 (s, 1H), 7.65 (s, 1H), 13.95 (br.s, 1H)

LCMS, m/z: 529.5 $(M+H)^+$, 551.3 $(M+Na)^+$.

Compound 34

Compound (33) (5 g, 9.5 mmol) was dissolved in THF (100 ml), and triethylamine (1.1 g, 11.4 mmol) added. The reaction mixture was cooled to 0° C., and ethylchloroformate (1.08 g, 10 mmol) added dropwise. Stirring was continued at −5° C. for 30 min before aqueous ammonia (150 mL) was added and the mixture stirred at room temperature overnight. The formed precipitate was filtered off, washed with water and air-dried to give compound (34) 4.4 g.

$^1$H-NMR (DMSO-$d_6$, δ, ppm): 2.33 (s, 3H), 2.39 (s, 3H), 2.69 (s, 3H), 3.28 (s, 3H), 3.37 (s, 3H), 3.38 (s, 3H), 3.64 (dd, 1H, $J_1$=10.5 Hz, $J_2$=4.5 Hz), 3.73 (dd, 1H, $J_1$=11.0 Hz, $J_2$=4.0 Hz), 3.89-4.08 (m, 2H), 4.11-4.47 (m, 4H), 4.61 (s, 2H), 4.69-4.87 (m, 5H), 7.48 (s, 1H), 7.64 (s, 1H), 7.79 (s, 1H), 8.27 (s, 1H)

LCMS, m/z: 528.3 $(M+H)^+$, 550.5 $(M+Na)^+$.

Compound 35

Compound (34) (2.1 g, 4 mmol) was dissolved in THF (50 ml). Pyridine (0.6 g, 8.0 mmol) was added under an inert atmosphere followed dropwise by trifluoroacetic anhydride (1.0 g, 4.8 mmol). The reaction mixture was stirred under an inert atmosphere at room temperature for 24 h. An additional amount of pyridine (0.6 g, 8.0 mmol) and trifluoroacetic anhydride (1 g, 4.8 mmol) was added and the stirring continued for 4 h. The reaction mixture was poured into water, extracted with EtOAc, dried over $Na_2SO_4$, concentrated and purified by column chromatography on silica gel eluting with 25-30% EtOAc in DCM to give compound (35) 1.5 g.

$^1$H-NMR (DMSO-$d_6$, δ, ppm): 2.34 (s, 3H), 2.43 (s, 3H), 2.71 (s, 3H), 3.28 (s, 3H), 3.37 (s, 3H), 3.38 (s, 3H), 3.63 (dd, 1H, $J_1$=11.5 Hz, $J_2$=5.3 Hz), 3.73 (dd, 1H, $J_1$=11.4, Hz, $J_2$=4 Hz), 3.93-4.06 (m, 2H), 4.16-4.41 (m, 4H), 4.61 (s, 2H), 4.74-4.84 (m, 5H), 7.55 (s, 1H), 7.71 (s, 1H)

LCMS, m/z: 511.0 $(M+H)^+$, 532.0 $(M+Na)^+$.

Compound 36

A mixture of compound (35) (1.5 g, 2.9 mmol), triethylammonium chloride (1.6 g, 11.6 mmol) and sodium azide (0.76 g, 11.6 mmol) in DMF (30 ml) was stirred at 120° C. for 5 h. The reaction mixture was concentrated under vacuum, diluted with water and extracted with EtOAc. The combined organic extracts were dried with $Na_2SO_4$ and evaporated to give compound (36) 1.5 g.

$^1$H-NMR (DMSO-$d_6$, δ, ppm): 2.35 (s, 3H), 2.42 (s, 3H), 2.66 (s, 3H), 3.28 (s, 3H), 3.37 (s, 3H), 3.38 (s, 3H), 3.66 (dd, 1H, $J_1$=10.5 Hz, $J_2$=5.3 Hz), 3.73 (dd, 1H, $J_1$=11.4 Hz, Hz, $J_2$=4.0 Hz), 3.93-4.11 (m, 2H), 4.14-4.49 (m, 4H), 4.61 (s, 2H), 4.71-4.99 (m, 6H), 7.53 (s, 1H), 7.72 (s, 1H)

LCMS, m/z: 553.5 $(M+H)^+$, 575.3 $(M+Na)^+$.

Compound 37 (Example 15)

Compound (36) (1.3 g, 2.3 mmol) was dissolved in MeOH (50 ml), and conc. HCl (10 mL) added. The reaction mixture was heated at 60° C. for 40 min. The formed precipitate was filtered off and washed with water to give compound (37) (Example 15) 0.45 g.

$^{1}$H-NMR (DMSO-$d_6$, δ, ppm): 2.35 (s, 3H), 2.41 (s, 3H), 3.22-3.38 (m, 4H), 3.42-3.50 (m, 1H), 3.60-3.66 (m, 3H), 4.18 (m, 1H), 4.36 (br.d, 1H, J=13.5 Hz), 4.40-4.56 (m, 1H), 4.62-4.83 (m, 3H), 5.00 (br.s, 1H), 7.66 (s, 1H), 7.75 (s, 1H), 16.8 (br.s, 1H).

$^{13}$C-NMR (DMSO-$d_6$, δ, ppm): 18.68, 20.45, 44.88, 63.47, 68.44, 68.49, 72.71, 73.75, 116.26, 130.06, 131.15, 132.24, 133.08, 139.99, 142.73, 150.96, 153.47.

LCMS, m/z: 377.6 $(M+H)^+$, 399.0 $(M+Na)^+$.

Synthesis of Compound 40 (Example 16)

Example 16 was synthesized according to the scheme below:

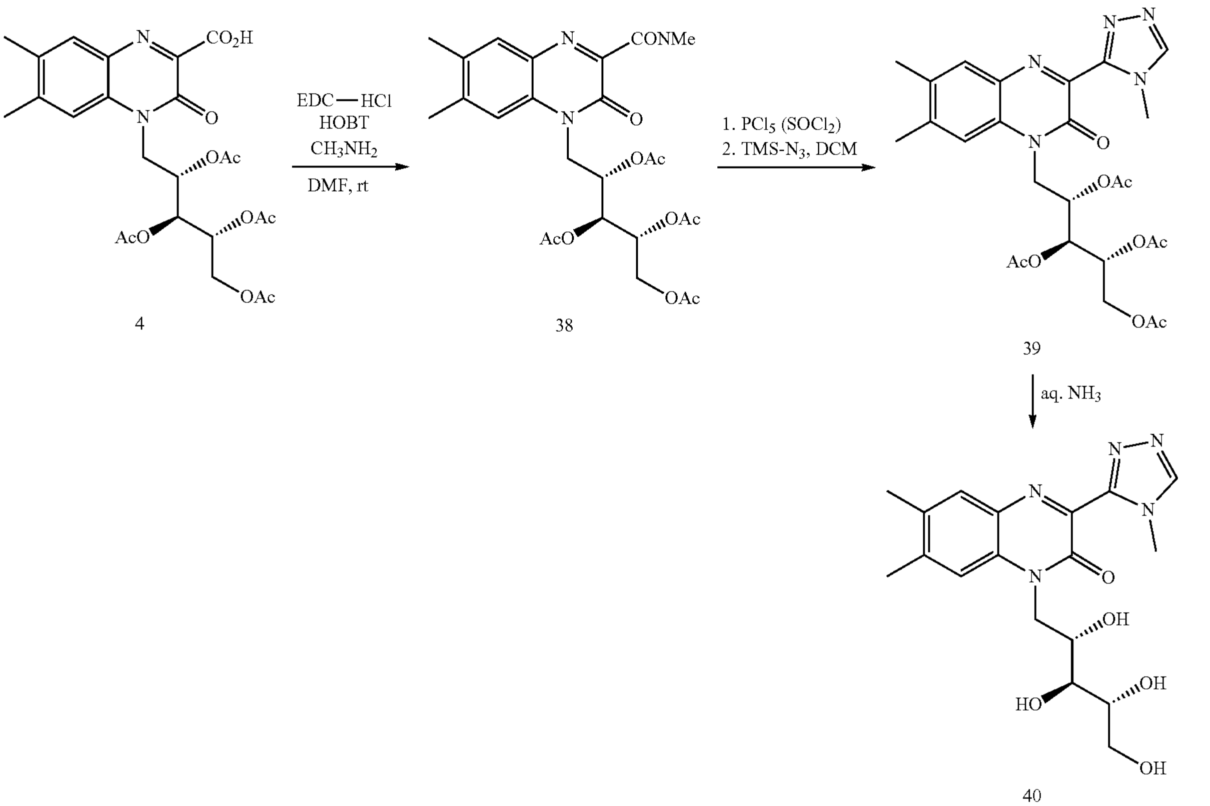

4

38

39

40
(Example 16)

Compound 38

To a solution of compound (4) (2 g, 3.8 mmol) in DMF (40 mL) was added methylamine hydrochloride (0.52 g, 7.6 mmol), EDCI (2.2 g, 11.4 mmol) and HOBt (1.17 g, 7.6 mmol). The mixture was stirred at room temperature for 18 h, diluted with water and extracted with EtOAc. The combined organic extracts were dried over $Na_2SO_4$ and evaporated to give compound (38) 0.9 g.

$^{1}$H-NMR (DMSO-$d_6$, δ, ppm): 1.69 (s, 3H), 2.0 (s, 3H), 2.11 (s, 3H), 2.12 (s, 3H), 2.33 (s, 3H), 2.42 (2, 3H), 2.8 (s, 3H), 4.11-4.23 (m, 1H), 4.3-4.39 (m, 1H), 4.43-4.54 (m, 1H), 4.61-4.74 (m, 1H), 5.26-5.44 (m, 3H), 7.48 (s, 1H), 7.64 (s, 1H), 8.77 (d, 1H, J=3.4 Hz).

LCMS, m/z: 534.3.0 $(M+H)^+$, 556.3 $(M+Na)^+$.

Compound 39

$PCl_5$ (0.28 g, 1.32 mmol) was added to a stirred solution of compound (38) (0.65 g, 1.2 mmol) in DCM under a nitrogen atmosphere. The stirred reaction mixture was cooled to −5° C., and $TMSN_3$ (0.56 g, 4.8 mmol) added dropwise before being allowed to warm to ambient temperature for 16 hours. The mixture was subsequently cooled to 0° C., and saturated $NaHCO_3$ added dropwise. The two layers were separated; the organic layer was washed with water, dried over $Na_2SO_4$ and evaporated to give compound (39) 0.26 g.

$^{1}$H-NMR (DMSO-$d_6$, δ, ppm): 1.69 (s, 3H), 2.0 (s, 3H), 1.99 (s, 3H), 2.09 (s, 3H), 2.13 (s, 3H), 2.36 (2, 3H), 2.47 (s, 3H), 4.12-4.21 (m, 3H), 4.3-4.39 (m, 1H), 4.51-4.6 (m, 1H), 4.69-4.78 (m, 1H), 5.29-5.47 (m, 3H), 7.59 (s, 1H), 7.75 (s, 1H).

LCMS, m/z: 559.2.0 $(M+H)^+$, 581.3 $(M+Na)^+$.

Compound 40 (Example 16)

Compound (39) (0.26 g, 0.4 mmol) was dissolved in MeOH (10 mL). Aqueous ammonia (5 mL) was added and the mixture stirred at ambient temperature overnight. The formed precipitate was filtered off and washed with water to give compound (40) (Example 16) 0.12 g.

$^{1}$H-NMR (DMSO-$d_6$, δ, ppm): 2.35 (s, 3H), 2.43 (s, 3H), 3.32 (s, 3H), 3.39-3.51 (m, 1H), 3.55-3.67 (m, 3H), 4.09-4.21 (m, 4H), 4.22-4.31 (d, 1H, J=3.7 In), 4.43-4.51 (m, 1H), 4.62-4.74 (m, 1H), 4.76-4.89 (m, 2H), 4.99 (d, 1H, J=4.0 III), 5.29-5.47 (m, 3H), 7.68 (s, 1H), 7.72 (s, 1H).

$^{13}$C-NMR (DMSO-$d_6$, δ, ppm): 18.65, 20.47, 35.32, 44.85, 63.53, 68.52, 72.79, 73.72, 116.26, 130.04, 131.04, 132.54, 132.97, 141.58, 142.99, 151.20, 153.40.

LCMS, m/z: 391.4 $(M+H)^+$, 413.6 $(M+Na)^+$.

Synthesis of Compound 43 (Example 17)

Example 17 was synthesized according to the scheme below:

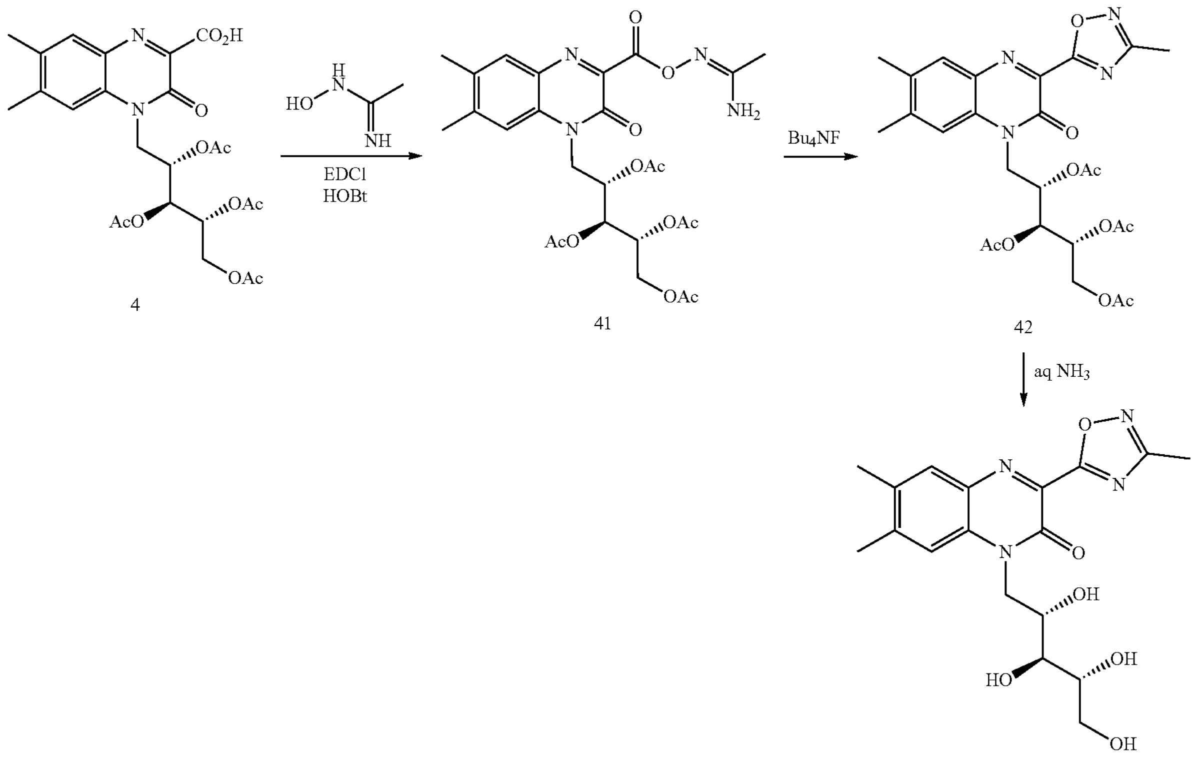

4 41 42

43
(Example 17)

Compound 41

A solution of compound (4) (2.0 g, 3.8 mmol), EDC-HCl (1.5 g, 7.6 mmol) and 1-hydroxybenzo-triazole (1.04 g, 7.6 mmol) in dry DCM (40 mL) was stirred at ambient temperature under nitrogen atmosphere for 30 minutes. N-hydroxyacetamidine (0.57 g, 7.6 mmol) was added and the reaction mixture stirred at ambient temperature for 12 h. The reaction mixture was quenched with water and extracted with DCM. Combined organic layers were washed with 10% sodium bicarbonate, water and brine, dried over $Na_2SO_4$, filtered and concentrated. The residue was passed through a silica gel pad eluting with 2% MeOH in DCM to give compound (41) 1.00 g.

$^1$H-NMR (DMSO-$d_6$, δ, ppm): 1.70 (s, 3H), 1.78 (s, 3H), 2.00 (s, 3H), 2.10 (s, 3H), 2.13 (s, 3H), 2.33 (s, 3H), 2.44 (s, 3H), 4.15-4.19 (m, 1H), 4.32-4.36 (m, 1H), 4.48-4.52 (m, 1H), 4.62-4.71 (m, 1H), 5.29-5.33 (m, 1H), 5.35-5.41 (m, 2H), 6.41-6.69 (m, 2H), 7.49 (s, 1H), 7.66 (s, 1H).

LCMS, m/z: 577.5 $(M+H)^+$, 599.2 $(M+Na)^+$.

Compound 42

To a solution of compound (41) (1.00 g, 1.7 mmol) in THF (30 mL) at ambient temperature was added TBAF (0.077 g, 1.7 mmol). The reaction mixture was stirred at ambient temperature for 12 h. The reaction mixture was dissolved in EtOAc, washed with water, 5% citric acid, water and brine, dried over $Na_2SO_4$, filtered and concentrated. The residue was passed through a silica gel pad eluting with 30% EtOAc in $CCl_4$ giving compound (42) 0.26 g.

$^1$H-NMR ($CDCl_3$, δ, ppm): 1.82 (s, 3H), 2.08 (s, 3H), 2.18 (s, 3H), 2.20 (s, 3H), 2.39 (s, 3H), 2.50 (s, 3H), 2.57 (s, 3H), 4.21-4.25 (m, 1H), 4.40-4.44 (m, 1H), 4.56-4.72 (m, 2H), 5.39-5.46 (m, 2H), 5.61-5.63 (m, 1H), 7.34 (s, 1H), 7.82 (s, 1H).

LCMS, m/z: 559.3 $(M+H)^+$, 581.3 $(M+Na)^+$.

Compound 43 (Example 17)

To a solution of compound (42) (0.26 g, 0.46 mmol) in MeOH (5 mL) at ambient temperature, was added aqueous $NH_3$ (5 mL). The reaction mixture was stirred at ambient temperature for 12 h. The reaction mixture was evaporated to ½ volume, and the pellet formed was filtered off and dried giving compound (43) (Example 17) 0.11 g.

$^1$H-NMR (DMSO-$d_6$, δ, ppm): 2.33 (s, 3H), 2.41 (s, 3H), 2.48 (s, 3H), 3.41-3.48 (m, 1H), 3.56-3.66 (m, 3H), 4.13-4.16 (m, 1H), 4.25-4.29 (m, 1H), 4.45-4.47 (m, 1H), 4.64-4.65 (m, 1H), 4.73-4.74 (m, 1H), 4.82 (br.s, 1H), 4.98 (br.s, 1H), 7.65 (s, 1H), 7.71 (s, 1H).

$^{13}$C-NMR (DMSO-$d_6$, δ, ppm): 11.34, 18.62, 20.53, 44.80, 63.50, 68.58, 72.73, 73.81, 116.25, 130.24, 130.75, 133.05, 139.61, 143.85, 152.56, 167.56, 171.70.

LCMS, m/z: 391.4 $(M+H)^+$, 413.6 $(M+Na)^+$.

Synthesis of Compound 44 (Example 7)

Example 7 can be synthesized according to the scheme below:

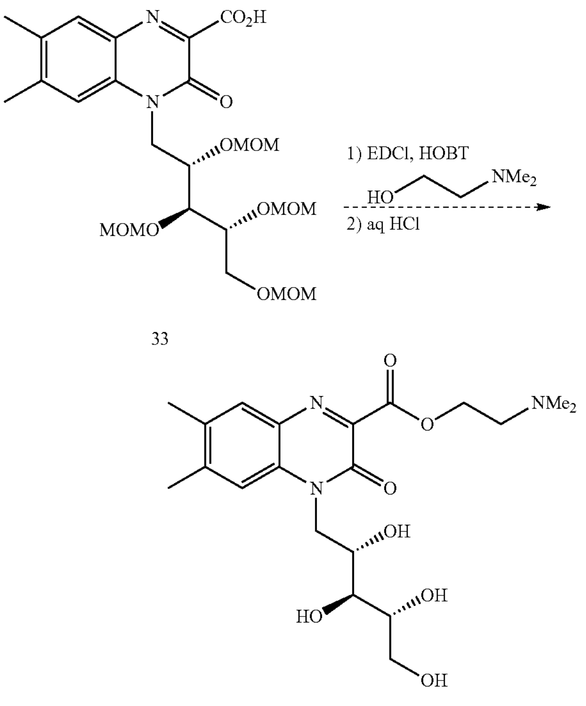

33

44
(Example 7)

Compound (33) is converted into compound (44) (Example 7) via coupling with 2-dimethylaminoethanol (CAS #108-01-0) and acid mediated removal of the MOM protecting groups.

Synthesis of Compound 50 (Example 18), Compound 52 (Example 19), Compound 54 Example 20

Examples 18-20 were synthesized according to the scheme below.

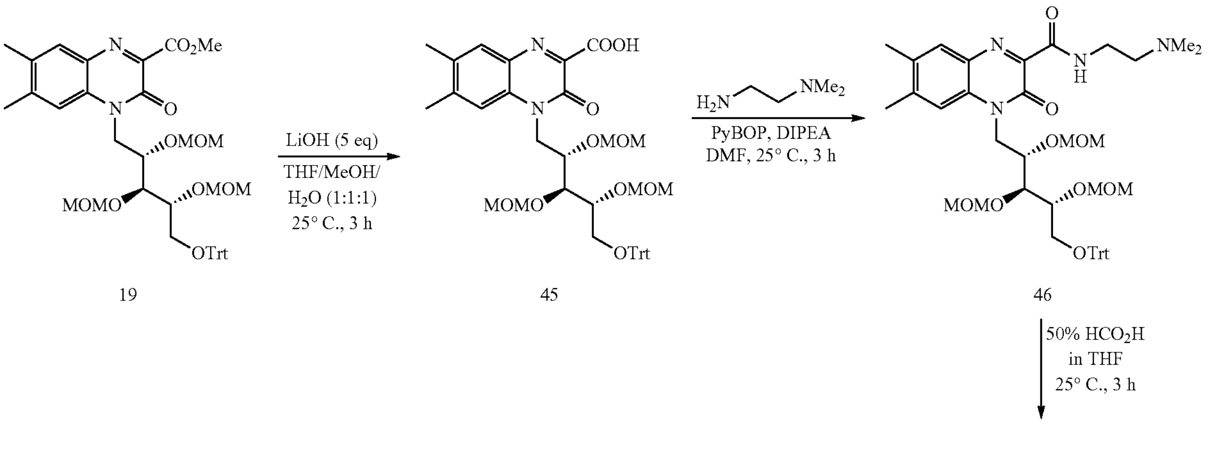

19 45 46

-continued

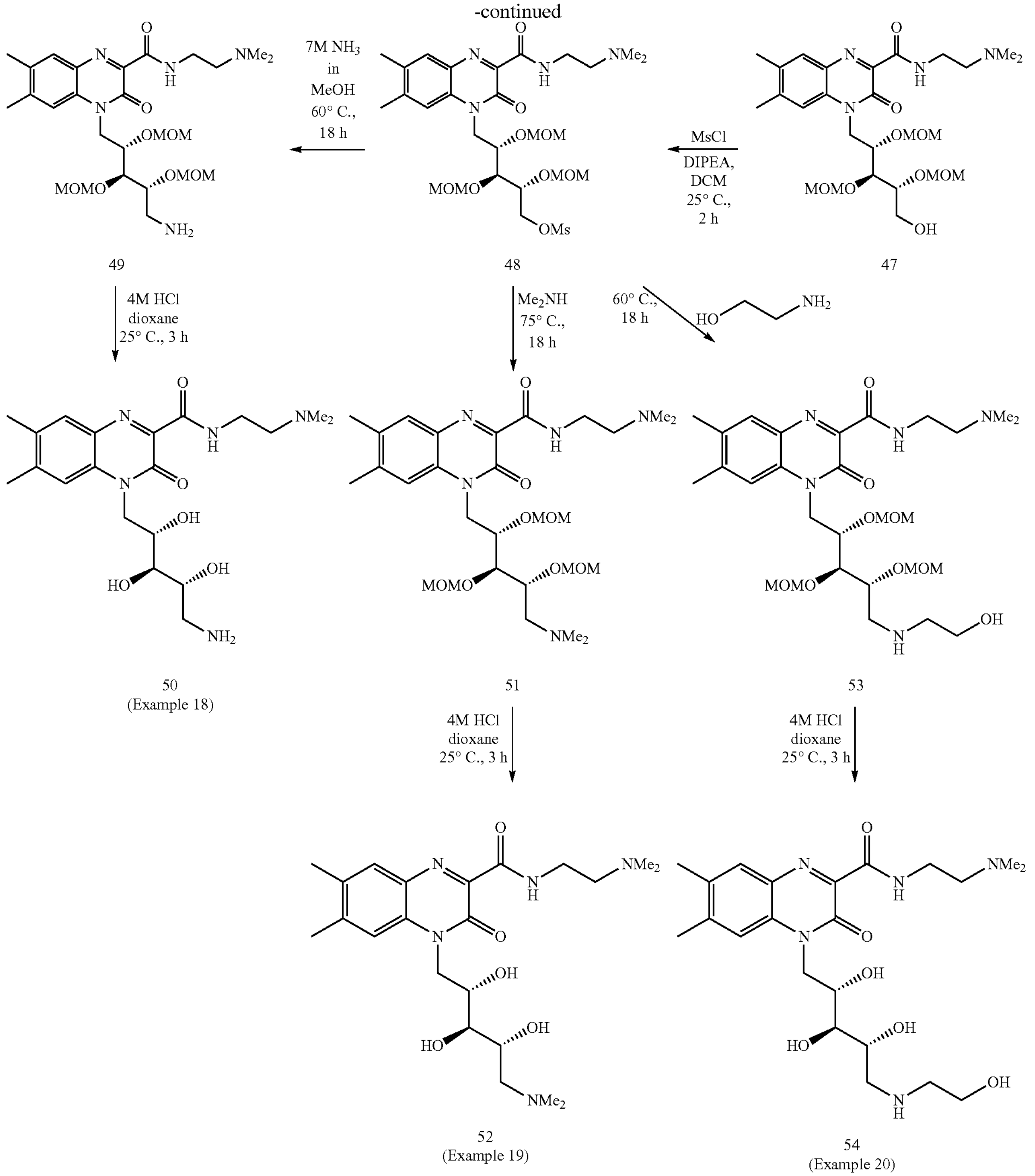

49 48 47

50
(Example 18)

51

53

52
(Example 19)

54
(Example 20)

Compound 45

Lithium hydroxide (6.47 g, 269.96 mmol) in water (120 mL) was added dropwise to a stirred solution of compound (19) (40.0 g, 53.99 mmol) in MeOH (120 mL) and THF (120 mL) at 0° C. The resulting mixture was stirred for 3 h at 0° C. The mixture was neutralized with 1M HCl to pH 7 and diluted with water (0.8 L). The resulting mixture was extracted with EtOAc (3×200 mL). The combined organic layers were washed with water (3×100 mL) and dried over anhydrous $Na_2SO_4$. After filtration, the filtrate was concentrated under reduced pressure to obtain compound (45) which was used directly in the next step without further purification.

LCMS: (ES, m/z): $[M+Na]^+=749.5$

Compound 46

To a 0° C. stirred solution of compound (45) (30.0 g, 41.27 mmol) and (2-aminoethyl)dimethylamine (7.28 g, 82.55 mmol) and DIPEA (16.0 g, 0.124 mol) in DMF (400 mL) was added PyBOP (42.99 g, 82.55 mmol) in portions. The resulting mixture was stirred for 3 h at 25° C. before being diluted with water (1.2 L). The resulting mixture was extracted with EtOAc (3×300 mL). The combined organic layers were washed with water (3×200 mL) and dried over anhydrous $Na_2SO_4$. After filtration, the filtrate was concentrated under reduced pressure to give compound (46) which was used directly in the next step without further purification.

LCMS: (ES, m/z): $[M+H]^+$=797.5

Compound 47

Formic acid (120 mL) was added dropwise to a 0° C. stirred solution of compound (46) (25.0 g, 31.37 mmol) in THF (120 mL). The resulting mixture was stirred for 3 h at 25° C. and adjusted to pH 10 with saturated aqueous $Na_2CO_3$. The mixture was subsequently diluted with water (0.8 L) and extracted with EtOAc (3×300 mL). The combined organic layers were washed with water (3×200 mL) and dried over anhydrous $Na_2SO^4$. After filtration, the filtrate was concentrated under reduced pressure. The residue was purified by reverse flash chromatography using the following conditions: column, C18 silica gel; mobile phase, acetonitrile in water (0.1% formic acid), 25% to 35% gradient in 20 min; detector, UV 254 nm to afford compound (47) as a yellow oil (8 g).

LCMS: (ES, m/z): [M+H]+=555.4

Compound 48

MsCl (6.20 g, 54.09 mmol) was added dropwise to a 0° C. stirred solution of compound (47) (6.00 g, 10.82 mmol) and DIPEA (13.98 mg, 108.18 mmol) in DCM under an argon atmosphere. The resulting mixture was stirred for 2 h at 25° C. and concentrated under reduced pressure. The residue was purified by reverse flash chromatography using the following conditions: column, C18 silica gel; mobile phase, acetonitrile in water (0.1% formic acid), 25% to 40% gradient in 20 min; detector, UV 254 nm to afford compound (48) as a yellow oil (5.2 g).

LCMS: (ES, m/z): $[M+H]^+$=633.3

Compound 49

In a 40 mL sealed tube were mixed compound (48) (400 mg) and 7M $NH_3$ (g) in MeOH (20 mL) at 25° C. The mixture was stirred for 18 h at 60° C. and concentrated under reduced pressure. The residue was purified by reverse flash chromatography using the following conditions: column, C18 silica gel; mobile phase, acetonitrile in water (0.1% formic acid), 25% to 40% gradient in 20 min; detector, UV 254 nm to afford compound (49) as a yellow oil (300 mg).

LCMS: (ES, m/z): $[M+H]^+$=554.4

Compound 50 (Example 18)

4M HCl in 1,4-dioxane (10 mL) was added dropwise to a 0° C. stirred solution of compound (49) (300 mg, 0.54 mmol) in THF (1 mL). The resulting mixture was stirred for 3 h at 0° C. under a nitrogen atmosphere. The mixture was subsequently concentrated under reduced pressure and purified by preparative HPLC using the following conditions: Column: X Bridge Shield RP18 OBD Column, 5 μm, 19×150 mm; Mobile Phase A: Water (10 mmol/L $NH_4HCO_3$), Mobile Phase B: Acetonitrile; flow rate: 25 mL/min; Gradient: 4% B to 18% B in 8 min; 220 nm; Rt: 7.8 min) to afford compound (50) (Example 18) as a yellow solid (55 mg).

LCMS: (ES, m/z): $[M+H]^+$=422.2

1H NMR (300 MHz, Methanol-d4) δ 7.82 (s, 1H), 7.66 (s, 1H), 4.64 (d, J=24.3 Hz, 2H), 4.19 (s, 1H), 4.03 (d, J=10.2 Hz, 1H), 3.76 (t, J=6.0 Hz, 1H), 3.65 (t, J=6.5 Hz, 2H), 3.16 (dd, J=12.9, 3.7 Hz, 1H), 3.04 (dd, J=12.9, 7.5 Hz, 1H), 2.65 (t, J=6.5 Hz, 2H), 2.46 (d, J=25.9 Hz, 3H), 2.36 (s, 9H).

Compound 51

To a 25° C. stirred solution of compound (48) (300 mg, 0.47 mmol) was added 2M dimethylamine in MeOH (5 mL). The resulting mixture was stirred for 18 h at 75° C. and concentrated under reduced pressure. The residue was purified by reverse flash chromatography using the following conditions: column, C18 silica gel; mobile phase, acetonitrile in water (0.1% formic acid), 25% to 40% gradient in 20 min; detector, UV 254 nm. to afford compound (51) as a yellow oil (200 mg).

LCMS: (ES, m/z): $[M+H]^+$=582.4

Compound 52 (Example 19)

4M HCl in 1,4-dioxane (10 mL) was added dropwise to a 0° C. solution of compound (51) (200 mg) in THF (10 mL) and stirred for 3 h at 0° C. The mixture was subsequently neutralized to pH 7 with saturated aqueous $NaHCO_3$. After filtration, the filtrate was concentrated under reduced pressure and the residue purified by preparative HPLC using the following conditions: Column: XBridge Shield RP18 OBD Column, 5 μm, 19×150 mm; Mobile Phase A: Water (10 mmol/L $NH_4HCO_3$), Mobile Phase B: Acetonitrile; flow rate: 25 mL/min; Gradient: 20% B to 50% B in 12 min; 220 nm; Rt: 11.8 min to afford compound (52) (Example 19) as a yellow solid (60 mg).

LCMS: (ES, m/z): $[M+H]^+$=450.2

1H NMR (300 MHz, DMSO-$d_6$) δ 9.15 (s, 1H), 7.63 (d, J=22.7 Hz, 2H), 4.91 (s, 2H), 4.72 (s, 1H), 4.55 (t, J=12.2 Hz, 1H), 4.31 (d, J=13.8 Hz, 1H), 4.05 (s, 1H), 3.77 (s, 1H), 3.58 (s, 3H), 2.41 (d, J=6.6 Hz, 7H), 2.33 (s, 3H), 2.26 (s, 6H), 2.20 (s, 6H).

Compound 53

To a solution of compound (48) (400 mg, 0.60 mmol) in THF (10 ml) at 25° C. was added 2-aminoethan-1-ol (10 mL). The resulting mixture was stirred for 18 h at 60° C., concentrated under reduced pressure and the residue purified by reverse flash chromatography using the following conditions: column, C18 silica gel; mobile phase, acetonitrile in water, 20% to 50% gradient in 25 min; detector, UV 254 nm. to afford compound (53) as a yellow solid (350 mg).

LCMS: (ES, m/z): $[M+H]^+$=598.4

Compound 54 (Example 20)

To a 0° C. stirred solution of compound (53) (300 mg, 0.50 mmol) in THF (10.00 mL) was added dropwise 4M HCl in 1,4-dioxane (10.00 mL). The resulting mixture was stirred for 3 h at 25° C. and neutralized to pH 7 with saturated aqueous $NaHCO_3$. After filtration, the filtrate was concentrated under reduced pressure and the residue purified by preparative HPLC using the following conditions: Column: Welch Xtimate C18 21.2×250 mm, 5 μm; Mobile Phase A: Water (0.05% TFA), Mobile Phase B: Acetonitrile; flow rate: 25 mL/min; Gradient: 13% B to 16% B in 9 min; 254 nm; Rt: 6.33 min. to afford compound (54) (Example 20) as a yellow solid (130 mg).

LCMS: (ES, m/z): $[M+H]^+$=466.3

1H NMR (300 MHz, Methanol-$d_4$) δ 7.80 (s, 1H), 7.66 (s, 1H), 4.70 (d, J=9.0 Hz, 1H), 4.59 (dd, J=14.0, 2.9 Hz, 1H), 4.25-4.11 (m, 2H), 3.92-3.80 (m, 5H), 3.45 (t, J=5.8 Hz, 2H), 3.30 (s, 1H), 3.27 (d, J=4.5 Hz, 1H), 3.21 (td, J=4.8, 2.0 Hz, 2H), 3.03 (s, 6H), 2.52 (s, 3H), 2.43 (s, 3H).

Synthesis of Compound 56 (Example 21)

Example 21 was synthesized according to the scheme below.

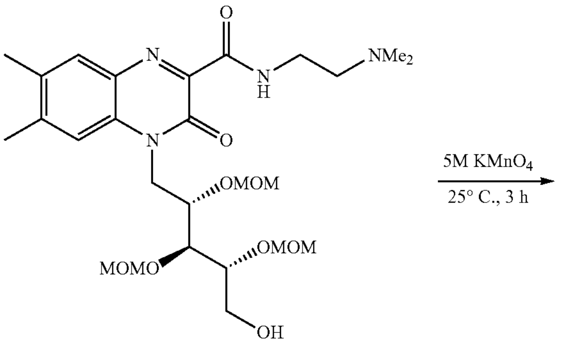

47

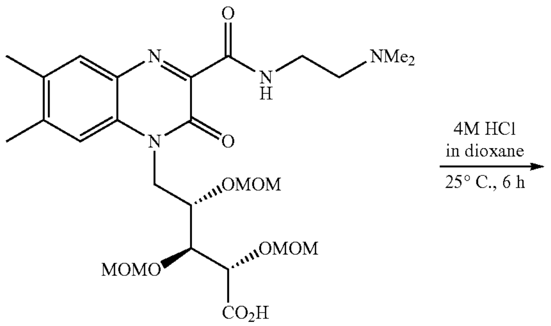

55

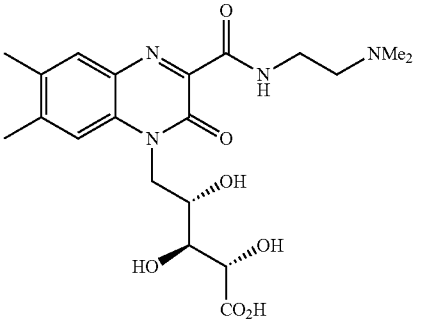

56
(Example 21)

Compound 55

$KMnO_4$ (854.79 mg, 5.41 mmol) in acetone (10 mL) was added dropwise to a 0° C. stirred solution of compound (47) (600 mg, 1.08 mmol) in acetone (10 mL). The resulting mixture was stirred for 3 h at 25° C. before being filtered and washed with water (3×5 mL). The filtrate was concentrated under reduced pressure and the residue purified by reverse flash chromatography using the following conditions: Column, C18 silica gel; mobile phase, ACN in water (0.1% aq$NH_3$), 10% to 50% gradient in 20 min; detector, UV 254 nm. to afford compound (55) (200 mg) as a yellow solid.

LCMS: (ES, m/z): $[M+H]^+$=569.4

Compound 56 (Example 21)

4M HCl in 1,4-dioxane (5.00 mL) was added dropwise to a 0° C. stirred solution of compound (55) (200 mg) in $H_2O$ (10.00 mL) under an argon atmosphere. The resulting mixture was stirred for 6 h at 25° C. before being neutralized to pH 7 with saturated aqueous $NaHCO_3$. The resulting mixture was concentrated under reduced pressure and the residue purified by preparative HPLC using the following conditions: Column: SunFire Prep C18 OBD Column 19×150 mm, 5 μm; Mobile Phase A: Water (0.1% formic acid), Mobile Phase B: ACN; Flow rate: 25 mL/min; Gradient: 15% B to 15% B in 6 min; 254/220 nm; Rt: 4.50 min. to afford compound (56) (Example 21) (31.9 mg) as a yellow solid.

LCMS: (ES, m/z): $[M+H]^+$=437.2

$^1H$ NMR (300 MHz, Methanol-d4) δ 8.07 (d, J=10.8 Hz, 1H), 7.75 (d, J=28.8 Hz, 2H), 4.81-4.75 (m, 1H), 4.62-4.46 (m, 2H), 4.28 (d, J=9.2 Hz, 1H), 3.88-3.75 (m, 3H), 3.74-3.57 (m, 5H), 3.12 (s, 1H), 2.98 (s, 2H), 2.46 (d, J=26.2 Hz, 6H).

Synthesis of Compound 59 (Example 22)

Example 22 was synthesized according to the scheme below.

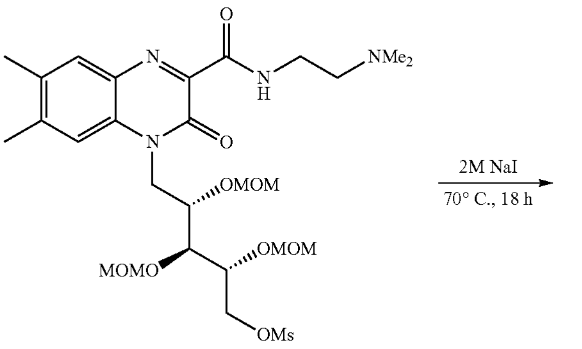

48

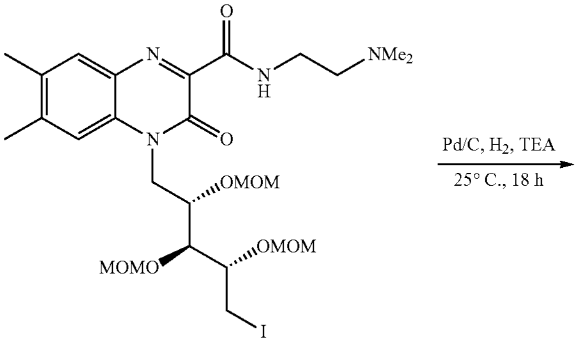

57

-continued

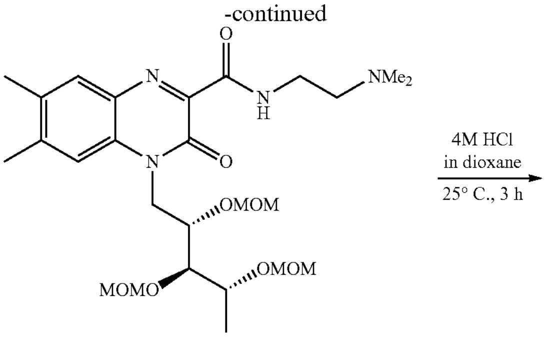

58

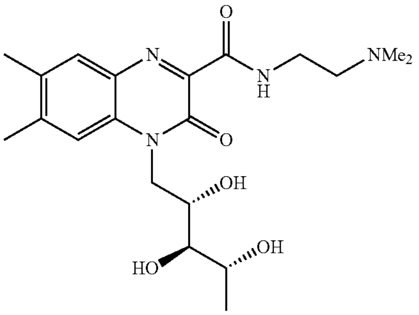

59
(Example 22)

Compound 57

In a sealed tube were combined compound (48) (350 mg, 0.55 mmol) and NaI (331.66 mg, 2.21 mmol) in acetone (20 mL). The resulting mixture was stirred for 18 h at 70° C. After cooling to 0° C. the mixture was concentrated under reduced pressure. The residue was subsequently purified by reverse flash chromatography using the following conditions: Column, C18 silica gel; mobile phase, ACN in water (0.1% formic acid), 25% to 45% gradient in 20 min; detector, UV 254 nm to afford compound 57 (280 mg) as a yellow oil.

LCMS: (ES, m/z): [M+H]+=665.2

Compound 58

A mixture of compound (57) (280 mg, 0.42 mmol), TEA (85.02 mg, 0.84 mmol) and Pd/C (60 mg) in MeOH (20 mL) was stirred for 18 h at 25° C. under a hydrogen atmosphere. The mixture was filtered and the residual solids washed with MeOH (3×5 mL). The combined filtrates were concentrated under reduced pressure to afford compound (58) (200 mg) as a yellow oil.

LCMS: (ES, m/z): $[M+H]^+$=539.3

Compound 59 (Example 22)

4M HCl in 1,4-dioxane (5 mL) was added dropwise to a 0° C. stirred solution of compound (58) (300 mg, 0.56 mmol) in MeOH (10 mL) under a nitrogen atmosphere. The resulting mixture was stirred for 3 h at 25° C. before being cooled to 0° C. and neutralized to pH 7 with saturated aqueous $NaHCO_3$. The mixture was concentrated under reduced pressure and the residue purified by reverse flash chromatography using the following conditions: Column: XBridge C18 OBD Prep Column, 100 Å, 5 μm, 19 mm×250 mm; Mobile Phase A: Water (10 mmol, $NH_4HCO_3$), mobile Phase B: ACN; Flow rate: 25 mL/min; Gradient: 19% B to 27% B in 11 min; 254 nm; Rt: 9.32 min to afford compound (59) (Example 22) (16.1 mg) as a yellow solid.

LCMS: (ES, m/z): $[M+H]^+$=407.3

$^1$H NMR (300 MHz, Methanol-d4) δ 7.82 (s, 1H), 7.69 (s, 1H), 4.61 (s, 1H), 4.18 (t, J=6.4 Hz, 1H), 3.96 (t, J=6.3 Hz, 1H), 3.69-3.58 (m, 4H), 2.65 (t, J=6.6 Hz, 2H), 2.50 (s, 3H), 2.42 (s, 3H), 2.36 (s, 6H), 1.29 (d, J=6.3 Hz, 3H).

Synthesis of Compound 61 (Example 23), Compound 63 (Example 24), Compound 65 Example 25

Examples 23-25 were synthesized according to the scheme below.

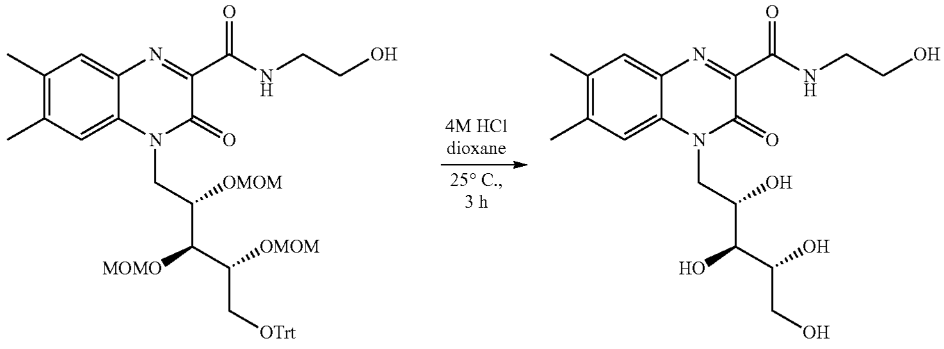

60

61
(Example 23)

-continued

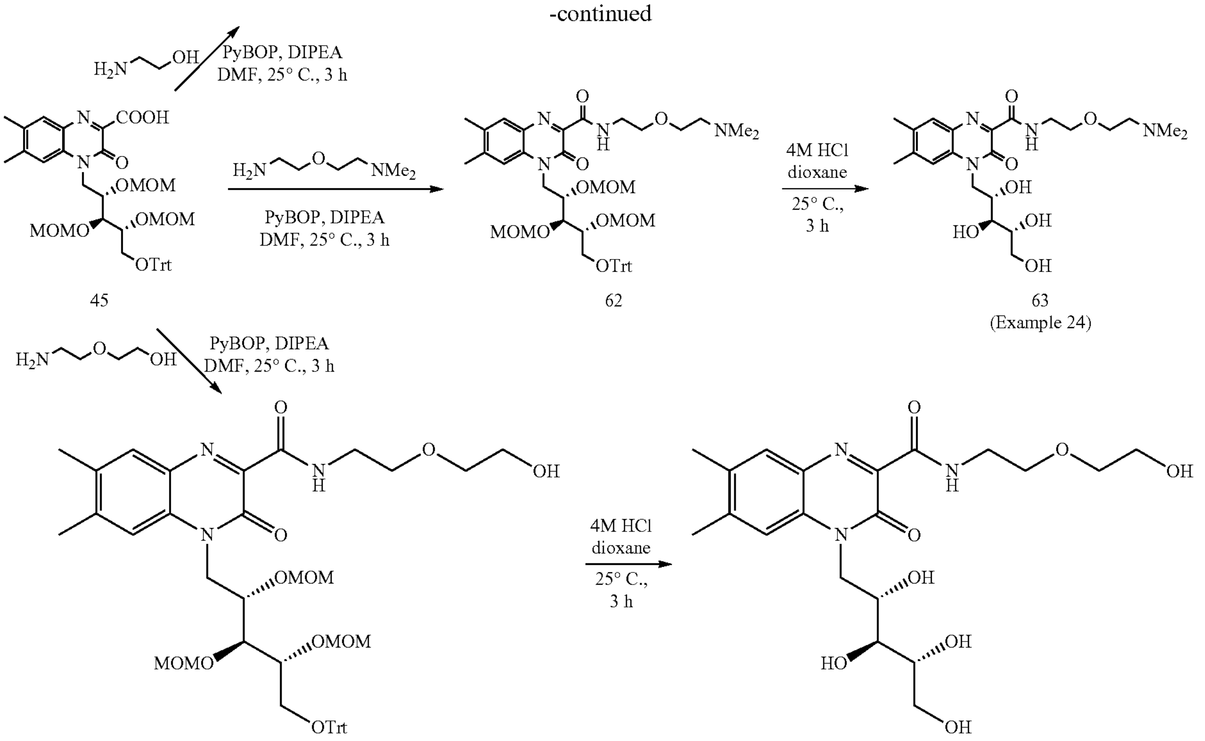

45 62 63 (Example 24)

64 65 (Example 25)

Compound 60

To a 0° C. stirred solution of compound (45) (300 mg, 0.41 mmol), 2-aminoethan-1-ol (240 mg, 3.93 mmol) and DIPEA (600 mg, 4.64 mmol) in DMF (10 ml) was added PyBOP (400 mg, 0.77 mmol) in portions. The resulting mixture was stirred for 3 h at 25° C. before being diluted with water (100 mL). The mixture was extracted with EtOAc (3×50 mL), the combined organic layers washed with water (3×50 mL) and dried over anhydrous $Na_2SO_4$. After filtration, the filtrate was concentrated under reduced pressure and purified by reverse flash chromatography using the following conditions: column, C18 silica gel; mobile phase, acetonitrile in water (0.1% formic acid), 25% to 40% gradient in 20 min; detector, UV 254 nm. to afford compound (60) as a yellow solid (250 mg).

LCMS: (ES, m/z): $[M+H]^+$=770.4

Compound 61 (Example 23)

4M HCl in 1,4-dioxane (10 mL) was added dropwise to a 0° C. solution of compound (60) (360 mg, 0.45 mmol) in THF (10 mL) and stirred for 3 h at 25° C. The mixture was subsequently neutralized to pH 7 with saturated aqueous $NaHCO_3$ and concentrated under reduced pressure. The residue was purified by preparative HPLC using the following conditions: Column: XBridge Shield RP18 OBD Column, 5 μm, 19×150 mm; Mobile Phase A: Water (10 mmol/L $NH_4HCO_3$), Mobile Phase B: Acetonitrile; Flow rate: 25 mL/min; Gradient: 8% B to 25% B in 8 min; 220 nm; Rt: 7.9 min to afford compound (61) (Example 23) as a yellow solid (90 mg).

LCMS: (ES, m/z): $[M+H]^+$=396.2

$^1$H NMR (300 MHz, DMSO-d6) δ 9.25 (t, J=5.5 Hz, 1H), 7.65 (d, J=16.5 Hz, 2H), 4.99 (d, J=3.9 Hz, 1H), 4.88-4.79 (m, 2H), 4.65 (dd, J=25.2, 8.7 Hz, 2H), 4.49 (t, J=5.3 Hz, 1H), 4.28-4.07 (m, 2H), 3.67-3.49 (m, 6H), 3.35 (d, 2H), 2.37 (d, J=19.4 Hz, 6H).

Compound 62

To a 0° C. stirred solution of compound (45) (300 mg, 0.41 mmol), [2-(2-aminoethoxy)ethyl] dimethylamine (109.14 mg, 0.83 mmol) and DIPEA (192.42 mg, 1.48 mmol) in DMF (10 mL) was added PyBOP (384.91 mg, 0.74 mmol) in portions. The resulting mixture was stirred for 3 h at 25° C. and subsequently diluted with water (100 mL). The mixture was extracted with EtOAc (3×50 mL) and the combined organic layers, washed with water (3×50 mL), and dried over anhydrous $Na_2SO_4$. After filtration, the filtrate was concentrated under reduced pressure. The residue was purified by reverse flash chromatography using the following conditions: column, C18 silica gel; mobile phase, acetonitrile in water (0.1% formic acid), 10% to 50% gradient in 20 min; detector, UV 254 nm. to afford compound (62) as a yellow solid (200 mg).

LCMS: (ES, m/z): $[M+H]^+$=841.5

Compound 63 (Example 24)

4M HCl in 1,4-dioxane (10 mL) was added dropwise to a 0° C. solution of compound (62) (200 mg, 0.24 mmol) in THF (10 mL) under a nitrogen atmosphere. The resulting mixture was stirred for 3 h at 25° C. and neutralized to pH 7 with saturated aqueous $NaHCO_3$. The mixture was concentrated under reduced pressure and purified by preparative HPLC using the following conditions: Column: X Bridge Shield RP18 OBD Column, 5 μm, 19×150 mm; Mobile Phase A: Water (10 mmol/L $NH_4HCO_3$), mobile Phase B: Acetonitrile; Flow rate: 25 mL/min; Gradient: 12% B to 40% B in 8 min; 220 nm; Rt: 7.9 min. to afford compound (63) (Example 24) as a yellow solid (70 mg).

LCMS: (ES, m/z): $[M+H]^+$=467.2

$^1$H NMR (300 MHz, DMSO-d6) δ 9.26 (d, J=5.8 Hz, 1H), 7.64 (d, J=13.5 Hz, 2H), 4.91 (d, J=48.1 Hz, 2H), 4.75-4.36 (m, 3H), 4.31-4.01 (m, 2H), 3.73-3.49 (m, 9H), 2.55-2.28 (m, 8H), 2.14 (s, 6H).

Compound 64

To a 0° C. stirred solution of compound (45) (300 mg, 0.41 mmol), 2-(2-aminoethoxy) ethan-1-ol (130.19 mg, 1.24 mmol) and DIPEA (214.56 mg, 1.65 mmol), in DMF (10 mL) was added PyBOP (429.59 mg, 0.83 mmol) in portions. The resulting mixture was stirred for 3 h at 25° C. and subsequently diluted with water (100 mL). The resulting mixture was extracted with EtOAc (3×50 mL). The combined organic layers were washed with water (3×50 mL) and dried over anhydrous $Na_2SO_4$. After filtration, the filtrate was concentrated under reduced pressure. The residue was purified by reverse flash chromatography using the following conditions: column, C18 silica gel; mobile phase, acetonitrile in water (0.1% formic acid), 25% to 50% gradient in 20 min; detector, UV 254 nm. to afford compound (64) as a yellow solid (200 mg).

LCMS: (ES, m/z): $[M+H]^+$=814.4

Compound 65 (Example 25)

4M HCl in 1,4-dioxane (10 mL) was added dropwise to a 0° C. solution of compound (64) (200 mg, 0.18 mmol) in THF (10 mL) under an argon atmosphere. The resulting mixture was stirred for 3 h at 25° C. and subsequently neutralized to pH 7 with saturated aqueous $NaHCO_3$. The resulting mixture was concentrated under reduced pressure and the residue purified by preparative HPLC using the following conditions: column, C18 silica gel; mobile phase, acetonitrile in water (0.1% formic acid), 20% to 35% gradient in 20 min; detector, UV 254 nm. to afford compound (65) (Example 25) as a yellow solid (50 mg).

LCMS: (ES, m/z): $[M+H]^+$=440

$^1$H NMR (300 MHz, DMSO-d6) δ 9.19 (t, J=5.5 Hz, 1H), 7.64 (d, J=14.0 Hz, 2H), 4.99 (d, J=4.5 Hz, 1H), 4.83 (d, J=3.5 Hz, 1H), 4.71-4.56 (m, 3H), 4.48 (t, J=5.4 Hz, 1H), 4.29-4.07 (m, 2H), 3.68-3.40 (m, 12H), 2.43-2.29 (m, 6H).

Synthesis of Compound 67 (Example 27) and Compound 69 (Example 26)

Examples 26 and 27 can be prepared according to the scheme below:

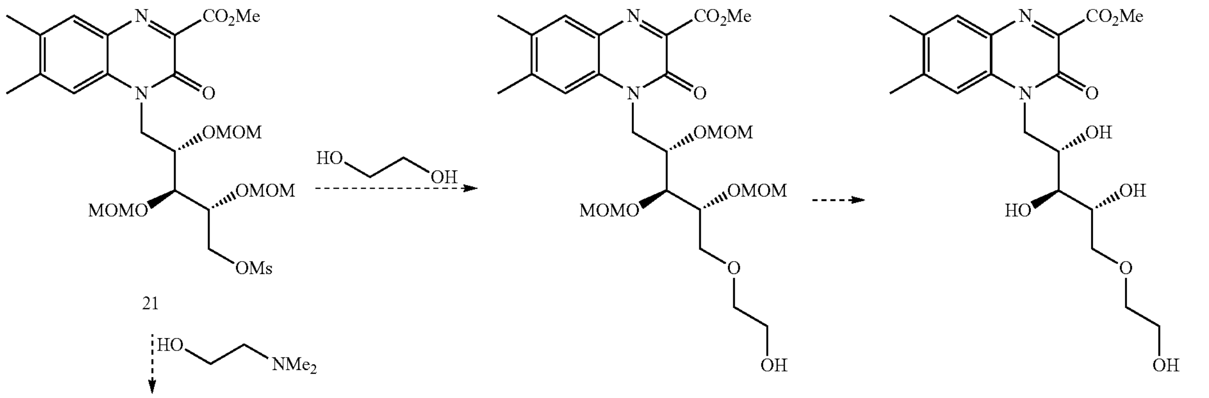

21

66

67
(Example 27)

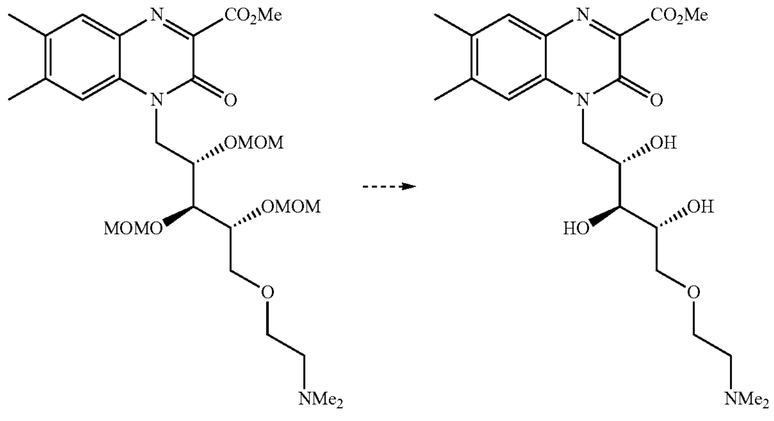

68

69
(Example 26)

Displacement of the OMs moiety in compound (21) with ethylene glycol affords compound (66), or displacement with 2-dimethylaminoethan-1-ol affords compound (68). Removal of the MOM protecting groups under acidic conditions on compound (66) leads to compound (67) (Example 27), removal of the MOM protecting groups on compound (68) leads to compound (69) (Example 26).

Synthesis of Compound 71 (Example 28) and Compound 73 (Example 29)

Examples 28 and 29 were synthesized according to the scheme below.

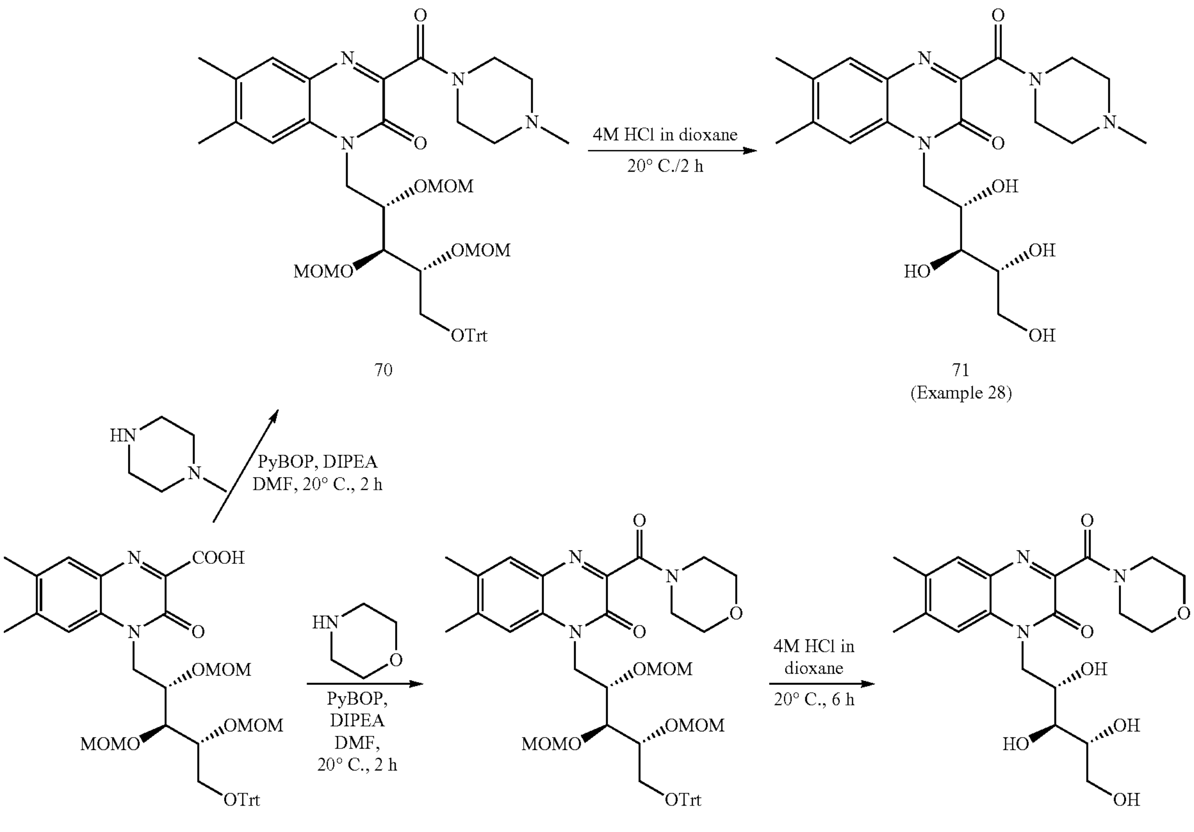

70

71 (Example 28)

45

72

73 (Example 29)

resulting mixture was stirred for 2 h at 20° C. and subsequently concentrated under reduced pressure. The crude product was purified by preparative HPLC using the following conditions: Column: XBridge Prep Phenyl OBD Column 5 μm, 19×250 mm; Mobile Phase A: Water (0.05% $NH_4OH$), Mobile Phase B: Acetonitrile; Flow rate: 25 mL/min; Gradient: 3% B to 3% B in 2 min; 254/220 nm; Rt: 8.50 min to afford compound (71) (Example 28) as a light yellow solid (90 mg).

LCMS: ESI-MS m/z=435.5 $[M+H]^+$ $^1$H-NMR (400 MHz, Methanol-d4): δ 7.72-7.65 (d, 2H), 4.95-4.83 (dd, J=14.1, 9.7 Hz, 1H), 4.45 (dd, J=14.1, 2.8 Hz, 1H), 4.28 (ddd, J=9.7, 4.6, 2.8 Hz, 1H), 3.91-3.80 (m, 5H), 3.80-3.74 (m, 1H), 3.45 (dd, J=5.9, 4.2 Hz, 2H), 2.60 (t, J=5.3 Hz, 2H), 2.48 (s, 5H), 2.38 (d, J=16.8 Hz, 6H).

Compound 70

To a 0° C. stirred solution of 1-methylpiperazine (82.69 mg, 0.83 mmol) and compound (45) (300 mg, 0.41 mmol) in DMF (5.00 mL) were added DIPEA (160.04 mg, 1.24 mmol) and PyBOP (279.23 mg, 0.54 mmol). The resulting mixture was stirred for 2 h at 20° C. The mixture was purified by reverse flash chromatography using the following conditions: column, C18 silica gel; mobile phase, A: 0.05% $NH_4HCO_3$ in water; B: Acetonitrile; detector, UV 254 nm; 40% B to afford compound (70) as yellow oil (500 mg).

ESI-MS m/z=809.8 $[M+H]^+$; 831.6 $[M+Na]^+$

Compound 71 (Example 28)

4M HCl in 1,4-dioxane (1.5 mL) was added dropwise to a 0° C. solution of compound (70) (300 mg, 0.37 mmol). The

Compound 72

To a 0° C. stirred solution of morpholine (71.92 mg, 0.83 mmol) and compound (45) (300 mg, 0.41 mmol) in DMF (3.00 mL) were added DIPEA (160.04 mg, 1.24 mmol) and PyBOP (279.23 mg, 0.54 mmol). The resulting mixture was stirred for 2 h at 20° C. and subsequently purified by reverse flash chromatography using the following conditions: column, C18 silica gel; mobile phase, A: 0.5% $NH_4HCO_3$ in water B: Acetonitrile, UV 254 nm, 40% B to afford compound (72) as a light yellow solid (300 mg).

ESI-MS m/z=818.4 $[M+Na]^+$

Compound 73 (Example 29)

4M HCl in dioxane (3.00 mL) was added to a solution of compound (72) (300 mg, 0.38 mmol) and stirred for 6 h at 20° C. The mixture was neutralized to pH 7 with saturated aqueous $NaHCO_3$ at 0° C. The resulting mixture was concentrated under reduced pressure and purified by preparative HPLC using the following conditions (Column: Welch Xtimate C18 21.2×250 mm, 5 μm; Mobile Phase A: 10 mmol $NH_4HCO_3$ Water, Mobile Phase B: Acetonitrile; Flow rate: 25 mL/min; Gradient: 21% B to 26% B in 9 min; detector 254 nm; Rt: 6.44 min) to afford compound (73) (Example 29) as a yellow solid (30.7 mg).

LCMS: ESI-MS m/z=422.2 $[M+H]^+$ $^1H$-NMR (300 MHz, Methanol-d4): δ 7.73-7.61 (d, 2H), 4.81-4.70 (m, 1H), 4.46 (dd, J=14.0, 2.8 Hz, 1H), 4.28 (dt, J=9.8, 3.2 Hz, 1H), 3.89-3.73 (m, 7H), 3.73-3.63 (m, 3H), 3.48-3.39 (m, 2H), 2.49 (s, 3H), 2.40 (s, 3H).

Synthesis of Compound 75 (Example 30) and Compound 78 (Example 32)

Examples 30 and 32 were synthesized according to the scheme below.

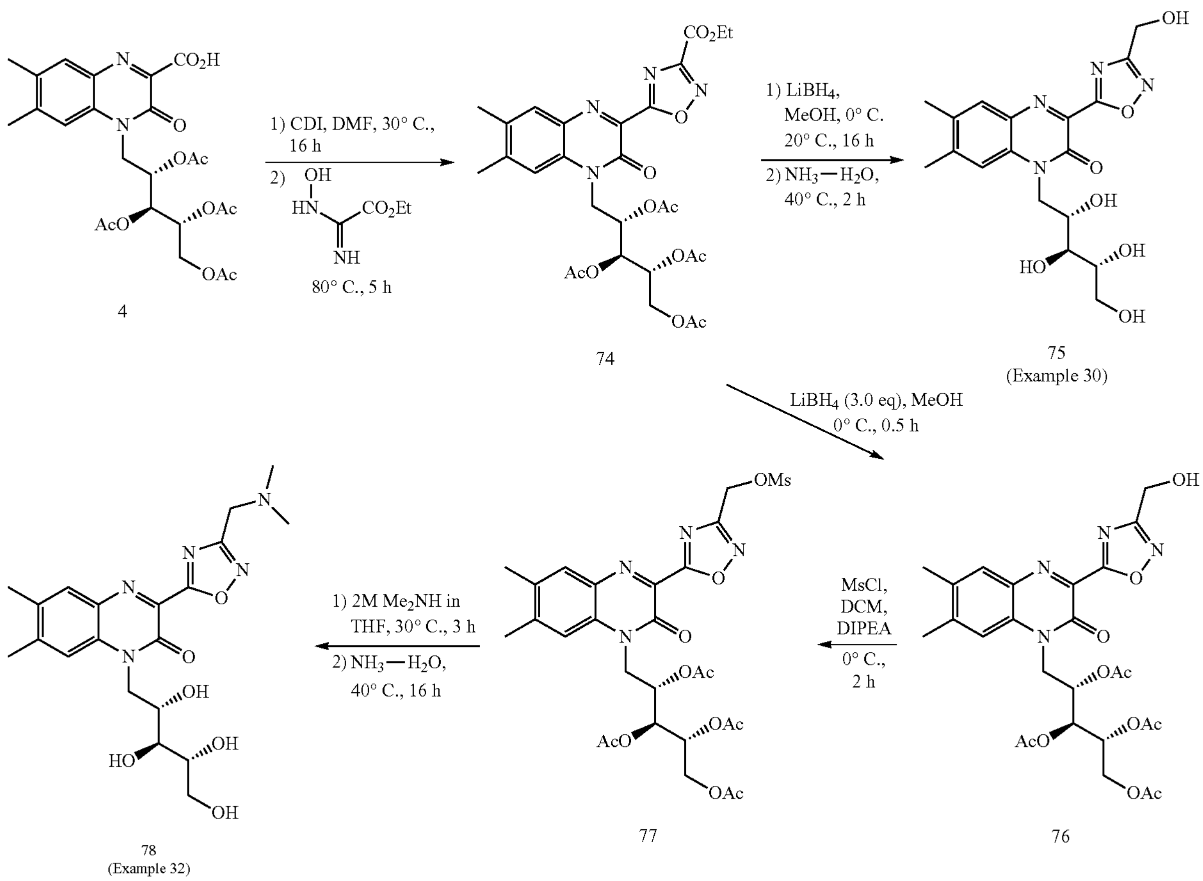

Compound 74

To a room temperature stirred solution of compound (4) (1 g, 1.92 mmol) in DMF (8 mL) was added CDI (800.63 mg, 4.94 mmol). The resulting mixture was stirred for 16 h at 30° C. and ethyl (N-hydroxycarbamimidoyl) formate (800 mg, 6.06 mmol) added. After a further 5 h at 80° C. the mixture was cooled to room temperature. The mixture was subsequently purified by reverse flash chromatography using the following conditions: column, C18 silica gel; mobile phase, A: 0.1% formic acid in water, B: ACN, 10% to 100% gradient in 30 min; detector, UV 254 nm, 70% B to afford compound (74) (350 mg) as a yellow semi-solid ESI-MS m/z=617.5 $[M+H]^+$ Compound 75 (Example 30)

To a 0° C. stirred solution of compound (74) (350 mg, 0.57 mmol) in MeOH (20 mL) was added $LiBH_4$ (61.83 mg, 2.84 mmol) in portions. The resulting mixture was stirred for 16 h at 20° C. Aqueous $NH_3$ (5 mL) was added dropwise at 20° C. to the mixture and stirring continued for an additional 2 h at 40° C. The resulting mixture was concentrated under reduced pressure and the residue purified by preparative HPLC using the following conditions (Column: XBridge Prep OBD C18 Column 19×250 mm, 5 μm; Mobile Phase A: Water (10 mmol $NH_4HCO_3$), Mobile Phase B: ACN; Flow rate: 25 mL/min; Gradient: 17% B to 21% B in 12 min; 254/220 nm; Rt: 8.13 min) to afford compound (75) (Example 30) (66.6 mg) as a light yellow solid.

LCMS ESI-MS m/z=407.15 $[M+H]^+$ $^1H$ NMR (300 MHz, DMSO-d6) δ 7.74 (s, 1H), 7.67 (s, 1H), 5.83 (t, J=6.3 Hz, 1H), 4.99 (d, J=4.4 Hz, 1H), 4.84 (s, 1H), 4.76 (d, J=6.0 Hz, 1H), 4.69 (d, J=6.3 Hz, 2H), 4.48 (t, J=5.5 Hz, 1H), 4.29 (d, J=14.0 Hz, 1H), 4.16 (s, 1H), 3.62 (s, 3H), 2.43 (s, 3H), 2.35 (s, 3H).

Compound 76

To a 0° C. stirred solution of compound (74) (700 mg, 1.16 mmol) in MeOH (10 mL) was added $LiBH_4$ (75.92 mg, 3.49 mmol) in portions. The resulting mixture was stirred for 0.5 h at 0° C. The mixture was quenched at 0° C. by the addition of water (1 mL) and purified by reverse flash chromatography using the following conditions: Column, C18 silica gel; mobile phase, A: 0.1% TFA in water, 0% to 100% gradient in 30 min; detector, UV 254 nm, 60% B to give compound (76) (300 mg) as a yellow oil.

LCMS: ESI-MS m/z=575.3 $[M+H]^+$

Compound 77

To a 0° C. stirred solution of compound (76) (300 mg, 0.52 mmol) in DCM (10 mL) was added DIPEA (202.45 mg, 1.57 mmol) and methanesulfonyl chloride (65.79 mg, 0.57 mmol) dropwise. The resulting mixture was stirred for 2 h at 0° C. and quenched with water. The organic layer was separated, washed with water (2×30 mL) and dried over anhydrous $Na_2SO_4$. After filtration, the filtrate was concentrated under reduced pressure to afford compound (77) (400 mg) as a yellow oil.

LCMS: ESI-MS m/z=653.4 $[M+H]^+$675.5 $[M+Na]^+$

Compound 78 (Example 32)

Compound (77) (400 mg) in 2M dimethylamine in THF (30 mL) was stirred for 3 h at 30° C. before being concentrated under reduced pressure. To the residue was added aqueous ammonia (10 mL) dropwise and the resulting mixture stirred for an additional 16 h at 40° C. The crude product was purified by preparative HPLC using the following conditions (Column: XBridge Prep OBD C18 Column 19×250 mm, 5 μm; Mobile Phase A: Water (0.05% aqueous $NH_3$), Mobile Phase B: ACN; Flow rate: 25 mL/min; Gradient: 19% B to 25% B in 15 min; 220/254 nm; Rt: 11.72 min) to afford compound (78) (Example 32) (25.5 mg) as a yellow solid.

LCMS: ESI-MS m/z=434.2 $[M+H]^+$ $^1$H NMR (300 MHz, Methanol-d4): δ 7.79 (s, 1H), 7.74 (s, 1H), 4.80 (s, 1H), 4.53 (dd, J=14.0, 2.8 Hz, 1H), 4.33 (dq, J=9.7, 3.1 Hz, 1H), 3.90-3.79 (m, 5H), 3.75-3.68 (m, 1H), 2.52 (s, 3H), 2.43 (d, J=1.6 Hz, 8H).

Synthesis of Compound 79 (Example 31)

Example 31 was synthesized according to the scheme below.

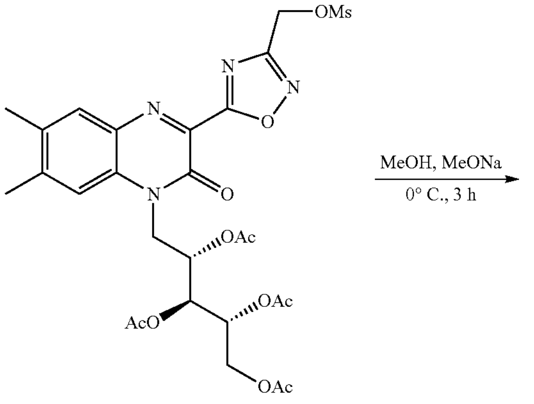

77

-continued

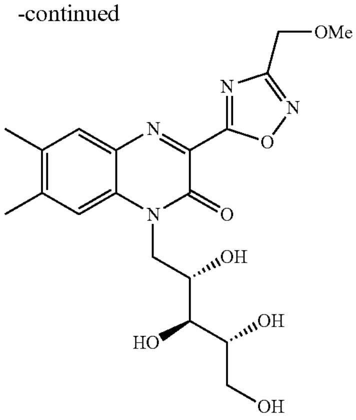

79
(Example 31)

Compound 78 (Example 32)

A solution of compound 77 (200 mg, 0.31 mmol) in MeOH (10 ml) was treated with sodium methoxide (200 mg, 3.70 mmol) in portions at 0° C. The mixture was stirred for 3 h at 0° C. before being concentrated under reduced pressure. The residue was purified by reverse flash chromatography using the following conditions: column, C18 silica gel; mobile phase, A: 0.1% TFA in water, B: ACN; 10% to 70% gradient in 20 min; detector, UV 254 nm to afford compound (79) (Example 31) (67 mg) as a yellow solid.

LCMS: ESI-MS m/z=421.20 $[M+H]^+$ $^1$H-NMR (300 MHz, Methanol-d4) δ 7.75 (d, J=16.5 Hz, 2H), 4.82 (s, 1H), 4.73 (s, 2H), 4.51 (dd, J=14.0, 2.7 Hz, 1H), 4.32 (ddd, J=9.8, 4.4, 2.7 Hz, 1H), 3.91-3.76 (m, 3H), 3.71 (dd, J=12.1, 6.2 Hz, 1H), 3.52 (s, 3H), 2.51 (s, 3H), 2.41 (s, 3H).

Synthesis of Compound 83 (Example 33)

Example 33 was synthesized according to the scheme below.

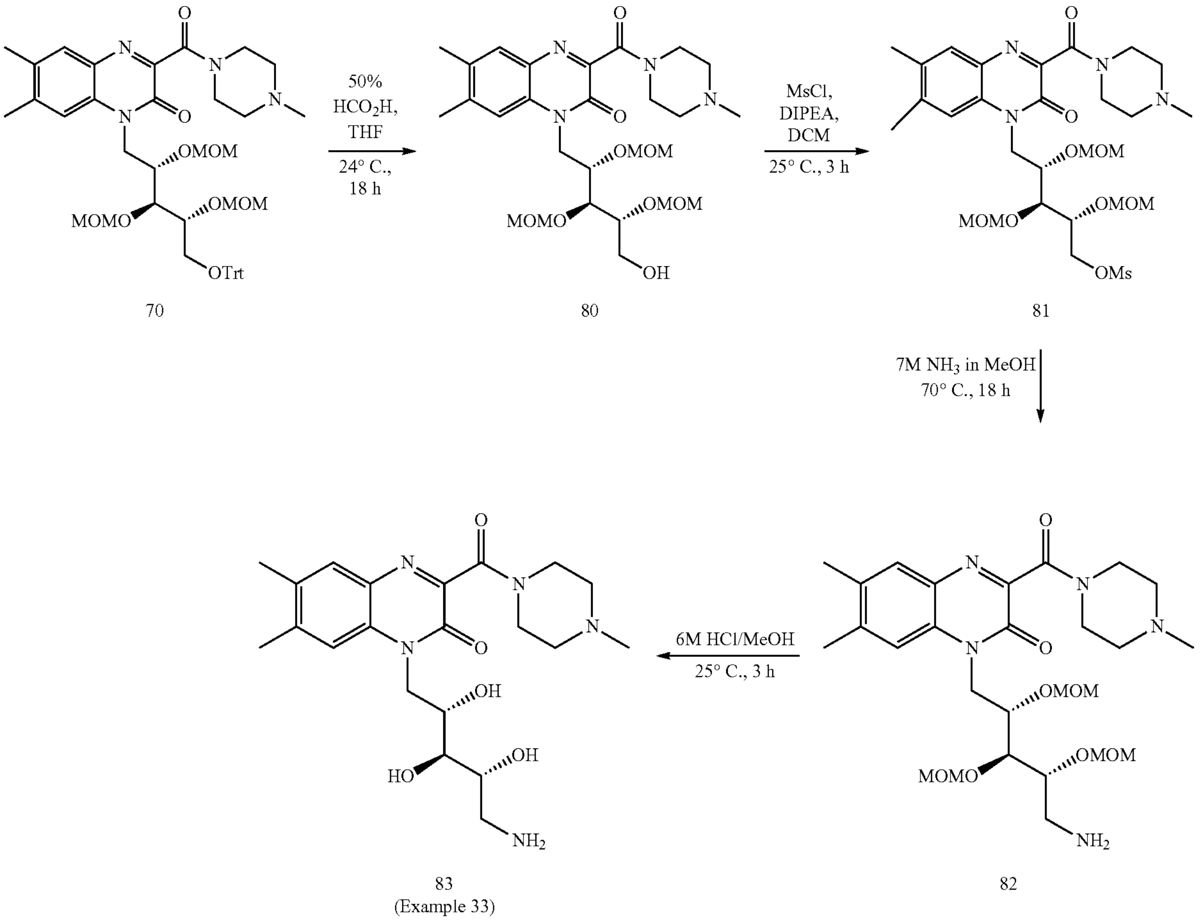

Compound 80

To a 0° C. stirred solution of compound (70) (2.0 g, 2.47 mmol) in THF (10 mL) was added formic acid (10 mL) dropwise. The resulting mixture was stirred for 18 h at 25° C. before being concentrated under reduced pressure. The residue was purified using reverse flash chromatography using the following conditions: column, C18 silica gel; mobile phase, ACN: water (0.1% FA), 10% to 50% ACN gradient over 20 min; detector, UV 254 nm to afford compound (80) (0.7 g) as a yellow oil.

LCMS: (ES, m/z): $[M+H]^+=567.4$

Compound 81

To a 0° C. stirred solution of compound (80) (0.70 g, 1.24 mmol) and DIPEA (803.01 mg, 6.178 mmol) in DCM (30 mL) under argon atmosphere was added a solution of MsCl (281.58 mg, 2.47 mmol) in DCM (30 mL) dropwise. The resulting mixture was stirred for 1 h at 25° C. under argon atmosphere before being diluted with water (50 mL). The resulting mixture was extracted with DCM (3x20 mL) and the combined organic layers washed with water (3x10 mL) and dried over anhydrous $Na_2SO_4$. After filtration, the filtrate was concentrated under reduced pressure and the residue purified by preparative thin layer chromatography eluting with (DCM/MeOH 10:1) to afford compound (81) (500 mg) as a yellow solid.

LCMS: (ES, m/z): $[M+H]^+=645.3$

Compound 82

Compound (81) (500 mg, 0.78 mmol) and 7M $NH_3$ (g) in MeOH (10 mL) were placed in a sealed tube and the mixture stirred for 16 h at 70° C. The mixture was subsequently concentrated under reduced pressure and the residue purified by reverse flash chromatography using the following conditions: column, C18 silica gel; mobile phase, ACN: water (0.1% FA), 10% to 50% ACN gradient over 10 min; detector, UV 254 nm to afford compound (82) (350 mg) as a yellow oil.

LCMS: (ES, m/z): $[M+H]^+=566.4$

Compound 83 (Example 33)

To a 0° C. stirred mixture of compound (82) (200 mg, 0.35 mmol) in MeOH (5 mL) was added HCl (6M in dioxane) (5 mL) dropwise. The resulting mixture was stirred for 3 h at 25° C. before being neutralized to pH 7 with saturated $NaHCO_3$ (aq.). The resulting mixture was concentrated under reduced pressure and the residue purified by reverse flash chromatography with the following conditions: Column: Gemini-NX C18 AXAI 21.2*150 mm, 5 μm; Mobile Phase A: Water (0.05% TFA), Mobile Phase B: ACN; Flow rate: 25 mL/min; Gradient: 7% B to 15% B in 10 min; 254/220 nm; Rt: 7.09 min to afford compound (83) (Example 33) (50 mg) as a yellow solid.

LCMS: (ES, m/z): $[M+H]^+$=434.2

$^1$H NMR (300 MHz, Methanol-d4) δ 7.66 (s, 2H), 4.65 (d, J=8.9 Hz, 1H), 4.55 (dd, J=14.0, 3.1 Hz, 1H), 4.20-4.04 (m, 3H), 3.77 (t, J=6.0 Hz, 2H), 3.38-3.34 (m, 4H), 3.27-3.06 (m, 4H), 2.96 (s, 3H), 2.50 (s, 3H), 2.41 (s, 3H).

Synthesis of Compound 84 (Example 34)

Example 34 was synthesized according to the scheme below.

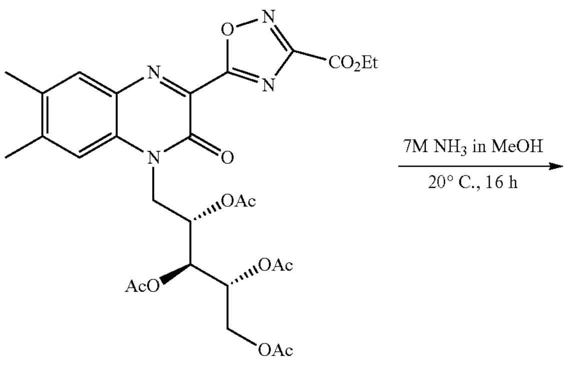

74

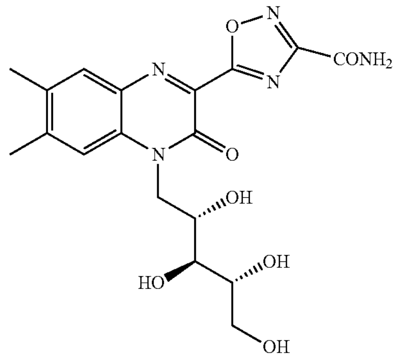

84
(Example 34)

Compound 84 (Example 34)

A solution of compound (74) (300 mg) in 7M $NH_3$ in MeOH (20 mL) was stirred for 16 h at 20° C. before being concentrated under reduced pressure. The residue was purified by reverse flash chromatography using the following conditions: Column, C18 silica gel; mobile phase A: 0.1% $NH_4HCO_3$ in water; mobile phase B: ACN, 0% to 50% gradient in 30 min; detector, UV 254 nm to afford compound (84) (Example 34) (85.9 mg) as a yellow solid.

LCMS: ESI-MS m/z=420.10 $[M+H]^+$ $^1$H-NMR: (300 MHz, DMSO-d6): δ 8.48 (s, 1H), 8.22 (s, 1H), 7.75 (s, 1H), 7.69 (s, 1H), 5.01 (d, J=4.0 Hz, 1H), 4.85 (s, 1H), 4.77 (d, J=5.9 Hz, 1H), 4.74-4.61 (m, 1H), 4.48 (d, J=5.5 Hz, 1H), 4.30 (d, J=14.1 Hz, 1H), 4.17 (s, 1H), 3.62 (s, 3H), 3.50-3.40 (m, 1H), 2.44 (s, 3H), 2.36 (s, 3H).

Synthesis of Compound 92 (Example 35)

Example 35 was synthesized according to the scheme below.

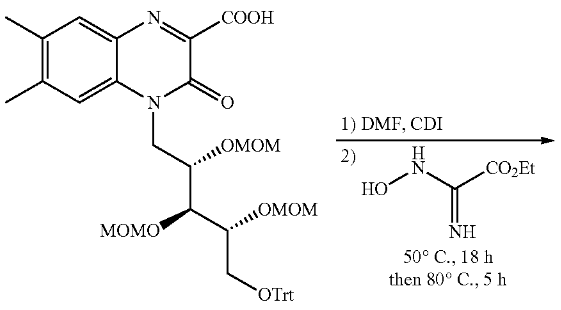

45

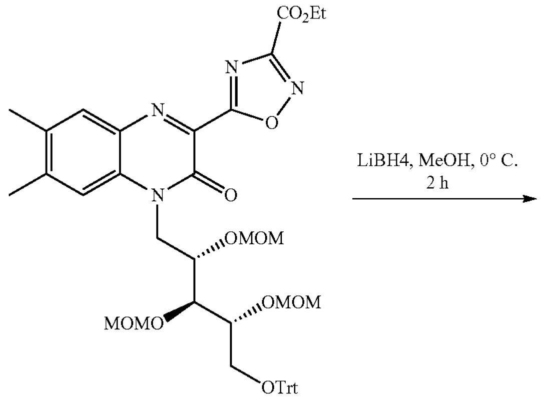

85

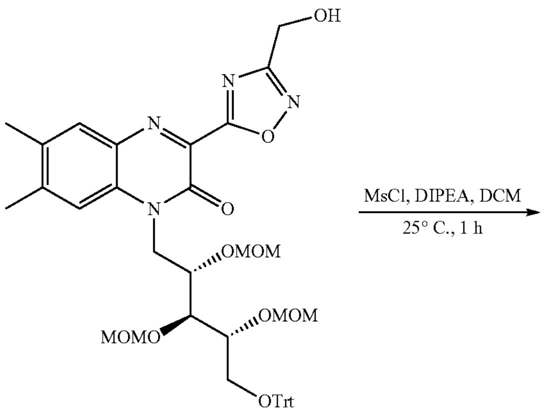

86

-continued

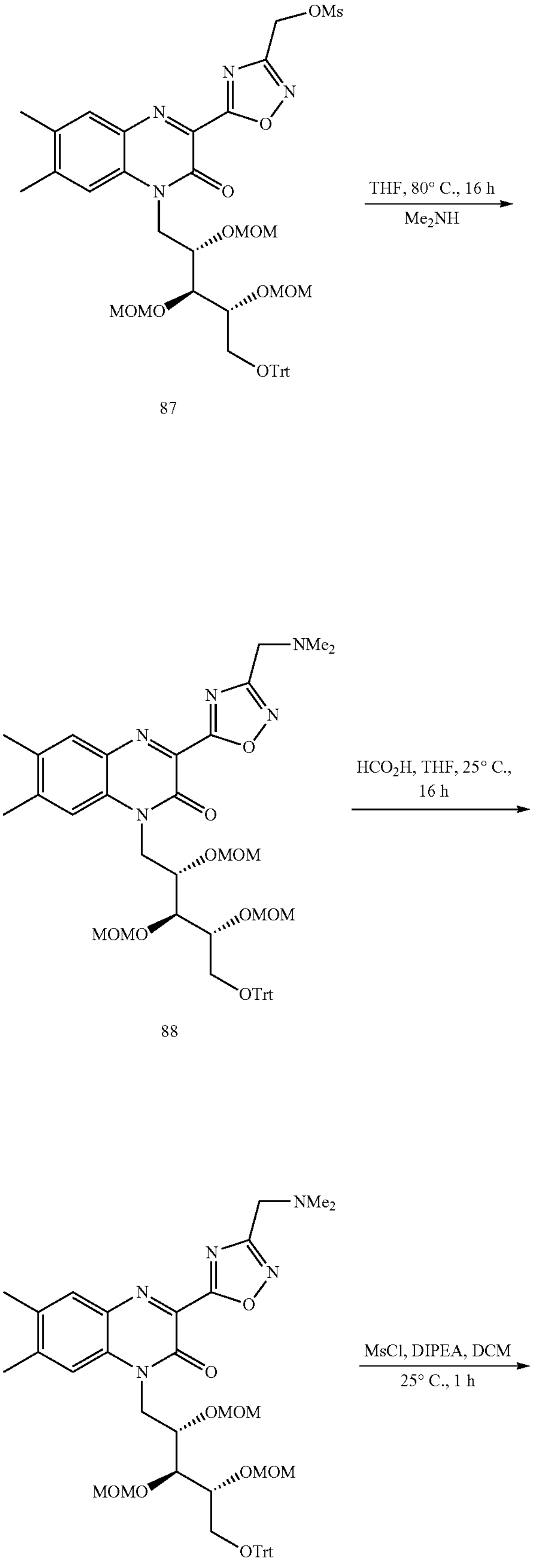

87

88

89

-continued

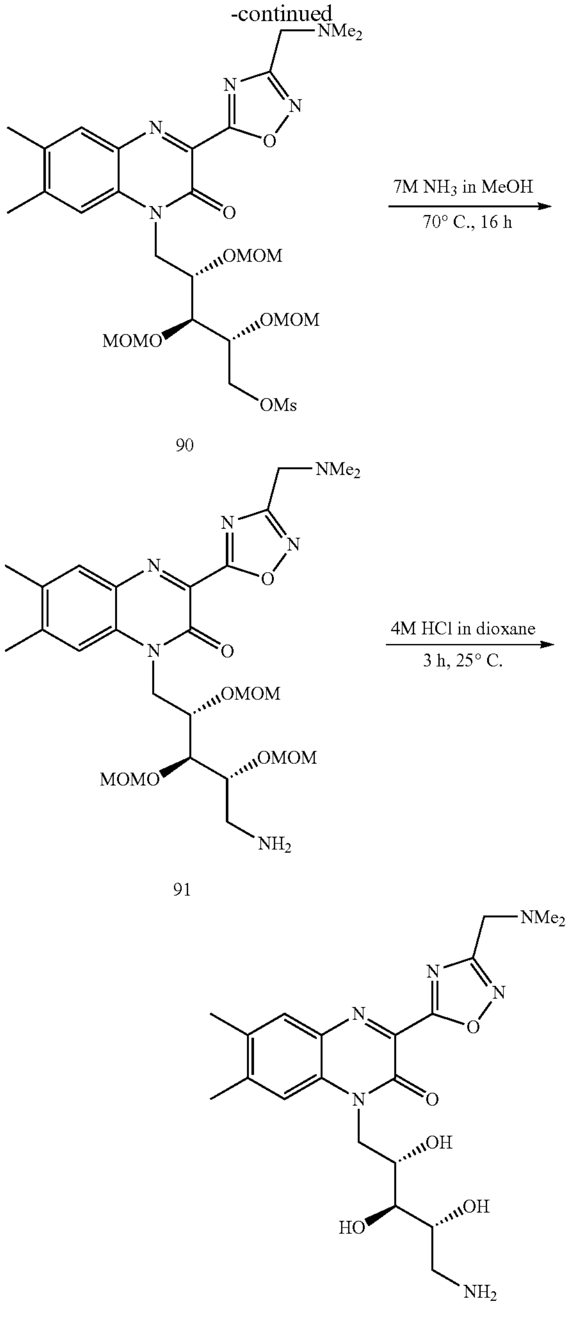

90

91

92
(Example 35)

Compound 85

To a stirred 25° C. solution of compound (45) (10 g, 13.76 mmol) in DMF (50 mL) was added CDI (6.69 g, 41.28 mmol) in portions followed by the addition of ethyl (N-hydroxycarbamimidoyl) formate (6.54 g, 49.5 mmol) in portions. The mixture was irradiated with microwave radiation for 18 h at 50° C. followed by 5 h at 80° C. The resulting mixture was diluted with water (200 mL) and extracted with EtOAc (3×30 mL). The combined organic layers were washed with water (3×20 mL), dried over anhydrous $Na_2SO_4$ and filtered. The filtrate was concentrated under reduced pressure and the residue purified by reverse flash chromatography using the following conditions: Column, C18 silica gel; mobile phase, ACN: water (0.1% FA), 60% to 85% gradient in 20 min; detector, UV 254 nm to afford compound (85) (4 g) as a yellow solid.

LCMS: (ES, m/z): $[M+Na]^+$=845.5

Compound 86

To a 0° C. stirred solution of compound (85) (4.0 g, 4.86 mmol) in MeOH (50 mL) was added $LiBH_4$ (1.06 g, 48.66 mmol) in portions. The resulting mixture was stirred for 2 h at 0° C. before being quenched with saturated $NH_4Cl$ (aq.) (10 mL). The mixture was diluted with water (200 mL) and extracted with EtOAc (3×100 mL). The combined organic layers were washed with water (3 200 mL), dried over anhydrous $Na_2SO_4$ and after filtration concentrated under reduced pressure. The residue was purified by silica gel column chromatography, eluted with PE/EtOAc (1:1) to afford compound (86) (3.5 g) as a yellow oil.

LCMS: (ES, m/z): $[M+Na]^+$=803.5

Compound 87

To a 0° C. stirred solution of compound (86) (2.0 g, 2.56 mmol) and DIPEA (3310.21 mg, 25.61 mmol) in DCM (20 mL) was added MsCl (1466.96 mg, 12.81 mmol) in DCM (1 mL) dropwise. The resulting mixture was stirred for 1 h at 25° C., before being concentrated under vacuum. The residue was purified by reverse flash chromatography using the following conditions: Column, C18 silica gel; mobile phase, ACN: water (0.1% FA), 10% to 70% gradient in 20 min; detector, UV 254 nm to afford compound (87) (2 g) as a yellow oil.

LCMS: (ES, m/z): $[M+Na]^+$=881.5

Compound 88

A solution of compound (87) (2.0 g, 2 mmol) and dimethylamine (2 M in MeOH) (5 mL) in THF (5 mL) was stirred for 16 h at 80° C. before being concentrated under vacuum. The residue was purified by reverse flash chromatography using the following conditions: Column, C18 silica gel; mobile phase, ACN: water (0.1% FA), 10% to 50% gradient in 20 min; detector, UV 254 nm to afford compound (88) (1.6 g) as a yellow oil.

LCMS: (ES, m/z): $[M+H]^+$=808.6

Compound 89

To a 0° C. stirred solution of compound (88) (1.60 g, 1.98 mmol) in THF (20 mL) was added formic acid (20 mL, 0.44 mmol) dropwise. The resulting mixture was stirred for 16 h at 25° C. before being concentrated under vacuum. The residue was purified by reverse flash chromatography with the following conditions: Column, C18 silica gel; mobile phase, ACN: water (0.1% FA), 10% to 50% gradient in 10 min; detector, UV 254 nm to afford compound (89) (700 mg) as a yellow oil.

LCMS: (ES, m/z): $[M+H]^+$=566.4

Compound 90

To a 0° C. stirred solution of compound (89) (700 mg, 1.24 mmol) and DIPEA (1599.48 mg, 12.38 mmol) in DCM was added MsCl (708.83 mg, 6.19 mmol) in DCM (1 mL) dropwise. The resulting mixture was stirred for 1 h at 25° C. before being concentrated under vacuum. The residue was purified by preparative thin layer chromatography eluted with (DCM/MeOH 10:1) to afford compound (90) (500 mg) as a yellow oil.

LCMS: (ES, m/z): $[M+H]^+$=644.5

Compound 91

Compound (90) (550 mg, 0.85 mmol) and $NH_3$ (g) in MeOH (12 mL, 422.77 mmol) were stirred in a sealed tube for 16 h at 70° C. The resulting mixture was concentrated under reduced pressure and the residue purified by reverse flash chromatography using the following conditions: Column, C18 silica gel; mobile phase, ACN: water (0.1% FA), 10% to 50% gradient in 20 min; detector, UV 254 nm to afford compound (91) (260 mg) as a yellow oil.

LCMS: (ES, m/z): $[M+H]^+$=565.5

Compound 92 (Example 35)

To a 0° C. stirred solution of compound (91) (240 mg, 0.43 mmol) in MeOH (4 mL, 98.8 mmol) was added 4M HCl (g) in 1,4-dioxane (4 mL, 131.65 mmol) dropwise. The resulting mixture was stirred for 3 h at 25° C. before being concentrated under vacuum. The residue was purified by reverse flash chromatography with the following conditions: Column: SunFire Prep C18 OBD Column, 19×150 mm, 5 μm; Mobile Phase A: Water (0.05% TFA), Mobile Phase B: ACN; Flow rate: 25 mL/min; Gradient: 8% B to 15% B in 12 min; 254/220 nm to afford compound (92) (Example 35) (40 mg) as a yellow solid.

LCMS: (ES, m/z): $[M+H]^+$=433.2

$^1$H NMR (400 MHz, Methanol-d4) δ 7.82 (s, 1H), 7.72 (s, 1H), 4.73 (s, 3H), 4.64 (dd, J=14.1, 2.9 Hz, 1H), 4.22 (ddd, J=9.2, 6.2, 2.8 Hz, 1H), 4.10 (ddd, J=8.2, 5.8, 3.6 Hz, 1H), 3.81 (t, J=6.0 Hz, 1H), 3.24 (dd, J=12.9, 3.7 Hz, 1H), 3.17-3.11 (m, 1H), 3.07 (s, 6H), 2.54 (s, 3H), 2.45 (d, J=0.9 Hz, 3H).

Synthesis of Compound 97 (Example 36)

Example 36 was synthesized according to the scheme below.

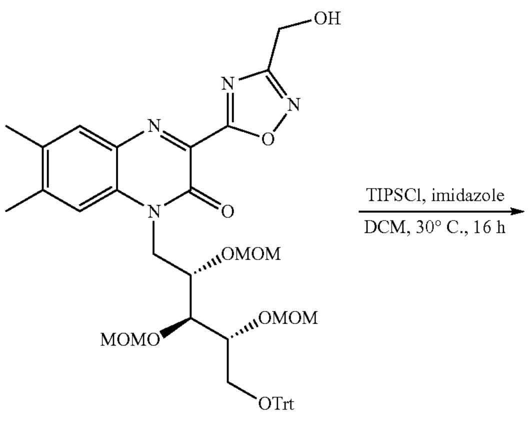

86

-continued

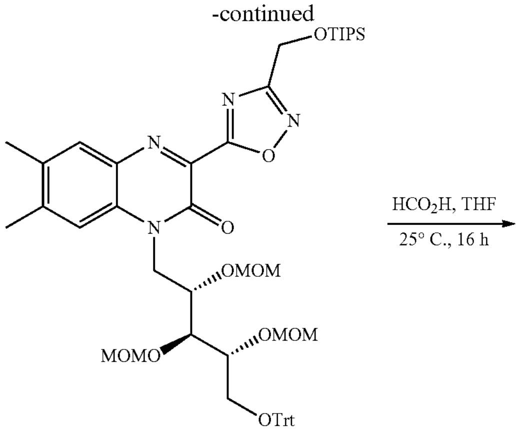

93

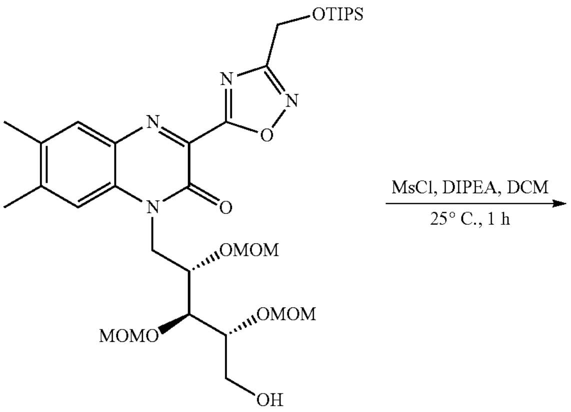

94

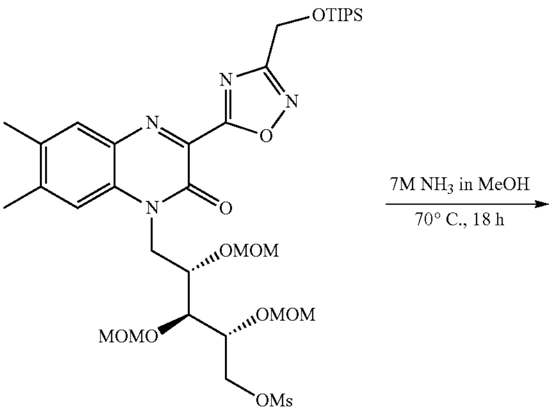

95

-continued

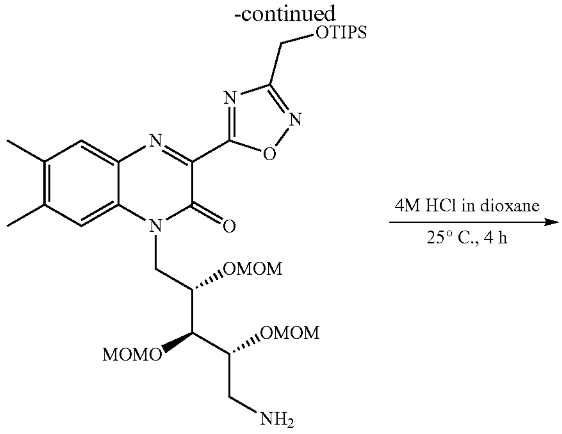

96

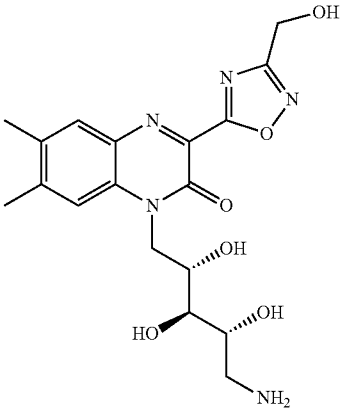

97
(Example 36)

Compound 93

To a 0° C. stirred solution of compound (86) (1.00 g, 1.28 mmol) and imidazole (261.54 mg, 3.84 mmol) in DCM (40 mL) was added chlorotriisopropylsilane (370.35 mg, 1.92 mmol) dropwise. The resulting mixture was stirred for 16 h at 30° C. before being diluted with water (200 mL) and extracted with EtOAc (3×50 mL). The combined organic layers were washed with water (3×50 mL), dried over anhydrous $Na_2SO_4$ and after filtration, the filtrate was concentrated under reduced pressure. The residue was purified by silica gel column chromatography eluted with PE/EtOAc (1:1) to afford compound (93) (1.1 g) as a yellow oil.

LCMS: (ES, m/z): $[M+Na]^+$=959.8

Compound 94

To a 0° C. stirred solution of compound (93) (1.1 g, 1.17 mmol) in THF (20 mL, 0.28 mmol) was added formic acid (20 mL, 0.44 mmol) dropwise. The resulting mixture was stirred for 16 h at 25° C. The resulting mixture was concentrated under vacuum and the residue purified by reverse flash chromatography using the following conditions: Column, C18 silica gel; mobile phase, MeOH: water, 10% to 50% gradient in 10 min; detector, UV 254 nm to afford compound (94) (220 mg) as a yellow oil.

LCMS: (ES, m/z): $[M+Na]^+$=717.6

Compound 95

To a 0° C. stirred solution of compound (94) (220 mg, 0.32 mmol) and DIPEA (409.18 mg, 3.17 mmol) in DCM (5 mL) was added MsCl (181.33 mg, 1.58 mmol) in DCM dropwise. The resulting mixture was stirred for 1 h at 25° C. before being concentrated under reduced pressure. The residue was purified by silica gel column chromatography eluted with PE/EtOAc (1:1) to afford compound (95) (230 mg) as a yellow solid.

LCMS: (ES, m/z): $[M+Na]^+$=881.5

Compound 96

Compound (95) (230 mg, 0.3 mmol) and 7M $NH_3$ (g) in MeOH (10 mL, 0.59 mmol) were stirred for 18 h at 70° C. in a sealed tube. The resulting mixture was concentrated under reduced pressure and the residue purified by reverse flash chromatography using the following conditions: Column, C18 silica gel; mobile phase, MeOH: water, 10% to 50% gradient in 10 min; detector, UV 254 nm to afford compound (96) (170 mg) as a yellow oil.

LCMS: (ES, m/z): $[M+H]^+$=694.6

Compound 97 (Example 36)

To a 0° C. stirred solution of compound (96) (170 mg, 0.25 mmol) in THF (4 mL, 0.055 mmol) was added 4M HCl (g) in 1,4-dioxane (4 mL, 0.11 mmol) dropwise. The resulting mixture was stirred for 4 h at 25° C. before being concentrated under reduced pressure. The residue was purified by preparative HPLC using the following conditions: Column: Gemini-NX C18 AXAI Packed, 21.2×150 mm, 5 μm; Mobile Phase A: Water (0.1% FA), Mobile Phase B: ACN; Flow rate: 25 mL/min; Gradient: 7% B to 28% B in 12 min; 254/220 nm to afford compound (97) (Example 36) (60 mg) as a yellow solid.

LCMS: (ES, m/z): $[M+H]^+$=406.3

$^1$H NMR (300 MHz, Methanol-d4) δ 8.55 (s, 1H), 7.75 (d, J=34.8 Hz, 2H), 4.83 (s, 2H), 4.65 (s, 2H), 4.15 (d, J=32.7 Hz, 2H), 3.79 (s, 1H), 3.21 (s, 1H), 3.12 (d, J=9.5 Hz, 1H), 2.48 (d, J=27.7 Hz, 6H).

Synthesis of Compound 99 (Example 37)

Example 37 was synthesized according to the scheme below.

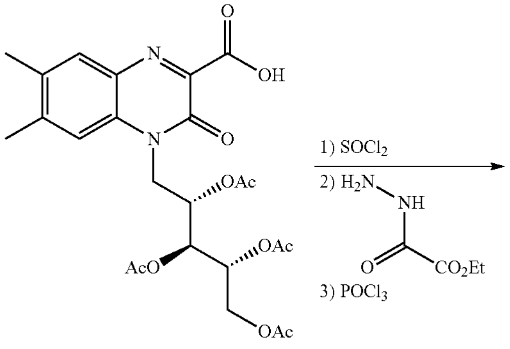

4

-continued

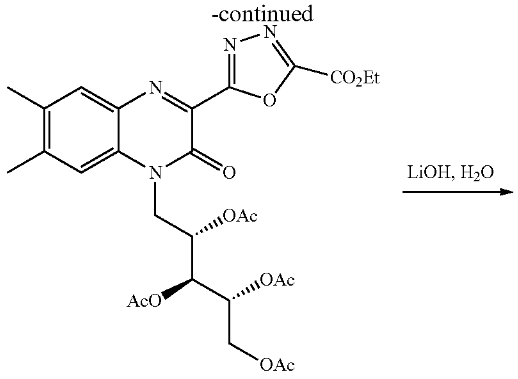

98

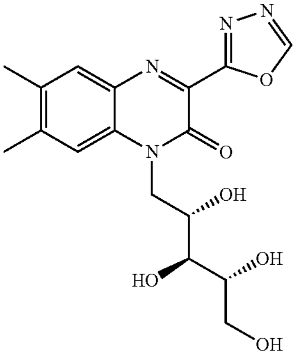

99
(Example 37)

Compound 98

A mixture of compound (4) (2 g, 3.84 mmol) in $SOCl_2$ (10 mL) was stirred for 5 h at 50° C. before being concentrated under reduced pressure. The residue was diluted with DCM (10 mL) and a solution of ethyl (hydrazinecarbonyl) formate (0.51 g, 3.86 mmol) and DIPEA (1.49 g, 11.53 mmol) in DCM (10 mL) added dropwise while stirred at 0° C. After 30 min the mixture was diluted with DCM (50 mL) washed with water (3×50 mL). The combined organic layers were concentrated under reduced pressure and the residue purified by reverse flash chromatography using the following conditions: Column, C18 silica gel; mobile phase A: 0.5% $NH_4HCO_3$, mobile phase B: ACN, 0% to 50% gradient in 3 min; detector, UV 254 nm to afford an intermediate as a yellow solid. The intermediate was subsequently stirred overnight at 70° C. in $POCH_3$ (10 mL) before being concentrated under vacuum. The residue was diluted with DCM (50 mL) and washed with water (3×50 mL). The combined organic layers were concentrated under reduced pressure and the residue purified by reverse flash chromatography using the following conditions: Column, C18 silica gel; mobile phase A: 0.1% TFA, mobile phase B: ACN, 0% to 70% gradient in 30 min; detector, UV 254 nm to afford compound (98) as a yellow solid.

Compound 99 (Example 37)

To a 0° C. stirred solution of compound (98) (200 mg, 0.32 mmol) in MeOH (5 mL) was added a solution of LiOH $H_2O$ (27.22 mg, 0.65 mmol) in water (2 mL) dropwise. The resulting mixture was stirred for 1 h at 0° C. before being concentrated under reduced pressure. The residue was purified by reverse flash chromatography using the following conditions: Column, C18 silica gel; mobile phase A: 0.1% TFA in water, mobile phase B: ACN: 0% to 50% gradient in 50 min; detector, UV 254 nm to afford compound (99) (Example 37) (41.8 mg) as a yellow solid.

LCMS: ESI-MS m/z=377.25 [M+H]$^+$ $^1$H-NMR: (300 MHz, DMSO-d6): δ 9.47 (s, 1H), 7.73-7.68 (d, 2H), 5.02-5.00 (m, 1H), 4.86-4.84 (m, 1H), 4.66-4.63 (m, 1H), 4.63-4.51 (m, 1H), 4.48-4.29 (m, 1H), 4.25-4.16 (m, 1H), 4.22-4.01 (m, 1H), 3.73-3.61 (s, 3H), 3.51-3.43 (s, 1H), 2.42 (s, 3H), 2.34 (s, 3H).

Synthesis of Compound 104 (Example 38) and Compound 105 (Example 39)

Examples 38 and 39 were synthesized according to the scheme below.

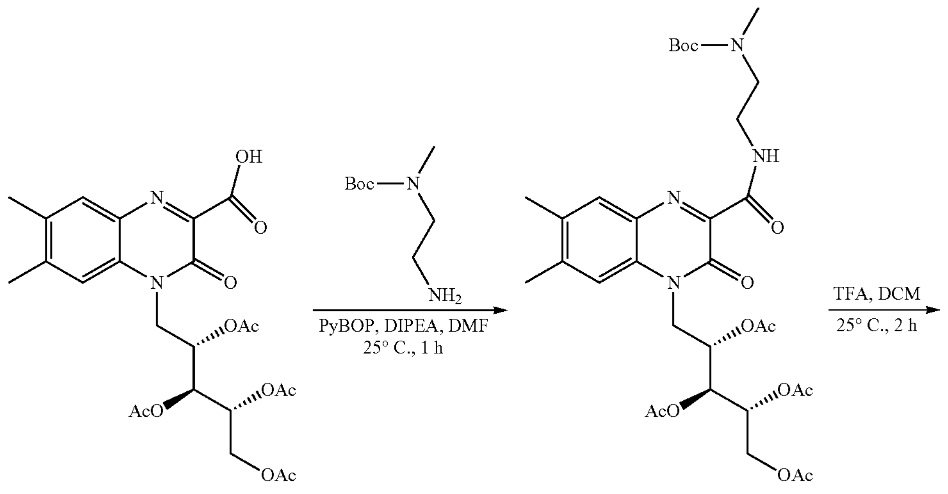

4

100

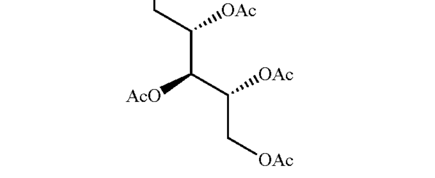

101

-continued

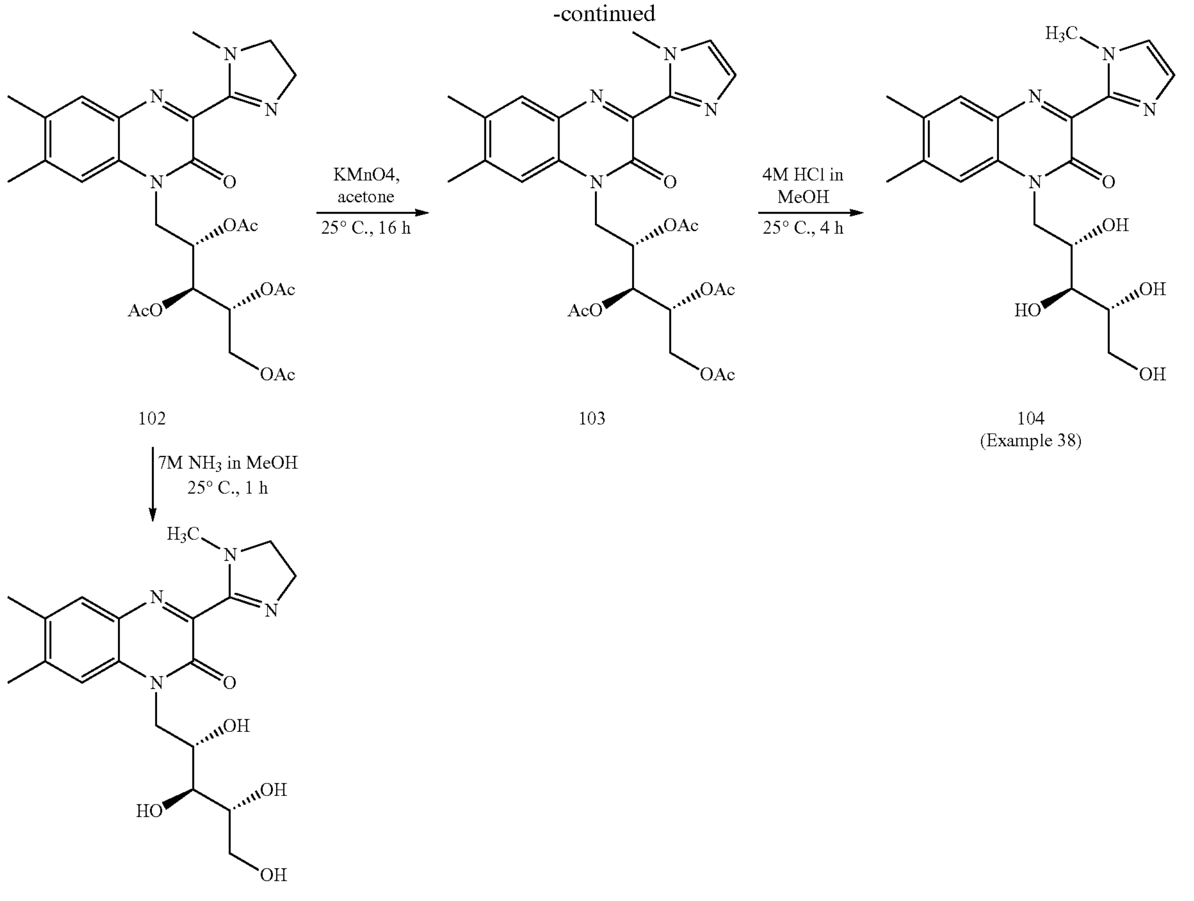

102 103 104 (Example 38)

105 (Example 39)

Compound 100

To a 0° C. stirred solution of compound (4) (3 g, 5.76 mmol) and DIPEA (3.72 g, 28.82 mmol) and tert-butyl N-(2-aminoethyl)-N-methylcarbamate (1.21 g, 6.94 mmol) in DMF (50 mL) was added PyBOP (6 g, 11.53 mmol) in portions. The resulting mixture was stirred for 1 h at 25° C. before being diluted with water (200 mL) and extracted with EtOAc (3×100 mL). The combined organic layers were washed with water (3×100 mL), dried over anhydrous $Na_2SO_4$ and after filtration, the filtrate concentrated under reduced pressure. The residue was purified by silica gel flash chromatography eluted with (EtOAc/PE=1:1) to afford compound (100) (2.8 g) as a yellow solid.

LCMS: (ES, m/z): $[M+H]^+$=677.2

Compound 101

To a 0° C. stirred solution of compound (100) (2.8 g, 4.14 mmol) in DCM (30 mL) was added TFA (15 mL) dropwise. The resulting mixture was stirred for 2 h at 25° C. before being concentrated under reduced pressure. The residue was purified by silica gel flash chromatography eluted with (EtOAc/PE=1:1) to afford compound (101) (2 g) as a yellow solid.

LCMS: (ES, m/z): $[M+H]^+$=577.2

Compound 102

To a 0° C. stirred solution of compound (101) (2 g, 3.47 mmol) in DCE (30 mL) was added $POCl_3$ (1.06 g, 6.91 mmol) dropwise. The resulting mixture was stirred for 4 h at 70° C. before being concentrated under reduced pressure. The residue was purified by reverse flash chromatography using the following conditions: Column, C18 silica gel; mobile phase, MeOH: water, 10% to 50% gradient in 10 min; detector, UV 254 nm to afford compound (102) (1.2 g) as a yellow solid.

LCMS: (ES, m/z): $[M+H]^+$=382.3

Compound 103

To a 0° C. stirred solution of compound (102) (600 mg, 1.07 mmol) in acetone (30 mL) was added $KMnO_4$ (509.25 mg, 3.22 mmol) in acetone (5 mL) dropwise. The resulting mixture was stirred for 16 h at 25° C. before being concentrated under reduced pressure. The residue was purified by reverse flash chromatography using the following conditions: Column, C18 silica gel; mobile phase, MeOH: water, 10% to 50% gradient in 10 min; detector, UV 254 nm to afford compound (103) (200 mg) as a yellow solid.

LCMS: (ES, m/z): $[M+H]^+$=557.1

Compound 104 (Example 38)

To a 0° C. stirred solution of compound (103) (300 mg, 0.54 mmol) in MeOH (5 mL) was added 4M HCl (g) in MeOH (21.41 mL, 704.64 mmol) dropwise. The resulting mixture was stirred for 4 h at 25° C. before being concentrated under reduced pressure. The residue was purified by reverse flash chromatography using the following conditions: Column, C18 silica gel; mobile phase, MeOH: water, 10% to 50% gradient in 10 min; detector, UV 254 nm to afford compound (104) (Example 38) (30 mg) as a yellow solid.

LCMS: (ES, m/z): $[M+H]^+$=389.2

$^1$H NMR: (400 MHz, Methanol-d4) δ 7.79 (d, J=18.3 Hz, 2H), 7.73-7.69 (m, 1H), 7.59-7.55 (m, 1H), 4.88-4.84 (m, 1H), 4.55 (dd, J=14.0, 2.7 Hz, 1H), 4.35 (d, J=10.0 Hz, 1H), 4.30 (s, 3H), 3.87-3.80 (m, 3H), 3.74-3.68 (m, 1H), 2.53 (s, 3H), 2.44 (s, 3H).

Compound 105 (Example 39)

Compound (102) (400 mg, 0.72 mmol) in 7M $NH_3$ (g) in MeOH (8 mL) was stirred at room temperature before being concentrated under reduced pressure. The residue was purified by preparative HPLC using the following conditions (Column: XBridge Shield RP18 OBD Column, 5 μm, 19×150 mm; Mobile Phase A: Water (0.05% FA), Mobile Phase B: ACN; Flow rate: 25 mL/min; Gradient: 31% B to 54% B in 10 min; 254 nm to afford compound (105) (Example 39) (60 mg) as a yellow solid.

LCMS: (ES, m/z): [M+H]=391.2

$^1$H NMR: (400 MHz, Methanol-d4) δ=8.55 (s, 1H), 7.79 (s, 2H), 4.88-4.82 (m, 1H), 4.53-4.49 (m, 1H), 4.32-4.21 (m, 1H), 4.20-4.06 (m, 4H), 3.89-3.79 (m, 3H), 3.73-3.68 (m, 1H), 3.57 (s, 2H), 2.54 (s, 3H), 2.41 (s, 3H).

Synthesis of Compound 110 (Example 40)

Example 40 was synthesized according to the scheme below.

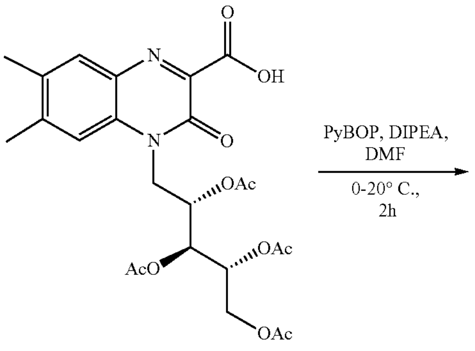

4

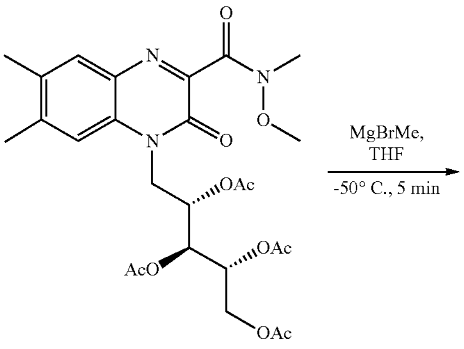

106

-continued

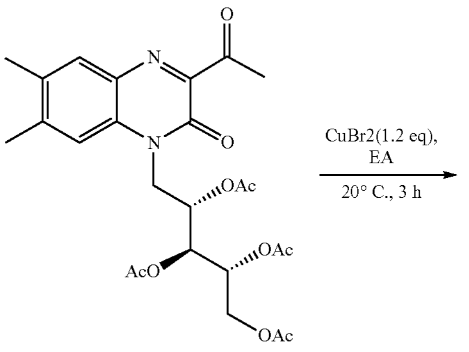

107

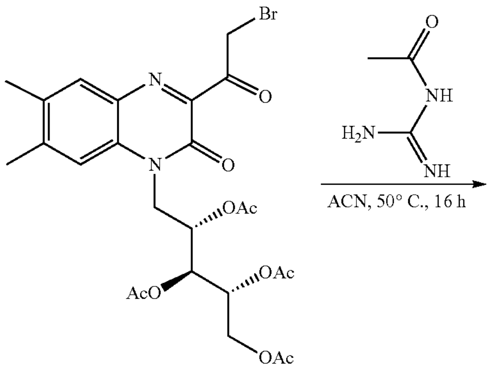

108

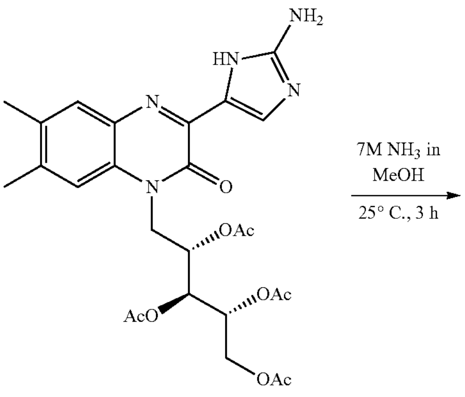

109

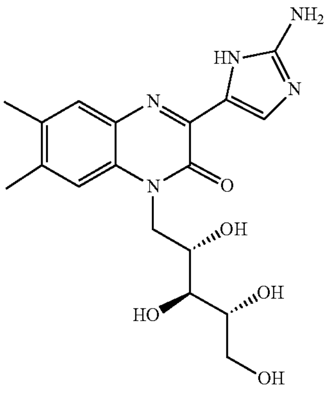

110
(Example 40)

Compound 106

To a 0° C. stirred mixture of compound (4) (10 g, 19.21 mmol) and N,O-dimethylhydroxylamine hydrochloride (3.52 g, 57.63 mmol) in DMF (150 mL) were added DIPEA (24.83 g, 192.12 mmol) and PyBOP (20 g, 38.43 mmol) in portions. The resulting mixture was stirred for 1 h at room temperature before being quenched with 1M HCl (200 mL) and extracted with EtOAc (3×150 mL). The combined organic layers were washed with saturated NaCl (aq) (3×200 mL), dried over anhydrous $Na_2SO_4$ and after filtration, the filtrate concentrated under reduced pressure. The residue was purified by silica gel column chromatography, eluted with PE/EtOAc (1:3) to afford compound (106) (8.5 g) as a yellow solid.

LCMS: (ES, m/z): $[M+H]^+=564.4$

Compound 107

To a −10° C. stirred mixture of compound (106) (8 g, 14.2 mmol) in THF (200 mL) under argon atmosphere was added methylmagnesium bromide (56.78 mL, 56.78 mmol) dropwise. The mixture was quenched with $NH_4Cl$ (200 mL) at 0° C. before being extracted with EtOAc (3×150 mL). The combined organic layers were washed with saturated NaCl (aq) (3×150 mL), dried over anhydrous $Na_2SO_4$ and after filtration, the filtrate concentrated under reduced pressure. The residue was purified by silica gel column chromatography, eluted with PE/EtOAc (1:1) to afford compound (107) (1.6 g) as a yellow oil.

LCMS: (ES, m/z): $[M+H]^+=519.4$

Compound 108

To a 0° C. stirred mixture of compound (107) (2 g, 3.86 mmol) in EtOAc (200 mL) was added $CuBr_2$ (1033.81 mg, 4.63 mmol) in portions. The resulting mixture was stirred for 3 h at room temperature. The mixture was subsequently washed with 1M HCl (2×100 mL) and extracted with EtOAc (3×100 mL). The combined organic layers were washed with water (3×100 mL), dried over anhydrous $Na_2SO_4$ and after filtration, the filtrate concentrated under reduced pressure. The residue was purified by reverse flash chromatography using the following conditions: Column, C18 silica gel; mobile phase, ACN: water, 10% to 100% gradient in 30 min; detector, UV 254 nm to afford compound (108) (800 mg) as a yellow oil.

LCMS: (ES, m/z): $[M+H]^+=597.1$

Compound 109

To a stirred room temperature solution of compound (108) (200 mg, 0.34 mmol) in ACN was added N-carbamimidoylacetamide (67.7 mg, 0.67 mmol) in portions. The resulting mixture was stirred for 16 h at 50° C. before being concentrated under reduced pressure. The residue was purified by reverse flash chromatography using the following conditions: Column, C18 silica gel; mobile phase, ACN: water (0.1% FA), 10% to 50% gradient in 10 min; detector, UV 254 nm to afford compound (109) (120 mg) as a yellow oil.

LCMS: (ES, m/z): $[M+H]^+=558.1$

Compound 110 (Example 40)

To a stirred solution of compound (109) (200 mg) in MeOH was added 7M $NH_3$ (g) in MeOH (3 mL) dropwise at 25° C. The resulting mixture was stirred for 3 h at 25° C. before being concentrated under reduced pressure. The residue was purified by reverse flash chromatography using the following conditions: Column, C18 silica gel; mobile phase, ACN: water, 10% to 50% gradient in 20 min; detector, UV 254 nm to afford compound (110) (Example 40) (70 mg) as a yellow solid.

LCMS: (ES, m/z): $[M+H]^+=390.2$ $^1H$ NMR: (400 MHz, Methanol-d4) δ 8.48 (s, 1H), 7.91 (s, 1H), 7.64 (d, J=4.1 Hz, 2H), 4.88-4.90 (m, 1H), 4.46 (dd, J=14.1, 2.7 Hz, 1H), 4.31 (ddd, J=9.6, 4.7, 2.5 Hz, 1H), 3.88-3.78 (m, 3H), 3.74-3.68 (m, 1H), 2.46 (s, 3H), 2.39 (s, 3H).

Synthesis of Compound 113 (Example 41)

Example 41 was synthesized according to the scheme below.

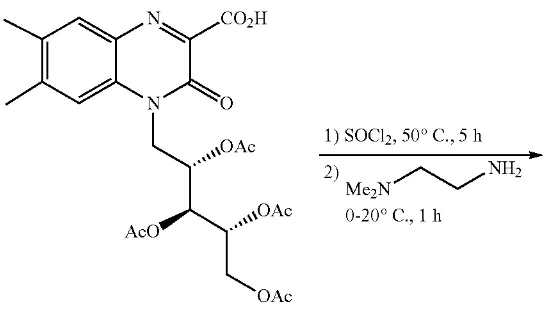

4

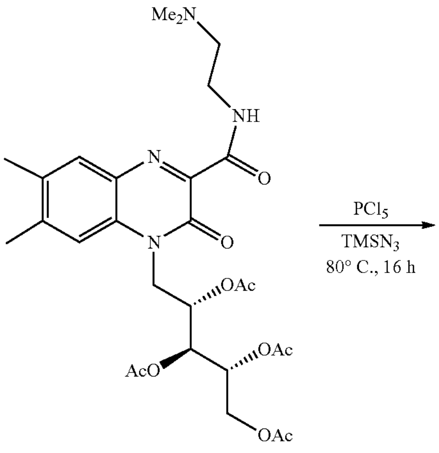

111

-continued

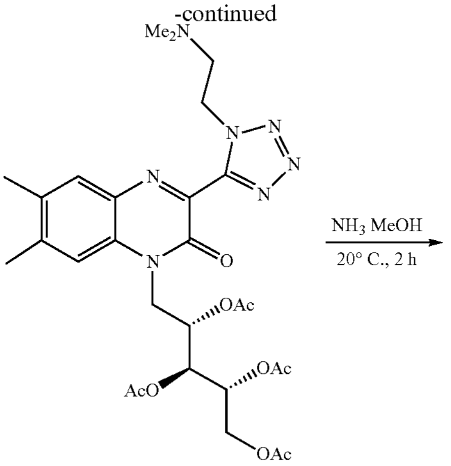

112

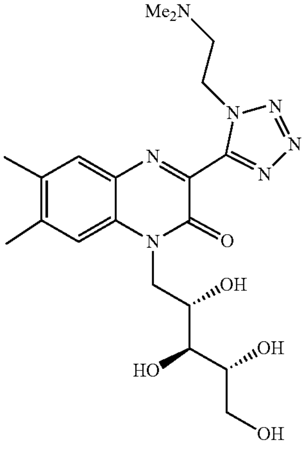

113
(Example 41)

Compound 111

A solution of compound (4) (2056 mg, 3.95 mmol) in $SOCl_2$ (15.00 mL) was stirred for 5 h at 50° C. before being concentrated under reduced pressure. The residue was dissolved in DCM (20 mL) and added dropwise to a 0° C. stirred solution of DIPEA (1531.12 mg, 11.85 mmol) and (2-aminoethyl)dimethylamine (1044.35 mg, 11.85 mmol) in THF (20 mL). The resulting mixture was stirred for 1 h at 20° C. before being diluted with DCM (50 mL) and washed with water (2×50 mL). The organic layers were dried over anhydrous $Na_2SO_4$ after filtration, the filtrate was concentrated under reduced pressure to give compound (111) which was used in the next step without further purification.

ESI-MS m/z=591.4 $[M+H]^+$

Compound 112

To a 0° C. stirred solution of compound (111) (500 mg, 0.85 mmol) in DCE (10 mL) was added $PCl_5$ (705.08 mg, 3.39 mmol) in portions. The mixture was cooled to −5° C. and trimethylsilyl azide (487.66 mg, 4.23 mmol) added dropwise. The resulting mixture was subsequently stirred for an additional 16 h at 80° C. before being diluted with DCM (20 mL) and quenched with sat. $NH_4CO_3$ (aq.) (30 mL) at room temperature. The mixture was washed with water (2×50 mL) and concentrated under reduced pressure. The residue was purified by reverse flash chromatography using the following conditions: Column, C18 silica gel; mobile phase A: 0.1% $NH_4HCO_3$ in water, mobile phase B: ACN; 0% to 100% gradient in 30 min; detector, UV 254 nm, to afford compound (112) (200 mg) as a yellow solid.

ESI-MS m/z=616.4 $[M+H]^+$

Compound 113 (Example 41)

To a stirred room temperature solution of compound (112) (200 mg, 0.33 mmol) in MeOH (10 mL) was added 7M $NH_3{\cdot}H_2O$ (8 mL) dropwise. The resulting mixture was stirred for 2 h at room temperature before being concentrated under reduced pressure. The residue was purified by preparative HPLC using the following conditions (Column: XBridge Shield RP18 OBD Column, 5 μm, 19×150 mm; Mobile Phase A: Water (10 mmol $NH_4HCO_3$), Mobile Phase B: ACN; Flow rate: 25 mL/min; Gradient: 5% B to 38% B in 8 min; 254/220 nm to afford compound (113) (Example 41) (60 mg) as a yellow solid.

LCMS: ESI-MS m/z=448.2 $[M+H]^+$ $^1$H-NMR: (400 MHz, DMSO-d6): δ 7.70 (d, J=8.5 Hz, 2H), 5.01 (d, J=4.0 Hz, 1H), 4.90-4.84 (m, 1H), 4.76 (d, J=6.2 Hz, 1H), 4.73-4.60 (m, 3H), 4.50 (t, J=5.4 Hz, 1H), 4.28 (dd, J=13.8, 2.5 Hz, 1H), 4.17 (s, 1H), 3.62 (d, J=4.6 Hz, 3H), 3.49-3.42 (m, 1H), 2.62 (t, J=6.1 Hz, 2H), 2.43 (s, 3H), 2.35 (s, 3H), 1.94 (s, 6H).

Synthesis of Compound 116 (Example 42)

Example 42 was synthesized according to the scheme below.

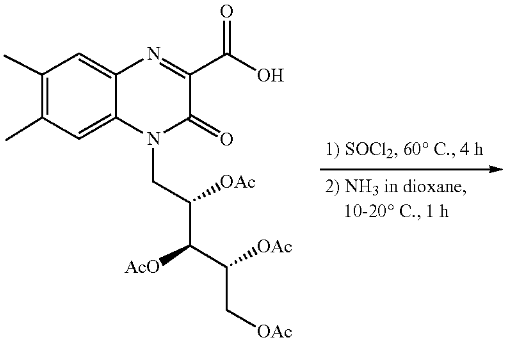

4

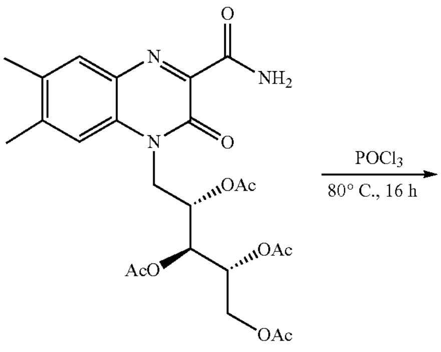

28

-continued

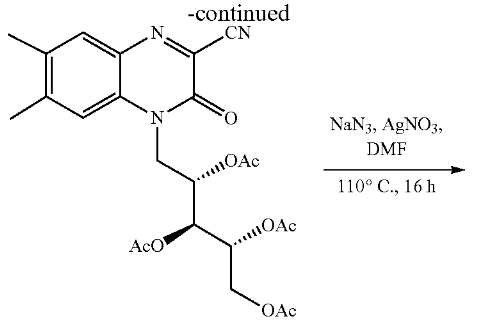

114

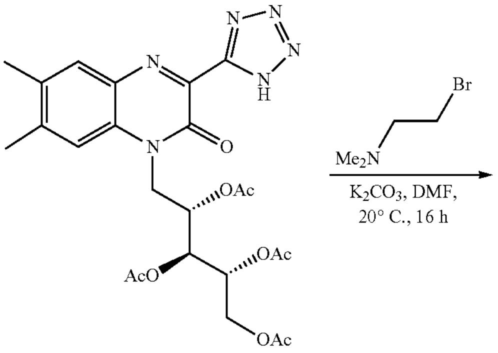

115

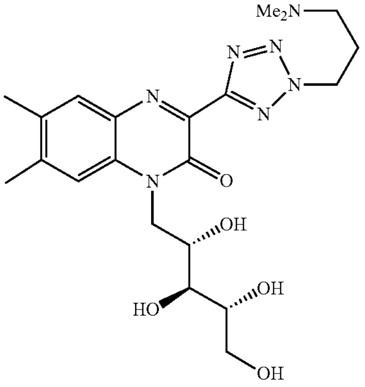

116
(Example 42)

Compound 114

Compound (4) (4 g, 7.69 mmol) in $SOCl_2$ (30 mL) was stirred for 5 h at 50° C. before being cooled down to room temperature and concentrated under reduced pressure. The residue (3.5 g) was diluted with DCM (20 mL) and stirred at room temperature while a solution of $NH_3$ (g) in 1,4-dioxane (0.4M) (200 mL) was added dropwise over 20 min. The resulting mixture was stirred for additional 1 h at 0° C. before being diluted with water (200 mL) and extracted with EtOAc (3×200 mL). The combined organic layers were washed with water (2×300 mL), dried over anhydrous $Na_2SO_4$ and after filtration, the filtrate concentrated under reduced pressure. The residue was dissolved in $POCl_3$ (40 mL) and stirred for 16 h at 80° C. The mixture was concentrated under reduced pressure, diluted with water (100 mL) and extracted with EtOAc (3×100 mL). The combined organic layers were washed with water (3×100 mL), dried over anhydrous $Na_2SO_4$ and after filtration, the filtrate concentrated under reduced pressure. The residue was purified by silica gel column chromatography, eluted with PE/EtOAc (1:1) to afford compound (114) (2.2 g) as a yellow solid.

ESI-MS m/z=502.3 $[M+H]^+$

Compound 115

A mixture of $AgNO_3$ (328.23 mg, 1.93 mmol) and $NaN_3$ (440.75 mg, 6.78 mmol) in DMF (15 mL) was stirred at room temperature for 10 minutes. A solution of compound (114) (1.70 g, 3.39 mmol) in DMF was then added dropwise at room temperature and the resulting mixture stirred for an additional 16 h at 110° C. The mixture was acidified to pH 5 with 1M HCl and extracted with EtOAc (3×50 mL). The combined organic layers were washed with water (2×100 mL), dried over anhydrous $Na_2SO_4$ and after filtration, the filtrate concentrated under reduced pressure. The residue was purified by reverse flash chromatography using the following conditions: Column, C18 silica gel; mobile phase, A: 0.1% FA in water, B: ACN, 10% to 50% gradient in 30 min; detector, UV 254 nm, 35% to afford compound (115) (1 g) as a yellow solid.

ESI-MS m/z=545.3 $[M+H]^+$

Compound 116 (Example 42)

To a 0° C. stirred solution of compound (115) (500 mg, 0.81 mmol) and $K_2CO_3$ (448.24 mg, 3.24 mmol) in DMF (10 mL) was added 1-bromo-3-methylbutane (300 mg, 1.99 mmol) in portions. The resulting mixture was stirred for 16 h at 20° C. before being concentrated under reduced pressure. The residue was purified by preparartive HPLC using the following conditions (Column: XBridge Shield RP18 OBD Column, 5 μm, 19×150 mm; Mobile Phase A: Water (10 mmol $NH_4HCO_3$), Mobile Phase B: ACN; Flow rate: 25 mL/min; Gradient: 5% B to 38% B in 8 min; 254/220 nm to afford compound (116) (Example 42) (48.9 mg) as a light yellow solid.

LCMS: ESI-MS m/z=448.2 $[M+H]^+$ $^1$H-NMR: (400 MHz, DMSO-d6): δ 7.69 (s, 1H), 7.64 (s, 1H), 4.99 (d, J=4.3 Hz, 1H), 4.89 (t, J=6.2 Hz, 2H), 4.84 (d, J=3.9 Hz, 1H), 4.75 (d, J=6.2 Hz, 1H), 4.66 (dd, J=13.8, 10.0 Hz, 1H), 4.48 (t, J=5.5 Hz, 1H), 4.27 (dd, J=13.8, 2.6 Hz, 1H), 4.16 (s, 1H), 3.62 (s, 3H), 3.49-3.42 (m, 1H), 2.89 (t, J=6.2 Hz, 2H), 2.41 (s, 3H), 2.34 (s, 3H), 2.19 (s, 6H).

Synthesis of Compound 117 (Example 43)

Example 43 was synthesized according to the scheme below.

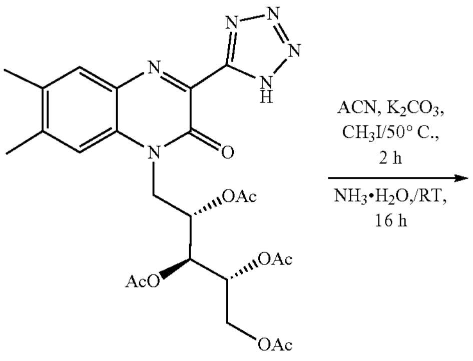

115

-continued

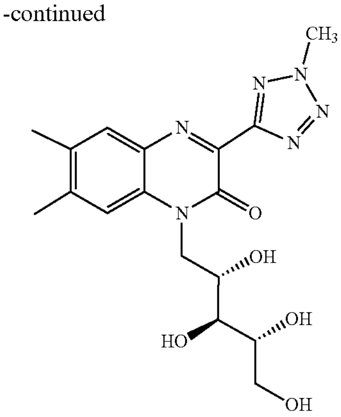

117
(Example 43)

Compound 117 (Example 43)

To a 50° C. stirred mixture of compound (115) (500 mg, 0.92 mmol) and $K_2CO_3$ (380.72 mg, 2.76 mmol) in ACN (15 mL) was added methyl iodide (391.00 mg, 2.76 mmol) dropwise. The resulting mixture was stirred for 2 h at 50° C. After cooling to room temperature ammonium hydroxide (10 mL) was added dropwise to the mixture and stirring continued for an additional 16 h at room temperature. After concentrating under reduced pressure the residue was purified by preparative HPLC using the following conditions (Column: Welch XB-C18, 21.2×250 mm, 5 μm; Mobile Phase A: Water (10 mmol $NH_4HCO_3$), Mobile Phase B: ACN; Flow rate: 25 mL/min; Gradient: 20% B, 254/220 nm to afford compound (117) (Example 43) (55.1 mg) as a light yellow solid.

ESI-MS m/z=391.15 $[M+H]^+$ $^1$H-NMR: (400 MHz, DMSO-d6): δ 7.66 (d, J=13.7 Hz, 2H), 4.98 (d, J=4.5 Hz, 1H), 4.83 (d, J=4.4 Hz, 1H), 4.74-4.65 (m, 2H), 4.49 (s, 4H), 4.27 (d, J=13.7 Hz, 1H), 4.16 (s, 1H), 3.62 (d, J=5.0 Hz, 3H), 3.50-3.40 (m, 1H), 2.41 (s, 3H), 2.34 (s, 3H).

Synthesis of Compound 121 (Example 44)

Example 44 was synthesized according to the scheme below.

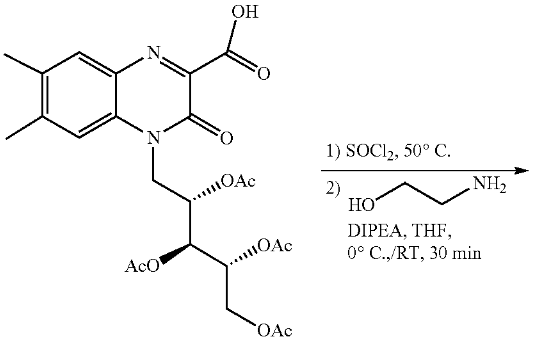

4

-continued

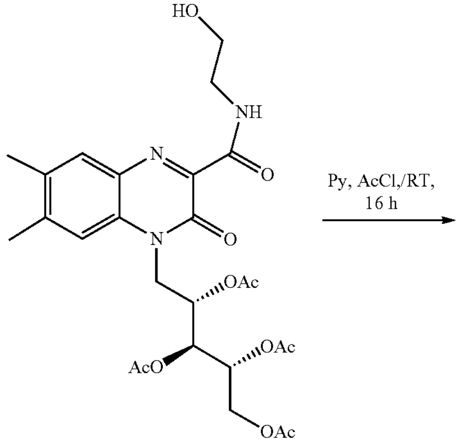

118

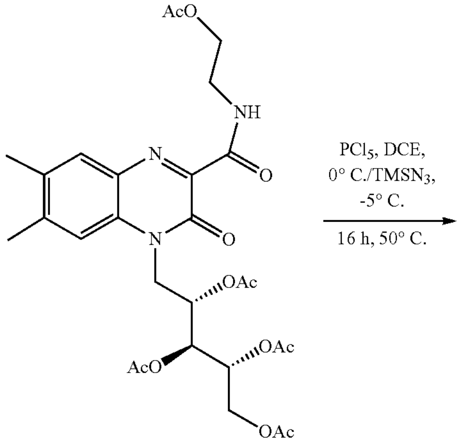

119

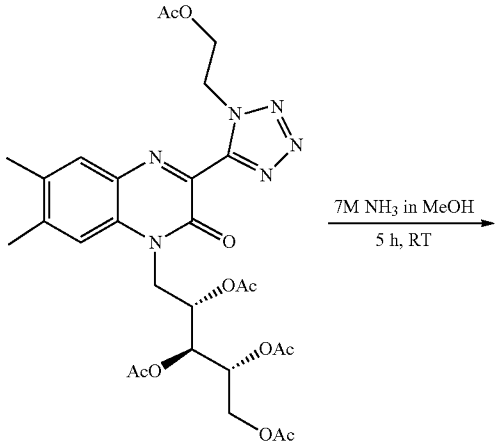

120

-continued

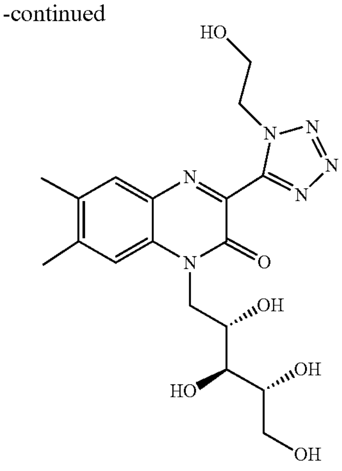

121
(Example 44)

Compound 118

A mixture of compound (4) (3 g, 5.76 mmol) in $SOCl_2$ (20 mL) was stirred for 5 h at 50° C. before being concentrated under vacuum. The residue was diluted with DCM (10 mL), cooled to 0° C. and a solution of ethanolamine (1056.23 mg, 17.29 mmol) and DIPEA (2.23 g) in THF (10 mL) added dropwise with stirring. The resulting mixture was stirred for 30 min at room temperature before being diluted with DCM (50 mL) and washed with water (100 mL). The organic layer was dried over anhydrous $Na_2SO_4$ and after filtration, the filtrate concentrated under reduced pressure. The residue of compound (118) was used in the next step directly without further purification.

Compound 119

A mixture of compound (118) (3.5 g, 6.21 mmol) and $Ac_2O$ (6.34 g, 62.10 mmol) in pyridine (15 mL) was stirred for 16 h at room temperature. The resulting mixture was concentrated under vacuum and the residue purified by reverse flash chromatography using the following conditions: Column, C18 silica gel; mobile phase A: 0.1% FA in water, mobile phase B: ACN; 0% to 100% gradient in 30 min; detector, UV 254 nm, to afford compound (119) (3.1 g) as a yellow solid.

Compound 120

To a 0° C. stirred solution of compound (119) (1 g, 1.65 mmol) in DCE (20 mL) was added phosphorus pentachloride (1375.30 mg, 6.61 mmol) in portions. The resulting mixture was stirred for 30 min at 0° C. After cooling to −5° C. trimethylsilyl azide (951.22 mg, 8.26 mmol) was added dropwise to the mixture. The mixture was stirred for additional 16 h at 50° C. before being diluted with DCM (100 mL) and quenched by the addition of saturated ammonium bicarbonate (100 mL) at 0° C. The resulting mixture was washed with water (2×100 mL) and the organic layers dried over anhydrous $Na_2SO_4$. After filtration, the filtrate was concentrated under reduced pressure. The residue was purified by reverse flash chromatography using the following conditions: Column, C18 silica gel; mobile phase A: 0.1% FA in water, mobile phase B: ACN; 0% to 100% B gradient in 30 min; detector, UV 254 nm to afford compound (120) (330 mg) as a yellow solid.

Compound 121 (Example 44)

A mixture of compound (120) (330 mg, 0.523 mmol) in 7M $NH_3$ in MeOH (5 mL) was stirred for 5 h at room temperature. After concentration under reduced pressure the residue was purified by preparative HPLC using the following conditions (Column: XBridge Prep OBD C18 Column, 19×250 mm, 5 μm; Mobile Phase A: Water (10 mmol $NH_4HCO_3$), Mobile Phase B: ACN; Flow rate: 25 mL/min; Gradient: 16% B to 24% B in 12 min; 254/220 nm to afford compound (121) (Example 44) (91.8 mg) as a yellow solid.

ESI-MS m/z=421.15 $[M+H]^+$ $^1$H-NMR: (400 MHz, DMSO-d6): δ 7.70 (d, J=10.6 Hz, 2H), 5.01 (d, J=3.9 Hz, 1H), 4.94 (t, J=5.4 Hz, 1H), 4.86 (d, J=3.9 Hz, 1H), 4.80 (d, J=6.0 Hz, 1H), 4.68-4.62 (m, 3H), 4.50 (t, J=5.4 Hz, 1H), 4.28 (dd, J=13.6, 2.6 Hz, 1H), 4.17 (s, 1H), 3.73 (q, J=5.5 Hz, 2H), 3.62 (s, 3H), 3.49-3.41 (m, 1H), 2.43 (s, 3H), 2.36 (s, 3H).

Synthesis of Compound 129 (Example 45)

Example 45 was synthesized according to the scheme below.

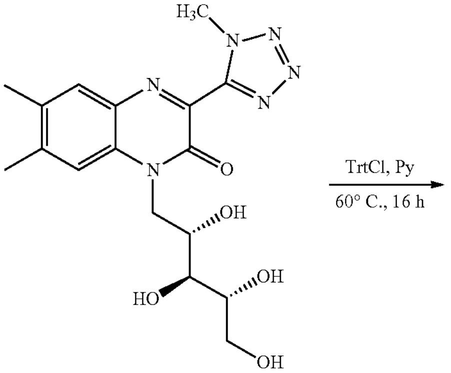

40

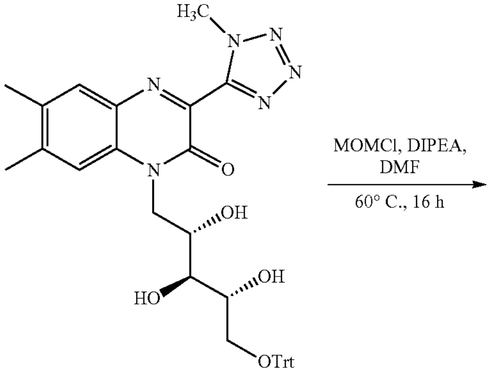

122

-continued

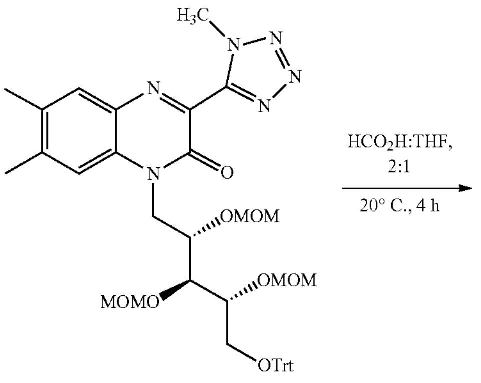

123

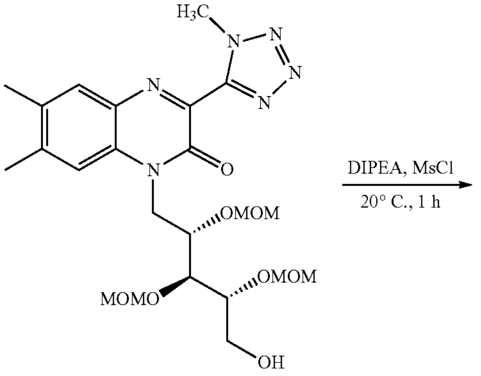

124

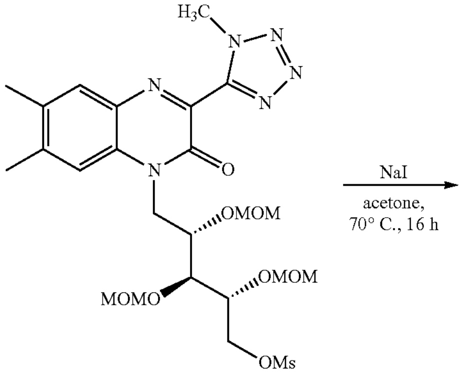

125

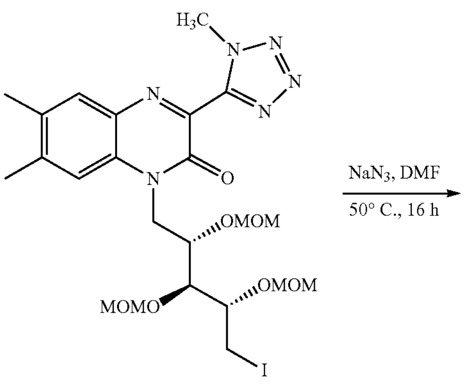

126

-continued

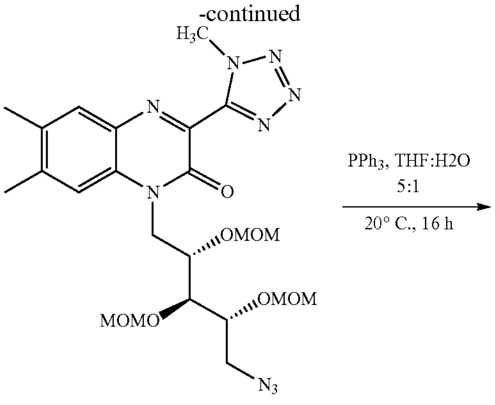

127

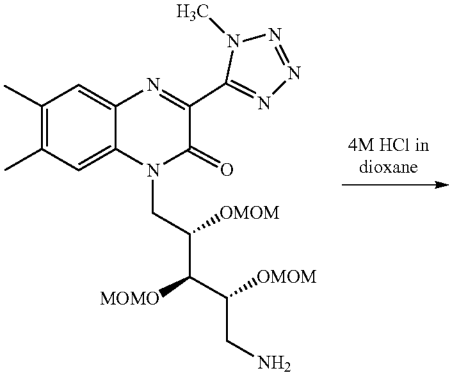

128

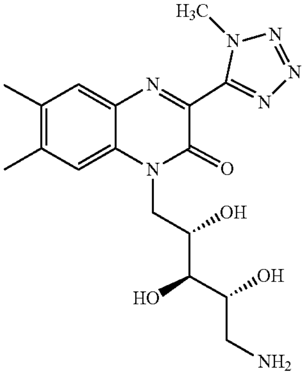

129
(Example 45)

Compound 122

To a 0° C. stirred solution of compound (40) (8 g, 20.49 mmol) in pyridine (200 mL) was added Trt-Cl (17.14 g, 61.48 mmol) in portions. The resulting mixture was stirred for 16 h at 70° C. before being diluted with water (600 mL) and extracted with EtOAc (3×200 mL). The combined organic layers were washed with water (3×100 mL), dried over anhydrous $Na_2SO_4$ and after filtration, the filtrate concentrated under reduced pressure. The residue was purified by silica gel column chromatography, eluted with PE/EtOAc (1:1) to afford compound (122) (10 g) as a yellow solid.

LCMS: (ES, m/z): $[M+Na]^+$=655.4

Compound 123

To a 0° C. stirred solution of compound (122) (3 g, 4.74 mmol) and DIPEA (18.39 g, 142.29 mmol) in DMF (300 mL) was added MOM-Cl (30.28 g, 455.43 mmol) in DMF (50 mL) dropwise. The resulting mixture was stirred for 18 h at 70° C. before being diluted with water (600 mL) and extracted with EtOAc (3×200 mL). The combined organic layers were washed with water (3×200 mL), dried over anhydrous $Na_2SO_4$ and after filtration, the filtrate concentrated under reduced pressure. The residue was purified by silica gel column chromatography, eluted with PE/EtOAc (2:1) to afford compound (123) (2 g) as a yellow solid.

LCMS: (ES, m/z): $[M+Na]^+=787.5$

Compound 124

To a 0° C. stirred solution of compound (123) (2 g, 2.62 mmol) in THF (10 mL) was added formic acid (10 mL, 217.26 mmol) dropwise. The resulting mixture was stirred for 4 h at 25° C. before being concentrated under reduced pressure. The residue was purified by reverse flash chromatography using the following conditions: Column, C18 silica gel; mobile phase, MeOH: water, 10% to 50% gradient in 10 min; detector, UV 254 nm to afford compound (124) (750 mg) as a yellow oil.

LCMS: (ES, m/z): $[M+H]^+=523.5$

Compound 125

To a 0° C. stirred solution of compound (124) (2.30 g, 4.45 mmol) and DIPEA (5.76 g, 44.57 mmol) in DCM (100 mL) was added Ms-Cl (2.55 g, 22.26 mmol) in DCM (10 mL) dropwise. The resulting mixture was stirred for 0.5 h at 25° C. before being concentrated under vacuum. The residue was purified by silica gel column chromatography, eluted with PE/EtOAc (1:1) to afford compound (125) (2 g) as a yellow oil.

LCMS: (ES, m/z): $[M+H]^+=601.5$

Compound 126

To a 25° C. stirred solution of compound (125) (300 mg, 0.5 mmol) in acetone (20 mL) was added NaI (374.34 mg, 2.5 mmol) in portions. The resulting mixture was stirred for 18 h at 70° C. before being concentrated under reduced pressure. The residue was purified by silica gel column chromatography, eluted with PE/EtOAc (1:1) to afford compound (126) (290 mg) as a yellow solid.

LCMS: (ES, m/z): $[M+H]^+=633.3$

Compound 127

To a 25° C. stirred mixture of compound (126) (290 mg, 0.46 mmol) in DMF (5 mL) was added $NaN_3$ (59.62 mg, 0.92 mmol) in portions. The resulting mixture was stirred for 18 h at 50° C. before being diluted with water (50 mL) and the solids filtered. The solids were washed with EtOAc (3×10 mL) and the filtrate concentrated under reduced pressure. The residue was purified by silica gel column chromatography, eluted with PE/EtOAc (1:1) to afford compound (127) (270 mg) as a yellow solid.

LCMS: (ES, m/z): $[M+H]^+=548.4$

Compound 128

To a 25° C. stirred solution of compound (127) (270 mg, 0.49 mmol) in water (1 mL) and THF (5 mL) was added triphenylphosphine (718.49 mg, 2.74 mmol) in portions. The resulting mixture was stirred for 16 h before being concentrated under reduced pressure. The residue compound (128) was used directly in the next step without further purification.

LCMS-PH-AVR-FTE0056-5: (ES, m/z): $[M+H]^+=522.4$

Compound 129 (Example 45)

To a stirred solution of compound (128) (230 mg, 0.44 mmol) in THF (10 mL) was added 6M HCl (5 mL) dropwise to maintain the temperature under 0° C. The resulting mixture was subsequently stirred for 4 h at 25° C. before being neutralized to pH 7 with saturated $NaHCO_3$ (aq.). The resulting mixture was concentrated under reduced pressure and the residue purified by reverse flash chromatography using the following conditions: Column, C18 silica gel; mobile phase, MeOH: water, 10% to 50% gradient in 10 min; detector, UV 254 nm to afford compound (129) (Example 45) (70 mg) as a yellow solid.

LCMS: (ES, m/z): $[M+H]^+=390.3$ $^1H$ NMR: (400 MHz, DMSO-d6) δ 7.71 (d, J=23.9 Hz, 2H), 5.14-4.73 (m, 2H), 4.61 (dd, J=13.8, 9.7 Hz, 2H), 4.33 (dd, J=13.9, 2.7 Hz, 2H), 4.16 (s, 4H), 3.62 (dq, J=11.6, 6.4, 5.0 Hz, 3H), 2.85 (dd, J=12.8, 3.7 Hz, 1H), 2.69 (dd, J=12.8, 6.1 Hz, 1H), 2.44 (s, 3H), 2.36 (s, 3H).

Synthesis of Compound 132 (Example 46)

Example 46 was synthesized according to the scheme below.

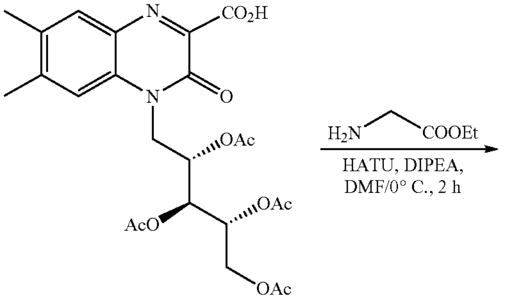

4

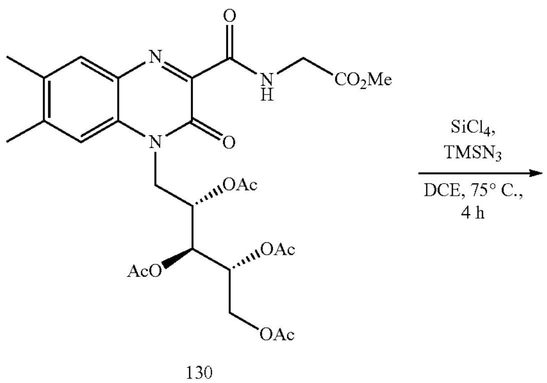

130

-continued

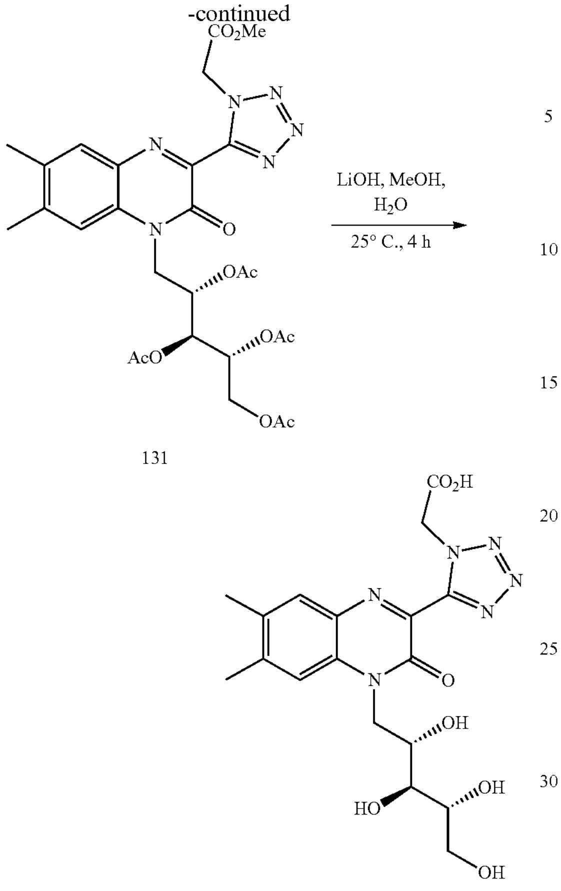

131

132
(Example 46)

Compound 130

To a 0° C. stirred solution of compound (4) (4 g, 7.69 mmol), glycine ethyl ester (1.19 g, 11.54 mmol) and DIPEA (2.98 g, 23.06 mmol) in DMF (50 mL) was added HATU (5.84 g, 15.37 mmol) in portions. The resulting mixture was stirred for 2 h at 0-20° C. before being diluted with water (200 mL) and extracted with EtOAc (3×200 mL). The combined organic layers were washed with water (3×300 mL), dried over anhydrous $Na_2SO_4$ and after filtration, the filtrate concentrated under reduced pressure.

The residue was purified by silica gel column chromatography, eluted with PE/EtOAc (1:1) to afford compound (130) (5 g) as a yellow solid.

Compound 131

To a 0° C. stirred solution of compound (130) (2.5 g, 4.23 mmol) in DCE (20 mL) was added silicon tetrachloride (2.15 g, 12.66 mmol) and trimethylsilyl azide (2.43 g, 21.09 mmol) dropwise. The resulting mixture was stirred for 16 h at 70° C. before being cooled to room temperature, diluted with DCM (100 mL) and washed with water (3×100 mL). The combined organic layers were dried over anhydrous $Na_2SO_4$ and after filtration, the filtrate concentrated under reduced pressure. The residue was purified by reverse flash chromatography using the following conditions: Column, C18 silica gel; mobile phase A: 0.1% FA in water; mobile phase B: ACN; 0% to 70% gradient in 30 min; detector, UV 254 nm to afford compound (131) (1.6 g) as a yellow solid.

Compound 132 (Example 46)

To a 0° C. stirred solution of compound (131) (300 mg, 0.49 mmol) in MeOH (5 mL) was added a solution of lithium hydroxide (58.26 mg, 2.433 mmol) in water dropwise. The resulting mixture was stirred for 1 h at 0° C. before being neutralized to pH 6 with 1M HCl and concentrated under reduced pressure. The residue was purified by reverse flash chromatography using the following conditions: Column, C18 silica gel; mobile phase A: 0.1% TFA in water, mobile phase B: ACN, 0% to 30% gradient in 30 min; detector, UV 254 nm to afford compound (132) (Example 46) (65 mg) as a yellow solid.

ESI-MS m/z=435.20 $[M+H]^+$ $^1$H-NMR: (400 MHz, MeOD-$d_4$): δ 7.76-7.71 (d, 2H), 5.68 (s, 2H), 4.83 (dd, J=14.1, 9.7 Hz, 1H), 4.53 (dd, J=14.1, 2.8 Hz, 1H), 4.31 (ddd, J=9.7, 4.7, 2.8 Hz, 1H), 3.89-3.80 (m, 3H), 3.75-3.66 (m, 1H), 2.51 (s, 3H), 2.47-2.39 (m, 3H).

Synthesis of Compound 135 (Example 47)

Example 47 was synthesized according to the scheme below.

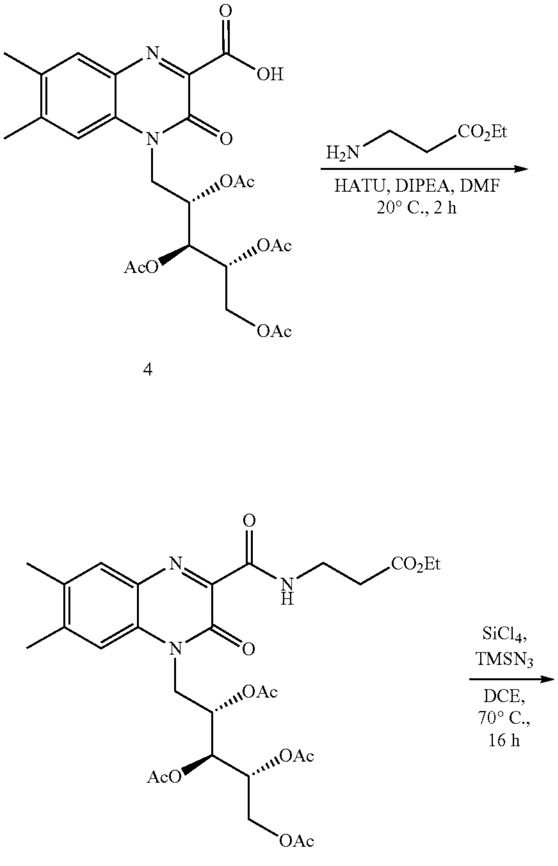

4

133

-continued

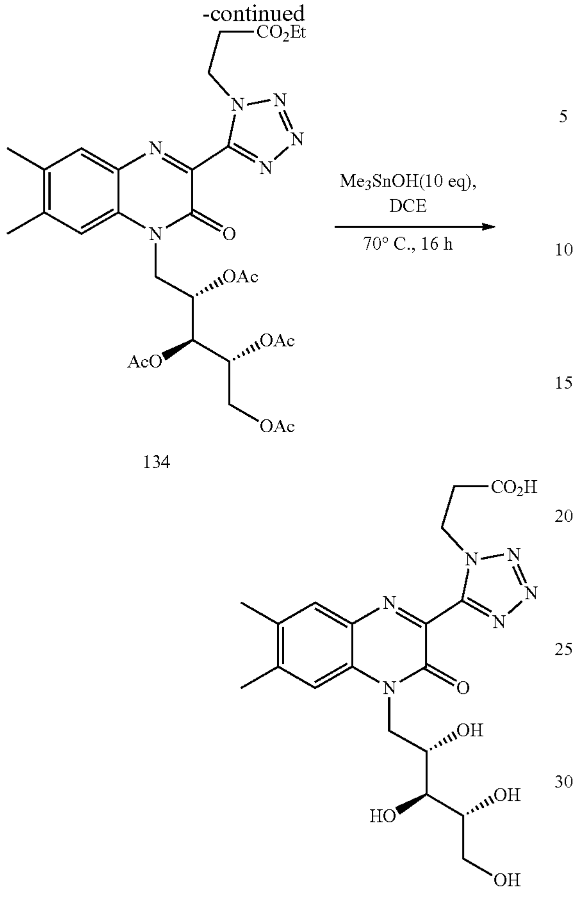

134

135
(Example 47)

Compound 133

To a 0° C. stirred solution of compound (4) (500 mg, 0.96 mmol), β-alanine ethyl ester (168.80 mg, 1.44 mmol) and DIPEA (620.78 mg, 4.80 mmol) in DMF (5 mL) was added HATU (474.84 mg, 1.25 mmol) in portions. The resulting mixture was stirred for 2 h at 0-20° C. before being diluted with water (20 mL) and extracted with EtOAc (3×20 mL). The combined organic layers were washed with water (2×50 mL), dried over anhydrous $Na_2SO_4$ and after filtration, the filtrate concentrated under reduced pressure. The residue was purified by preparative thin layer chromatography eluted with (EtOAc) to afford compound (133) (530 mg) as a yellow solid.

Compound 134

To a 0° C. stirred mixture of compound (133) (585 mg, 0.94 mmol) in DCE (10 mL) was added $SiCl_4$ (481.21 mg, 2.83 mmol) and trimethylsilyl azide (543.87 mg, 4.72 mmol) in portions. The resulting mixture was stirred for 16 h at 70° C. before being diluted with DCM (20 mL), washed with water (3×20 mL), dried over anhydrous $Na_2SO_4$ and after filtration, the filtrate concentrated under reduced pressure. The residue was purified by preparative thin layer chromatography eluted with (PE/EtOAc 2:3) to afford compound (134) (500 mg) as a yellow solid.

Compound 135 (Example 47)

To a 0° C. stirred solution of compound (134) (200 mg, 0.31 mmol) in DCE (10 mL) was added trimethyltin hydroxide (673.2 mg, 3.72 mmol) in portions. The resulting mixture was stirred for 16 h at 80° C. before being allowed to cool to room temperature and concentrated under reduced pressure. The residue was diluted with MeOH (5 mL), acidified to pH 6 with HCl (aq.) and purified by reverse flash chromatography using the following conditions: Column, C18 silica gel; mobile phase A: 0.1 FA % in water, mobile phase B: ACN, 0% to 30% gradient in 20 min; detector, UV 254 nm to afford compound (135) (Example 47) (56 mg) as a yellow solid.

ESI-MS m/z=449.15 $[M+H]^+$ $^1$H-NMR: (400 MHz, MeOD-$d_4$): δ 7.76 (d, J=4.7 Hz, 2H), 4.95 (s, 2H), 4.81 (s, 1H), 4.53 (dd, J=14.1, 2.8 Hz, 1H), 4.33 (ddd, J=9.7, 4.6, 2.8 Hz, 1H), 3.89-3.77 (m, 3H), 3.70 (dd, J=12.2, 6.4 Hz, 1H), 3.08 (t, J=6.7 Hz, 2H), 2.52 (s, 3H), 2.42 (s, 3H).

Synthesis of Compound 137 (Example 48)

Example 48 was synthesized according to the scheme below.

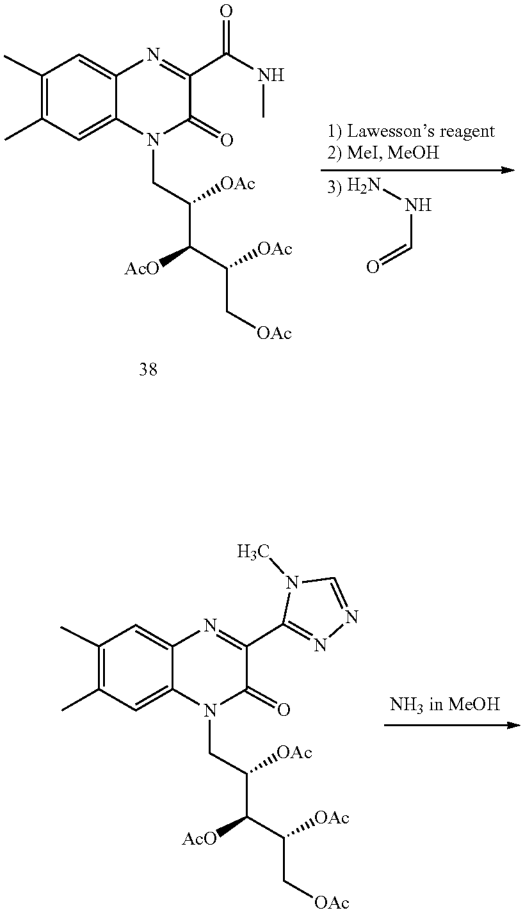

38

136

-continued

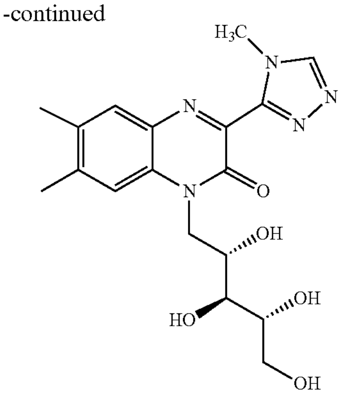

137
(Example 48)

Compound 136

To a 25° C. stirred mixture of compound (38) (900 mg, 1.69 mmol) in toluene (30 mL) was added Lawessons Reagent (682.28 mg, 1.69 mmol) in portions. The resulting mixture was stirred for 4 h at 120° C. before being concentrated under reduced pressure. The residue was dissolved in THF (10 mL) and methyl iodide (2394.32 mg, 16.87 mmol) added dropwise to the stirred mixture at 25° C. The mixture was stirred for 18 h at 25° C. before being concentrated under reduced pressure. To the residue was added N-formylhydrazine (202.61 mg, 3.37 mmol) at 25° C. and the resulting mixture stirred for 18 h at 70° C. before being concentrated under reduced pressure. The residue was purified by preparative thin layer chromatography eluted with (PE/EtOAc 1:1) to afford compound (136) (300 mg) as a yellow solid.

LCMS: (ES, m/z): $[M+H]^+=558.3$

Compound 137 (Example 48)

A mixture of compound (136) (300 mg, 0.54 mmol) and $NH_3$ (g) in MeOH (10 mL) were stirred for 2 h at 25° C. before being concentrated under reduced pressure. The residue was purified by reverse flash chromatography using the following conditions: Column, C18 silica gel; mobile phase, MeOH: water, 10% to 50% gradient in 10 min; detector, UV 254 nm to afford compound (137) (Example 48) (100 mg) as a yellow solid.

LCMS: (ES, m/z): $[M+H]^+=390.2$ $^1H$ NMR: (400 MHz, DMSO-d6) δ 8.63 (s, 1H), 7.67 (d, J=12.1 Hz, 2H), 5.01 (d, J=3.7 Hz, 1H), 4.88-4.84 (m, 1H), 4.80 (d, J=6.1 Hz, 1H), 4.67 (dd, J=13.8, 10.0 Hz, 1H), 4.50 (t, J=5.3 Hz, 1H), 4.25 (dd, J=13.8, 2.6 Hz, 1H), 4.16 (td, J=6.8, 3.4 Hz, 1H), 3.70 (s, 3H), 3.65-3.57 (m, 3H), 3.47-3.43 (m, 1H), 2.42 (s, 3H), 2.35 (s, 3H).

Synthesis of Compound 141 (Example 49)

Example 49 was synthesized according to the scheme below.

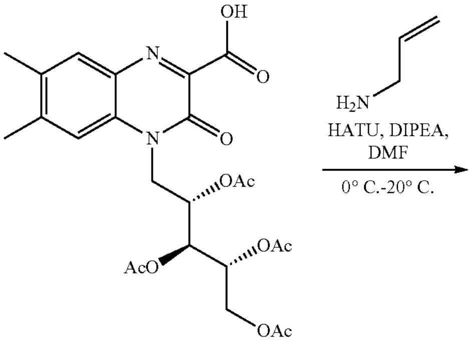

4

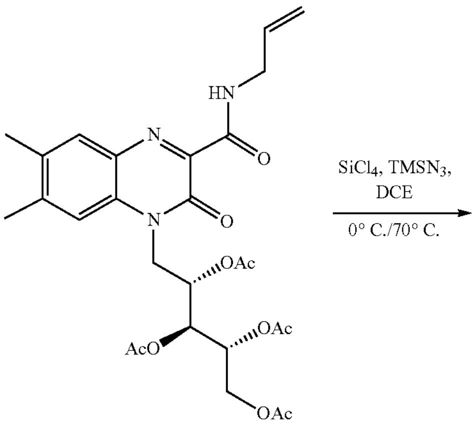

138

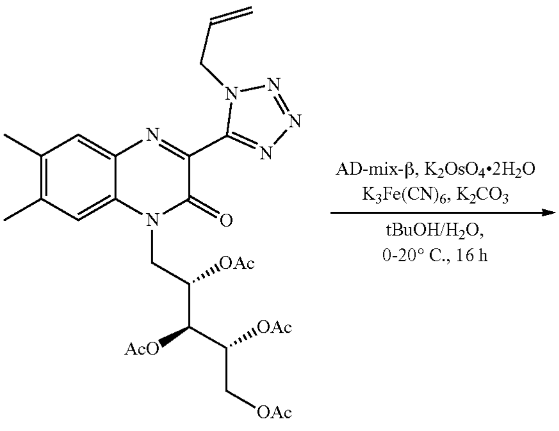

139

-continued

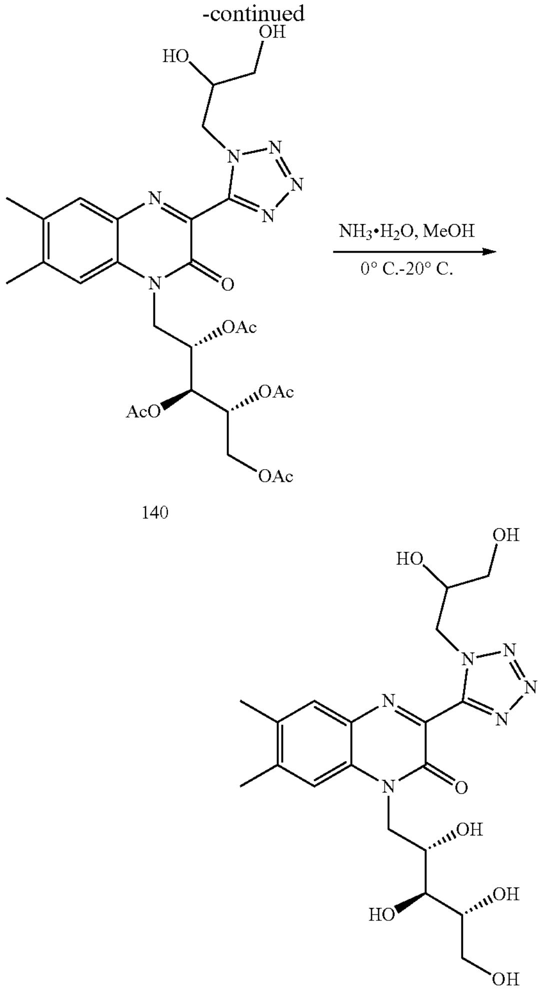

140

141
(Example 49)

Compound 138

To a 0° C. stirred solution of compound (4) (1 g, 1.92 mmol) and DIPEA (744.93 mg, 5.76 mmol) in DMF (10 mL) were added allylamine (164.54 mg, 2.88 mmol) and HATU (1095.78 mg, 2.88 mmol) dropwise. The resulting mixture was stirred for 2 h at 0-20° C. before being diluted with water (50 mL) and extracted with EtOAc (3×50 mL). The combined organic layers were washed with water (2×100 mL), dried over anhydrous $Na_2SO_4$ and after filtration, the filtrate concentrated under reduced pressure. The residue was purified by silica gel column chromatography, eluted with PE/EtOAc (1:1) to afford compound (138) (1 g) as a yellow solid.

Compound 139

To a 0° C. stirred mixture of compound (138) (800 mg, 1.43 mmol) in DCE (10 mL) was added silicon tetrachloride (728.66 mg, 4.29 mmol) and trimethylsilyl azide (823.57 mg, 7.15 mmol) dropwise. The resulting mixture was stirred for 16 h at 70° C. then cooled room temperature. DCM (50 mL) was added and the mixture washed with water (3×50 mL), dried over anhydrous $Na_2SO_4$ and after filtration, the filtrate was concentrated under reduced pressure. The residue was purified by preparative thin layer chromatography eluted with (PE/EtOAc 1:2) to afford compound (139) (500 mg) as a yellow solid.

Compound 140

To a 0° C. stirred mixture of compound (139) (200 mg, 0.34 mmol) in $H_2O$/t-BuOH (10 mL) was added $K_2CO_3$ (141.85 mg, 1.03 mmol), $K_2OsO_4$·$2H_2O$ (1.26 mg, 0.003 mmol), $K_3Fe(CN)_6$ (11.26 mg, 0.034 mmol) and ad-mix-beta(dhqd)$_2$phal (26.65 mg, 0.034 mmol) in portions. The resulting mixture was stirred for 16 h at 0-20° C. before being concentrated under reduced pressure. The residue was purified by reverse flash chromatography using the following conditions: Column, C18 silica gel; mobile phase A: 0.1% FA in water, mobile phase B: ACN; 10% to 50% gradient in 20 min; detector, UV 254 nm to afford compound (140) (120 mg) as a yellow solid.

Compound 141 (Example 49)

To a 0° C. stirred solution of compound (140) (200 mg) in MeOH (4 mL) was added $NH_3$·$H_2O$ (2 mL) dropwise. The resulting mixture was stirred for 2 h at room temperature before being concentrated under reduced pressure. The residue was purified by reverse flash chromatography using the following conditions: Column, C18 silica gel; mobile phase A: 0.1% FA in water, mobile phase B: ACN; 0% to 30% gradient in 20 min; detector, UV 254 nm to afford compound (141) (Example 49) (56 mg) as a yellow solid.

ESI-MS m/z=451.20 $[M+H]^+$ $^1$H-NMR: (400 MHz, DMSO-$d_6$): δ 7.70 (d, J=10.6 Hz, 2H), 5.03 (dd, J=8.9, 4.7 Hz, 2H), 4.87 (d, J=3.7 Hz, 1H), 4.79 (t, J=5.4 Hz, 2H), 4.77-4.62 (m, 2H), 4.49 (dt, J=17.7, 6.9 Hz, 2H), 4.27 (d, J=13.8 Hz, 1H), 4.16 (s, 1H), 3.79 (s, 1H), 3.62 (d, J=4.5 Hz, 3H), 3.45 (m, 1H), 3.32 (m, 1H), 3.21 (m, 1H), 2.43 (s, 3H), 2.35 (s, 3H).

Synthesis of Compound 143 (Example 50)

Example 50 was synthesized according to the scheme below.

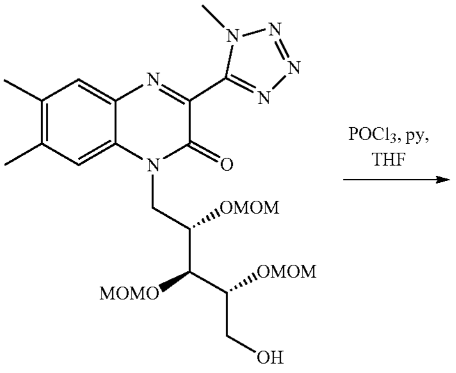

124

-continued

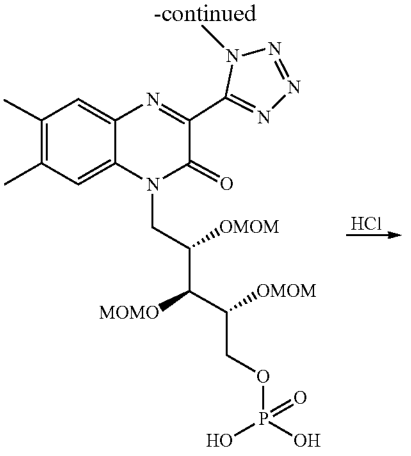

142

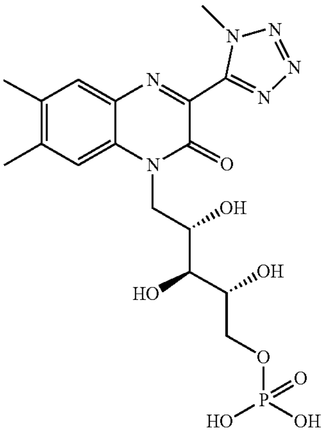

143
(Example 50)

Compound 142

To a 0° C. stirred solution of compound (124) (200 mg, 0.38 mmol) and pyridine (151.37 mg, 1.91 mmol) in THF was added $POCl_3$ (176.06 mg, 1.148 mmol) dropwise. The resulting mixture was stirred for 3 h at 20° C. before being concentrated under reduced pressure. The residue compound (142) was used directly in the next step without further purification.

LCMS: (ES, m/z): $[M+H]^+$=603.2

Compound 143 (Example 50)

To a 20° C. stirred solution of compound (142) (200 mg, 0.33 mmol) in THF (5 mL) was added 4M HCl (gas) in 1,4-dioxane (5.00 mL, 0.14 mmol) dropwise. The resulting mixture was stirred for 2 h at 20° C. before being concentrated under reduced pressure. The residue was purified by reverse flash chromatography using the following conditions: Column, C18 silica gel; mobile phase, ACN: water, 10% to 50% gradient in 30 min; detector, UV 254 nm to afford compound (143) (Example 50) (60 mg) as a yellow solid.

LCMS: (ES, m/z): $[M+H]^+$=471.1

$^1$H NMR: (400 MHz, Methanol-d4) δ 7.77 (d, J=13.2 Hz, 2H), 4.84-4.76 (m, 1H), 4.52 (dd, J=14.1, 2.8 Hz, 1H), 4.38-4.24 (m, 5H), 4.13 (dt, J=10.8, 6.5 Hz, 1H), 4.03-3.98 (m, 1H), 3.84 (dd, J=7.4, 4.9 Hz, 1H), 2.53 (d, J=6.2 Hz, 3H), 2.43 (s, 3H).

Synthesis of Compound 145 (Example 51)

Example 51 was synthesized according to the scheme below.

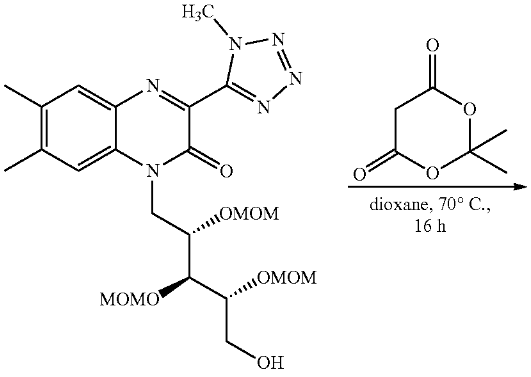

124

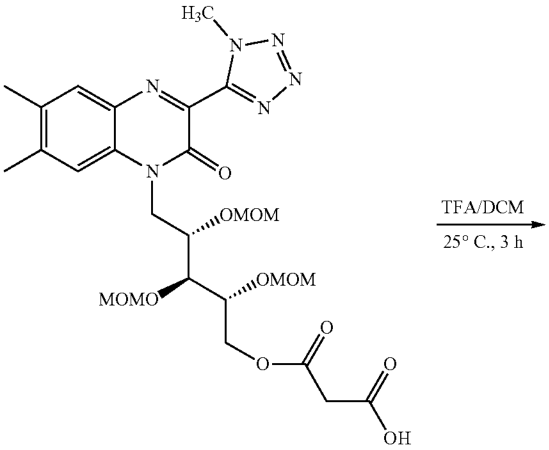

144

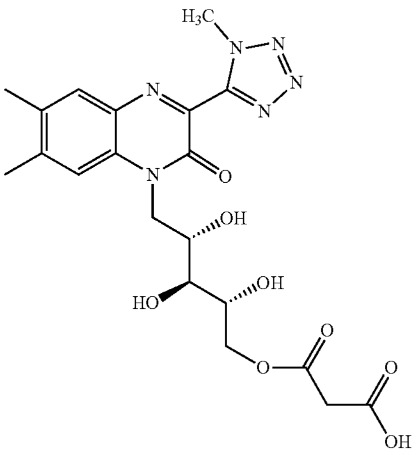

145
(Example 51)

Compound 144

To a stirred 25° C. solution of compound (124) (300 mg, 0.57 mmol) in dioxane (5 mL) was added meldrums acid (165.48 mg, 1.15 mmol) in portions. The resulting mixture was stirred for 18 h at 70° C. before being concentrated under vacuum. The residue was purified by silica gel column chromatography, eluted with PE/EtOAc (1:1) to afford compound (144) (300 mg) as a yellow solid.

LCMS: (ES, m/z): $[M+H]^+$=609.3

Compound 145 (Example 51)

To a 0° C. stirred solution of compound (144) (200 mg, 0.33 mmol) in DCM (3 mL) was added TFA (3 mL) dropwise. The resulting mixture was stirred for 3 h at 25° C. before being concentrated under reduced pressure. The residue was purified by reverse flash chromatography using the following conditions: Column, C18 silica gel; mobile phase, MeOH: water, 10% to 50% gradient in 10 min; detector, UV 254 nm to afford compound (145) (Example 51) (40 mg) as a yellow solid.

LCMS: (ES, m/z): $[M+H]^+$=506.3

$^1$H NMR: (400 MHz, Methanol-$d_4$) δ 7.77 (s, 1H), 7.73 (s, 1H), 4.83-4.78 (m, 3H), 4.55-4.43 (m, 2H), 4.35-4.28 (m, 5H), 4.06 (tt, J=7.0, 3.5 Hz, 1H), 3.82 (dd, J=7.2, 5.1 Hz, 1H), 2.52 (s, 3H), 2.42 (s, 3H).

Synthesis of Compound 147 (Example 52)

Example 52 was synthesized according to the scheme below.

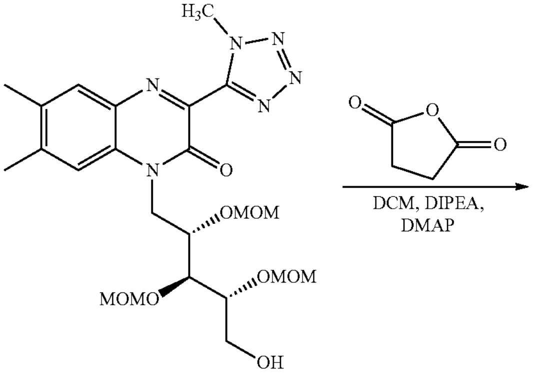

124

-continued

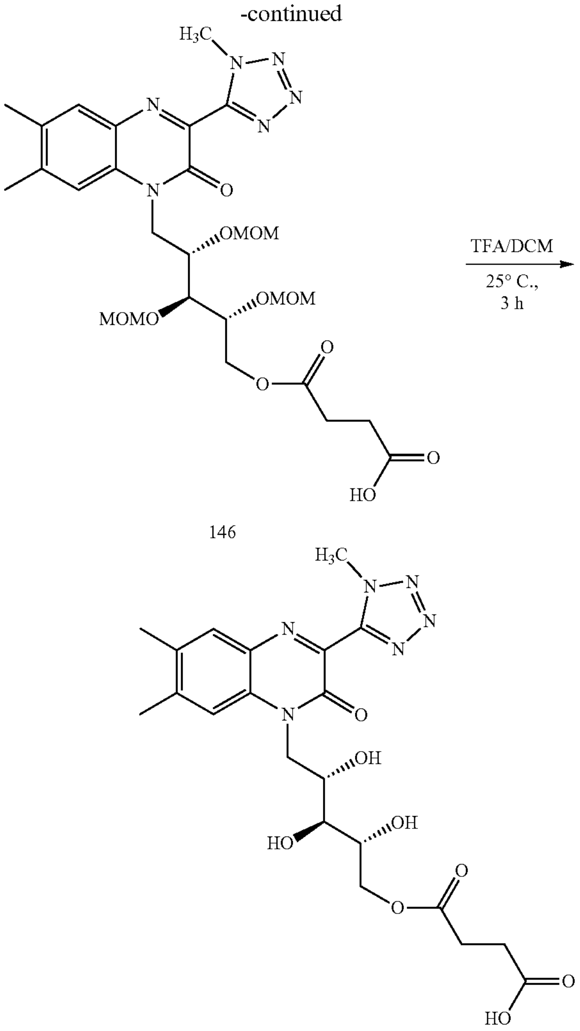

146

147
(Example 52)

Compound 146

To a 0° C. stirred solution of compound (124) (300 mg, 0.57 mmol) and DIPEA (370.99 mg, 2.87 mmol) and DMAP (14.03 mg, 0.12 mmol) in DCM (10 mL) was added succinic anhydride (120.07 mg, 1.2 mmol) in portions. The resulting mixture was stirred for 18 h at 25° C. before being concentrated under reduced pressure. The residue was purified by silica gel column chromatography, eluted with PE/EtOAc (1:1) to afford compound (146) (300 mg) as a yellow solid.

LCMS: (ES, m/z): $[M+H]^+$=623.3

Compound 147 (Example 52)

To a 0° C. stirred mixture of compound (146) (200 mg, 0.32 mmol) in DCM was added TFA (2 mL) in DCM (1 mL) dropwise. The resulting mixture was stirred for 3 h at 25° C. before being concentrated under vacuum. The residue was purified by reverse flash chromatography using the following conditions: Column: XSelect CSH Prep C18 OBD Column, 5 μm, 19×150 mm; Mobile Phase A: Water (0.05% FA), Mobile Phase B: ACN; Flow rate: 25 mL/min;

Gradient: 12% B to 26% B in 16 min; 254 nm to afford compound (147) (Example 52) (70 mg) as a yellow solid.

LCMS: (ES, m/z): $[M+H]^+$=491.2

$^1$H NMR: (400 MHz, DMSO-d6) δ12.48-11.52 (m, 1H), 7.74 (s, 1H), 7.66 (s, 1H), 5.27-5.17 (m, 2H), 4.96 (d, J=5.9 Hz, 1H), 4.64 (dd, J=13.8, 9.9 Hz, 1H), 4.34-4.23 (m, 2H), 4.16 (s, 4H), 4.03 (dd, J=11.2, 7.2 Hz, 1H), 3.85 (s, 1H), 3.63 (t, J=5.9 Hz, 1H), 2.57-2.53 (m, 4H), 2.44 (s, 3H), 2.36 (s, 3H).

Synthesis of Compound 150 (Example 53)

Example 53 was synthesized according to the scheme below.

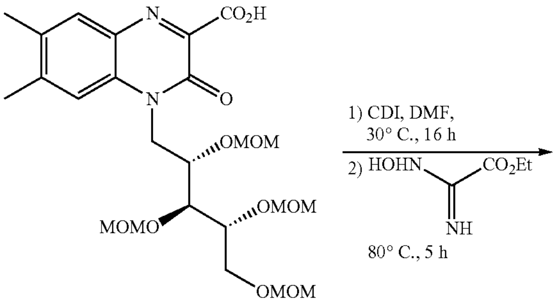

33

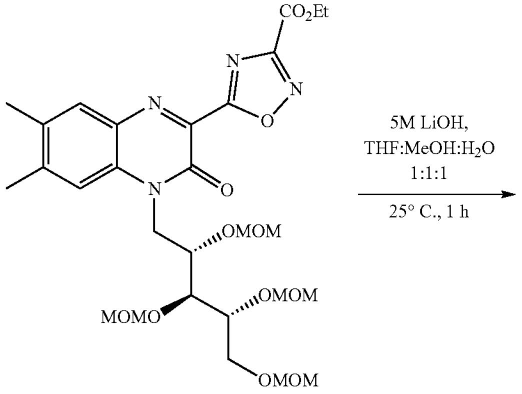

148

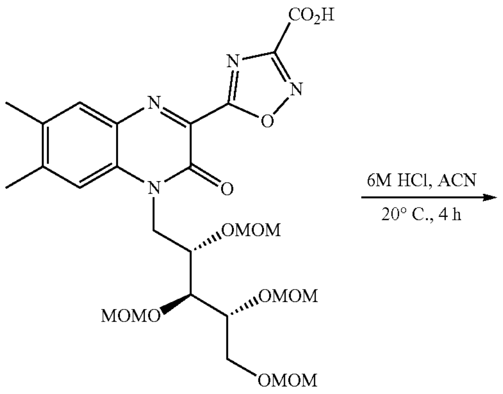

149

-continued

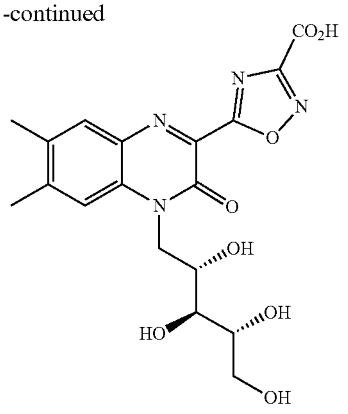

150
(Example 53)

Compound 148

To a 20° C. stirred solution of compound (33) (1.9 g, 3.24 mmol) in DMF (17 mL) was added CDI (1.34 g, 8.28 mmol). The resulting mixture was stirred for 16 h at 30° C. before ethyl (N-hydroxycarbamimidoyl) formate (1.35 g, 10.19 mmol) was added and the mixture was stirred for additional 5 h at 80° C. After concentrating under reduced pressure the residue was purified by reverse flash chromatography using the following conditions: Column, C18 silica gel; mobile phase, A: 0.05% FA in water, B: ACN, 0% to 100% gradient in 30 min; detector, UV 254 nm to afford compound (148) (1 g) as a yellow oil.

Compound 149

To a 0° C. stirred solution of compound (148) (200 mg, 0.32 mmol) in MeOH (2 mL) and THF (2 mL) was added LiOH (38.34 mg, 1.60 mmol) in $H_2O$ (2 mL) dropwise. The resulting mixture was stirred for 1 h at 25° C. before being neutralized to pH 7 with HCl (aq.) and extracted with EtOAc (3×10 mL). The combined organic layers were washed with water (3×10 mL), dried over anhydrous $Na_2SO_4$ and after filtration, the filtrate was concentrated under reduced pressure. The residue compound (149) was used directly in the next step without further purification.

LCMS: (ES, m/z): $[M+H]^+$=597.4

Compound 150 (Example 53)

To a 0° C. stirred solution of compound (149) (170 mg, 0.29 mmol) in ACN (4 mL) was added 6M HCl (4 mL) dropwise. The resulting mixture was stirred for 3 h at 20° C. before being concentrated under reduced pressure. The residue was purified by preparative HPLC using the following conditions: Column: Gemini-NX C18 AXAI Packed, 21.2×150 mm, 5 μm; Mobile Phase A: Water (0.1% FA), Mobile Phase B: ACN; Flow rate: 25 mL/min; Gradient: 10% B to 31% B in 11 min; 254/220 nm to afford compound (150) (Example 53) (80 mg) as a yellow solid.

LCMS: (ES, m/z): $[M+H]^+$=421.1

$^1$H NMR: (400 MHz, Methanol-d4) δ 7.81 (s, 1H), 7.75 (s, 1H), 4.54 (d, J=13.9 Hz, 1H), 4.36-4.29 (m, 1H), 3.88-3.79 (m, 3H), 3.68 (dq, J=18.2, 6.0 Hz, 2H), 2.52 (s, 3H), 2.43 (s, 3H), 2.34 (d, J=7.8 Hz, 1H).

Synthesis of Compound 153 (Example 54)

Example 54 was synthesized according to the scheme below.

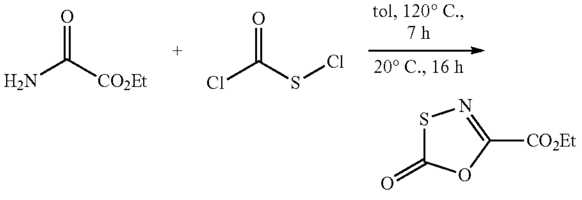

151

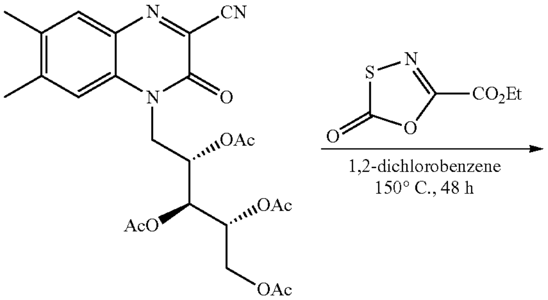

114

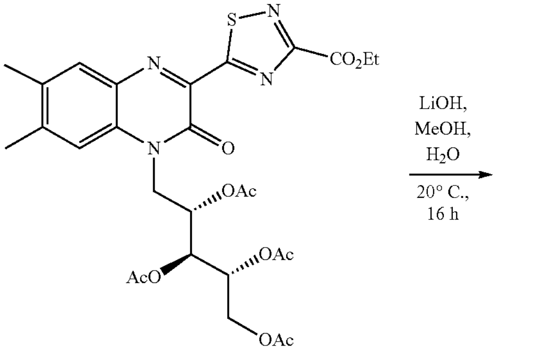

152

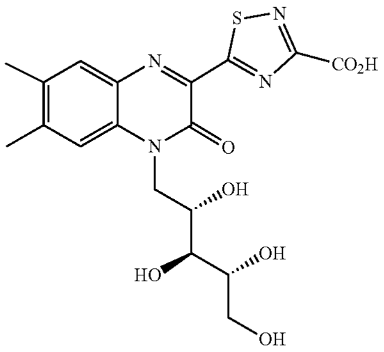

153
(Example 54)

Compound 151

To a 20° C. stirred solution of ethylcarbamoylformate (8.80 g, 75.15 mmol) in toluene under an argon atmosphere was added chloro (chlorosulfanyl) methanone (9841.99 mg, 75.15 mmol). The resulting mixture was stirred for 7 h at 120° C. then for 16 h at 20° C. before being concentrated under vacuum. The residue was purified by silica gel column chromatography, eluted with PE/EtOAc (5:1) to afford compound (151) (7.3 g) as a yellow oil.

Compound 152

To a 20° C. stirred mixture of compound (114) (1 g, 1.99 mmol) in 1,2-dichlorobenzene under an argon atmosphere was added compound (151) (1047.83 mg, 5.98 mmol). The resulting mixture was stirred for 2 days at 150° C. under an argon atmosphere. After cooling to 20° C. the mixture was concentrated under reduced pressure and the residue purified by reverse flash chromatography using the following conditions: Column, C18 silica gel; mobile phase, ACN in water, 0% to 100% gradient in 30 min; detector, UV 254 nm to afford compound (152) (70 mg) as a yellow solid.

Compound 153 (Example 54)

To a 0° C. stirred solution of compound (152) (240 mg, 0.38 mmol) in MeOH (5 mL) and $H_2O$ (2 mL) was added LiOH $H_2O$ (79.60 mg, 1.9 mmol) in portions. The resulting mixture was stirred for 16 h at 20° C. before being concentrated under reduced pressure. The residue was purified by preparative HPLC using the following conditions (Column: XBridge Shield RP18 OBD; 5 μm, 19×150 mm; Mobile Phase A: Water (0.05% FA), Mobile Phase B: ACN; Flow rate: 25 mL/min; Gradient: 10% B to 25% B in 8 min; 254/220 nm to afford compound (153) (Example 54) (54.5 mg) as a yellow solid.

LCMS: ESI-MS m/z=437.05 $[M+H]^+$ $^1$H-NMR: (300 MHz, DMSO-$d_6$): δ 7.90 (s, 1H), 7.75 (s, 1H), 5.06 (s, 1H), 4.99-4.70 (m, 3H), 4.53 (m, 2H), 4.23 (s, 1H), 3.66 (d, J=8.8 Hz, 3H), 3.47 (m, 2H), 2.45 (s, 3H), 2.39 (s, 3H).

Synthesis of Compound 158 (Example 55)

Example 55 was synthesized according to the scheme below.

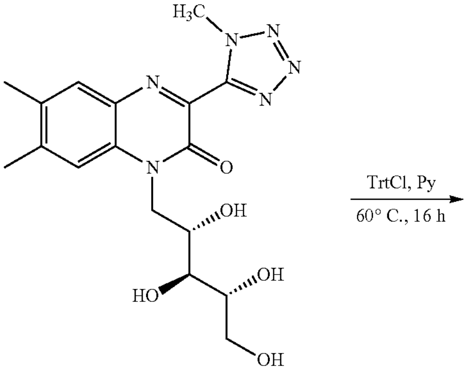

40

-continued

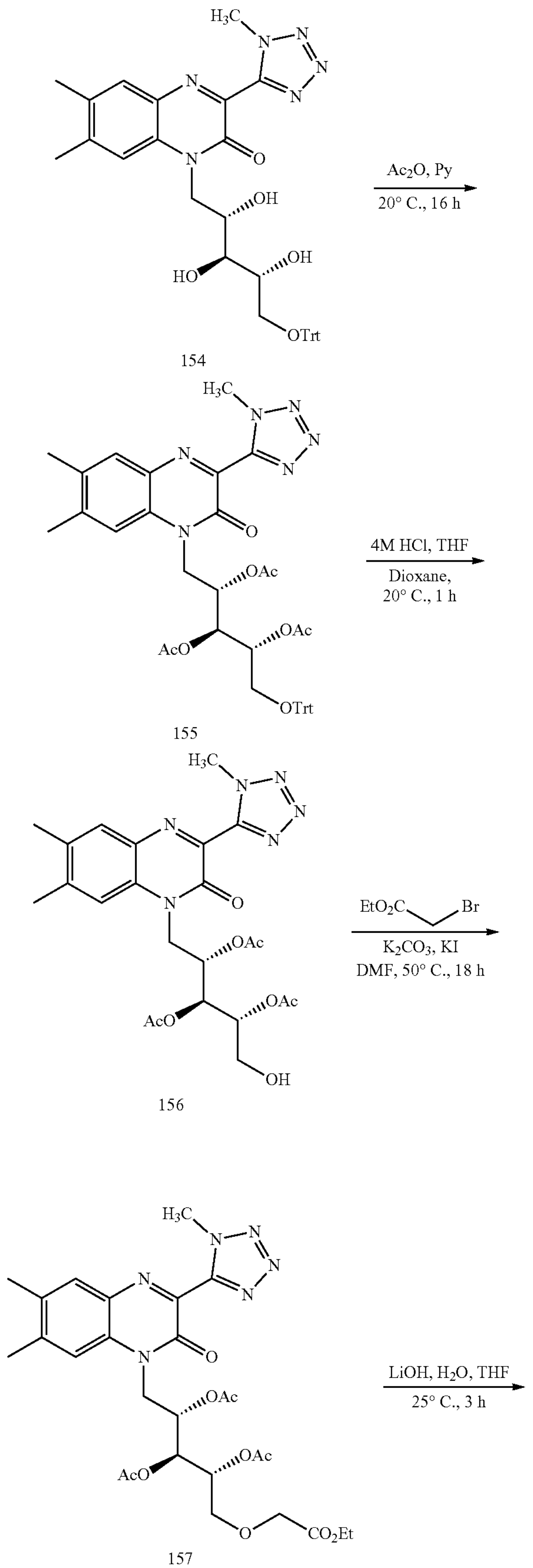

154

155

156

157

-continued

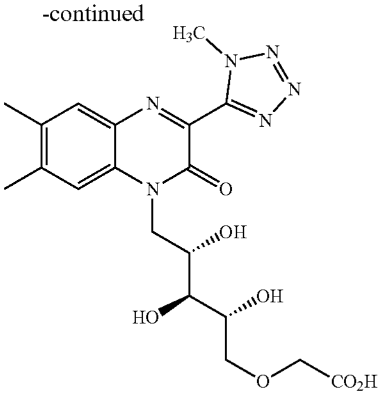

158
(Example 55)

Compound 154

To a 0° C. stirred solution of compound (40) (12 g, 30.74 mmol) in pyridine (200 mL) was added Trt-Cl (25.71 g, 92.23 mmol) in portions. The resulting mixture was stirred for 16 h at 70° C. before being concentrated under reduced pressure. The residue was diluted with water (0.6 L) and extracted with EtOAc (3×200 mL). The combined organic layers were washed with water (3×100 mL), dried over anhydrous $Na_2SO_4$ and after filtration, the filtrate concentrated under reduced pressure. The residue was purified by silica gel column chromatography, eluted with EtOAc to afford compound (154) (15 g) as a yellow solid.

LCMS: (ES, m/z): $[M+Na]^+$=655.4

Compound 155

To a 25° C. stirred solution of compound (154) (15 g, 23.71 mmol) in pyridine (100 mL) was added $Ac_2O$ (24.20 g, 237.05 mmol) dropwise. The resulting mixture was stirred for 16 h at 25° C. before being concentrated under reduced pressure. The residue was diluted with water (300 mL) and extracted with EtOAc (3×100 mL). The combined organic layers were washed with water (3×100 mL), dried over anhydrous $Na_2SO_4$. After filtration, the filtrate was concentrated under reduced pressure. The residue was purified by silica gel column chromatography, eluted with PE/EtOAc (1:1) to afford compound (155) (15 g) as a yellow solid.

LCMS: (ES, m/z): $[M+Na]^+$=781.3

Compound 156

To a 25° C. stirred mixture of compound (155) (15 g, 19.77 mmol) in THF was added 4M HCl in Dioxane (100 mL) dropwise. The resulting mixture was stirred for 1 h at 25° C. before being concentrated under reduced pressure. The residue was purified by reverse flash chromatography using the following conditions: Column, C18 silica gel; mobile phase, ACN: water (0.1% FA), 10% to 50% gradient in 30 min; detector, UV 254 nm. to afford compound (156) (9 g) as a yellow solid.

LCMS: (ES, m/z): $[M+H]^+$=517.3

Compound 157

To a 25° C. stirred mixture of compound (156) (200 mg, 0.39 mmol) and KI (39.85 mg, 0.24 mmol) and $K_2CO_3$ (107.03 mg, 0.77 mmol) in DMF (10 mL) was added ethyl bromoacetate (77.6 mg, 0.47 mmol) in DMF (1 mL) dropwise. The resulting mixture was stirred for 18 h at 50° C. before being cooled to 25° C., diluted with water (30 mL) and extracted with EtOAc (3×10 mL). The combined organic layers were washed with water (3×10 mL), dried over anhydrous $Na_2SO_4$ and after filtration, the filtrate concentrated under reduced pressure. The residue compound (157) was used directly in the next step without further purification.

LCMS: (ES, m/z): $[M+H]^+$=603.4

Compound 158 (Example 55)

To a 25° C. stirred solution of compound (157) (200 mg, 0.33 mmol) in THF (3 mL) was added lithium hydroxide (79.49 mg, 3.32 mmol) in water (3 mL) dropwise. The resulting mixture was stirred for 3 h at 25° C. before being acidified to pH 1 with conc. HCl and concentrated under reduced pressure. The residue was purified by reverse flash chromatography using the following conditions: Column, C18 silica gel; mobile phase, ACN: water (01% FA), 10% to 50% gradient in 10 min; detector, UV 254 nm to afford compound (158) (Example 55) (80 mg) as a yellow solid.

LCMS: (ES, m/z): $[M+H]^+$=449.3

$^1H$ NMR: (400 MHz, DMSO-$d_6$) δ 7.71 (d, J=19.4 Hz, 2H), 5.09-5.32 (m, 2H), 5.07 (s, 1H), 4.75 (dd, J=13.6, 9.9 Hz, 1H), 4.66-4.48 (m, 1H), 4.35 (s, 2H), 4.30 (dd, J=9.5, 4.9 Hz, 2H), 4.16 (s, 3H), 3.75-3.70 (m, 1H), 3.65-3.59 (m, 2H), 3.51 (dd, J=11.2, 5.7 Hz, 1H), 2.44 (s, 3H), 2.36 (s, 3H).

Synthesis of Compound 160 (Example 56)

Example 56 was synthesized according to the scheme below.

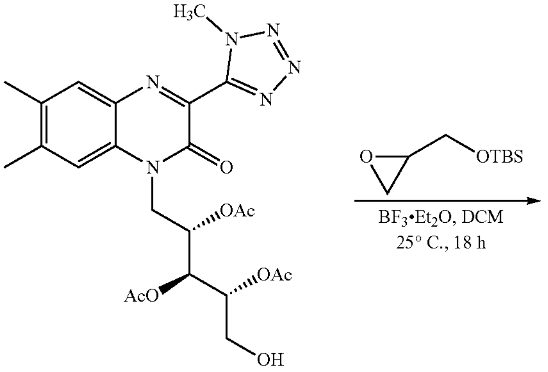

156

-continued

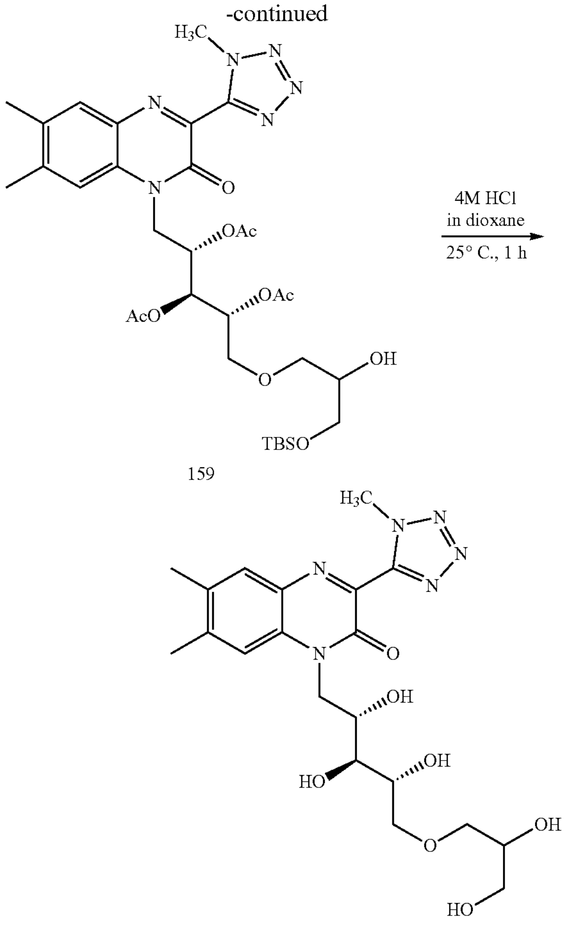

159

160
(Example 56)

Compound 159

A mixture of compound (156) (250 mg, 0.48 mmol), $BF_3 \cdot Et_2O$ (13.74 mg, 0.1 mmol) and tert-butyldimethyl (oxiran-2-ylmethoxy) silane (273.48 mg, 1.45 mmol) in DCM (5 mL) was stirred for 18 h at 25° C. before being concentrated under reduced pressure. The residue was diluted with water (20 mL) and extracted with EtOAc (3×10 mL). The combined organic layers were washed with water (3×10 mL), dried over anhydrous $Na_2SO_4$ and after filtration, the filtrate concentrated under reduced pressure. The residue was purified by reverse flash chromatography using the following conditions: Column, $C_{18}$ silica gel; mobile phase, MeOH: water, 10% to 50% gradient in 10 min; detector, UV 254 nm to afford compound (159) (250 mg) as a yellow solid.

LCMS: (ES, m/z): $[M+H]^+$=705.5

Compound 160 (Example 56)

To a 0° C. stirred mixture of compound (160) (250 mg, 0.36 mmol) in MeOH was added 4M HCl (gas) in 1,4-dioxane (5 mL, 0.14 mmol) dropwise. The resulting mixture was stirred for 1 h at 25° C. before being concentrated under reduced pressure. The residue was purified by reverse flash chromatography using the following conditions: Column, C18 silica gel; mobile phase, MeOH: water, 10% to 50% gradient in 10 min; detector, UV 254 nm to afford compound (160) (Example 56) (70 mg) as a yellow solid.

LCMS: (ES, m/z): $[M+H]^+$=465.2 1H NMR: (300 MHz, Methanol-d4) δ 7.87 (d, J=3.8 Hz, 2H), 5.21-4.92 (m, 3H), 4.56 (dd, J=14.0, 2.8 Hz, 1H), 4.51 (s, 3H), 4.34 (d, J=9.4 Hz, 1H), 4.07 (dq, J=8.5, 4.9, 4.2 Hz, 1H), 3.88-3.78 (m, 3H), 3.74-3.66 (m, 1H), 3.60 (dd, J=11.5, 4.5 Hz, 1H), 3.50 (dd, J=11.4, 5.9 Hz, 1H), 2.58 (s, 3H), 2.46 (d, J=0.9 Hz, 3H).

Synthesis of Compound 161 (Example 57)

Example 57 was synthesized according to the scheme below.

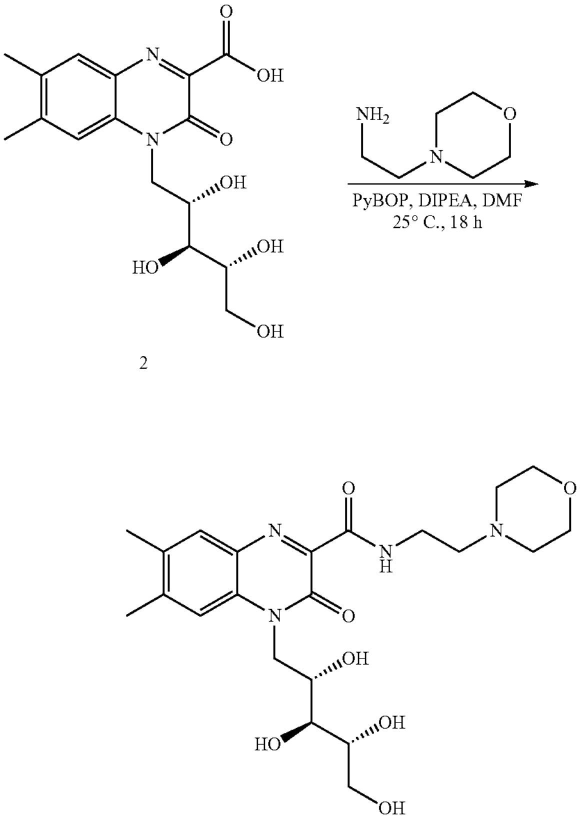

2

161
(Example 57)

Compound 161 (Example 57)

To a 0° C. stirred mixture of compound (2) (300 mg, 0.85 mmol), DIPEA (1100.43 mg, 8.51 mmol) and N-aminoethylmorpholine (221.70 mg, 1.70 mmol) in DMF (10 mL) was added PyBOP (886.17 mg, 1.70 mmol) in portions. The resulting mixture was stirred for 18 h at 25° C. before being concentrated under reduced pressure. The residue was purified by reverse flash chromatography using the following conditions: Column, C18 silica gel; mobile phase, ACN: water (0.1% FA), 10% to 25% gradient in 25 min; detector, UV 254 nm to afford compound (161) (Example 57) (200 mg) as a yellow solid.

LCMS: (ES, m/z): $[M+H]^+$=465.2

$^1$H NMR: (400 MHz, Methanol-$d_4$) δ 8.23 (s, 1H), 7.80 (s, 1H), 7.71 (s, 1H), 4.78-4.82 (m, 1H), 4.50 (dd, J=14.1, 2.7 Hz, 1H), 4.30 (d, J=8.5 Hz, 1H), 3.89-3.75 (m, 6H), 3.72 (t, J=6.2 Hz, 3H), 2.87 (t, J=6.2 Hz, 2H), 2.80 (s, 3H), 2.50 (s, 3H), 2.42 (s, 3H).

Synthesis of Compound 162 (Example 58)

Example 58 was synthesized according to the scheme below.

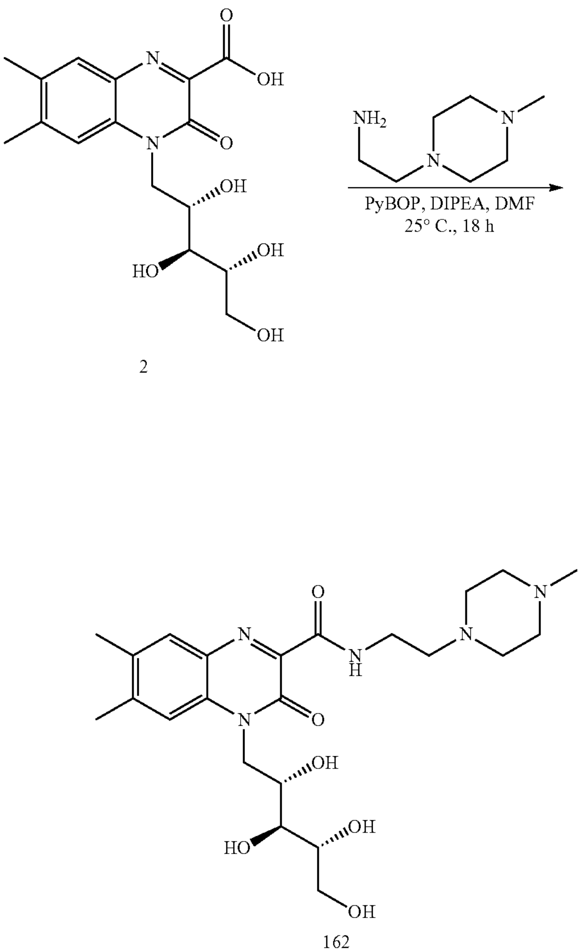

2

162
(Example 58)

Compound 162 (Example 58)

To a 0° C. stirred mixture of compound (2) (300 mg, 0.85 mmol) and DIPEA (1100.43 mg, 8.51 mmol) and 2-(4-methylpiperazin-1-yl) ethanamine (365.87 mg, 2.55 mmol) in DMF (10 mL) was added PyBOP (886.17 mg, 1.70 mmol) in portions. The resulting mixture was stirred for 18 h at 25° C. before being concentrated under reduced pressure. The residue was purified by reverse flash chromatography using the following conditions: Column, C18 silica gel; mobile phase, ACN: water (0.1% FA), 10% to 25% gradient in 25 min; detector, UV 254 nm to afford compound (162) (Example 58) (180 mg) as a yellow solid.

LCMS: (ES, m/z): $[M+H]^+$=478.2

$^1$H NMR: (300 MHz, Methanol-d4) δ 8.46 (s, 1H), 7.77 (d, J=27.9 Hz, 2H), 4.87-4.76 (m, 2H), 4.51 (dd, J=14.1, 2.7 Hz, 1H), 4.34-4.26 (m, 1H), 3.90-3.76 (m, 3H), 3.69 (dt, J=17.5, 6.3 Hz, 3H), 3.16 (s, 4H), 2.77 (d, J=2.5 Hz, 8H), 2.51 (s, 3H), 2.42 (s, 3H).

Synthesis of Compound 163 (Example 59)

Example 59 was synthesized according to the scheme below.

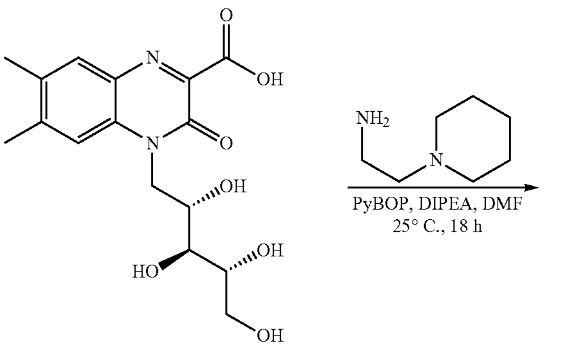

2

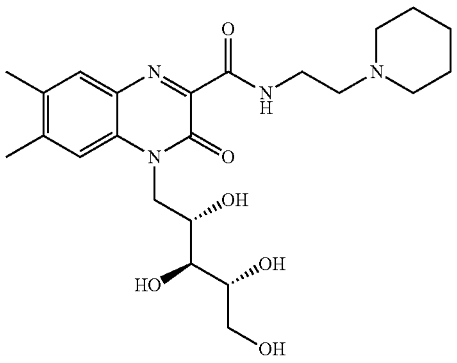

163
(Example 59)

Compound 163 (Example 59)

To a 0° C. stirred mixture of compound (2) (300 mg, 0.85 mmol), DIPEA (1100.43 mg, 8.51 mmol) and 2-(piperidin-1-yl) ethanamine (327.51 mg, 2.55 mmol) in DMF (10 mL) was added PyBOP (886.17 mg, 1.7 mmol) in portions. The resulting mixture was stirred for 18 h at 25° C. before being concentrated under reduced pressure. The residue was purified by reverse flash chromatography using the following conditions: Column, C18 silica gel; mobile phase, ACN: water (0.1% FA), 10% to 25% gradient in 25 min; detector, UV 254 nm to afford compound (163) (Example 59) (150 mg) as a yellow solid.

LCMS: (ES, m/z): $[M+H]^+$=463.3

$^1H$ NMR: (300 MHz, Methanol-d4) δ 8.49 (s, 1H), 7.69 (d, J=13.6 Hz, 2H), 4.83-4.75 (m, 1H), 4.46 (dd, J=14.0, 2.7 Hz, 1H), 4.34-4.26 (m, 1H), 3.90-3.77 (m, 5H), 3.75-3.68 (m, 1H), 3.38-3.34 (m, 2H), 3.31 (s, 4H), 2.49 (s, 3H), 2.40 (s, 3H), 1.91 (p, J=5.7 Hz, 4H), 1.71 (d, J=6.3 Hz, 2H).

Synthesis of Compound 165 (Example 60)

Example 60 was synthesized according to the scheme below.

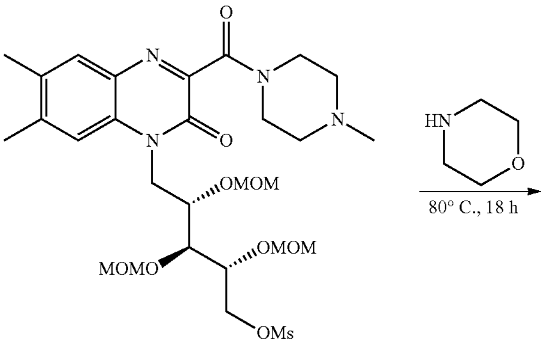

81

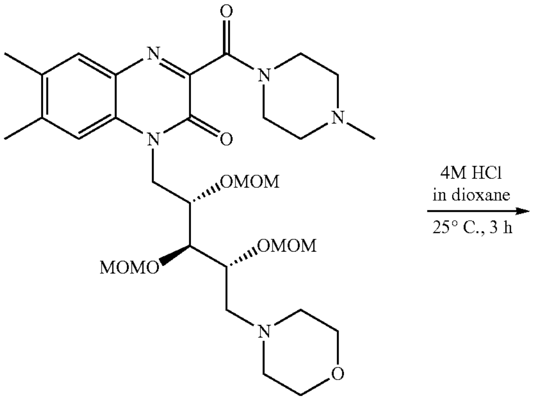

164

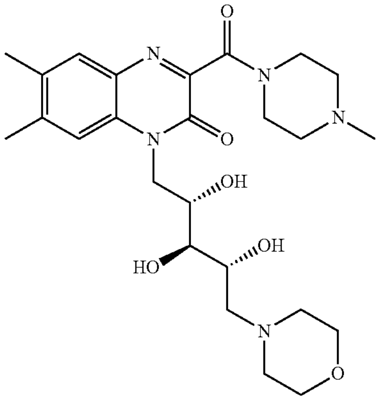

165
(Example 60)

Compound 164

Compound (81) (500 mg, 0.78 mmol) in THF (2 mL) and morpholine (2 mL) were stirred for 16 h at 80° C. before being concentrated under reduced pressure. The residue was purified by reverse flash chromatography using the following conditions: Column, C18 silica gel; mobile phase, ACN: water (0.1% FA), 10% to 50% gradient in 30 min; detector, UV 254 nm to afford compound (164) (300 mg) as a yellow oil.

LCMS: (ES, m/z): $[M+H]^+$=636.6

Compound 165 (Example 60)

To a 0° C. stirred solution of compound (164) (200 mg, 0.32 mmol) in MeOH (1 mL) was added 4M HCl (gas) in 1,4-dioxane (4 mL) dropwise. The resulting mixture was stirred for 3 h at 25° C. before being concentrated under vacuum. The residue was purified by reverse flash chromatography using the following conditions: Column, C18 silica gel; mobile phase, ACN: water (0.1% $NH_4HCO_3$), 10% to 50% gradient in 20 min; detector, UV 254 nm to afford compound (165) (Example 60) (90 mg) as a yellow solid.

LCMS: (ES, m/z): $[M+H]^+$=504.5

$^1$H NMR: (300 MHz, Methanol-d4) δ 7.66 (d, J=9.5 Hz, 2H), 4.71 (dd, J=14.0, 9.4 Hz, 1H), 4.49 (dd, J=14.1, 3.0 Hz, 1H), 4.23 (ddd, J=9.1, 5.2, 2.9 Hz, 1H), 3.99 (td, J=6.7, 4.9 Hz, 1H), 3.83 (q, J=5.0 Hz, 2H), 3.74 (dt, J=9.4, 5.2 Hz, 5H), 3.45 (t, J=5.0 Hz, 2H), 2.74 (dd, J=12.9, 4.9 Hz, 1H), 2.59 (dq, J=12.7, 6.7 Hz, 7H), 2.49 (s, 5H), 2.38 (d, J=13.1 Hz, 6H).

Synthesis of Compound 167 (Example 61)

Example 61 was synthesized according to the scheme below.

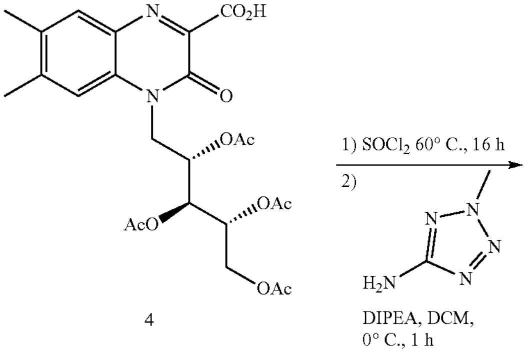

4

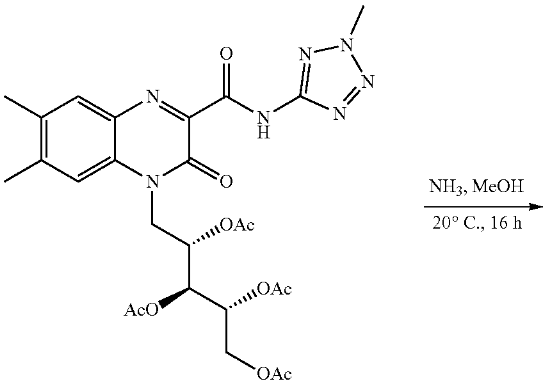

166

-continued

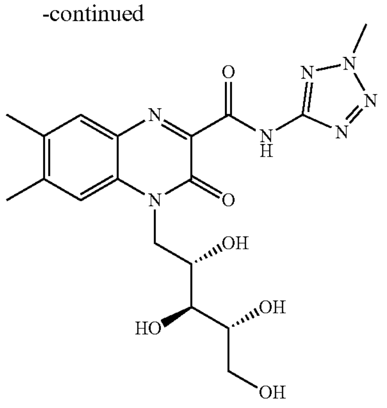

167
(Example 61)

Compound 166

Compound (4) (1 g, 1.92 mmol) in $SOCl_2$ (10 mL) was stirred for 5 h at 50° C. before being concentrated under reduced pressure. The residue was diluted with DCM (10 mL) and added dropwise to a 0° C. stirred solution of 2-methyl-1, 2, 3, 4-tetrazol-5-amine (190.39 mg, 1.92 mmol) and DIPEA (744.93 mg, 5.76 mmol) in DCM (30 mL). The mixture was stirred for 1 h at room temperature before being washed with water (3×100 mL), dried over anhydrous $Na_2SO_4$ and after filtration, the filtrate concentrated under reduced pressure. The residue was purified by reverse flash chromatography using the following conditions: Column, C18 silica gel; mobile phase A: 0.1% FA in water; mobile phase B: ACN, 0% to 70% gradient in 30 min; detector, UV 254 nm to afford compound (166) (800 mg) as a yellow solid.

ESI-MS m/z=602.2 $[M+H]^+$

Compound 167 (Example 61)

A solution of compound (166) (400 mg, 0.67 mmol) and ammonium hydroxide (2 mL) in methanol (5 mL) was stirred for 16 h at room temperature. The resulting mixture was washed with MeOH (3×5 mL) and ACN (3×5 mL) and the resulting solid dried in an oven to afford compound (167) (Example 61) (185.0 mg) as a yellow solid.

LCMS: ESI-MS m/z=434.15 $[M+H]^+$ $^1$H: (400 MHz, DMSO-$d_6$): δ 11.25 (s, 1H), 7.73-7.68 (d, 1H), 5.05-4.99 (m, 1H), 4.87 (d, J=3.6 Hz, 1H), 4.73 (d, J=6.0 Hz, 1H), 4.66 (t, J=12.0 Hz, 1H), 4.50 (t, J=5.4 Hz, 1H), 4.37 (s, 2H), 4.29 (d, J=13.7 Hz, 1H), 4.20-4.00 (m, 2H), 3.65-3.60 (m, 3H), 3.49-3.42 (m, 1H), 2.38 (d, J=28.5 Hz, 6H).

Synthesis of Compound 170 (Example 62)

Example 62 was synthesized according to the scheme below.

-continued

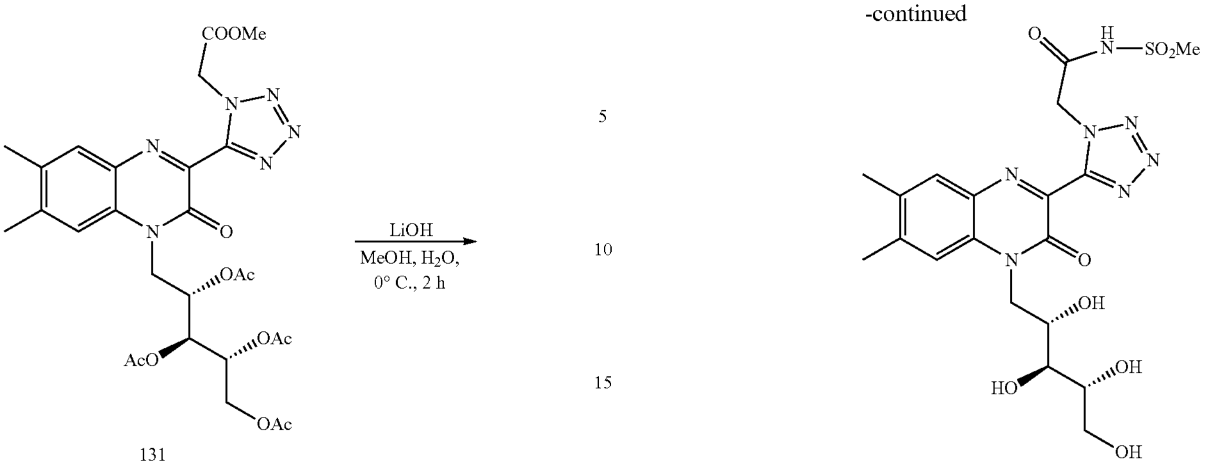

131

170
(Example 62)

Compound 168

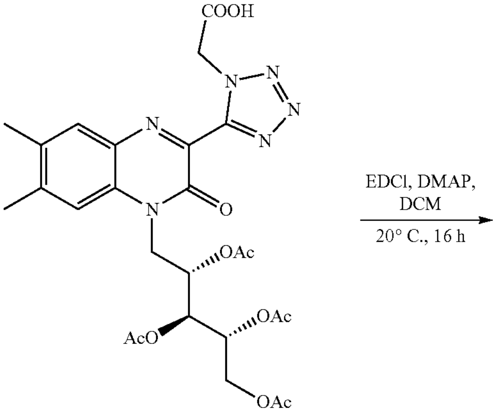

168

To a 0° C. stirred solution of compound (131) (500 mg, 0.81 mmol) in THF (5 mL) was added a solution of LiOH (21.36 mg, 0.89 mmol) in water dropwise. The resulting mixture was stirred for 1 h at 0° C. before being concentrated under reduced pressure. The residue was purified by reverse flash chromatography using the following conditions: Column, C18 silica gel; mobile phase A: 0.1% TFA in water, mobile phase B: ACN; 0% to 60% gradient in 30 min; detector, UV 254 nm to afford compound (168) (200 mg) as a yellow solid.

Compound 169

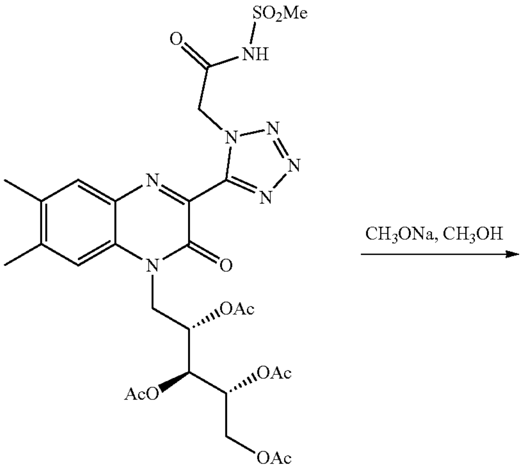

169

To a 0° C. stirred mixture of compound (168) (180 mg, 0.30 mmol), methanesulfonamide (56.80 mg, 0.60 mmol) and DMAP (73.00 mg, 0.60 mmol) in DCE (5 mL) was added EDCI (115.00 mg, 0.60 mmol) in portions. The resulting mixture was stirred for 16 h at 20° C. before being diluted with DCM (50 mL) and washed with water (3×50 mL). The organic layer was washed with brine (1×100 mL), dried over anhydrous $Na_2SO_4$ and after filtration, the filtrate concentrated under reduced pressure. The residue compound (169) was used directly in the next step without further purification.

ESI-MS m/z=680.2 $[M+H]^+$

Compound 170 (Example 62)

To a 0° C. stirred solution of compound (169) (130 mg, 0.19 mmol) in MeOH (3 mL) was added MeONa (10.33 mg, 0.19 mmol) in portions. The resulting mixture was stirred for 2 h at 0-20° C. before being concentrated under reduced pressure. The residue was purified by reverse flash chromatography using the following conditions: Column, C18 silica gel; mobile phase A: 0.1% FA in water, mobile phase B: ACN; 0% to 30% gradient in 30 min; detector, UV 254 nm to afford compound (170) (Example 62) (55.6 mg) as a yellow solid.

ESI-MS m/z=512.15 $[M+H]^+$ $^1H$-NMR: (300 MHz, MeOD-$d_4$): δ 7.85 (s, 1H), 7.71 (s, 1H), 5.64 (s, 2H), 4.60-4.50 (d, 1H), 4.35-4.29 (m, 1H), 3.91-3.76 (m, 3H), 3.70 (dd, J=12.1, 6.4 Hz, 1H), 3.25 (m, 1H), 3.08 (s, 3H), 2.50 (s, 3H), 2.42 (s, 3H).

Synthesis of Compound 171 (Example 63)

Example 63 was synthesized according to the scheme below.

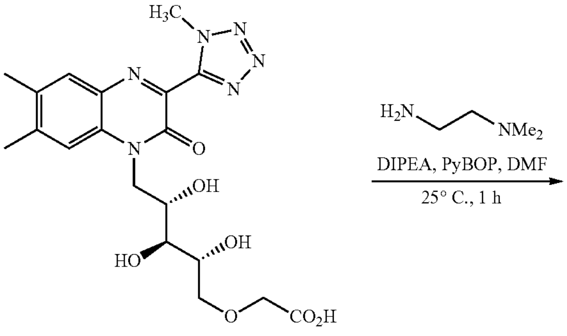

158

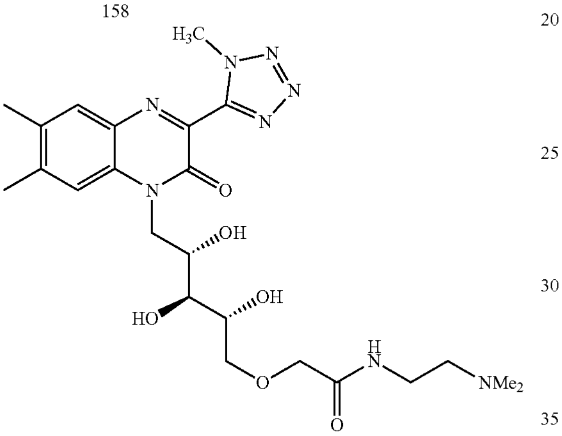

171
(Example 63)

Compound 171 (Example 63)

To a 0° C. stirred solution of compound (158) (120 mg, 0.27 mmol), (2-aminoethyl)dimethylamine (47.18 mg, 0.54 mmol) and DIPEA (172.93 mg, 1.34 mmol) in DMF (5 mL) was added PyBOP (278.51 mg, 0.54 mmol) in portions. The resulting mixture was stirred for 1 h at 25° C. before being concentrated under reduced pressure. The residue was purified by reverse flash chromatography using the following conditions: Column: Gemini-NX C18 AXAI Packed, 21.2×150 mm, 5 μm; Mobile Phase A: Water (0.1% FA), Mobile Phase B: ACN; Flow rate: 25 mL/min; Gradient: 8% B to 17% B in 10 min; 254/220 nm to afford compound (171) (Example 63) (50 mg) as a yellow solid.

LCMS: (ES, m/z): $[M+H]^+=519.3$ $^1H$ NMR: (400 MHz, Methanol-d4) δ 8.51 (s, 1H), 7.83 (s, 1H), 7.71 (s, 1H), 5.18 (dd, J=14.1, 10.4 Hz, 1H), 4.55 (dt, J=10.3, 3.2 Hz, 1H), 4.43 (d, J=3.0 Hz, 1H), 4.39 (s, 4H), 4.27-4.20 (m, 1H), 3.92-3.85 (m, 1H), 3.85-3.79 (m, 2H), 3.75 (dd, J=11.6, 4.6 Hz, 1H), 3.67 (q, J=5.6 Hz, 2H), 3.26 (d, J=6.1 Hz, 1H), 2.85 (s, 5H), 2.78 (s, 1H), 2.53 (s, 3H), 2.44 (s, 3H).

Synthesis of Compound 173 (Example 64)

Example 64 was synthesized according to the scheme below.

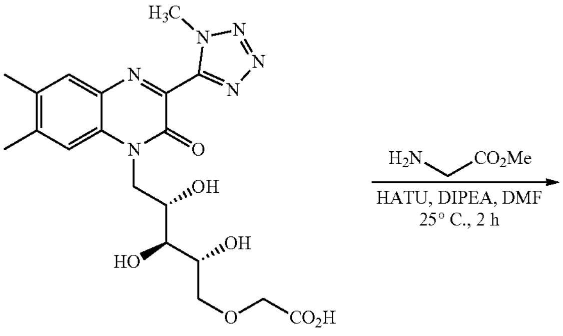

158

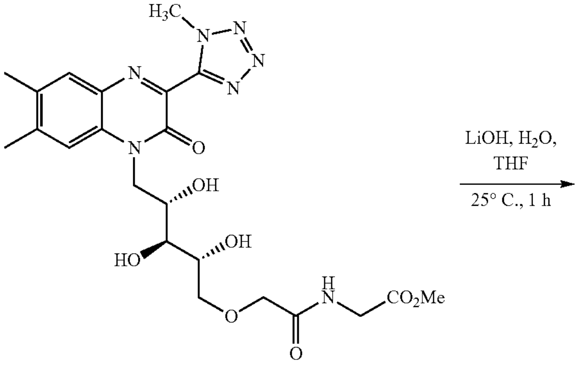

172

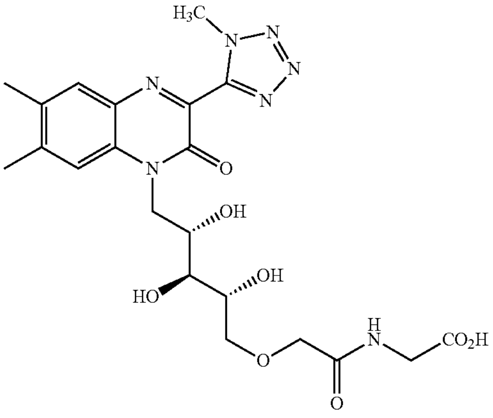

173
(Example 64)

Compound 172

To a 0° C. stirred solution of compound (158) (2 g, 4.46 mmol) and methyl 2-aminoacetate (476.83 mg, 5.35 mmol) and DIPEA (1729.25 mg, 13.38 mmol) in DMF was added HATU (3391.61 mg, 8.92 mmol) in portions. The resulting mixture was stirred for 2 h at 25° C. before being diluted with water (200 mL) and extracted with EtOAc (3×100 mL). The combined organic layers were washed with water (3×200 mL), dried over anhydrous $Na_2SO_4$ and after filtration, the filtrate concentrated under reduced pressure. The residue was purified by reverse flash chromatography using the following conditions: Column, C18 silica gel; mobile phase, MeOH: water, 10% to 50% gradient in 10 min; detector, UV 254 nm to afford compound (172) (2 g) as a yellow solid.

LCMS: (ES, m/z): $[M+H]^+=520.2$

Compound 173 (Example 64)

To a 0° C. stirred solution of compound (172) (200 mg, 0.39 mmol) in THF (5 mL) was added LiOH (32.31 mg, 0.77 mmol) in water (1 mL) dropwise. The resulting mixture was stirred for 1 h at 25° C. before being concentrated under reduced pressure. The residue was purified by reverse flash chromatography using the following conditions: Column: Welch XB-C18, 21.2×250 mm, 5 μm; Mobile Phase A: Water (0.05% FA), Mobile Phase B: ACN; Flow rate: 25 mL/min; Gradient: 18% B to 33% B in 10 min; 254 nm to afford compound (173) (Example 64) (70 mg) as a yellow solid.

LCMS: (ES, m/z): $[M+H]^+$=506.3

$^1H$ NMR: (400 MHz, Methanol-d4) δ 7.77 (d, J=8.0 Hz, 2H), 4.88-4.84 (m, 1H), 4.60 (dd, J=14.1, 2.8 Hz, 1H), 4.51-4.45 (m, 1H), 4.38 (s, 2H), 4.32 (s, 3H), 4.00 (d, J=9.4 Hz, 3H), 3.85-3.75 (m, 3H), 2.52 (s, 3H), 2.43 (s, 3H).

Synthesis of Compound 175 (Example 65)

Example 65 was synthesized according to the scheme below.

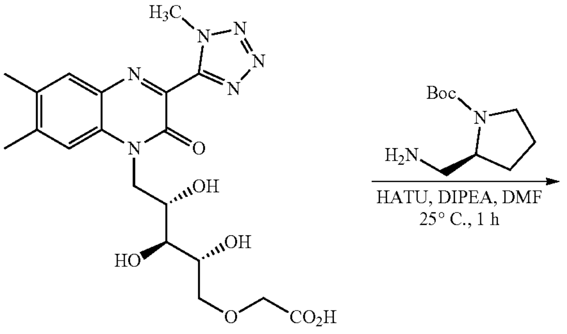

158

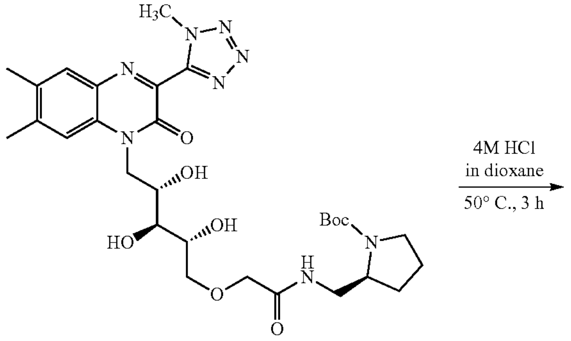

174

-continued

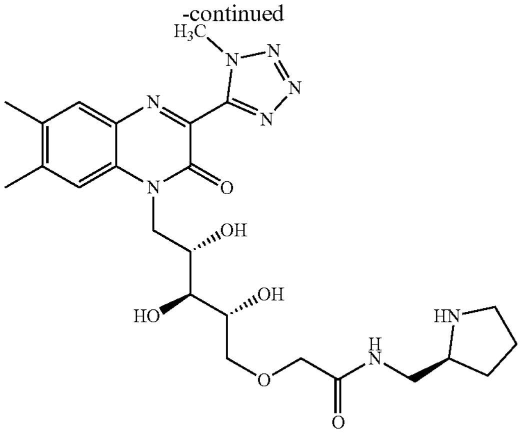

175
(Example 65)

Compound 174

To a room temperature stirred mixture of compound (158) (150 mg, 0.34 mmol) and tert-butyl(2S)-2-(aminomethyl) pyrrolidine-1-carboxylate (80.39 mg, 0.40 mmol) in DMF (5 mL) was added DIPEA (129.69 mg, 1.0 mmol) and HATU (254.37 mg, 0.67 mmol) in portions. The resulting mixture was stirred for 1 h at room temperature before being concentrated under reduced pressure. The residue was purified by reverse flash chromatography using the following conditions: Column, C18 silica gel; mobile phase, MeOH: water, 10% to 50% gradient in 10 min; detector, UV 254 nm to afford compound (174) (130 mg) as a yellow solid LCMS: (ES, m/z): $[M+H]^+$=631.2

Compound 175 (Example 65)

4M HCl in dioxane (3 mL) was added dropwise to a 0° C. stirred solution of compound (174) (130 mg, 0.21 mmol) in dioxane. The resulting mixture was stirred for 3 h at 50° C. before being concentrated under reduced pressure. The residue was purified by reverse flash chromatography using the following conditions: Column, C18 silica gel; mobile phase, MeOH: water, 10% to 50% gradient in 10 min; detector, UV 254 nm to afford compound (175) (Example 65) (70 mg) as a yellow solid.

LCMS: (ES, m/z): $[M+H]^+$=531.3

$^1H$ NMR: (400 MHz, Methanol-d4) δ 8.53 (s, 1H), 7.83 (s, 1H), 7.64 (s, 1H), 5.24 (dd, J=14.0, 10.5 Hz, 1H), 4.54 (dt, J=10.6, 3.3 Hz, 1H), 4.48 (s, 3H), 4.43 (s, 1H), 4.37-4.29 (m, 2H), 4.18 (d, J=15.7 Hz, 1H), 3.86-3.71 (m, 7H), 3.51-3.38 (m, 2H), 3.28 (ddd, J=11.4, 7.3, 4.4 Hz, 1H), 2.52 (s, 3H), 2.43 (s, 3H), 2.23 (tdd, J=13.0, 6.8, 3.8 Hz, 2H), 2.14-2.03 (m, 1H), 1.79 (dq, J=12.8, 9.2, 8.5 Hz, 1H).

Synthesis of Compound 177 (Example 66)

Example 66 was synthesized according to the scheme below.

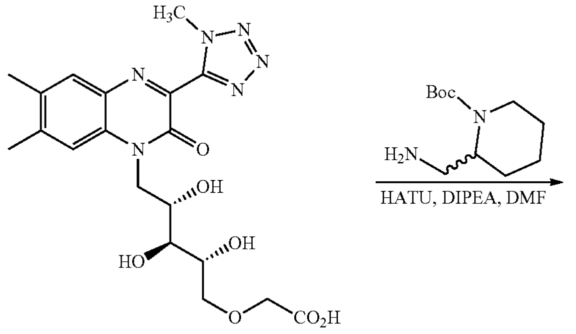

158

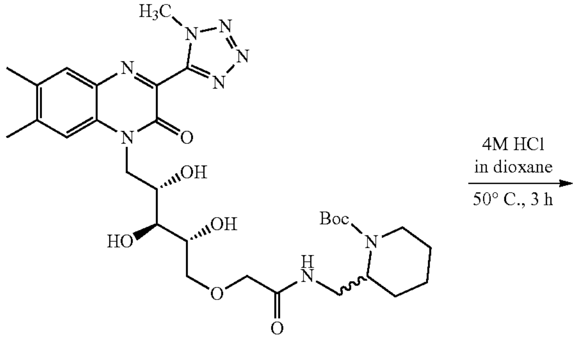

176

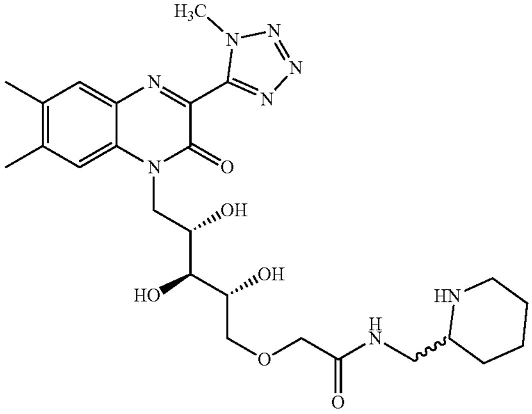

177
(Example 66)

Compound 176

To a room temperature stirred mixture of compound (158) (200 mg, 0.45 mmol) and tert-butyl 2-(aminomethyl) piperidine-1-carboxylate (114.70 mg, 0.54 mmol) in DMF (5 mL) was added DIPEA (172.93 mg, 1.34 mmol) and HATU (339.16 mg, 0.89 mmol) in portions. The resulting mixture was stirred for 1 h at room temperature before being concentrated under reduced pressure. The residue was purified by reverse flash chromatography using the following conditions: Column, C18 silica gel; mobile phase, MeOH: water, 10% to 50% gradient in 10 min; detector, UV 254 nm to afford compound (176) (170 mg) as a yellow solid.

LCMS: (ES, m/z): $[M+H]^+$=645.3

Compound 177 (Example 66)

4M HCl in dioxane (3 mL) was added dropwise to a 0° C. stirred solution of compound (176) (130 mg, 0.206 mmol, 1.00 equiv). The resulting mixture was stirred for 3 h at 50° C. before being concentrated under reduced pressure. The residue was purified by reverse flash chromatography using the following conditions: Column, C18 silica gel; mobile phase, MeOH: water, 10% to 50% gradient in 10 min; detector, UV 254 nm. to afford compound (177) (Example 66) (70 mg) as a yellow solid.

LCMS: (ES, m/z): $[M+H]^+$=531.3

$^1$H NMR: (400 MHz, Methanol-d4) δ 8.55 (s, 1H), 7.86 (d, J=4.9 Hz, 1H), 7.67 (d, J=9.5 Hz, 1H), 5.33 (ddd, J=42.4, 14.1, 10.6 Hz, 1H), 4.58 (d, J=10.9 Hz, 2H), 4.53-4.43 (m, 4H), 4.43-4.31 (m, 1H), 4.17 (dd, J=15.7, 5.7 Hz, 1H), 3.89-3.80 (m, 3H), 3.75 (dd, J=11.5, 4.1 Hz, 1H), 3.59-3.53 (m, 1H), 3.46-3.37 (m, 2H), 3.05 (dtd, J=33.8, 12.6, 4.3 Hz, 1H), 2.54 (s, 3H), 2.45 (s, 3H), 2.11-1.81 (m, 4H), 1.64 (q, J=11.3, 10.9 Hz, 2H).

Synthesis of Compound 180 (Example 67)

Example 67 was synthesized according to the scheme below.

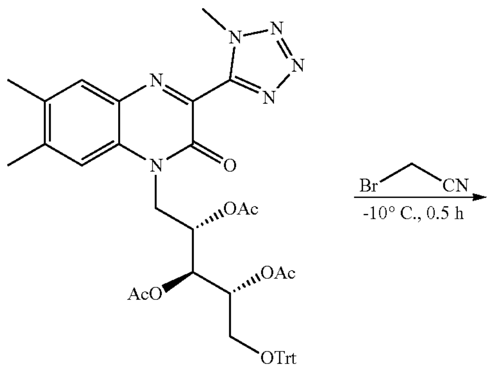

156

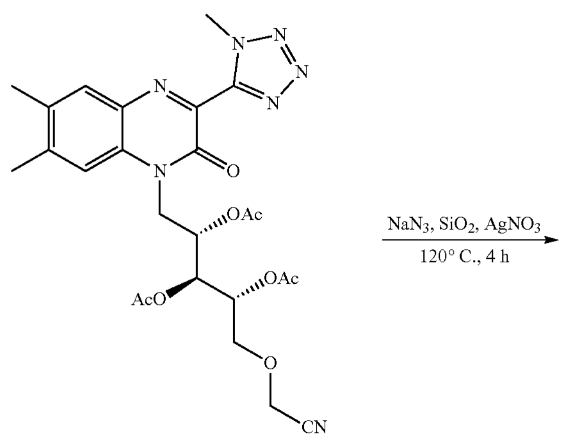

178

-continued

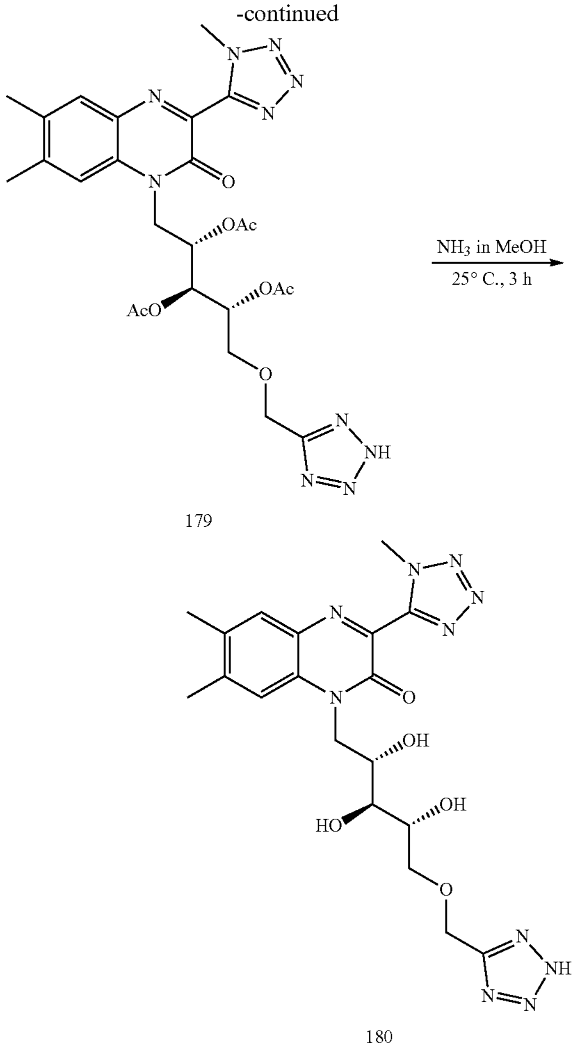

179

180
(Example 67)

Compound 178

A mixture of compound (156) (1 g, 1.94 mmol) and NaH (92.92 mg, 3.87 mmol) in ACN (15 mL) was stirred for 30 min at −10° C. under an argon atmosphere before 2-bromoacetonitrile (464.46 mg, 3.87 mmol) in ACN (5 mL) was added dropwise. The resulting mixture was stirred for 2 h at −10° C. under an argon atmosphere. The mixture was quenched by the addition of sat. $NH_4Cl$ (aq) (100 mL) at −10° C. and extracted with EtOAc (3×30 mL). The combined organic layers were washed with water (3×20 mL), dried over anhydrous $Na_2SO_4$ and after filtration, the filtrate concentrated under reduced pressure. The residue was purified by reverse flash chromatography using the following conditions: Column, C18 silica gel; mobile phase, MeOH: water, 10% to 50% gradient in 10 min; detector, UV 254 nm to afford compound (178) (600 mg) as a yellow solid.

LCMS: (ES, m/z): $[M+H]^+$=556.4

Compound 179

To a stirred mixture of $AgNO_3$ (36.69 mg, 0.22 mmol) and $NaN_3$ (46.81 mg, 0.72 mmol) in DMF (5 mL) was added compound (178) (200 mg, 0.36 mmol) in DMF (1 mL) and $SiO_2$ (20 mg, 0.33 mmol). The resulting mixture was stirred for 4 h at 120° C. before being acidified to pH 6 with 1M HCl. The resulting mixture was diluted with water (50 mL) and extracted with EtOAc (3×20 mL). The combined organic layers were washed with water (3×50 mL), dried over anhydrous $Na_2SO_4$ and after filtration, the filtrate concentrated under reduced pressure. The residue was purified by reverse flash chromatography using the following conditions: Column, C18 silica gel; mobile phase, ACN: water, 10% to 50% gradient in 10 min; detector, UV 254 nm to afford compound (179) (150 mg) as a yellow solid.

Compound 180 (Example 67)

To a 25° C. stirred solution of compound (179) (200 mg, 0.34 mmol) in MeOH was added 7M $NH_3$ (g) in MeOH (20 mL) dropwise. The resulting mixture was stirred for 3 h at 25° C. before being concentrated under reduced pressure. The residue was purified by reverse flash chromatography using the following conditions: Column, C18 silica gel; mobile phase, ACN: water, 10% to 50% gradient in 10 min; detector, UV 254 nm to afford compound (180) (Example 67) (80 mg) as a yellow solid.

LCMS: (ES, m/z): $[M+H]^+$=473.2

$^1H$ NMR: (400 MHz, Methanol-d4) δ 7.78 (s, 1H), 7.71 (s, 1H), 5.26 (d, J=4.6 Hz, 2H), 4.96-4.92 (m, 1H), 4.53 (dt, J=10.4, 3.1 Hz, 2H), 4.33 (d, J=2.7 Hz, 3H), 3.95 (dtd, J=10.3, 7.1, 3.6 Hz, 2H), 3.82-3.73 (m, 2H), 2.49 (d, J=3.4 Hz, 3H), 2.43 (s, 3H).

Synthesis of Compound 181 (Example 68)

Example 68 was synthesized according to the scheme below.

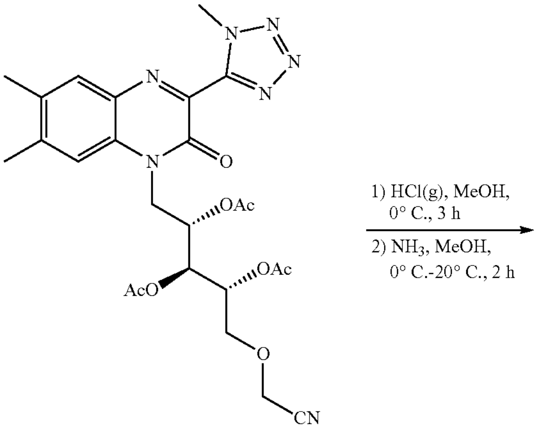

178

-continued

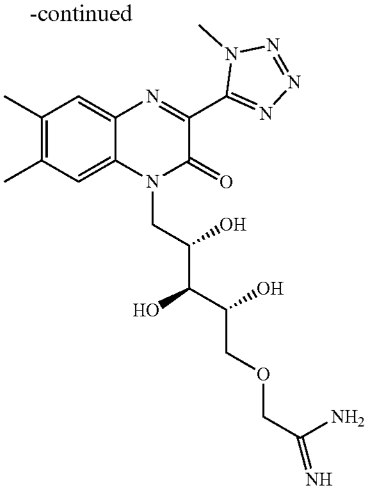

181
(Example 68)

Compound 181 (Example 68)

A solution of compound (178) (300 mg, 0.54 mmol) in MeOH was treated with HCl (g) in MeOH (5 mL) for 3 h at 0° C. under a nitrogen atmosphere followed by the dropwise addition at 0° C. of $NH_3$ (g) in MeOH (5 mL). The resulting mixture was stirred for 2 h at 20° C. before being concentrated under reduced pressure. The residue was purified by reverse flash chromatography using the following conditions: Column: Gemini-NX C18 AXAI Packed, 21.2×150 mm 5 μm; Mobile Phase A: Water (0.05% FA), Mobile Phase B: ACN; Flow rate: 25 mL/min; Gradient: 16% B to 18% B in 10 min; 254 nm to afford compound (181) (Example 68) (70 mg) as a yellow solid.

LCMS: (ES, m/z): $[M+H]^+$=447.2

$^1H$ NMR: (400 MHz, Methanol-d4) δ 7.81 (s, 1H), 7.71 (s, 1H), 5.00 (dd, J=14.0, 10.0 Hz, 1H), 4.74 (s, 2H), 4.55 (dd, J=10.0, 3.1 Hz, 1H), 4.47 (dd, J=14.0, 2.9 Hz, 1H), 4.35 (s, 3H), 3.93 (dtd, J=10.4, 7.4, 3.5 Hz, 2H), 3.80 (qd, J=11.6, 3.9 Hz, 2H), 2.52 (s, 3H), 2.44 (s, 3H).

Synthesis of Compound 183 (Example 69)

Example 69 was synthesized according to the scheme below.

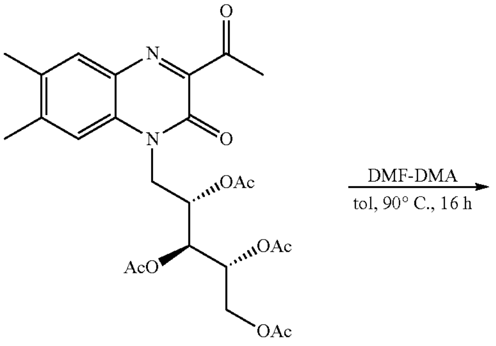

107

-continued

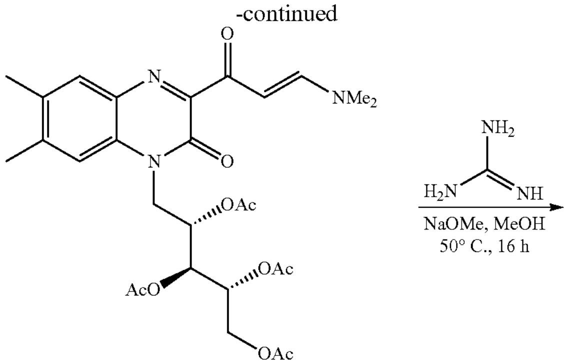

182

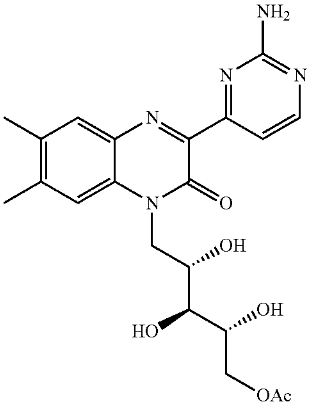

183
(Example 69)

Compound 182

To a 25° C. stirred solution of compound (107) (300 mg, 0.58 mmol) in toluene (10 mL) was added DMF-DMA (2 mL, 14.94 mmol) dropwise. The resulting mixture was stirred for 16 h at 90° C. before being concentrated under reduced pressure. The residue was purified by reverse flash chromatography using the following conditions: Column, C18 silica gel; mobile phase, ACN: water (0.1% FA), 10% to 90% gradient in 30 min; detector, UV 254 nm to afford compound (182) (200 mg) as a yellow oil.

LCMS: (ES, m/z): $[M+H]^+$=574.3

Compound 183 (Example 69)

To a 25° C. stirred solution of compound (182) (200 mg, 0.35 mmol) and guanidine (65.91 mg, 1.12 mmol) in MeOH was added NaOMe (114.41 mg, 1.4 mmol) in portions. The resulting mixture was stirred for 16 h at 50° C. before being concentrated under reduced pressure. The residue was purified by reverse flash chromatography using the following conditions: Column, C18 silica gel; mobile phase, ACN; water, 0% to 50% gradient in 20 min; detector, UV 254 nm to afford compound (183) (Example 69) (70 mg) as a yellow solid.

LCMS: (ES, m/z): $[M+H]^+$=402.3

$^1H$ NMR: (400 MHz, Methanol-d4) δ 8.44 (d, J=5.2 Hz, 1H), 7.75 (s, 1H), 7.69 (s, 1H), 7.49 (d, J=5.1 Hz, 1H), 4.80-4.77 (m, 1H) 4.50 (dd, J=14.1, 2.7 Hz, 1H), 4.32 (ddd, J=9.7, 4.8, 2.7 Hz, 1H), 3.88-3.78 (m, 3H), 3.73-3.68 (m, 1H), 2.49 (s, 3H), 2.41 (s, 3H).

Methods for Evaluating Compounds:

Porcine Eye Corneal Flattening Assay

Protocol 1 (For Examples 8, 9, 10, 17, 18, 19, 20, 28, and 29): Porcine whole globes in saline at 4° C. were warmed to room temperature. The corneas were then de-epithelialized with a dulled scalpel blade and the eyes placed into custom movable eye holders in a horizontal position with the cornea facing upward. The eye holders were then positioned inside an enclosed chamber that allows for the control of atmosphere, temperature and humidity (typically a water bath at 37.0° C.). IOP is maintained at a constant pressure by the insertion of a blood bank buffered saline line from an IV bag at a standard height inserted into each eye via a syringe needle. 5% Dextran T500 in blood bank buffered saline is dropped onto the surface of the cornea of each eye every 90 sec for 2 hours to allow the eyes to stabilize. The dextran drops were discontinued and a solution of a test compound held in place by a small rubber O-ring on the center of the cornea is allowed to soak into the corneal surface of the test eye. After a set soaking time (typically 10 minutes) the O-ring is removed and any excess test solution washed away with saline. The test eye is then orientated in a vertical position and the pre-treatment surface keratometry of the cornea measured using a Pentacam® HR device fine cornea 100 scan. The eye is then returned to the horizontal position and a specific pattern of UVA light at 365 nm is administered to the cornea over a desired dosing period. After a further 1.5 hours during which the 5% dextran drops are resumed the eye is orientated back to the vertical position and the post-treatment surface keratometry of the cornea measured using a Pentacam® HR device fine cornea 100 scan as before. The difference map between the pre and post treatment corneal images is obtained and the overall change in keratometry (Km) of the central 3 mm zone recorded as a change in diopters.

Protocol 2 (For Examples 16, 21, and 54): Porcine whole globes in saline at 4° C. were warmed to room temperature. The eyes were either immediately placed into custom movable eye holders with the cornea facing upward or were first de-epithelialized with a dulled scalpel blade before being placed in the holder. The eye holders were placed inside an enclosed chamber that allows for the control of atmosphere, temperature and humidity (typically a water bath at 37.0° C.). Intra ocular pressure (IOP) was maintained by inserting a blood bank buffered saline line from an IV bag at a standard height into each eye via a needle. 0.5% to 10% (typically 5%) Dextran T500 in blood bank buffered saline was dropped onto the cornea of each eye every 90 sec for 2 hours to allow the eyes to stabilize. The test eye is then orientated in a vertical position and a pre-treatment surface keratometry scan of the cornea taken using a Pentacam® HR device (fine cornea 100 scan). The eye is then returned to the horizontal position and the dextran drops replaced by a solution of the test compound (typically 0.22% w/v in saline) held in place by a small rubber O-ring on the center of the cornea. After a set soaking time 5-30 minutes (typically 10 minutes) the O-ring is removed and excess test solution washed away with saline. The cornea is then illuminated with a specific pattern of UVA light at 365 nm over a desired dosing period. After a further 1.5 hours during which the dextran drops are resumed the eye is returned to the vertical position and a post-treatment surface keratometry scan of the cornea taken using a Pentacam® HR device (fine cornea 100 scan). The difference map between the pre and post treatment corneal images is obtained. Overall change in keratometry (Km) of the central 3 mm zone were recorded as a change in diopters.

Representative porcine de-epithelialized corneal flattening data* for selected examples of the present disclosure are listed in Table B-1, below:

TABLE B-1

| Example # | Compound # | Refractive Change (D) |
|---|---|---|
| 8 | Compound 15 | −1.1 |
| 9 | Compound 16 | −1.3 |
| 10 | Compound 24 | −1.81.8 |
| 16 | Compound 40@ | −2.5, (−1.9)# |
| 17 | Compound 43 | −0.93 |
| 18 | Compound 50 | −1.9 |
| 19 | Compound 52 | −1.85 |
| 20 | Compound 54 | −1.8 |
| 21 | Compound 56 | −2.7, (−18)# |
| 28 | Compound 71 | −1.64 |
| 29 | Compound 73 | −0.7 |
| 54 | Compound 153 | −1.1 |

*UVA light administered in a 4 mm circle at 365 nm, 30 mW/cm$^2$ irradiance, pulsed 1 second on: 1 second off, for 16.2 min, 15 J total dose under a 90% + oxygen atmosphere at 37.0° C..

#Epithelial intact

@(0.11% w/v in saline)

*UVA light administered in a 4 mm circle at 365 nm, 30 mW/cm$^2$ irradiance, pulsed 1 second on: 1 second off, for 16.2 min, 15 J total dose under a 90%+ oxygen atmosphere at 37.0° C.

#Epithelial intact

@ (0.11% w/v in saline)

Porcine Eye Corneal Stiffening Assay

Protocol 1 (for Examples 8, 9, 10, 17, 18, 19, 20, 24, 28, and 29): Porcine whole globes in saline at 4° C. were warmed to room temperature. The eyes were either immediately placed into custom movable eye holders in a horizontal position with the cornea facing upward or were first de-epithelialized with a dulled scalpel blade before being placed in the holder. The eye holders were then positioned inside an enclosed chamber that allows for the control of atmosphere, temperature and humidity (typically a water bath at 37.0° C.). A solution of test compound held in place by a small rubber O-ring on the center of the cornea is then allowed to soak into the cornea surface of the test eye. After a set soaking time (typically 10 minutes) the O-ring is removed and any excess test solution washed away with saline. A specific pattern of UVA light at 365 nm is administered to the test eye cornea over a desired dosing period. A corneal flap of desired thickness (typically 200 μm is then excised from the eyes using a femtosecond laser (Zeimer, LDV1). The corneal flap is placed in saline at ambient temperature for 20 minutes and then mounted onto a biaxial extensiometer (CellScale Biotester5000, Waterloo, ON), using biorake attachments (5 times spanning a width of 3.5 mm). The corneal flap is stretched at a constant rate of 4 μm/s in saline at 37° C. until sample failure. The maximum slope of the force vs distance curve is calculated and compared to that obtained from an untreated cornea.

Protocol 2 (for Examples: 16, 21, 33, 35, 36, 38, 39, 40, 41, 42, 45, 46, 47, 49, 50, 51, 52, 53, 54, 55, 62, 63, 64, 65, 66, 67): Porcine whole globes in saline at 4° C. were warmed to room temperature. The eyes were either immediately placed into custom movable eye holders with the cornea facing upward or were first de-epithelialized with a dulled scalpel blade before being placed in the holder. The eye holders were then positioned inside an enclosed chamber that allows for the control of atmosphere, temperature and humidity (typically a water bath at 37.0° C.). A solution of the test compound (typically 0.22% w/v in saline) is held in place by a small rubber O-ring on the center of the cornea. After a set soaking time of 5-30 minutes (typically 10 minutes) the O-ring is removed and excess test solution washed away with saline. The cornea is then illuminated with a specific pattern of UVA light at 365 nm over a desired dosing period. A corneal flap of desired thickness and diameter (typically 200 μm thick by 8 mm diameter) is then excised from the eyes using a femtosecond laser (Zeimer, LDV1). The corneal flap is either placed in saline at ambient temperature for 20 minutes and then mounted in saline onto a biaxial extensiometer (CellScale Biotester5000, Waterloo, ON) or mounted directly onto the tester in 5% Dextran T500/saline. Biorake attachments (5 tines spanning a width of 3.5 mm) are used to hold the flap as it is stretched at 37° C. and a constant rate of 4 μm/s in both X (5 N load cell) and Y (10 N load cell) directions simultaneously. The maximum slope of the force vs distance curve is calculated (stiffening value) and compared to that obtained from an untreated cornea.

Representative porcine stiffening data** for selected examples of the present disclosure are listed in Table C-1, below:

TABLE C-1

| Example # | Name/ID # | Stiffening value |
|---|---|---|
| 8 | Compound 15 | 13.73 |
| 9 | Compound 16 | 11.81 |
| 10 | Compound 24 | 11.12 |
| 16 | Compound 40$^{@}$ | **16.3$^{†§}$,13.2$^{§}$** |
| 17 | Compound 43 | 11.8 |
| 18 | Compound 50 | 11.73 |
| 19 | Compound 52 | 11.18 |
| 20 | Compound 54 | 10.57 |
| 21 | Compound 56 | **14.1$^{§}$** |
| 24 | Compound 63 | 10.28 |
| 28 | Compound 71 | 11.03 |
| 29 | Compound 73 | 11.35 |
| 33 | Compound 83 | 10.95$^{§}$ |
| 35 | Compound 92 | **11.8$^{§}$** |
| 36 | Compound 97 | **10.2$^{§}$** |
| 38 | Compound 104 | **15.2$^{§}$** |
| 39 | Compound 105 | **14.7$^{§}$** |
| 40 | Compound 110 | **12.6$^{§}$** |
| 41 | Compound 113 | **11.9$^{§}$** |
| 42 | Compound 116 | **11.1$^{§}$** |
| 45 | Compound 129 | **10.4$^{§}$** |
| 46 | Compound 132 | **12.5$^{§}$** |
| 47 | Compound 135 | **10.1$^{§}$** |
| 49 | Compound 141 | **10.9$^{§}$** |
| 50 | Compound 143 | **16.3$^{§}$** |
| 51 | Compound 145 | **15.8$^{§}$** |
| 52 | Compound 147 | **13.5$^{§}$** |
| 53 | Compound 150 | 12.8$^{§}$ |
| 54 | Compound 153 | **13.5$^{§}$** |
| 55 | Compound 158 | **12.6$^{§}$** |
| 62 | Compound 170 | **10.4$^{§}$** |
| 63 | Compound 171 | **15.4$^{§}$** |
| 64 | Compound 173 | **15.6$^{§}$** |
| 65 | Compound 175 | **17.2$^{§}$** |
| 66 | Compound 177 | **15.4$^{§}$** |
| 67 | Compound 180 | **13.4$^{§}$** |

**UVA light administered in a 9 mm circle at 365 nm, 30 mW/cm$^2$ irradiance, pulsed 1 second on: 1 second off, for 16.2 min, 15 J total dose under a 90%+ oxygen atmosphere at 37.0° C., eyes were not de-epithelialized prior to treatment,
Untreated control cornea max slope value = 10.1
§stiffening value calculated as stress at 10% strain from data curves aligned at 0.1N load.
†de-epithelialized
Bold (mounted directly in 5% Dextran)
@ (0.11% w/v in saline)

** UVA light administered in a 9 mm circle at 365 nm, 30 mW/cm$^2$ irradiance, pulsed 1 second on: 1 second off, for 16.2 min, 15 J total dose under a 90%+ oxygen atmosphere at 37.0° C., eyes were not de-epithelialized prior to treatment,
Untreated control cornea max slope value=10.1
§ stiffening value calculated as stress at 10% strain from data curves aligned at 0.1N load.
† de-epithelialized
Bold (mounted directly in 5% Dextran)
@ (0.11% w/v in saline)

A number of embodiments of the invention have been described. Nevertheless, it will be understood that various modifications may be made without departing from the spirit and scope of the invention. Accordingly, other embodiments are within the scope of the following claims

What is claimed is:

1. A compound having formula (I):

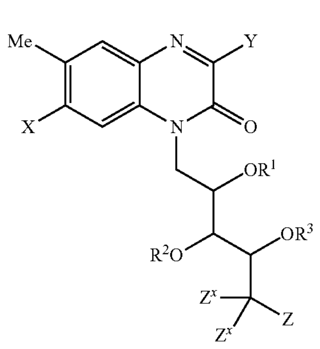

(I)

or a pharmaceutically acceptable salt thereof;

wherein:

X is $C_1$-$C_6$ alkyl;

Y is selected from the group consisting of:

(i) $C(O)NR^{4Y}R^{5Y}$;

(ii) heteroaryl including from 5-6 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-2 independently selected $R^c$; and (iii) heterocycloalkenyl including from 5-6 ring atoms, wherein from 1-4 ring atoms are heteroatoms, each independently selected from the group consisting of N, N(H), N($R^4$), O, and S, and wherein one or more of the heterocycloalkenyl ring carbon atoms are optionally substituted with from 1-2 independently selected $R^b$;

Z is selected from the group consisting of:

(i) H, (ii) $NR^{4Z}R^{5Z}$, (iii) $OR^{6Z}$, (iv) $OC(O)R^{7Z}$, (v) $OP(O)OR^{8Z}OR^{9Z}$, and (vi) heterocyclyl including from 4-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $R^h$;

each $Z^x$ is H; or each $Z^x$ together with the carbon to which each is attached forms C═O;

each of $R^1$, $R^2$, and $R^3$ is $R^{6A}$;

ach of $R^{4Y}$ and $R^{5Y}$ is independently selected from the group consisting of:

(i) H;

(ii) $C_{1-12}$ alkyl, which is optionally substituted with 1-6 $R^a$;

(iii) heteroaryl including from 5-10 ring atoms, wherein from 1-4 ring atoms are heteroatoms, each independently selected from the group consisting of N, N(H), N($R^d$), O, and S, and wherein one or more of the heteroaryl ring carbon atoms are optionally substituted with from 1-4 independently selected $R^h$;

(iv) —$(W^1—W^2)_n$—$W^3$, wherein:

$W^1$ is in each occurrence is independently $C_{1-3}$ alkylene optionally substituted with from 1-4 $R^a$;

$W^2$ is in each occurrence independently —N(H)—, —N($R^d$)—, —O—, or —S—;

$W^3$ is H or $C_{1-7}$ alkyl optionally substituted with from 1-4 $R^a$; and n is 2-4;

and (v) $R^{4Y}$ and $R^{5Y}$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms in addition to the nitrogen atom attached to $R^{4Y}$ and $R^{5Y}$, which are each independently selected from the group consisting of N(H), N($R^d$), O, and S;

each of $R^{4Z}$ and $R^{5Z}$ is independently selected from the group consisting of:

(i) H; and (ii) $C_{1-10}$ alkyl optionally substituted with 1-6 independently selected $R^a$;

$R^{6A}$ in each occurrence is H;

$R^{6Z}$ is independently selected from the group consisting of:

(i) H;

(ii) $C_{1-10}$ alkyl optionally substituted with from 1-6 independently selected $R^a$;

(iii) —($C_{0-2}$ alkylene)-($C_{6-10}$ aryl), wherein the $C_{6-10}$ aryl is optionally substituted with from 1-2 independently selected $R^h$;

(iv) —($C_{0-2}$ alkylene)-(heteroaryl), wherein the heteroaryl includes from 5-10 ring atoms, wherein from 1-4 ring atoms are heteroatoms, each independently selected from the group consisting of N, N(H), N($C_{1-3}$ alkyl), O, and S, and wherein one or more of the heteroaryl ring carbon atoms are optionally substituted with from 1-4 independently selected $R^h$, and (v) —($C_{1-2}$ alkylene)-C(═O)NH—($C_{1-3}$ alkylene)-$R^{6Z'}$;

$R^{6Z'}$ is selected from the group consisting of:

C(═O)OH, N($C_{1-4}$ alkyl)$_2$, $NH_2$, NH($C_{1-4}$ alkyl), and heterocyclyl including from 3-10 ring atoms, wherein from 1-3 ring atoms are heteroatoms, each independently selected from the group consisting of N, N(H), N($R^d$), and O, and wherein one or more of the heterocyclyl ring carbon atoms are optionally substituted with from 1-4 independently selected $C_{1-3}$ alkyl;

each of $R^{7Z}$ at each occurrence, is independently $C_{1-10}$ alkyl optionally substituted with from 1-6 independently selected $R^a$;

each of $R^{8Z}$ and $R^{9Z}$ in each occurrence is H;

each occurrence of $R^a$ is independently selected from the group consisting of: —OH; $NR^eR^f$; $C_{1-4}$ alkoxy; —C(═O)OH; —CON(R')(R"); C(═NH)N(R')(R");

each occurrence of $R^b$ is $C_{1-6}$ alkyl;

each occurrence of $R^c$ is independently selected from the group consisting of:

(i) $C_{1-10}$ alkyl;

(ii) $C_{1-10}$ alkyl substituted with from 1-6 independently selected $R^a$;

(iii) —$NR^eR^f$, (iv) —C(═O)OH; and (v) —C(═O)N(R')(R");

$R^d$ is $C_{1-6}$ alkyl optionally substituted with from 1-3 independently selected $R^g$;

each occurrence of $R^e$ and $R^f$ is independently selected from the group consisting of: H and $C_{1-6}$ alkyl;

or $R^e$ and $R^f$ together with the nitrogen atom to which each is attached forms a ring including from 3-8 ring atoms, wherein the ring includes: (a) from 1-7 ring carbon atoms, each of which is substituted with from 1-2 substituents independently selected from H and $C_{1-3}$ alkyl; and (b) from 0-3 ring heteroatoms in addition to the nitrogen atom attached to $R^e$ and $R^f$, which are each independently selected from the group consisting of N(H), N($R^d$), O, and S;

each occurrence of $R^h$ is $C_{1-3}$ alkyl;

and each occurrence of R' and R" is H;

with the proviso that the compound is not:

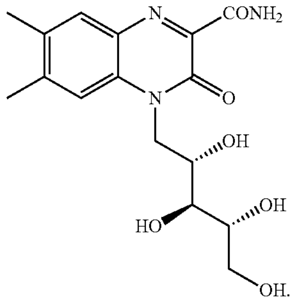 [SMILES: Cc1cc2nc(C(N)=O)c(=O)n(C[C@H](O)[C@H](O)[C@H](O)CO)c2cc1C]

2. The compound of claim 1, wherein Z is $OR^{6Z}$.

3. The compound of claim 2, wherein $R^{6Z}$ is selected from H and $C_{1-3}$ alkyl, optionally substituted with 1 $R^a$.

4. The compound of claim 3, wherein $R^{6Z}$ is H.

5. The compound of claim 1, wherein Y is $CONR^{4Y}R^{5Y}$.

6. The compound of claim 5, wherein each of $R^{4Y}$ and $R^{5Y}$ is independently H or $C_{1-4}$ alkyl optionally substituted with from 1-2 independently selected $R^a$.

7. The compound of claim 6, wherein each of $R^{4Y}$ and $R^{5Y}$ is independently H or

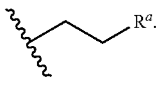

8. The compound of claim 7, wherein $R^{4Y}$ is H; and $R^a$ on $R^{5Y}$ is selected from —OH and —$NR^eR^f$—.

9. The compound of claim 8, wherein $R^{5Y}$ is

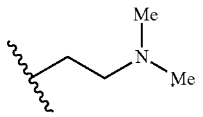 [SMILES: *CCN(C)C]

10. The compound of claim 1, wherein Y is heteroaryl including from 5 ring atoms wherein from 1-4 ring atoms are heteroatoms, each independently selected from the group consisting of N, N(H), N($R^d$), O, and S, and wherein one or more of the heteroaryl ring carbon atoms are optionally substituted with from 1-2 independently selected $R^c$.

11. The compound of claim 10, wherein Y is selected from tetrazolyl, triazolyl, oxadiazolyl, and oxazolyl, wherein one or more of the heteroaryl ring carbon atoms are optionally substituted with from 1-2 independently selected $R^c$; and one of the heteroaryl ring nitrogen atoms is optionally substituted with $R^d$.

12. The compound of claim 1, wherein each $Z^x$ is H.

13. The compound of claim 1, wherein each $Z^x$ together with the carbon to which each is attached forms C═O.

14. The compound of claim 1, wherein the compound is selected from:

| Example # | Compound | Name/ID # |
|---|---|---|
| 8 | 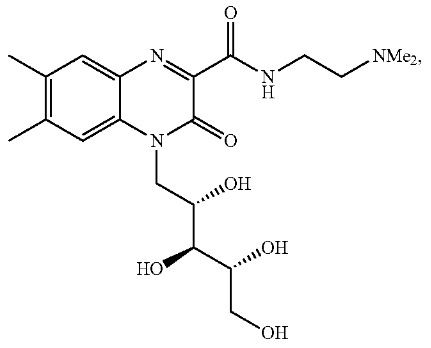 [SMILES: Cc1cc2nc(C(=O)NCCN(C)C)c(=O)n(C[C@H](O)[C@H](O)[C@H](O)CO)c2cc1C] | Compound 15 |
| 14 | 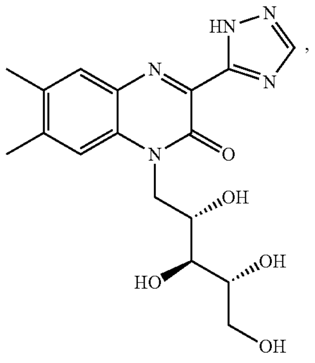 [SMILES: Cc1cc2nc(-c3ncn[nH]3)c(=O)n(C[C@H](O)[C@H](O)[C@H](O)CO)c2cc1C] | Compound 31 |
| 15 | 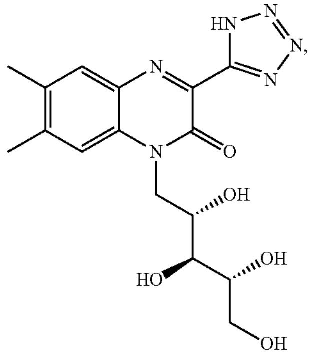 [SMILES: Cc1cc2nc(-c3nnn[nH]3)c(=O)n(C[C@H](O)[C@H](O)[C@H](O)CO)c2cc1C] | Compound 37 |

-continued
| Example # | Compound | Name/ID # |
|---|---|---|
| 16 | 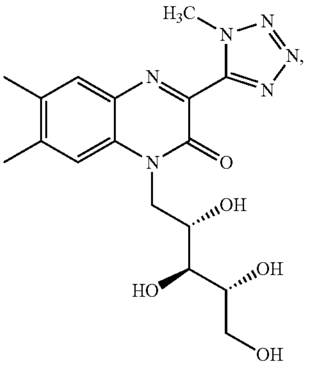 | Compound 40 |
| 17 | 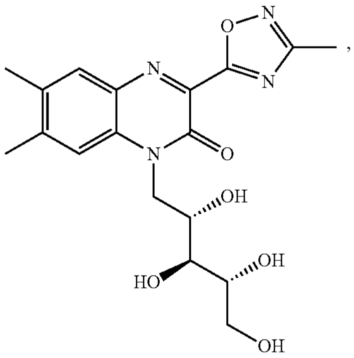 | Compound 43 |
| 18 | 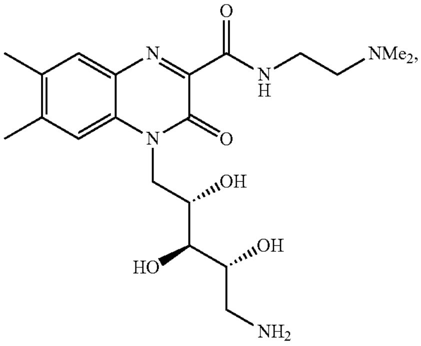 [SMILES: Cc1cc2nc(C(=O)NCCN(C)C)c(=O)n(C[C@H](O)[C@H](O)[C@H](O)CN)c2cc1C] | Compound 50 |
| 19 | 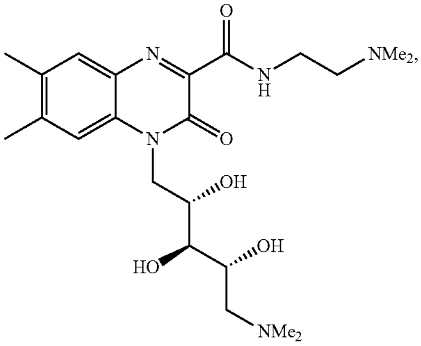 | Compound 52 |

-continued
| Example # | Compound | Name/ID # |
|---|---|---|
| 20 | 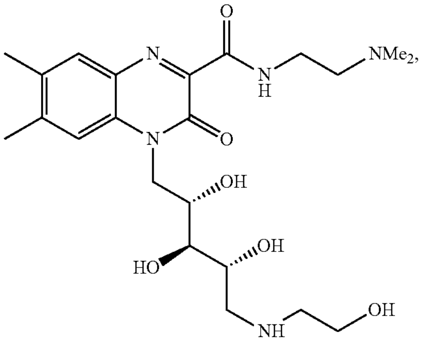 [SMILES: Cc1cc2nc(C(=O)NCCN(C)C)c(=O)n(C[C@H](O)[C@H](O)[C@H](O)CNCCO)c2cc1C] | Compound 54 |
| 21 | 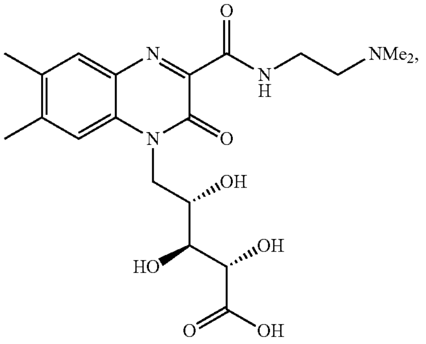 [SMILES: Cc1cc2nc(C(=O)NCCN(C)C)c(=O)n(C[C@H](O)[C@H](O)[C@H](O)C(=O)O)c2cc1C] | Compound 56 |
| 22 | 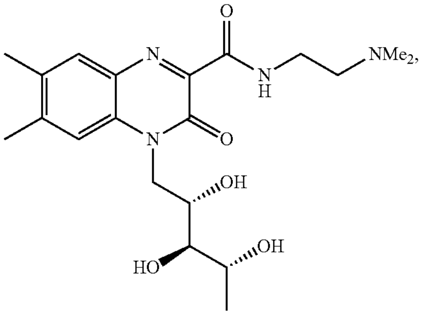 [SMILES: Cc1cc2nc(C(=O)NCCN(C)C)c(=O)n(C[C@H](O)[C@H](O)[C@@H](C)O)c2cc1C] | Compound 59 |
| 23 | 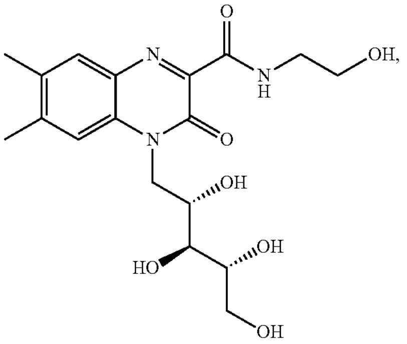 [SMILES: Cc1cc2nc(C(=O)NCCO)c(=O)n(C[C@H](O)[C@H](O)[C@H](O)CO)c2cc1C] | Compound 61 |

-continued
| Example # | Compound | Name/ID # |
|---|---|---|
| 24 | 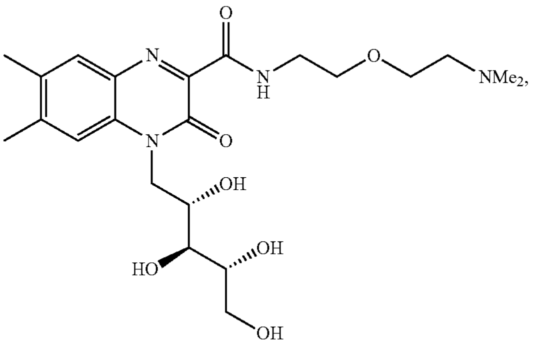 [SMILES: Cc1cc2nc(C(=O)NCCOCCN(C)C)c(=O)n(C[C@H](O)[C@H](O)[C@H](O)CO)c2cc1C] | Compound 63 |
| 25 | 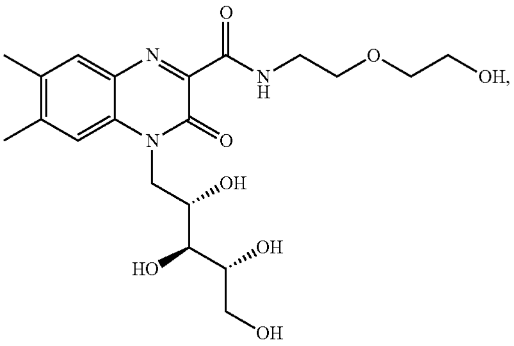 [SMILES: Cc1cc2nc(C(=O)NCCOCCO)c(=O)n(C[C@H](O)[C@H](O)[C@H](O)CO)c2cc1C] | Compound 65 |
| 28 | 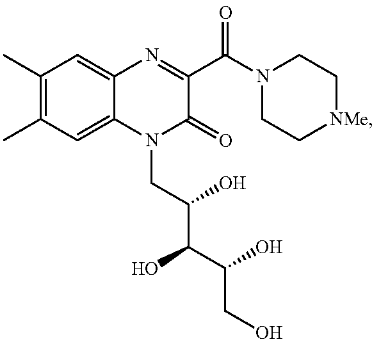 [SMILES: Cc1cc2nc(C(=O)N3CCN(C)CC3)c(=O)n(C[C@H](O)[C@H](O)[C@H](O)CO)c2cc1C] | Compound 71 |
| 29 | 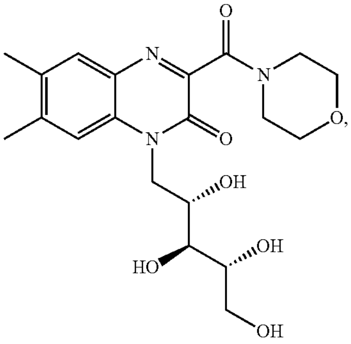 [SMILES: Cc1cc2nc(C(=O)N3CCOCC3)c(=O)n(C[C@H](O)[C@H](O)[C@H](O)CO)c2cc1C] | Compound 73 |

-continued
| Example # | Compound | Name/ID # |
|---|---|---|
| 30 | 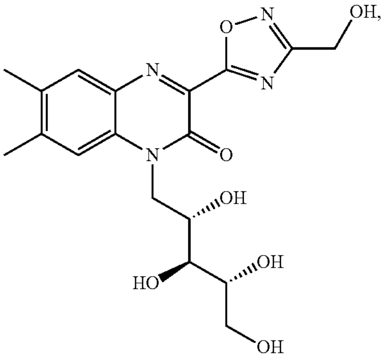 [SMILES: Cc1cc2nc(-c3nc(CO)no3)c(=O)n(C[C@H](O)[C@H](O)[C@H](O)CO)c2cc1C] | Compound 75 |
| 31 | 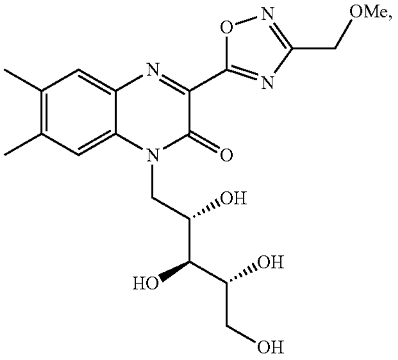 [SMILES: COCc1noc(-c2nc3cc(C)c(C)cc3n(C[C@H](O)[C@H](O)[C@H](O)CO)c2=O)n1] | Compound 79 |
| 32 | 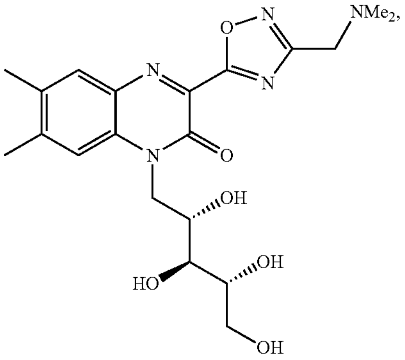 [SMILES: Cc1cc2nc(-c3nc(CN(C)C)no3)c(=O)n(C[C@H](O)[C@H](O)[C@H](O)CO)c2cc1C] | Compound 78 |
| 33 | 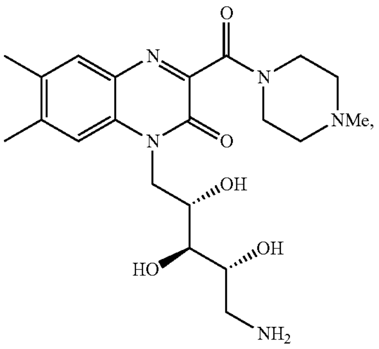 [SMILES: Cc1cc2nc(C(=O)N3CCN(C)CC3)c(=O)n(C[C@H](O)[C@H](O)[C@H](O)CN)c2cc1C] | Compound 83 |

-continued
| Example # | Compound | Name/ID # |
|---|---|---|
| 34 | 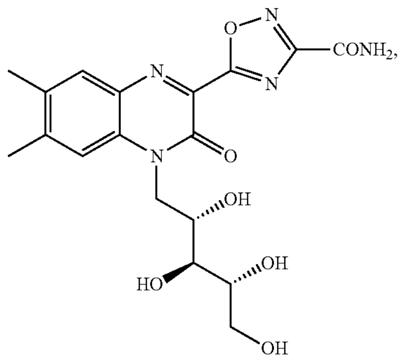 [SMILES: Cc1cc2nc(-c3nc(C(N)=O)no3)c(=O)n(C[C@H](O)[C@H](O)[C@H](O)CO)c2cc1C] | Compound 84 |
| 35 | 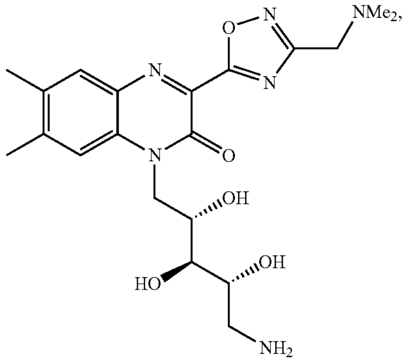 [SMILES: Cc1cc2nc(-c3nc(CN(C)C)no3)c(=O)n(C[C@H](O)[C@H](O)[C@H](O)CN)c2cc1C] | Compound 92 |
| 36 | 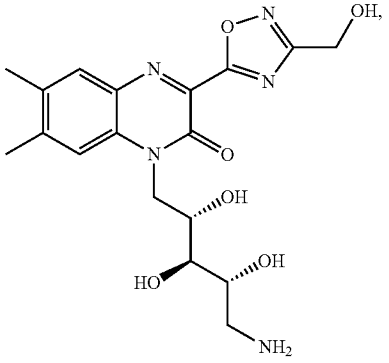 [SMILES: Cc1cc2nc(-c3nc(CO)no3)c(=O)n(C[C@H](O)[C@H](O)[C@H](O)CN)c2cc1C] | Compound 97 |
| 37 | 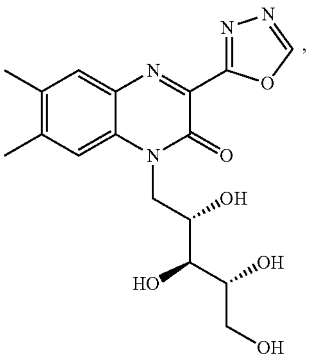 [SMILES: Cc1cc2nc(-c3nnco3)c(=O)n(C[C@H](O)[C@H](O)[C@H](O)CO)c2cc1C] | Compound 99 |

-continued
| Example # | Compound | Name/ID # |
|---|---|---|
| 38 | 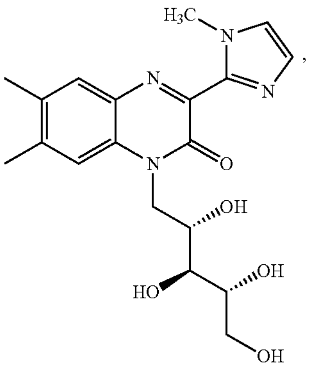 [SMILES: Cc1cc2nc(-c3nccn3C)c(=O)n(C[C@H](O)[C@H](O)[C@H](O)CO)c2cc1C] | Compound 104 |
| 39 | 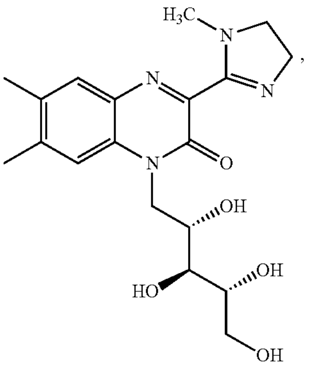 [SMILES: Cc1cc2nc(C3=NCCN3C)c(=O)n(C[C@H](O)[C@H](O)[C@H](O)CO)c2cc1C] | Compound 105 |
| 40 | 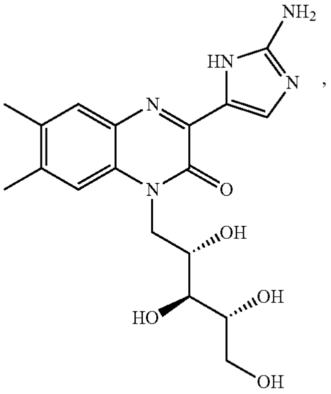 [SMILES: Cc1cc2nc(-c3cnc(N)[nH]3)c(=O)n(C[C@H](O)[C@H](O)[C@H](O)CO)c2cc1C] | Compound 110 |
| 41 | 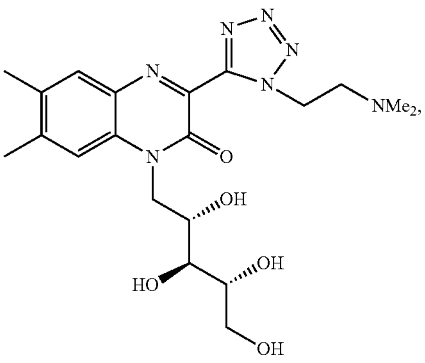 [SMILES: Cc1cc2nc(-c3nnnn3CCN(C)C)c(=O)n(C[C@H](O)[C@H](O)[C@H](O)CO)c2cc1C] | Compound 113 |

-continued
| Example # | Compound | Name/ID # |
|---|---|---|
| 42 | 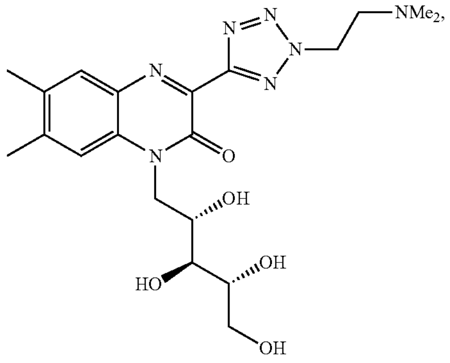 [SMILES: Cc1cc2nc(-c3nnn(CCN(C)C)n3)c(=O)n(C[C@H](O)[C@H](O)[C@H](O)CO)c2cc1C] | Compound 116 |
| 43 | 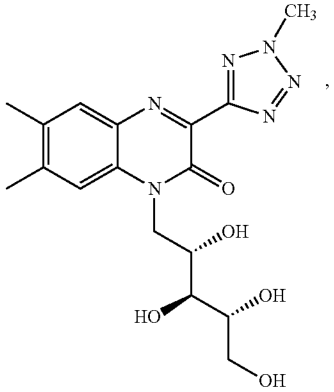 [SMILES: Cc1cc2nc(-c3nnn(C)n3)c(=O)n(C[C@H](O)[C@H](O)[C@H](O)CO)c2cc1C] | Compound 117 |
| 44 | 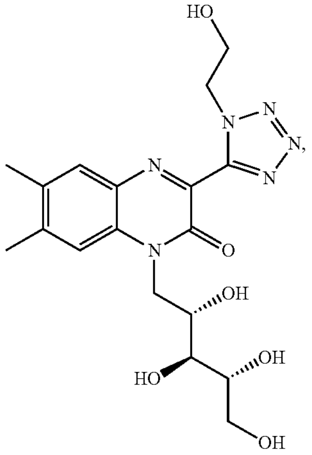 [SMILES: Cc1cc2nc(-c3nnnn3CCO)c(=O)n(C[C@H](O)[C@H](O)[C@H](O)CO)c2cc1C] | Compound 121 |
| 45 | 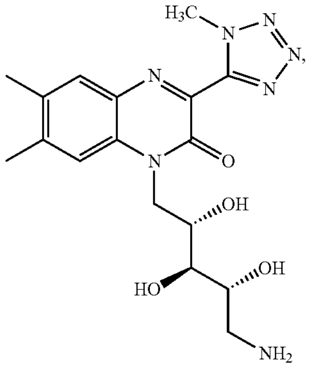 [SMILES: Cc1cc2nc(-c3nnnn3C)c(=O)n(C[C@H](O)[C@H](O)[C@H](O)CN)c2cc1C] | Compound 129 |

-continued
| Example # | Compound | Name/ID # |
|---|---|---|
| 46 | 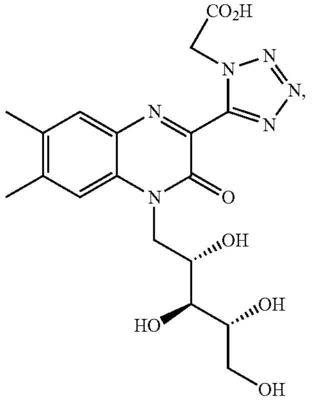 [SMILES: Cc1cc2nc(-c3nnnn3CC(=O)O)c(=O)n(C[C@H](O)[C@H](O)[C@H](O)CO)c2cc1C] | Compound 132 |
| 47 | 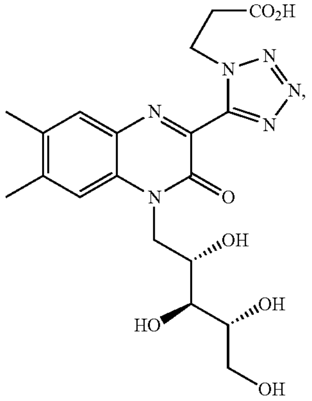 [SMILES: Cc1cc2nc(-c3nnnn3CCC(=O)O)c(=O)n(C[C@H](O)[C@H](O)[C@H](O)CO)c2cc1C] | Compound 135 |
| 48 | 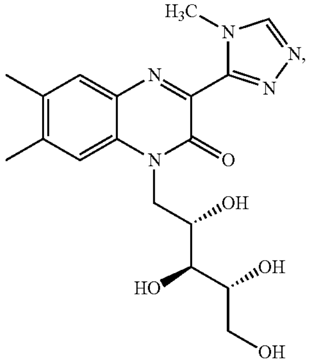 [SMILES: Cc1cc2nc(-c3nncn3C)c(=O)n(C[C@H](O)[C@H](O)[C@H](O)CO)c2cc1C] | Compound 137 |
| 49 | 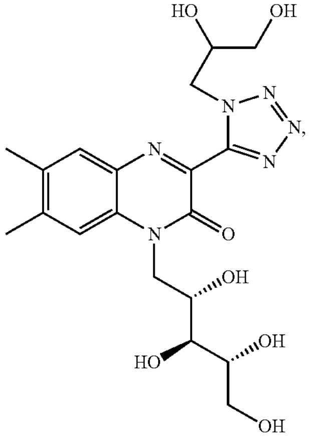 [SMILES: Cc1cc2nc(-c3nnnn3CC(O)CO)c(=O)n(C[C@H](O)[C@H](O)[C@H](O)CO)c2cc1C] | Compound 141 |

-continued
| Example # | Compound | Name/ID # |
|---|---|---|
| 50 | 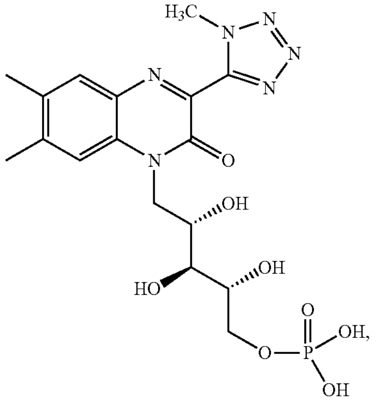 [SMILES: Cc1cc2nc(-c3nnnn3C)c(=O)n(C[C@H](O)[C@H](O)[C@H](O)COP(=O)(O)O)c2cc1C] | Compound 143 |
| 51 | 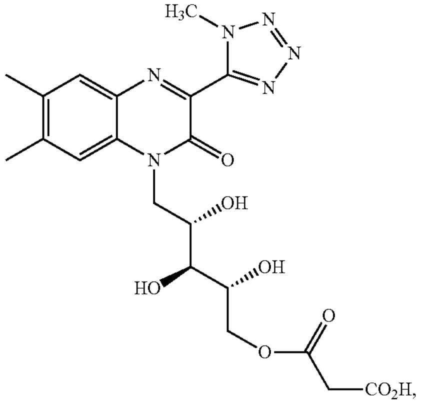 [SMILES: Cc1cc2nc(-c3nnnn3C)c(=O)n(C[C@H](O)[C@H](O)[C@H](O)COC(=O)CC(=O)O)c2cc1C] | Compound 145 |
| 52 | 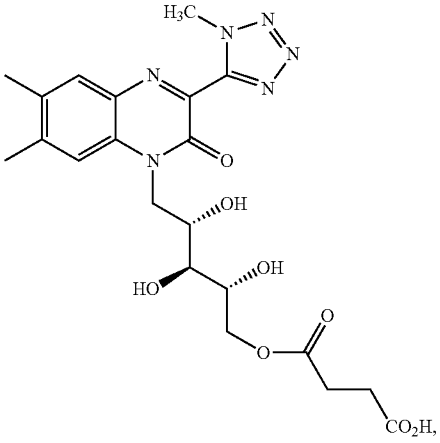 [SMILES: Cc1cc2nc(-c3nnnn3C)c(=O)n(C[C@H](O)[C@H](O)[C@H](O)COC(=O)CCC(=O)O)c2cc1C] | Compound 147 |

-continued
| Example # | Compound | Name/ID # |
|---|---|---|
| 53 | 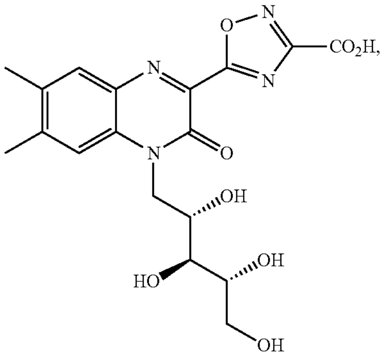 [SMILES: Cc1cc2nc(-c3nc(C(=O)O)no3)c(=O)n(C[C@H](O)[C@H](O)[C@H](O)CO)c2cc1C] | Compound 150 |
| 54 | 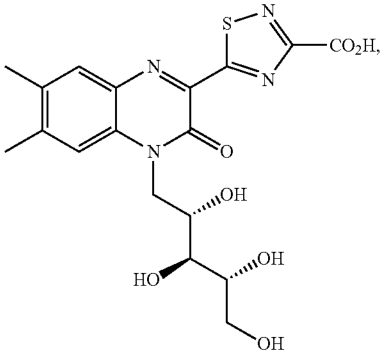 | Compound 153 |
| 55 | 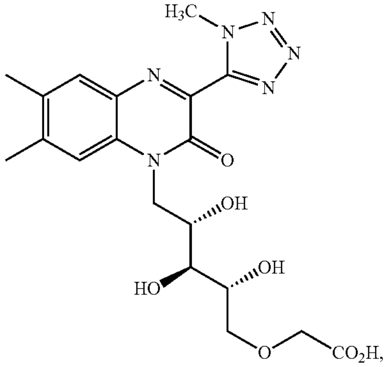 [SMILES: Cc1cc2nc(-c3nnnn3C)c(=O)n(C[C@H](O)[C@H](O)[C@H](O)COCC(=O)O)c2cc1C] | Compound 158 |
| 56 | 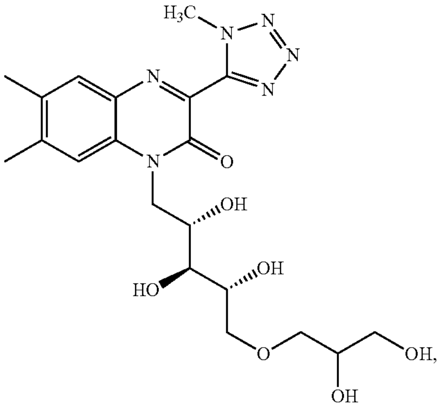 [SMILES: Cc1cc2nc(-c3nnnn3C)c(=O)n(C[C@H](O)[C@H](O)[C@H](O)COCC(O)CO)c2cc1C] | Compound 160 |

-continued
| Example # | Compound | Name/ID # |
|---|---|---|
| 57 | 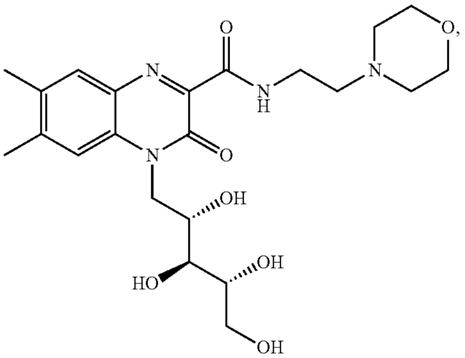 [SMILES: Cc1cc2nc(C(=O)NCCN3CCOCC3)c(=O)n(C[C@H](O)[C@H](O)[C@H](O)CO)c2cc1C] | Compound 161 |
| 58 | 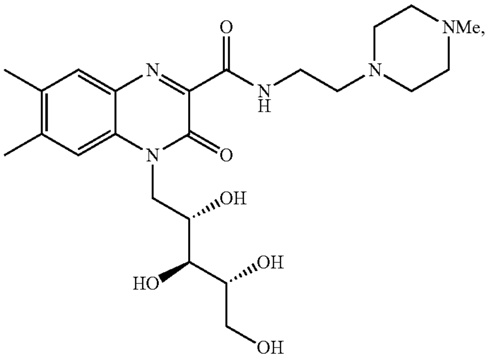 [SMILES: Cc1cc2nc(C(=O)NCCN3CCN(C)CC3)c(=O)n(C[C@H](O)[C@H](O)[C@H](O)CO)c2cc1C] | Compound 162 |
| 59 | 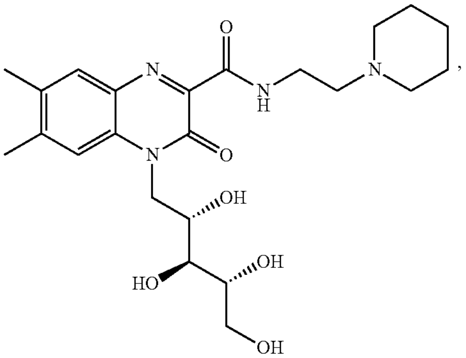 [SMILES: Cc1cc2nc(C(=O)NCCN3CCCCC3)c(=O)n(C[C@H](O)[C@H](O)[C@H](O)CO)c2cc1C] | Compound 163 |
| 60 | 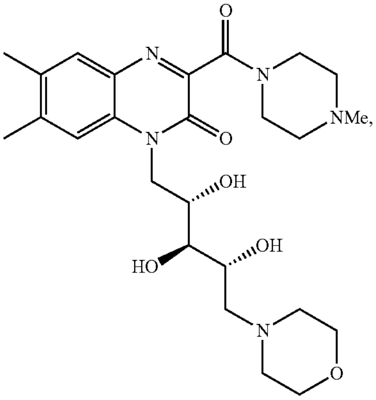 [SMILES: Cc1cc2nc(C(=O)N3CCN(C)CC3)c(=O)n(C[C@H](O)[C@H](O)[C@H](O)CN3CCOCC3)c2cc1C] | Compound 165 |

-continued
| Example # | Compound | Name/ID # |
|---|---|---|
| 61 | 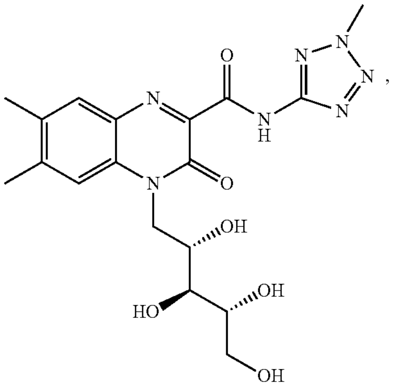 [SMILES: Cc1cc2nc(C(=O)Nc3nnn(C)n3)c(=O)n(C[C@H](O)[C@H](O)[C@H](O)CO)c2cc1C] | Compound 167 |
| | 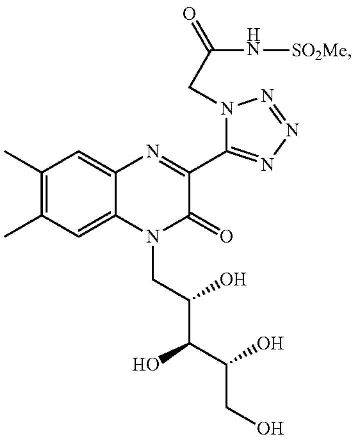 [SMILES: Cc1cc2nc(-c3nnnn3CC(=O)NS(C)(=O)=O)c(=O)n(C[C@H](O)[C@H](O)[C@H](O)CO)c2cc1C] | |
| 63 | 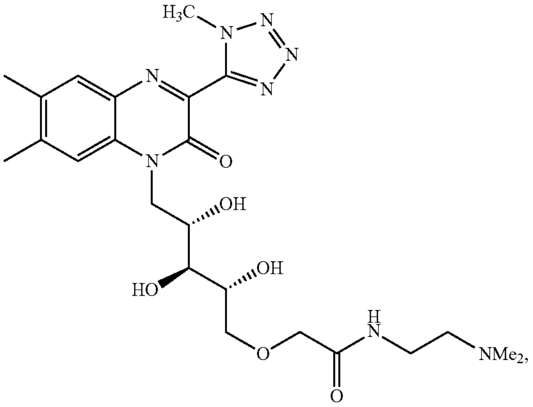 [SMILES: Cc1cc2nc(-c3nnnn3C)c(=O)n(C[C@H](O)[C@H](O)[C@H](O)COCC(=O)NCCN(C)C)c2cc1C] | Compound 171 |

-continued
| Example # | Compound | Name/ID # |
|---|---|---|
| 64 | 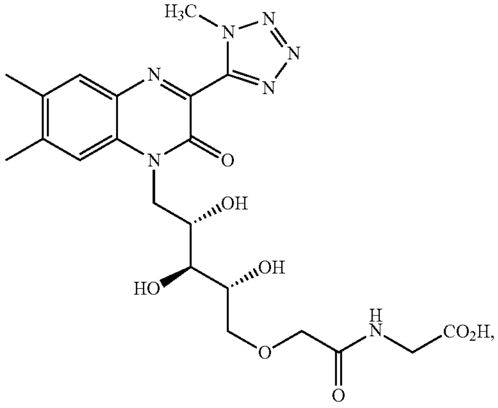 [SMILES: Cc1cc2nc(-c3nnnn3C)c(=O)n(C[C@H](O)[C@H](O)[C@H](O)COCC(=O)NCC(=O)O)c2cc1C] | Compound 173 |
| 65 | 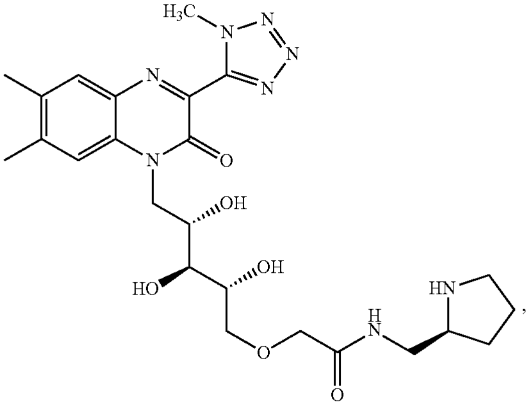 [SMILES: Cc1cc2nc(-c3nnnn3C)c(=O)n(C[C@H](O)[C@H](O)[C@H](O)COCC(=O)NC[C@@H]3CCCN3)c2cc1C] | Compound 175 |
| 66 | 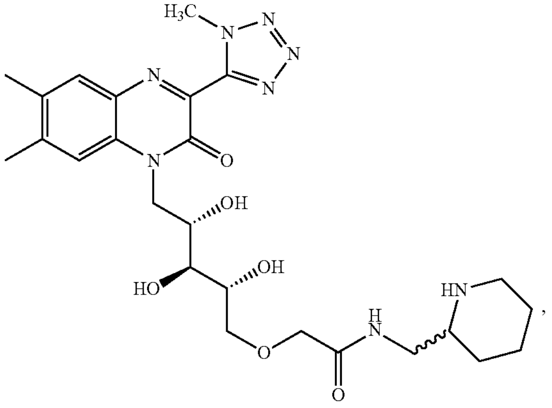 [SMILES: Cc1cc2nc(-c3nnnn3C)c(=O)n(C[C@H](O)[C@H](O)[C@H](O)COCC(=O)NCC3CCCCN3)c2cc1C] | Compound 177 |

-continued

| Example # | Compound | Name/ID # |
|---|---|---|
| 67 | 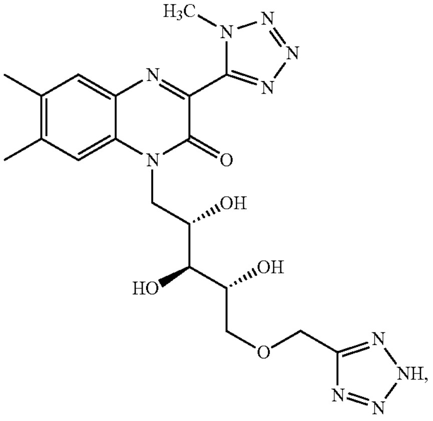 [SMILES: Cc1cc2nc(-c3nnnn3C)c(=O)n(C[C@H](O)[C@H](O)[C@H](O)COCc3nn[nH]n3)c2cc1C] | Compound 180 |
| 68 | 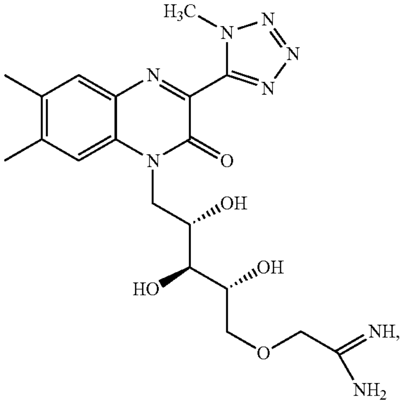 and | Compound 181 |
| 69 | 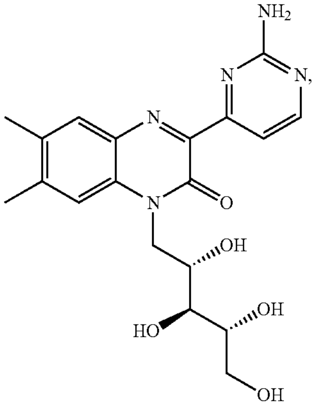 [SMILES: Cc1cc2nc(-c3ccnc(N)n3)c(=O)n(C[C@H](O)[C@H](O)[C@H](O)CO)c2cc1C] | Compound 183 |

or a pharmaceutically acceptable salt thereof.

15. A pharmaceutical composition comprising a compound of claim 1, or a pharmaceutically acceptable salt thereof, and a pharmaceutically acceptable excipient.

16. A method for applying treatment to a cornea of an eye, comprising:

administering a compound of claim 1, or a pharmaceutically acceptable salt thereof, to the cornea of a subject in need thereof; and applying an electromagnetic radiation to the cornea, thereby generating cross-linking in the cornea.

17. The method according to claim 16, wherein the method is used to treat one or more corneal ectatic disorders selected from the group consisting of keratoconus, keratoglobus, pellucid marginal degeneration, post-operative ectasia, and Terrien's marginal degeneration.

18. The method according to claim 16, wherein the electromagnetic radiation is selected from the group consisting of ultraviolet light and laser radiation.

19. The method according to claim 16, further comprising administering to the cornea an additional cross-linking agent; administering to the cornea one or more additives that are different from the cross-linking agent; administering to the cornea an additional ophthalmic therapeutic for inflammation, cataracts, or lens disorder and/or applying a selected concentration of oxygen to the eye, where the selected concentration is greater than a concentration of oxygen in atmosphere.
20. The compound of claim 11, wherein Y is selected from the group consisting of:
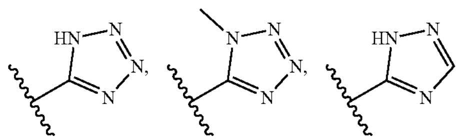
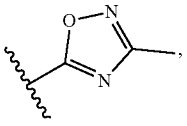
, and
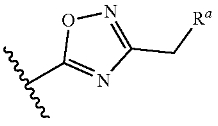
,
wherein $R^a$ is selected from —OH, —OMe, and —$NMe_2$.
* * * * *